(12) United States Patent
Kostenuik et al.

(10) Patent No.: US 8,992,925 B2
(45) Date of Patent: Mar. 31, 2015

(54) RANKL ANTIBODY-PTH/PTHRP CHIMERIC MOLECULES

(75) Inventors: Paul Kostenuik, Newbury Park, CA (US); Wenyan Shen, Palo Alto, CA (US); Thomas C. Boone, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 1829 days.

(21) Appl. No.: 11/599,629

(22) Filed: Nov. 13, 2006

(65) Prior Publication Data

US 2007/0134245 A1 Jun. 14, 2007

Related U.S. Application Data

(60) Provisional application No. 60/736,664, filed on Nov. 14, 2005.

(51) Int. Cl.

| A61K 39/395 | (2006.01) |
|---|---|
| C07K 16/24 | (2006.01) |
| A01K 67/027 | (2006.01) |
| C07K 14/635 | (2006.01) |
| C07K 14/705 | (2006.01) |
| C07K 16/28 | (2006.01) |
| A61K 39/00 | (2006.01) |

(52) U.S. Cl.
CPC ........... *C07K 16/241* (2013.01); *A01K 67/0278* (2013.01); *C07K 14/635* (2013.01); *C07K 14/70575* (2013.01); *C07K 16/2875* (2013.01); *A01K 2207/15* (2013.01); *A01K 2217/00* (2013.01); *A01K 2227/105* (2013.01); *A01K 2267/03* (2013.01); *A61K 2039/505* (2013.01); *C07K 2317/21* (2013.01); *C07K 2317/76* (2013.01); *C07K 2319/00* (2013.01)
USPC ................ 424/145.1; 530/388.24; 530/391.1; 424/178.1

(58) Field of Classification Search
CPC .................... A61K 2300/00; A61K 2039/505; A61K 39/395; A61K 39/3955; A61K 38/29; A61K 38/1875; C07K 2319/00; C07K 14/635; C07K 14/525; C07K 14/54; C07K 14/521
USPC ........................................ 530/387.3; 435/328
See application file for complete search history.

(56) References Cited

U.S. PATENT DOCUMENTS

| 6,316,408 | B1 | 11/2001 | Boyle |
|---|---|---|---|
| 6,884,598 | B2 | 4/2005 | Dougall |
| 7,097,834 | B1 | 8/2006 | Boyle |
| 2003/0021785 | A1 | 1/2003 | Dougall |
| 2003/0103978 | A1 | 6/2003 | Deshpande et al. |
| 2003/0176647 | A1 | 9/2003 | Yamaguchi et al. |
| 2003/0208045 | A1 | 11/2003 | Yamaguchi et al. |
| 2004/0033535 | A1* | 2/2004 | Boyle et al. ..................... 435/7.2 |
| 2004/0101904 | A1* | 5/2004 | Pardridge et al. .............. 435/7.1 |
| 2005/0003457 | A1 | 1/2005 | Yamaguchi et al. |

FOREIGN PATENT DOCUMENTS

| EP | 0 911 342 A1 | 4/1999 |
|---|---|---|
| WO | WO 98/46751 A1 | 10/1998 |
| WO | WO 98/54201 A1 | 12/1998 |
| WO | WO 01/81415 A2 | 11/2001 |
| WO | WO 01/83525 A2 | 11/2001 |
| WO | WO 03/002713 A2 | 1/2003 |
| WO | WO 2004/001384 A2 | 12/2003 |
| WO | WO 2004/060386 A1 | 7/2004 |

OTHER PUBLICATIONS

Hendy et al. Nucleotide sequence of cloned cDNAs encoding human preproparathyroid hormone. Proc Natl Acad Sci U S A. Dec. 1981;78(12):7365-9.*
McGrath et al. Bifunctional fusion between nerve growth factor and a transferrin receptor antibody. J Neurosci Res. Jan. 15, 1997;47(2):123-33.*
Paul W. E. Fundamental Immunology, 3rd edition, 1993, pp. 292-295.*
Rudikoff et al. Single amino acid substitution altering antigen-binding specificity. Proc Natl Acad Sci U S A. Mar. 1982;79(6):1979-83.*
Vajdos et al. Comprehensive functional maps of the antigen-binding site of an anti-ErbB2 antibody obtained with shotgun scanning mutagenesis. J Mol Biol. Jul. 5, 2002;320(2):415-28.*
Alberts et al. 1994. Molecular Biology of the Cell, Third Edition, Garland Publishing, Inc. New York & London, pp. 129-130.*
Body et al, "A study of the biological receptor activator of nuclear factor-κB ligand inhibitor, denosumab, in patients with multiple myeloma or bone metastases from breast cancer," *Clin. Cancer Res.*, 12:1221-1228 (2006).
Hofbauer et al, "Osteoprotegerin and its cognate ligand: a new paradigm of osteoclastogenesis," *Eur. J. of Endocrin.*, 139(2):152-154 (1998).
Hofbauer et al., "Stimulation of osteoprotegerin ligand and inhibition of osteoprotegerin production by glucocorticoids in human osteoblastic lineage cells: potential paracrine mechanisms of glucocorticoid-induced osteoporosis," *Endocrin.*, 140(10):4382-4389 (1999).
Hofbauer et al., "The role of receptor activator of nuclear factor -κB ligand and osteoprotegerin in the pathogenesis and treatment of metabolic bone disease," *J. Clin. Endocrin. Metab.*, 85:2355-2363 (2000).
Kodaira et al., "Cloning and characterization of the gene encoding mouse osteoclast differentiation factor," *Gene*, 230:121-127 (1999).
Kong et al., "OPGL is a key regulator of osteoclastogenesis, lymphocyte development and lymph-node organogenesis," *Nature*, 397:315-323 (1999).

(Continued)

*Primary Examiner* — Gregory S Emch
(74) *Attorney, Agent, or Firm* — Scott L. Ausenhus

(57) ABSTRACT

Chimeric molecules comprising receptor activator of NF-κB ligand (RANKL) antibodies and parathyroid hormone/parathyroid hormone-related protein (PTH/PTHrP) peptides are described. Compositions and methods for the treatment of bone diseases are also described.

62 Claims, 29 Drawing Sheets

(56) References Cited

OTHER PUBLICATIONS

Kong et al., "Osteoprotegerin ligand: a regulator of immune responses and bone physiology," *Immun. Today*, 21(10): 495-502 (2000).

Kostenuik et al., "OPG and PTH-(1-34) have addictive effects on bone density and mechanical strength in osteopenic ovariectomized rats," *Endocrin.*, 142(10):4295-4304 (2001).

Mannstadt et al., "Receptors for PTH and PTHrP: their biological importance and functional properties," *Journal of the American Physiological Society*, 277:F665-F675 (1999).

Nagai et al., "Cancer cells responsible for humoral hypercalcemia express mRNA encoding a secreted form of ODF/TRANCE that induces osteoclast formation," *Biochem. Biophys. Res. Comm.*, 269:532-536 (2000).

Nakagawa et al., "RANK is the essential signaling receptor for osteoclast differentiation factor in osteoclastogenesis," *Biochem. Biophys. Res. Comm.*, 253:395-400 (1998).

Oyajobi et al., "Therapeutic efficacy of a soluble receptor activator of nuclear factor κB-IgG Fc fusion protein in suppressing bone resorption and hypercalcemia in a model of humoral hypercalcemia of malignancy," *Cancer Res.*, 61:2572-2578 (2001).

Rosen et al., "Anabolic therapy for osteoporosis," *J. Clin. Endocrin. Metab.*, 86(3):957-964 (Mar. 2001).

Takahashi et al., "A new member of tumor necrosis factor ligand family, ODF/OPGL/TRANCE/RANKL, regulates osteoclast differentiation and function," *Biochem. Biophys. Res. Comm.*, 256(3):449-455 (1999).

Tsukii et al., "Osteoclast differentiation factor mediates an essential signal for bone resorption induced by $1\alpha$, 25-dihydroxyvitamin $D_3$, prostaglandin $E_2$, or parathyroid hormone in the microenvironment of bone," *Biochem. Biophys. Res. Comm.*, 246(2):337-341 (1998).

Yasuda et al., "Osteoclast differentiation factor is a ligand for ssteoprotegerin/ osteoclastogenesis-inhibitory factor and is identical to TRANCE/RANKL," *Proc. NatL Acad. Sci USA*, 95:3597-3602 (1998).

Amendment and Response to Paper No. 12 with Exhibits A to D, filed in U.S. Appl. No. 09/705,985, on Apr. 9, 2003.

Office Action in U.S. Appl. No. 09/705,985, mailed on Jul. 28, 2006.

Office Action in U.S. Appl. No. 09/211,297, mailed on Mar. 27, 2003.

Office Action in U.S. Appl. No. 09/211,315, mailed on Aug. 13, 2003.

Communication pursuant to Article 96(2) EPC in European Patent Application No. 02749660.3-1222 dated Jun. 9, 2006.

English translation of Office Action in Taiwan Patent Application No. 91114055, dated Sep. 7, 2005.

First Office Action and Text of the First Office Action in Chinese Patent Application No. 02816680.9, dated Feb. 24, 2006, with English translation.

English translation of Official Notification on the necessity of submitting additional materials dated Sep. 4, 2006, in Eurasian Patent Application No. 200400063/28, with English translation.

Summons to attend oral proceedings pursuant to Rule 71(1) EPC dated Jan. 16, 2007, in European Patent Application No. 01911158.2-1222.

Kostenuik et al., "OPG and PTH-(1-34) have additive effects on bone density and mechanical strength in osteopenic ovariectomized rats," *Endocrinology*, 142:4295-4304 (2001).

Schett et al., "Additive bone-protective effects of anabolic treatment when used in conjunction with RANKL and tumor necrosis factor inhibition in two rat arthritis models," *Arthritis & Rheumatism*, 52:1604-1611 (2005).

Schwarz et al., "Receptor activator of nuclear κB ligand and osteoprotegerin: where are we now and what about future treatment uses?" *Current Opinion in Orthopedics*, 16:370-375 (2005).

Valenta et al., "Combined treatment with PTH (1-34) and OPG increases bone volume and uniformity of mineralization in aged ovariectomized rats," *Bone*, 37:87-95 (2005).

PCT Notification of Transmittal of the International Search Report and the Written Opinion of the International Searching Authority, or the Declaration, mailed Jun. 25, 2007, in International Application No. PCT/US2006/044199.

PCT Notification Concerning Transmittal of International Preliminary Report on Patentability, International Preliminary Report on Patentability, and Written Opinion of the International Searching Authority, mailed May 22, 2008, for International Application No. PCT/US2006/044199.

Communication in Cases for which No Other Form is Applicable; PCT Notification of Transmittal of the International Search Report and the Written Opinion of the International Searching Authority, or the Declaration; International Search Report; and Written Opinion of the International Search Authority, mailed Aug. 7, 2007, in International Application No. PCT/US2006/044199.

Examiner's First Report, mailed Feb. 28, 2011, for Australian Patent Application No. 2006315542 (2 pages).

Examiner's first substantive report, mailed May 11, 2010, with translation, for Chilean Patent Application No. 3076-2006 (10 pages).

Request for Entry into the European Phase, with amended claims, filed Mar. 31, 2008, for European Patent Application No. 06837570.8 (24 pages).

Communication pursuant to Article 94(3) EPC, mailed Feb. 20, 2009, for European Patent Application No. 06837570.8 (6 pages).

Response to the Official Communication dated Feb. 20, 2009, filed Sep. 2, 2009, for European Patent Application No. 06837570.8 (39 pages).

Supplemental response to the Official Communication dated Feb. 20, 2009, filed Oct. 28, 2009, for European Patent Application No. 06837570.8 (2 pages).

Invitation pursuant to Article 94(3) and Rule 71(1) EPC, mailed Jan. 28, 2010, for European Patent Application No. 06837570.8 (3 pages).

Noting of loss of rights pursuant to Rule 112(1) EPC, mailed Sep. 14, 2010, for European Patent Application No. 06837570.8 (1 page).

Response to the Official Notification dated Sep. 14, 2010, and Response to Official Communication dated Jan. 28, 2010, filed Nov. 24, 2010, for European Patent Application No. 06837570.8 (122 pages).

Decision on the request for further processing under Rule 135(3) EPC, mailed Dec. 9, 2010, for European Patent Application No. 06837570.8 (1 page).

Communication pursuant to Article 94(3) EPC, mailed Feb. 24, 2011, for European Patent Application No. 06837570.8 (7 pages).

Technical Report CJE 12-2010, with English translation, mailed Mar. 31, 2010, for Peruvian Patent Application No. 001412-2006/OIN (27 pages).

Technical Report CJE No. 12-2010a, with English translation, mailed Sep. 24, 2010, for Peruvian Patent Application No. 001412-2006/OIN (27 pages).

Resolution No. 000168-2011/DIN-INDECOPI, mailed Feb. 23, 2011, for Peruvian Patent Application No. 001412-2006/OIN (22 pages).

Preliminary Amendment, filed Nov. 21, 2013, for U.S. Appl. No. 13/843,987 (13 pages).

Response to Official Report, filed Aug. 30, 2012, for Australian Patent App. No. 2006315542 (53 pages).

Notice of Acceptance, mailed Sep. 25, 2012, for Australian Patent App. No. 2006315542 (3 pages).

Statement of Proposed Amendments, filed Dec. 31, 2012, for Australian Patent App. No. 2006315542 (4 pages).

Acceptance of post-allowance amendments, mailed Jan. 31, 2013, for Australian Patent App. No. 2006315542 (1 page).

Grant of post-allowance amendments, mailed May 22, 2013, for Australian Patent App. No. 2006315542 (1 page).

Official Action, mailed Jun. 11, 2013, for Canadian Patent App. No. 2,628,628 (6 pages).

Human Precursor PTH, entry version 141, updated May 1, 2013, from http://www.unitprot.org/uniprot/P01270 (6 pages).

Human Precursor PTHrH, entry version 152, updated May 1, 2013, from http://www.unitprot.org/uniprot/P12272 (8 pages).

Response to Official Action, filed Dec. 11, 2013, for Canadian Patent App. No. 2,628,628 (53 pages).

Response to Official Communication dated Feb. 24, 2011, filed Sep. 6, 2011, for European Patent App. No. 06837570.8 (42 pages).

Invitation pursuant to Article 94(3) and Rule 71(1) EPC, mailed Oct. 5, 2011, for European Patent App. No. 06837570.8 (3 pages).

(56) References Cited

OTHER PUBLICATIONS

Response to Official Communication dated Oct. 5, 2011, filed Apr. 16, 2012, for European Patent App. No. 06837570.8 (41 pages).
Invitation pursuant to Article 94(3) and Rule 71(1) EPC, mailed Sep. 19, 2012, for European Patent App. No. 06837570.8 (4 pages).
Response to Official Communication dated Sep. 19, 2012, filed Mar. 28, 2013, for European Patent App. No. 06837570.8 (40 pages).
Communication under Rule 71(3) EPC, mailed Jul. 18, 2013, for European Patent App. No. 06837570.8 (209 pages).
Decision to grant a European patent pursuant to Article 97(1) EPC, mailed Dec. 12, 2013, for European Patent App. No. 06837570.8 (2 pages).
Response to invitation to remedy deficiencies (Rule 58 EPC), filed Jun. 3, 2011, for European Patent App. No. 11156478.7 (8 pages).
Communication of the extended European search report and opinion, mailed Oct. 6, 2011, for European Patent App. No. 11156478.7 (9 pages).
Communication pursuant to Rule 69 EPC, mailed Nov. 7, 2011, for European Patent App. No. 11156478.7 (2 pages).
Response to the Communication under Rule 70(a) dated Nov. 7, 2011/response to the Opinion accompanying the European Search Report, filed Aug. 21, 2012, for European Patent App. No. 11156478.7 (10 pages).
Communication pursuant to Article 94(3) EPC, mailed Oct. 22, 2013, for European Patent App. No. 11156478.7 (9 pages).
Response to the Official Communication dated Oct. 22, 2013, filed Aug. 5, 2014, for European Patent App. No. 11156478.7 (8 pages).
Invitation to remedy deficiencies (R. 58 EPC) (claims), mailed May 19, 2014, for European Patent App. No. 14166902.8 (1 page).
Invitation to remedy deficiencies (R. 58 EPC) (drawings), mailed May 19, 2014, for European Patent App. No. 14166902.8 (3 pages).
Response to the two Communications pursuant Rule 58 EPC dated May 19, 2014, filed Jul. 29, 2014, for European Patent App. No. 14166902.8 (36 pages).

Notice of Rejection ($1^{st}$ Official Action), with translation, mailed Apr. 17, 2012, for Japanese Patent App. No. 2008-540279 (7 pages).
Response to Notice of Rejection, with translation of amended claims, filed Oct. 16, 2012, for Japanese Patent App. No. 2008-540279 (17 pages).
Written Statement, with translation of amended claims, filed Nov. 13, 2012, for Japanese Patent App. No. 2008-540279 (13 pages).
Examiner's Decision of Rejection, with translation, mailed Apr. 2, 2013, for Japanese Patent App. No. 2008-540279 (6 pages).
Response, with translation of amended claims, filed Aug. 1, 2013, for Japanese Patent App. No. 2008-540279 (10 pages).
Amendment, with translation of amended claims, filed Nov. 27, 2013, for Japanese Patent App. No. 2008-540279 (10 pages).
Voluntary Amendment filed Nov. 13, 2012, for Japanese Patent App. No. 2012-229099, with translation of amended claims (9 pages).
Notice of Rejection ($1^{st}$ Official Action), mailed Apr. 15, 2014, for Japanese Patent App. No. 2012-229099, with translation (7 pages).
Translation of the Requirements Stated by the Examiner for Mexican Patent App. No. MX/a/2008/005927 (2 pages) (2012).
Court Order No. 1678-2012/TPI-INDECOPI, with translation, mailed Sep. 20, 2012, for Peruvian Patent App. No. 001412-2006/OIN (47 pages).
Office Action, with translation, mailed Jun. 18, 2012, for Taiwanese Patent App. No. 095141718 (22 pages).
Friedman et al., "PTH(1-84)/PTH(7-84): a balance of power," *Am. J. Physiol. Renal Physiol.*, 290: F975-F984 (2006).
Decision of Rejection, with translation, mailed Apr. 17, 2013, for Taiwanese Patent App. No. 095141718 (11 pages).
Examination Report, mailed Aug. 12, 2013, for Gulf Coast Cooperation Patent App. No. GCC/P/2006/7192 (6 pages).
Examination Report, mailed May 26, 2014, for Gulf Coast Cooperation Patent App. No. GCC/P/2006/7192 (3 pages).
Communication enclosing the Extended European Search Report, mailed Nov. 26, 2014, for European Patent App. No. 14166902.8 (10 pages).

\* cited by examiner

FIGURE 1

αRANKL-1 (also called αOPGL-1) heavy chain cDNA

```
   1 AAGCTTGACC ACCATGGAGT TTGGGCTGAG CTGGCTTTTT CTTGTGGCTA TTTTAAAAGG
  61 TGTCCAGTGT GAGGTGCAGC TGTTGGAGTC TGGGGGAGGC TTGGTACAGC CTGGGGGGTC
 121 CCTGAGACTC TCCTGTGCAG CCTCTGGATT CACCTTTAGC AGCTATGCCA TGAGCTGGGT
 181 CCGCCAGGCT CCAGGGAAGG GGCTGGAGTG GGTCTCAGGT ATTACTGGGA GTGGTGGTAG
 241 TACATACTAC GCAGACTCCG TGAAGGGCCG GTTCACCATC TCCAGAGACA ATTCCAAGAA
 301 CACGCTGTAT CTGCAAATGA ACAGCCTGAG AGCCGAGGAC ACGGCCGTAT ATTACTGTGC
 361 GAAAGATCCA GGGACTACGG TGATTATGAG TTGGTTCGAC CCCTGGGGCC AGGGAACCCT
 421 GGTCACCGTC TCCTCAGCCT CCACCAAGGG CCCATCGGTC TTCCCCCTGG CGCCCTGCTC
 481 CAGGAGCACC TCCGAGAGCA CAGCGGCCCT GGGCTGCCTG GTCAAGGACT ACTTCCCCGA
 541 ACCGGTGACG GTGTCGTGGA ACTCAGGCGC TCTGACCAGC GGCGTGCACA CCTTCCCAGC
 601 TGTCCTACAG TCCTCAGGAC TCTACTCCCT CAGCAGCGTG GTGACCGTGC CTCCAGCAA
 661 CTTCGGCACC CAGACCTACA CCTGCAACGT AGATCACAAG CCCAGCAACA CCAAGGTGGA
 721 CAAGACAGTT GAGCGCAAAT GTTGTGTCGA GTGCCCACCG TGCCCAGCAC CACCTGTGGC
 781 AGGACCGTCA GTCTTCCTCT TCCCCCCAAA ACCCAAGGAC ACCCTCATGA TCTCCCGGAC
 841 CCCTGAGGTC ACGTGCGTGG TGGTGGACGT GAGCCACGAA GACCCCGAGG TCCAGTTCAA
 901 CTGGTACGTG GACGGCGTGG AGGTGCATAA TGCCAAGACA AAGCCACGGG AGGAGCAGTT
 961 CAACAGCACG TTCCGTGTGG TCAGCGTCCT CACCGTTGTG CACCAGGACT GGCTGAACGG
1021 CAAGGAGTAC AAGTGCAAGG TCTCCAACAA AGGCCTCCCA GCCCCCATCG AGAAAACCAT
1081 CTCCAAAACC AAAGGGCAGC CCCGAGAACC ACAGGTGTAC ACCCTGCCCC CATCCCGGGA
1141 GGAGATGACC AAGAACCAGG TCAGCCTGAC CTGCCTGGTC AAAGGCTTCT ACCCCAGCGA
1201 CATCGCCGTG GAGTGGGAGA GCAATGGGCA GCCGGAGAAC AACTACAAGA CCACACCTCC
1261 CATGCTGGAC TCCGACGGCT CCTTCTTCCT CTACAGCAAG CTCACCGTGG ACAAGAGCAG
1321 GTGGCAGCAG GGGAACGTCT TCTCATGCTC CGTGATGCAT GAGGCTCTGC ACAACCACTA
1381 CACGCAGAAG AGCCTCTCCC TGTCTCCGGG TAAATGATAA GTCGAC      (SEQ ID NO: 1)
```

FIGURE 2

αRANKL-1 (also called αOPGL-1) heavy chain amino acid sequence

```
  1 MEFGLSWLFL VAILKGVQCE VQLLESGGGL VQPGGSLRLS CAASGFTFSS YAMSWVRQAP
 61 GKGLEWVSGI TGSGGSTYYA DSVKGRFTIS RDNSKNTLYL QMNSLRAEDT AVYYCAKDPG
121 TTVIMSWFDP WGQGTLVTVS Sastkgpsvf plapcsrsts estaalgclv kdyfpepvtv
181 swnsgaltsg vhtfpavlqs sglyslssvv tvpssnfgtq tytcnvdhkp sntkvdktve
241 rkccvecppc pappvagpsv flfppkpkdt lmisrtpevt cvvvdvshed pevqfnwyvd
301 gvevhnaktk preeqfnstf rvvsvltvvh qdwlngkeyk ckvsnkglpa piektisktk
361 gqprepqvyt lppsreemtk nqvsltclvk gfypsdiave wesngqpenn ykttppmlds
421 dgsfflyskl tvdksrwqqg nvfscsvmhe alhnhytqks lslspgk (SEQ ID NO: 2)
```

FIGURE 3

αRANKL-1 (also called αOPGL-1) kappa light chain cDNA

```
  1 TCTAGACCAC CATGGAAACC CCAGCGCAGC TTCTCTTCCT CCTGCTACTC TGGCTCCCAG
 61 ATACCACCGG AGAAATTGTG TTGACGCAGT CTCCAGGCAC CCTGTCTTTG TCTCCAGGGG
121 AAAGAGCCAC CCTCTCCTGT AGGGCCAGTC AGAGTGTTCG CGGCAGGTAC TTAGCCTGGT
181 ACCAGCAGAA ACCTGGCCAG GCTCCCAGGC TCCTCATCTA TGGTGCATCC AGCAGGGCCA
241 CTGGCATCCC AGACAGGTTC AGTGGCAGTG GGTCTGGGAC AGACTTCACT CTCACCATCA
301 GCAGACTGGA GCCTGAAGAT TTTGCAGTGT TTTACTGTCA GCAGTATGGT AGTTCACCTC
361 GGACGTTCGG CCAAGGGACC AAGGTGGAAA TCAAACGAAC TGTGGCTGCA CCATCTGTCT
421 TCATCTTCCC GCCATCTGAT GAGCAGTTGA AATCTGGAAC TGCCTCTGTT GTGTGCCTGC
481 TGAATAACTT CTATCCCAGA GAGGCCAAAG TACAGTGGAA GGTGGATAAC GCCCTCCAAT
541 CGGGTAACTC CCAGGAGAGT GTCACAGAGC AGGACAGCAA GGACAGCACC TACAGCCTCA
601 GCAGCACCCT GACGCTGAGC AAAGCAGACT ACGAGAAACA CAAAGTCTAC GCCTGCGAAG
661 TCACCCATCA GGGCCTGAGC TCGCCCGTCA CAAAGAGCTT CAACAGGGGA GAGTGTTGAT
721 AAGTCGAC                                            (SEQ ID NO: 3)
```

FIGURE 4

αRANKL-1 (also called αOPGL-1) kappa light chain amino acid sequence

```
  1 METPAQLLFL LLLWLPDTTG EIVLTQSPGT LSLSPGERAT LSCRASQSVR
 51 GRYLAWYQQK PGQAPRLLIY GASSRATGIP DRFSGSGSGT DFTLTISRLE
101 PEDFAVFYCQ QYGSSPRTFG QGTKVEIKrt vaapsvfifp psdeqlksgt
151 asvvcllnnf ypreakvqwk vdnalqsgns qesvteqdsk dstyslsstl
201 tlskadyekh kvyacevthq glsspvtksf nrgec (SEQ ID NO: 4)
```

Circular Plasmid Map of αRANKL-1-kappa/pDSRα19

(also called αOPGL-1-kappa/pDSRα19)

Circular Plasmid Map of αRANKL-1-IgG2/pDSRα19

(also called αOPGL-1- IgG2/pDSRα19)

FIGURE 7 synPTH cDNA sequence

```
  1  TCTAGACCAC CATGATCCCC GCCAAGGACA TGGCCAAGGT GATGATCGTG
 51  ATGCTGGCCA TTTGTTTCCT GACCAAGAGC GATGGCAAGT CCGTGAAGAA
101  GAGATCCGTG AGCGAGATCC AGCTGATGCA CAACCTGGGC AAGCACCTGA
151  ACTCCATGGA GAGAGTGGAG TGGCTGCGCA AGAAGCTGCA GGACGTGCAC
201  AACTTCGGCG GCGGCGCGCC C          (SEQ ID NO: 5)
```

FIGURE 8 synPTH amino acid sequence

```
1    MIPAKDMAKV MIVMLAICFL TKSDGKSVKK RSVSEIQLMH NLGKHLNSME
51   RVEWLRKKLQ DVHNFGGGAP              (SEQ ID NO: 6)
```

FIGURE 9 synPTH-αRANKL-1 light chain cDNA sequence

| | | | | | |
|---|---|---|---|---|---|
| 1 | TCTAGACCAC | <u>CATGATCCCC</u> | <u>GCCAAGGACA</u> | <u>TGGCCAAGGT</u> | <u>GATGATCGTG</u> |
| 51 | <u>ATGCTGGCCA</u> | <u>TTTGTTTCCT</u> | <u>GACCAAGAGC</u> | <u>GATGGCAAGT</u> | <u>CCGTGAAGAA</u> |
| 101 | <u>GAGATCCGTG</u> | AGCGAGATCC | AGCTGATGCA | CAACCTGGGC | AAGCACCTGA |
| 151 | ACTCCATGGA | GAGAGTGGAG | TGGCTGCGCA | AGAAGCTGCA | GGACGTGCAC |
| 201 | AACTTC*GGCG* | *GCGGCGCGCC* | CGAAATTGTG | TTGACGCAGT | CTCCAGGCAC |
| 251 | CCTGTCTTTG | TCTCCAGGGG | AAAGAGCCAC | CCTCTCCTGT | AGGGCCAGTC |
| 301 | AGAGTGTTCG | CGGCAGGTAC | TTAGCCTGGT | ACCAGCAGAA | ACCTGGCCAG |
| 351 | GCTCCCAGGC | TCCTCATCTA | TGGTGCATCC | AGCAGGGCCA | CTGGCATCCC |
| 401 | AGACAGGTTC | AGTGGCAGTG | GGTCTGGGAC | AGACTTCACT | CTCACCATCA |
| 451 | GCAGACTGGA | GCCTGAAGAT | TTTGCAGTGT | TTTACTGTCA | GCAGTATGGT |
| 501 | AGTTCACCTC | GGACGTTCGG | CCAAGGGACC | AAGGTGGAAA | TCAAACGAAC |
| 551 | TGTGGCTGCA | CCATCTGTCT | TCATCTTCCC | GCCATCTGAT | GAGCAGTTGA |
| 601 | AATCTGGAAC | TGCCTCTGTT | GTGTGCCTGC | TGAATAACTT | CTATCCCAGA |
| 651 | GAGGCCAAAG | TACAGTGGAA | GGTGGATAAC | GCCCTCCAAT | CGGGTAACTC |
| 701 | CCAGGAGAGT | GTCACAGAGC | AGGACAGCAA | GGACAGCACC | TACAGCCTCA |
| 751 | GCAGCACCCT | GACGCTGAGC | AAAGCAGACT | ACGAGAAACA | CAAAGTCTAC |
| 801 | GCCTGCGAAG | TCACCCATCA | GGGCCTGAGC | TCGCCCGTCA | CAAAGAGCTT |
| 851 | CAACAGGGGA | GAGTGTTGAG | TCGAC | (SEQ ID NO: 7) | |

FIGURE 10 synPTH-αRANKL-1 light chain amino acid sequence

```
  1    MIPAKDMAKV MIVMLAICFL TKSDGKSVKK RSVSEIQLMH NLGKHLNSME
 51    RVEWLRKKLQ DVHNFGGGAP EIVLTQSPGT LSLSPGERAT LSCRASQSVR
101    GRYLAWYQQK PGQAPRLLIY GASSRATGIP DRFSGSGSGT DFTLTISRLE
151    PEDFAVFYCQ QYGSSPRTFG QGTKVEIKRT VAAPSVFIFP PSDEQLKSGT
201    ASVVCLLNNF YPREAKVQWK VDNALQSGNS QESVTEQDSK DSTYSLSSTL
251    TLSKADYEKH KVYACEVTHQ GLSSPVTKSF NRGEC    (SEQ ID NO: 8)
```

FIGURE 11 synPTH-αRANKL-1 heavy chain cDNA sequence

```
   1    TCTAGACCAC CATGATCCCC GCCAAGGACA TGGCCAAGGT GATGATCGTG
  51    ATGCTGGCCA TTTGTTTCCT GACCAAGAGC GATGGCAAGT CCGTGAAGAA
 101    GAGATCCGTG AGCGAGATCC AGCTGATGCA CAACCTGGGC AAGCACCTGA
 151    ACTCCATGGA GAGAGTGGAG TGGCTGCGCA AGAAGCTGCA GGACGTGCAC
 201    AACTTCGGCG GCGGCGCGCC CGAGGTGCAG CTGTTGGAGT CTGGGGGAGG
 251    CTTGGTACAG CCTGGGGGGT CCCTGAGACT CTCCTGTGCA GCCTCTGGAT
 301    TCACCTTTAG CAGCTATGCC ATGAGCTGGG TCCGCCAGGC TCCAGGGAAG
 351    GGGCTGGAGT GGGTCTCAGG TATTACTGGG AGTGGTGGTA GTACATACTA
 401    CGCAGACTCC GTGAAGGGCC GGTTCACCAT CTCCAGAGAC AATTCCAAGA
 451    ACACGCTGTA TCTGCAAATG AACAGCCTGA GAGCCGAGGA CACGGCCGTA
 501    TATTACTGTG CGAAAGATCC AGGGACTACG GTGATTATGA GTTGGTTCGA
 551    CCCCTGGGGC CAGGGAACCC TGGTCACCGT CTCCTCAGCC TCCACCAAGG
 601    GCCCATCGGT CTTCCCCCTG GCGCCCTGCT CCAGGAGCAC CTCCGAGAGC
 651    ACAGCGGCCC TGGGCTGCCT GGTCAAGGAC TACTTCCCCG AACCGGTGAC
 701    GGTGTCGTGG AACTCAGGCG CTCTGACCAG CGGCGTGCAC ACCTTCCCAG
 751    CTGTCCTACA GTCCTCAGGA CTCTACTCCC TCAGCAGCGT GGTGACCGTG
 801    CCCTCCAGCA ACTTCGGCAC CCAGACCTAC ACCTGCAACG TAGATCACAA
 851    GCCCAGCAAC ACCAAGGTGG ACAAGACAGT TGAGCGCAAA TGTTGTGTCG
 901    AGTGCCCACC GTGCCCAGCA CCACCTGTGG CAGGACCGTC AGTCTTCCTC
 951    TTCCCCCCAA AACCCAAGGA CACCCTCATG ATCTCCCGGA CCCCTGAGGT
1001    CACGTGCGTG GTGGTGGACG TGAGCCACGA AGACCCCGAG GTCCAGTTCA
1051    ACTGGTACGT GGACGGCGTG GAGGTGCATA ATGCCAAGAC AAAGCCACGG
1101    GAGGAGCAGT TCAACAGCAC GTTCCGTGTG GTCAGCGTCC TCACCGTTGT
1151    GCACCAGGAC TGGCTGAACG GCAAGGAGTA CAAGTGCAAG GTCTCCAACA
1201    AAGGCCTCCC AGCCCCATC GAGAAAACCA TCTCCAAAAC CAAAGGGCAG
1251    CCCCGAGAAC CACAGGTGTA CACCCTGCCC CCATCCCGGG AGGAGATGAC
1301    CAAGAACCAG GTCAGCCTGA CCTGCCTGGT CAAAGGCTTC TACCCCAGCG
1351    ACATCGCCGT GGAGTGGGAG AGCAATGGGC AGCCGGAGAA CAACTACAAG
1401    ACCACACCTC CCATGCTGGA CTCCGACGGC TCCTTCTTCC TCTACAGCAA
1451    GCTCACCGTG GACAAGAGCA GGTGGCAGCA GGGGAACGTC TTCTCATGCT
1501    CCGTGATGCA TGAGGCTCTG CACAACCACT ACACGCAGAA GAGCCTCTCC
1551    CTGTCTCCGG GTAAATGAGT CGAC        (SEQ ID NO: 9)
```

FIGURE 12 synPTH-αRANKL-1 heavy chain amino acid sequence

```
  1  MIPAKDMAKV MIVMLAICFL TKSDGKSVKK RSVSEIQLMH NLGKHLNSME
 51  RVEWLRKKLQ DVHNFGGGAP EVQLLESGGG LVQPGGSLRL SCAASGFTFS
101  SYAMSWVRQA PGKGLEWVSG ITGSGGSTYY ADSVKGRFTI SRDNSKNTLY
151  LQMNSLRAED TAVYYCAKDP GTTVIMSWFD PWGQGTLVTV SSASTKGPSV
201  FPLAPCSRST SESTAALGCL VKDYFPEPVT VSWNSGALTS GVHTFPAVLQ
251  SSGLYSLSSV VTVPSSNFGT QTYTCNVDHK PSNTKVDKTV ERKCCVECPP
301  CPAPPVAGPS VFLFPPKPKD TLMISRTPEV TCVVVDVSHE DPEVQFNWYV
351  DGVEVHNAKT KPREEQFNST FRVVSVLTVV HQDWLNGKEY KCKVSNKGLP
401  APIEKTISKT KGQPREPQVY TLPPSREEMT KNQVSLTCLV KGFYPSDIAV
451  EWESNGQPEN NYKTTPPMLD SDGSFFLYSK LTVDKSRWQQ GNVFSCSVMH
501  EALHNHYTQK SLSLSPGK             (SEQ ID NO: 10)
```

Circular plasmid map of synPTH-αRANKL-1-kappa/pDSRα20

Circular plasmid map of synPTH-αRANKL-1-IgG2/pDSRα20

Blood ionized calcium levels in aged huRANKL mice or wild-type mice

MicroCT of Vertebra From HuRANKL Mice
• Images represent median sample from each group (n = 6) based on % bone volume MicroCT of Prox Tibia From HuRANKL Mice
•Images represent median sample from each group (n = 6) based on % bone volume MicroCT of Femurs From HuRANKL Mice
•Images represent median sample from each group (n = 6) based on % bone volume

FIGURE 28

αRANKL-1 (also called αOPGL-1) Heavy Chain Variable Region Amino Acid Sequence

```
  1 EVQLLESGGG LVQPGGSLRL SCAASGFTFS SYAMSWVRQA
 41 PGKGLEWVSG ITGSGGSTYY ADSVKGRFTI SRDNSKNTLY
 81 LQMNSLRAED TAVYYCAKDP GTTVIMSWFD PWGQGTLVTV
121 SS                              (SEQ ID NO: 11)
```

FIGURE 29

αRANKL-1 (also called αOPGL-1) Light Chain Variable Region Amino Acid Sequence

```
 1 EIVLTQSPGT LSLSPGERAT LSCRASQSVR GRYLAWYQQK
41 PGQAPRLLIY GASSRATGIP DRFSGSGSGT DFTLTISRLE
81 PEDFAVFYCQ QYGSSPRTFG QGTKVEIK (SEQ ID NO: 12)
```

RANKL ANTIBODY-PTH/PTHRP CHIMERIC MOLECULES

This application claims the benefit of U.S. Provisional Application No. 60/736,664, filed Nov. 14, 2005. U.S. Provisional Application No. 60/736,664 is incorporated by reference herein in its entirety for any purpose.

FIELD

Chimeric molecules comprising antibodies that bind receptor activator of NF-κB ligand (RANKL) and parathyroid hormone/parathyroid hormone-related protein (PTH/PTHrP) peptides (RANKL antibody-PTH/PTHrP chimeric molecules) are provided. Compositions and methods for the treatment of bone diseases are also described.

BACKGROUND

Bone tissue provides support for the body and includes mineral (including calcium and phosphorous), a matrix of collagenous and noncollagenous proteins, and cells. Living bone tissue exhibits a dynamic equilibrium between formation of bone, which is called deposition, and break-down of bone, which is called resorption. Three types of cells found in bone, osteocytes, osteoblasts and osteoclasts, are involved in this equilibrium. Osteoblasts promote formation of bone tissue whereas osteoclasts are associated with resorption. Resorption, or the dissolution of bone matrix and mineral, is a fast and efficient process compared to bone formation and can release large amounts of mineral from bone. Osteoclasts are involved in the regulation of the normal remodeling of skeletal tissue and in resorption induced by hormones. For instance, resorption is stimulated by the secretion of parathyroid hormone in response to decreasing concentrations of calcium ion in extracellular fluids. In contrast, inhibition of resorption is a function of calcitonin. In addition, metabolites of vitamin D alter the responsiveness of bone to parathyroid hormone and calcitonin.

Receptor activator of NF-κB ligand (RANKL; also called osteoprotegerin ligand, or OPGL), which is a member of the TNF family of cytokines, promotes formation of osteoclasts through binding to the receptor activator of NF-κB (RANK, also called osteoclast differentiation and activation receptor, or ODAR). Osteoprotegerin (OPG), on the other hand, inhibits the formation of osteoclasts by sequestering RANKL and preventing RANKL association with RANK. Thus, the amount of RANKL associated with RANK correlates with the equilibrium between bone deposition and resorption.

After skeletal maturity, the amount of bone in the skeleton reflects the balance (or imbalance) of bone formation and bone resorption. Peak bone mass occurs after skeletal maturity prior to the fourth decade. Between the fourth and fifth decades, the equilibrium shifts and bone resorption dominates. The inevitable decrease in bone mass with advancing years starts earlier in females than males and is distinctly accelerated after menopause in some females (principally those of Caucasian and Asian descent).

Parathyroid hormone (PTH) is secreted in response to hypocalcemia. PTH activates osteoclasts, possibly through binding to and activating the PTH1 receptor. PTH1 receptor activation leads to secretion of RANKL, which stimulates bone resorption and an increase in serum calcium levels.

Paradoxically, intermittent administration of PTH or PTH-related protein (PTHrP) can actually cause an increase in bone density. That increase is due to activation of osteoblasts, which increase bone formation, in addition to activation of osteoclasts, which increase bone resorption. When osteoblast activation outpaces osteoclast activation, the net result is an increase in bone density. However, strong stimulation of osteoblasts has been associated with osteosarcoma in mice.

Osteopenia is a condition relating generally to any decrease in bone mass to below normal levels. Such a condition may arise from a decrease in the rate of bone synthesis or an increase in the rate of bone destruction or both. A common form of osteopenia is primary osteoporosis, also referred to as postmenopausal and senile osteoporosis. This form of osteoporosis is a consequence of the universal loss of bone with age and is often a result of increase in bone resorption with a normal rate of bone formation. Many white females in the United States develop symptomatic osteoporosis. A direct relationship exists between osteoporosis and the incidence of hip, femoral, neck and inter-trochanteric fracture in women 45 years and older. Elderly males may develop symptomatic osteoporosis between the ages of 50 and 70.

SUMMARY OF THE INVENTION

In certain embodiments, a receptor activator of NF-κB ligand (RANKL) antibody-parathyroid hormone/parathyroid hormone related protein (PTH/PTHrP) chimeric molecule is provided. In certain embodiments, the RANKL antibody-PTH/PTHrP chimeric molecule comprises an antibody that binds to RANKL and a PTH/PTHrP peptide.

In certain embodiments a RANKL antibody-PTH/PTHrP chimeric molecule comprises an antibody that binds to RANKL. In certain embodiments, a RANKL antibody-PTH/PTHrP chimeric molecule comprises a heavy chain having an amino acid sequence as set forth in SEQ ID NO:2 or a fragment thereof. In certain embodiments, a RANKL antibody-PTH/PTHrP chimeric molecule comprises a light chain having an amino acid sequence as set forth in SEQ ID NO:4 or a fragment thereof.

In certain embodiments, a RANKL antibody-PTH/PTHrP chimeric molecule comprises a heavy chain comprising a first variable region comprising an amino acid sequence as set forth in SEQ ID NO: 11 or a fragment thereof. In certain embodiments, a RANKL antibody-PTH/PTHrP chimeric molecule comprises a light chain comprising a second variable region comprising an amino acid sequence as set forth in SEQ ID NO: 12 or a fragment thereof.

In certain embodiments, a RANKL antibody-PTH/PTHrP chimeric molecule comprises a heavy chain comprising a first variable region that comprises a sequence that has at least 92% identity to the amino acid sequence set forth in SEQ ID NO: 11. In certain embodiments, a RANKL antibody-PTH/PTHrP chimeric molecule comprises a light chain comprising a second variable region that comprises a sequence that has at least 90% identity to the amino acid sequence set forth in SEQ ID NO: 12.

In certain embodiments, a RANKL antibody-PTH/PTHrP chimeric molecule comprises a heavy chain comprising a first variable region that comprises a sequence that has at least 95% identity to the amino acid sequence set forth in SEQ ID NO: 11. In certain embodiments, a RANKL antibody-PTH/PTHrP chimeric molecule comprises a light chain comprising a second variable region that comprises a sequence that has at least 95% identity to the amino acid sequence set forth in SEQ ID NO: 12.

In certain embodiments, a RANKL antibody-PTH/PTHrP chimeric molecule comprises a heavy chain comprising a first variable region that comprises a sequence that has at least 99% identity to the amino acid sequence set forth in SEQ ID NO: 11. In certain embodiments, a RANKL antibody-PTH/

PTHrP chimeric molecule comprises a light chain comprising a second variable region that comprises a sequence that has at least 99% identity to the amino acid sequence set forth in SEQ ID NO: 12.

In certain embodiments, a RANKL antibody-PTH/PTHrP chimeric molecule comprises an antibody selected from a single-chain Fv antibody (scFv), a Fab antibody, a Fab' antibody, a (Fab')2 antibody, a domain antibody, a nanobody, a minibody, a maxibody, and a diabody. In certain embodiments, a RANKL antibody-PTH/PTHrP chimeric molecule comprises a RANKL antibody that is fully human.

In certain embodiments, a PTH/PTHrP peptide is operably linked to the RANKL antibody. In certain embodiments, a PTH/PTHrP peptide comprises a prepro domain and a PTH/PTHrP modulating domain. In certain embodiments, a PTH/PTHrP peptide is operably linked to a heavy chain of a RANKL antibody. In certain embodiments, a PTH/PTHrP peptide is operably linked to a light chain of a RANKL antibody. In certain embodiments, a PTH/PTHrP peptide is fused to the N-terminus of a heavy chain of a RANKL antibody. In certain embodiments, a PTH/PTHrP peptide is fused to the N-terminus of a light chain of a RANKL antibody.

In certain embodiments, a RANKL antibody-PTH/PTHrP chimeric molecule comprises a first PTH/PTHrP peptide and a second PTH/PTHrP peptide. In certain embodiments, a first PTH/PTHrP peptide is operably linked to a light chain and a second PTH/PTHrP peptide is operably linked to a heavy chain. A first and second PTH/PTHrP peptides may be the same or different. In certain embodiments, the first PTH/PTHrP peptide is operably linked to a heavy chain. In certain embodiments, the first PTH/PTHrP peptide is operably linked to the N-terminus of a heavy chain. In certain embodiments, the first PTH/PTHrP peptide is fused to a heavy chain. In certain embodiments, the second PTH/PTHrP peptide is operably linked to a light chain. In certain embodiments, the second PTH/PTHrP peptide is operably linked to the N-terminus of a light chain. In certain embodiments, the second PTH/PTHrP peptide is fused to a light chain.

In certain embodiments, a RANKL antibody-PTH/PTHrP chimeric molecule comprises a PTH/PTHrP peptide comprising a PTH/PTHrP modulating domain selected from the polypeptides of formula I:

$$X^N NHX^{10}X^{11}X^{12}KX^{14}X^{15}X^{16}X^{17}X^{18}X^{19}RX^{21}X^{22}X^{23}X^{24}X^{25}X^{26}X^{27}X^{28}X^C$$
(Formula I; SEQ ID NO: 13)

wherein:
$X^N$ is absent or is $X^3X^4X^5X^6X^7$, $X^2X^3X^4X^5X^6X^7$, $X^1X^2X^3X^4X^5X^6X^7$, or $YX^1X^2X^3X^4X^5X^6X^7$;
$X^1$ through $X^7$, $X^{10}$, $X^1$, $X^{12}$, $X^{14}$ through $X^{28}$ are each independently selected amino acid residues;
$X^C$ is absent or is $X^{29}$, $X^{29}X^{30}$, $X^{29}X^{30}X^{31}$, $X^{29}X^{30}X^{31}X^{32}$, $X^{29}X^{30}X^{31}X^{32}X^{33}$, $X^{29}X^{30}X^{31}X^{32}X^{33}X^{34}$, $X^{29}X^{30}X^{31}X^{32}X^{33}X^{34}X^{35}$, or $X^{29}X^{30}X^{31}X^{32}X^{33}X^{34}X^{35}X^{36}$;
$X^{29}$ through $X^{36}$ are each independently selected amino acid residues;
provided that one or more of $X^{14}$ through $X^{36}$ is a cysteine residue.

In certain embodiments, the PTH/PTHrP peptide binds to a PTH-1 receptor or a PTH-2 receptor. In certain embodiments, the PTH/PTHrP peptide further comprises a prepro domain. In certain embodiments, the prepro domain is selected from SEQ ID NOs: 188 to 207.

In certain embodiments, a RANKL antibody-PTH/PTHrP chimeric molecule comprises a PTH/PTHrP peptide comprising a PTH/PTHrP modulating domain selected from polypeptides of formula II:

$$J^N J^7 J^8 HNJ^{11}J^{12}KHLJ^{16}SJ^{18}J^{19}RJ^{21}EWLRKKLJ^C$$
(Formula II; SEQ ID NO: 14)

wherein:
$J^N$ is absent or is $J^1J^2J^3J^4J^5J^6$, $J^2J^3J^4J^5J^6$, or $J^3J^4J^5J^6$;
$J^1$ through $J^8$, $J^{12}$, $J^{16}$, $J^{18}$, and $J^{21}$ are each independently selected amino acid residues;
$J^{11}$ is a nonfunctional or basic residue;
$J^{19}$ is an acidic or basic residue;
$J^C$ is absent or is $J^{29}$, $J^{29}J^{30}$, $J^{29}J^{30}J^{31}$, $J^{29}J^{30}J^{31}J^{32}$, $J^{29}J^{30}J^{31}J^{32}J^{33}$, or $J^{29}J^{30}J^{31}J^{32}J^{33}J^{34}$;
$J^{29}$ through $J^{34}$ are each independently selected amino acid residues;
provided that one or more of $J^{14}$ through the C-terminal residue of the PTH/PTHrP modulating domain is a cysteine residue.

In certain embodiments, the PTH/PTHrP peptide binds to a PTH-1 receptor or a PTH-2 receptor. In certain embodiments, the PTH/PTHrP peptide further comprises a prepro domain. In certain embodiments, the prepro domain is selected from SEQ ID NOs: 188 to 207.

In certain embodiments, a RANKL antibody-PTH/PTHrP chimeric molecule comprises a PTH/PTHrP peptide comprising a PTH/PTHrP modulating domain selected from polypeptides of formula III:

$$O^N LHO^{10}O^{11}O^{12}KSIO^{15}O^{16}O^{17}LRRRFO^{23}LHHLIO^C$$
(Formula III; SEQ ID NO: 15)

wherein:
$O^N$ is absent or is $YO^1O^2O^3O^4O^5O^6O^7$, $O^1O^2O^3O^4O^5O^6O^7$, $O^2O^3O^4O^5O^6O^7$, $O^3O^4O^5O^6O^7$, $O^4O^5O^6O^7$, $O^5O^6O^7$, $O^6O^7$, or $O^7$;
$O^1$ through $O^7$, $O^{10}$ through $O^{12}$, $O^{15}$ through $O^{17}$ and $O^{23}$ are each independently selected amino acid residues;
$O^C$ is absent or is $O^{29}$, $O^{29}O^{30}$, $O^{29}O^{30}O^{31}$, $O^{29}O^{30}O^{31}O^{32}$, $O^{29}O^{30}O^{31}O^{32}O^{33}$, $O^{29}O^{30}O^{31}O^{32}O^{33}O^{34}$, $O^{29}O^{30}O^{31}O^{32}O^{33}O^{34}O^{35}$, or $O^{29}O^{30}O^{31}O^{32}O^{33}O^{34}O^{35}O^{36}$;
$O^{29}$ through $O^{35}$ are each independently amino acid residues;
provided that one or more of O14 through the C-terminal residue of the PTH/PTHrP modulating domain is a cysteine residue.

In certain embodiments, the PTH/PTHrP peptide binds to a PTH-1 receptor or a PTH-2 receptor. In certain embodiments, the PTH/PTHrP peptide further comprises a prepro domain. In certain embodiments, the prepro domain is selected from SEQ ID NOs: 188 to 207.

In certain embodiments, a RANKL antibody-PTH/PTHrP chimeric molecule comprises a PTH/PTHrP peptide comprising a modulating domain comprising a sequence selected from SEQ ID NOs: 16 to 67. In certain embodiments, a RANKL antibody-PTH/PTHrP chimeric molecule comprises a PTH/PTHrP peptide comprising a modulating domain comprising a sequence selected from SEQ ID NOs: 68 to 89. In certain embodiments, a RANKL antibody-PTH/PTHrP chimeric molecule comprises a PTH/PTHrP peptide comprising a modulating domain comprising a sequence selected from SEQ ID NOs: 90 to 107 except that one or more residues at position 14 through the C-terminus of the PTH/PTHrP modulating domain is substituted with a cysteine residue.

In certain embodiments, a RANKL antibody-PTH/PTHrP chimeric molecule comprises a first polypeptide having an amino acid sequence of SEQ ID NO: 2 and a second polypeptide having an amino acid sequence of SEQ ID NO: 8. In certain embodiments, a RANKL antibody-PTH/PTHrP chimeric molecule comprises a first polypeptide having an amino acid sequence of SEQ ID NO: 10 and a second polypeptide having an amino acid sequence of SEQ ID NO: 4. In certain embodiments, a RANKL antibody-PTH/PTHrP chimeric molecule comprises a first polypeptide having an amino acid sequence of SEQ ID NO: 10 and a second polypeptide having an amino acid sequence of SEQ ID NO: 8.

In certain embodiments, a RANKL antibody-PTH/PTHrP chimeric molecule inhibits binding of RANKL to a receptor activator of NF-κB (RANK).

In certain embodiments, a pharmaceutical composition comprising a RANKL antibody-PTH/PTHrP chimeric molecule is provided.

In certain embodiments, a pharmaceutical composition further comprises at least one therapeutic agent selected from a bone anti-resorptive agent, a bone anabolic agent, an anti-inflammatory agent, an immune suppressing agent, and a cancer therapy agent. In certain embodiments, a pharmaceutical composition further comprises at least one therapeutic agent is selected from, anakinra, etanercept, infliximab, adalimumab, and methotrexate. In certain embodiments, a pharmaceutical composition further comprises at least one cancer therapy agent selected from radiation therapy and chemotherapy. In certain embodiments, a pharmaceutical composition further comprises at least one cancer therapy agent selected from an epidermal growth factor receptor (EGFR) inhibitor, a HER2 inhibitor, a vegF inhibitor, a vegF receptor inhibitor, a hepatocyte growth factor (HGF)/scatter factor (SF) inhibitor, a c-Met inhibitor, an angiopoietin inhibitor, a Tie2 inhibitor, a platelet derived growth factor receptor (PDGFR) inhibitor, an insulin-like growth factor receptor (IGFR) inhibitor, a mucin-like glycoprotein inhibitor, a CDC20 inhibitor, and a CDC33 inhibitor.

In certain embodiments, a pharmaceutical composition further comprises at least one therapeutic antibody. In certain embodiments, at least one therapeutic antibody is selected from a Her2 antibody, a CDC20 antibody, an EGFR antibody, a vegF antibody, a vegF receptor antibody, a hepatocyte growth factor (HGF)/scatter factor (SF) antibody, an insulin-like growth factor receptor (IFGR) antibody, and a CDC33 antibody.

In certain embodiments, a method of treating bone loss in a patient is provided. In certain embodiments a method of treating bone loss comprises administering a pharmaceutical composition comprising a RANKL antibody-PTH/PTHrP chimeric molecule. In certain embodiments, a method comprises administering a pharmaceutical composition comprising a RANKL antibody-PTH/PTHrP chimeric molecule and at least one agent selected from a bone anti-resorptive agent, a bone anabolic agent, an anti-inflammatory agent, an immune suppressing agent, and a cancer therapy agent. In certain embodiments, a method comprises administering a pharmaceutical composition comprising a RANKL antibody-PTH/PTHrP chimeric molecule and at least one therapeutic agent selected from a bone morphogenic factor, transforming growth factor-β (TGF-β), an interleukin-1 (IL-1) inhibitor, IL-1 ra, anakinra, a TNFα inhibitor, a soluble TNFα receptor, etanercept, an anti-TNFα antibody, infliximab, adalimumab, a prostaglandin, a bisphosphonate, alendronate, fluoride, calcium, a non-steroidal anti-inflammatory drug (NSAID), a COX-2 inhibitor, celecoxib, rofecoxib, an immunosuppressant, methotrexate, leflunomide, a serine protease inhibitor, a secretory leukocyte protease inhibitor (SLPI), an IL-6 inhibitor, an IL-6 antibody, an IL-8 inhibitor, an IL-8 antibody, an IL-18 inhibitor, an IL-18 binding protein, an IL-18 antibody, an Interleukin-1 converting enzyme (ICE) modulator, a fibroblast growth factor (FGF), an FGF modulator, a PAF antagonist, a keratinocyte growth factor (KGF), a KGF-related molecule, a KGF modulator; a matrix metalloproteinase (MMP) modulator, a nitric oxide synthase (NOS) modulator, a modulator of glucocorticoid receptor, a modulator of glutamate receptor, a modulator of lipopolysaccharide (LPS) levels, a noradrenaline, a noradrenaline mimetic, and a noradrenaline modulator.

In certain embodiments, a method of treating an inflammatory condition with attendant bone loss is provided. In certain embodiments, a method of treating an autoimmune condition with attendant bone loss is provided. In certain embodiments, a method of treating an rheumatoid arthritis is provided. In certain embodiments, a method of treating bone loss associated with cancer is provided. In certain embodiments, the method comprises administering a pharmaceutical composition comprising a RANKL antibody-PTH/PTHrP chimeric molecule.

BRIEF DESCRIPTION OF THE FIGURES

FIG. 1 shows a cDNA sequence encoding the αRANKL-1 (also called αOPGL-1) antibody heavy chain (SEQ ID NO: 1). The cDNA sequence begins at a HindIII site and ends at a SalI site. The start codon begins at nucleotide 14 and the stop codon begins at nucleotide 1415.

FIG. 2 shows the amino acid sequence of the αRANKL-1 (also called αOPGL-1) antibody heavy chain (SEQ ID NO: 2). The heavy chain signal peptide is underlined. The variable region is in capital letters and is not underlined. The constant region is in lower case.

FIG. 3 shows a cDNA sequence encoding the αRANKL-1 (also called αOPGL-1) antibody light chain (SEQ ID NO: 3). The cDNA sequence begins at an XbaI site and ends at a SalI site. The start codon begins at nucleotide 12 and the stop codon begins at nucleotide 717.

FIG. 4 shows the amino acid sequence of the αRANKL-1 (also called αOPGL-1) antibody light chain (SEQ ID NO: 4). The kappa signal peptide is underlined. The variable region is in capital letters and is not underlined. The constant region is in lower case.

FIG. 7 shows a cDNA sequence encoding synPTH (SEQ ID NO: 5). The XbaI (TCTAGA) site and Kozak sequence (CCACC) are in bold. The prepro domain is underlined. An exemplary PTH/PTHrP modulating domain is in plain text. The sequence encoding the GGGAP linker (SEQ ID NO: 212) is in italics. A BssHII site (GCGCGC) is located within the linker sequence.

FIG. 8 shows the amino acid sequence of synPTH (SEQ ID NO: 6). The prepro domain is underlined. An exemplary modulating domain is in plain text. The GGGAP linker (SEQ ID NO: 212) is in italics.

FIG. 9 shows a cDNA sequence encoding synPTH-αRANKL-1 light chain (also called synPTH-αRANKL-1 kappa; SEQ ID NO: 7). The XbaI (TCTAGA) site and Kozak sequence (CCACC) are in bold at the beginning of the sequence. The prepro domain is underlined. The sequence encoding the GGGAP linker (SEQ ID NO: 212) is in italics. The stop codon begins at nucleotide 867. A SalI site is in bold at the end of the sequence.

FIG. 10 shows the amino acid sequence of synPTH-αRANKL-1 light chain (also called synPTH-αRANKL-1 kappa; SEQ ID NO: 8). The prepro domain is underlined. The GGGAP linker (SEQ ID NO: 212) is in italics.

FIG. 11 shows a cDNA sequence encoding synPTH-αRANKL-1 heavy chain (also called synPTH-αRANKL-1 IgG2; SEQ ID NO: 9). The XbaI (TCTAGA) site and Kozak sequence (CCACC) are in bold at the beginning of the sequence. The prepro domain is underlined. The sequence encoding the GGGAP linker (SEQ ID NO: 212) is in italics. The stop codon begins at nucleotide 1566. A SalI site is in bold at the end of the sequence.

FIG. 12 shows the amino acid sequence of synPTH-αRANKL-1 heavy chain (also called synPTH-αRANKL-1 IgG2; SEQ ID NO: 10). The prepro domain is underlined. The GGGAP linker (SEQ ID NO: 212) is in italics.

FIG. 28 shows the amino acid sequence of the αRANKL-1 antibody heavy chain variable region (SEQ ID NO: 11).

FIG. 29 shows the amino acid sequence of the αRANKL-1 antibody light chain variable region (SEQ ID NO: 12).

DETAILED DESCRIPTION OF CERTAIN EMBODIMENTS

Figure 5:
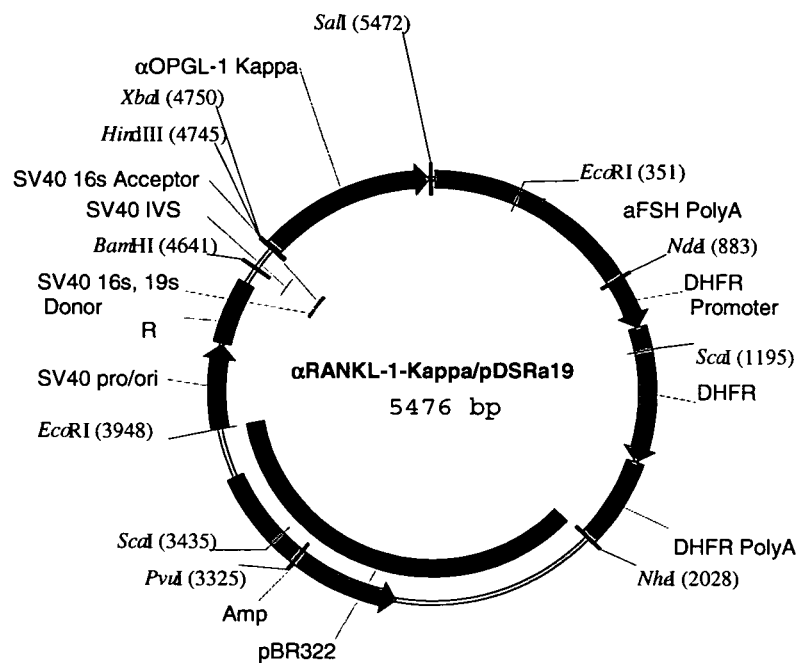
FIG. 5 shows a schematic diagram of the αRANKL-1 kappa light chain expression plasmid αRANKL-1-Kappa/pDSRa19 (also called αOPGL-1-Kappa/pDSRa19; see, e.g., U.S. Patent Publication No. U.S. 2004/0033535 A1 and PCT Publication No. WO 2003/002713 A3).
Figure 6:
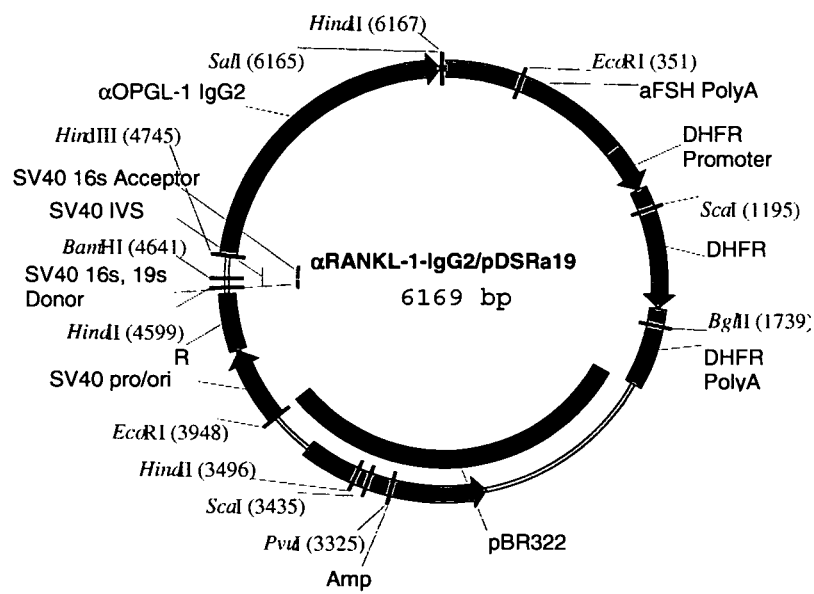
FIG. 6 shows a schematic diagram of the αRANKL-1 IgG2 heavy chain expression plasmid, αRANKL-1-IgG2/pDSRα19 (also called αOPGL-1-IgG2/pDSRa19; see, e.g., U.S. Patent Publication No. U.S. 2004/0033535 A1 and PCT Publication No. WO 2003/002713 A3).

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference herein in their entirety for any purpose.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Definitions

As utilized in accordance with the present disclosure, the following terms, unless otherwise indicated, shall be understood to have the following meanings:

The terms "polypeptide," "peptide," and "protein" are used interchangeably herein and refer to a polymer of two or more amino acids joined together by peptide bonds or modified peptide bonds. The terms apply to amino acid polymers containing naturally occurring amino acids as well as amino acid polymers in which one or more amino acid residues is a non-naturally occurring amino acid or a chemical analogue of a naturally occurring amino acid. An amino acid polymer may contain one or more amino acid residues that has been modified by one or more natural processes, such as post-translational processing, and/or one or more amino acid residues that has been modified by one or more chemical modification techniques known in the art.

The term "isolated polypeptide" refers to any polypeptide that (1) is free of at least some polypeptides with which it would normally be found, or (2) is essentially free of other polypeptides from the same source, e.g., that are found in the same environment, such as in the same cell or fluid, or (3) is expressed by a cell of a different species from the species of origin of the polypeptide, (4) is expressed in a cell-free expression system, (5) is prepared synthetically, or (6) does not occur in nature.

A "fragment" of a reference polypeptide refers to a contiguous stretch of amino acids from any portion of the reference polypeptide. A fragment may be of any length that is less than the length of the reference polypeptide.

A "variant" of a reference polypeptide refers to a polypeptide having one or more amino acid substitutions, deletions, or insertions relative to the reference polypeptide.

Variants of a reference polypeptide include, but are not limited to, cysteine variants. Cysteine variants include variants in which one or more cysteine residues of the reference polypeptide are replaced by one or more non-cysteine residues; and/or one or more non-cysteine residues of the reference polypeptide are replaced by one or more cysteine residues. Cysteine variants may be useful, in certain embodiments, when a particular polypeptide must be refolded into a biologically active conformation, e.g., after the isolation of insoluble inclusion bodies. In certain embodiments, cysteine variants of a reference polypeptide have fewer cysteine residues than the reference polypeptide. In certain embodiments, cysteine variants have more cysteine residues that the reference polypeptide. In certain embodiments, cysteine variants of a reference polypeptide have an even number of cysteines to minimize interactions resulting from unpaired cysteines.

Variants of a reference polypeptide include, but are not limited to, glycosylation variants. Glycosylation variants include variants in which the number and/or type of glycosylation sites have been altered as compared to the reference polypeptide. In certain embodiments, glycosylation variants of a reference polypeptide comprise a greater or a lesser number of N-linked glycosylation sites than the reference polypeptide. In certain embodiments, an N-linked glycosylation site is characterized by the sequence Asn-X-Ser or Asn-X-Thr, wherein the amino acid residue designated as X may be any amino acid residue except proline. In certain embodiments, glycosylation variants include rearrangements of N-linked carbohydrate chains wherein one or more N-linked glycosylation sites (including, but not limited to, naturally-occurring glycosylation sites) are eliminated and one or more new N-linked glycosylation sites are created.

A "derivative" of a reference polypeptide refers to a polypeptide (1) having one or more modifications of one of more amino acid residues of the reference polypeptide; and/or (2) in which one or more peptidyl linkages has been replaced with one or more non-peptidyl linkages; and/or (3) in which the N-terminus and/or the C-terminus has been modified.

In certain embodiments, polypeptides may be branched and/or cyclic. Cyclic, branched and branched cyclic polypeptides may result from post-translation natural processes (including, but not limited to, ubiquitination) or may be made by synthetic methods.

The term "polypeptide" encompasses RANKL antibody-PTH/PTHrP chimeric molecules. In certain embodiments, the term "polypeptide" encompasses RANKL antibody-PTH/PTHrP chimeric molecules, wherein one or more RANKL antibodies and one or more PTH/PTHrP peptides have been translated from a single coding sequence to produce a single contiguous polypeptide. In certain embodiments, the term "polypeptide" encompasses RANKL antibody-PTH/PTHrP chimeric molecules, wherein one or more RANKL antibodies and one or more PTH/PTHrP peptides have been chemically synthesized as a single contiguous polypeptide. In certain embodiments, the term "polypeptide" encompasses RANKL antibody-PTH/PTHrP chimeric molecules, wherein one or more RANKL antibodies and one or more PTH/PTHrP peptides have been produced separately, either enzymatically or chemically, and then chemically or enzymatically linked to one another.

In certain embodiments, a polypeptide comprises one or more randomized amino acids and/or stretches of amino acids. In certain embodiments, a polynucleotide comprises one or more randomized nucleotides and/or stretches of nucleotides.

The term "randomized" refers to a residue or stretch of residues that are randomly substituted. A stretch of residues comprises two or more contiguous residues. In certain embodiments, random substitution means that a particular amino acid position is substituted randomly with an amino acid selected from a pool of two or more amino acids. In certain embodiments, a particular amino acid position is substituted randomly with an amino acid selected from a pool of five or more amino acids. In certain embodiments, a particular amino acid position is substituted randomly with an amino acid selected from a pool of ten or more amino acids. In certain embodiments, a particular amino acid position is substituted randomly with an amino acid selected from a pool of fifteen or more amino acids. In certain embodiments, a particular amino acid position is substituted randomly with an amino acid selected from a pool of twenty or more amino acids. In certain embodiments, a polypeptide having a desired characteristic may be selected from a pool of randomized polypeptides using at least one technique selected from phage display, E. coli display, ribosome display, RNA-peptide screening, chemical screening, and the like.

In certain embodiments, random substitution means that a particular nucleotide position is substituted randomly with a nucleotide selected from a pool of two or more nucleotides. In certain embodiments, a particular nucleotide position is substituted randomly with a nucleotide selected from a pool of three or more nucleotides. In certain embodiments, a particular nucleotide position is substituted randomly with a nucleotide selected from a pool of four or more nucleotides. In certain embodiments, a polynucleotide having one or more randomized nucleotides and/or stretches of nucleotides encodes a polypeptide having one or more randomized amino acids and/or stretches of amino acids.

The term "PTH/PTHrP modulating domain" refers to a polypeptide that binds to a PTH-1 receptor and/or a PTH-2 receptor. In certain embodiments, a PTH/PTHrP modulating domain comprises a naturally-occurring sequence. In certain embodiments, a PTH/PTHrP modulating domain comprises at least one randomized residue and/or sequence. Certain exemplary PTH/PTHrP modulating domains are discussed in or can be identified or derived from the documents listed for Tables 1A and 2.

The term "PTH/PTHrP" or "PTH/PTHrP peptide" refers to a polypeptide comprising a PTH/PTHrP modulating domain. In certain embodiments, a PTH/PTHrP peptide comprises a prepro domain in addition to a PTH/PTHrP modulating domain. In certain embodiments, a PTH/PTHrP peptide comprises a portion of a prepro domain in addition to a PTH/PTHrP modulating domain. The term "PTH/PTHrP peptide" encompasses mature PTH/PTHrP peptides that result from processing a PTH/PTHrP peptide having a prepro domain to remove that prepro domain. The term "PTH/PTHrP peptide" encompasses any intermediates that are formed during processing of a PTH/PTHrP peptide having a prepro domain, even if those intermediates are not further processed.

The term "PTH agonist" refers to a molecule that binds to a PTH-1 receptor and/or a PTH-2 receptor and causes a similar response in one or more PTH activity assays as full-length PTH. In certain embodiments, a "similar response" means that the PTH agonist increases a signal in a PTH activity assay relative to a control under the same conditions that full-length PTH increases the signal relative to the control in the same PTH activity assay. In certain embodiments, a "similar response" means that the PTH agonist decreases a signal relative to a control in a PTH activity assay under the same conditions that full-length PTH decreases the signal relative to the control in the same PTH activity assay. Certain exemplary PTH activity assays are described, e.g., in Example 5 and in PCT Publication No. WO 01/81415.

The term "PTH antagonist" refers to a molecule that binds to a PTH-1 receptor and/or a PTH-2 receptor and blocks or prevents the normal effect that full-length PTH has on the receptor. Certain exemplary PTH activity assays are described, e.g., in Example 5 and in PCT Publication No. WO 01/81415.

The term "naturally-occurring" as applied to an object means that the object can be found in nature. For example, a polypeptide or polynucleotide that is present in an organism (including viruses) that can be isolated from a source in nature is naturally-occurring.

The term "chimeric molecule" refers to a molecule that comprises at least two components that are not normally part of the same molecule. Each component of a chimeric molecule is linked to at least one other component of the chimeric molecule. In certain embodiments, a first component of a chimeric molecule may be covalently linked to a second component that is the same as, or different from, the first component. Thus, as a non-limiting example, in a chimeric molecule that comprises one RANKL antibody and two PTH/PTHrP peptides having the same sequence, the RANKL antibody may be linked to the first PTH/PTHrP peptide and the second PTH/PTHrP peptide may also be linked to the first PTH/PTHrP peptide.

The term "linked" refers to components that are associated either covalently or non-covalently such that they remain substantially associated under physiological conditions. In certain embodiments, a first polypeptide and a second polypeptide may be covalently linked. In certain embodiments, a first polypeptide and a second polypeptide may be covalently linked by translating the first and second polypeptides as single contiguous polypeptide. In certain embodiments, a first polypeptide and a second polypeptide may be covalently linked by synthesizing the first and second polypeptides as a single contiguous polypeptide. In certain embodiments, a first polypeptide and a second polypeptide may be covalently linked by translating and/or synthesizing the first and second polypeptides separately, and then linking them together chemically and/or enzymatically.

In certain embodiments, when a first and second polypeptide are translated as a single contiguous polypeptide, a linker sequence may be included between the C-terminus of the first polypeptide and the N-terminus of the second polypeptide. In certain embodiments, a linker sequence is between 1 and 100 amino acids long. In certain embodiments, a linker sequence is between 5 and 50 amino acids long. In certain embodiments, a linker sequence is between 10 and 30 amino acids long.

In certain embodiments, a first polypeptide and a second polypeptide are covalently linked. In certain embodiments, a first polypeptide and a second polypeptide are produced separately, and then covalently linked to one another. Certain exemplary peptide and non-peptide covalent linkers are known in the art and/or are discussed herein.

In certain embodiments, a first polypeptide and a second polypeptide are linked noncovalently. In certain embodiments, a first polypeptide and a second polypeptide are linked noncovalently by incorporating into a first polypeptide sequence a first member of a binding pair and incorporating into a second polypeptide sequence a second member of a binding pair, such that when the first and second polypeptides are exposed to one another under appropriate conditions, the first and second members of the binding pair interact and noncovalently link the polypeptides.

As used herein, the term "binding pair" refers to two molecules that specifically bind to one another. Certain exemplary binding pairs include biotin and avidin, biotin and streptavidin, His₆ tag and nickel, human serum albumin and its binding peptides, human serum albumin and an antibody fragment, an antibody and its antigen, an antibody fragment and its antigen, a Nanobody™ and its antigen, and a domain antibody and its antigen. Certain exemplary Nanobodies™ are described, e.g., in PCT Publication Nos. WO 03/050531, WO 04/041862, WO 04/041863, WO 04/041865, WO 04/041867, WO 04/062551, and European Application No. 1456410. Certain exemplary domain antibodies are described, e.g., in U.S. Pat. No. 6,696,245, and PCT Publication Nos. WO 04/058821, WO 04/003019 and WO 03/002609.

The term "operably linked" refers to components that are in a relationship permitting them to function in their intended manner. For example, in the context of a polynucleotide sequence, a control sequence may be "operably linked" to a coding sequence when the control sequence and coding sequence are associated in such a way that expression of the coding sequence is achieved under conditions compatible with the functioning of the control sequence.

The term "control sequence" refers to polynucleotide sequences which may effect the expression and processing of coding sequences to which they are associated. The nature of such control sequences may differ depending upon the host organism. Certain exemplary control sequences for prokaryotes include, but are not limited to, promoters, ribosomal binding sites, and transcription termination sequences. Certain exemplary control sequences for eukaryotes include, but are not limited to, promoters and transcription termination sequences.

In certain embodiments, a first polynucleotide coding sequence is operably linked to a second polynucleotide coding sequence when the first and second polynucleotide coding sequences are transcribed into a single contiguous mRNA that can be translated into a single contiguous polypeptide.

In the context of polypeptides, two or more polypeptides are "operably linked" if each linked polypeptide is able to function in its intended manner. A polypeptide that is able to function in its intended manner when operably linked to another polypeptide may or may not be able to function in its intended manner when not operably linked to another polypeptide. For example, in certain embodiments, a first polypeptide may be unable to function in its intended manner when unlinked, but may be stabilized by being linked to a second polypeptide such that it becomes able to function in its intended manner. Alternatively, in certain embodiments, a first polypeptide may be able to function in its intended manner when unlinked, and may retain that ability when operably linked to a second polypeptide.

As used herein, two or more polypeptides are "fused" when the two or more polypeptides are linked by translating them as a single contiguous polypeptide sequence or by synthesizing them as a single contiguous polypeptide sequence. In certain embodiments, two or more fused polypeptides may have been translated in vivo from two or more operably linked polynucleotide coding sequences. In certain embodiments, two or more fused polypeptides may have been translated in vitro from two or more operably linked polynucleotide coding sequences.

As used herein, two or more polypeptides are "operably fused" if each linked polypeptide is able to function in its intended manner.

In certain embodiments, a first polypeptide that contains two or more distinct polypeptide units is considered to be linked to a second polypeptide so long as at least one of the distinct polypeptide units of the first polypeptide is linked to the second polypeptide. As a non-limiting example, in certain embodiments, an antibody is considered linked to a second polypeptide in all of the following instances: (a) the second polypeptide is linked to one of the heavy chain polypeptides of the antibody; (b) the second polypeptide is linked to one of the light chain polypeptides of the antibody; (c) a first molecule of the second polypeptide is linked to one of the heavy chain polypeptides of the antibody and a second molecule of the second polypeptide is linked to one of the light chain polypeptides of the antibody; and (d) first and second molecules of the second polypeptide are linked to the first and second heavy chain polypeptides of the antibody and third and fourth molecules of the second polypeptide are linked to first and second light chain polypeptides of the antibody.

In certain embodiments, the language "a first polypeptide linked to a second polypeptide" encompasses situations where: (a) only one molecule of a first polypeptide is linked to only one molecule of a second polypeptide; (b) only one molecule of a first polypeptide is linked to more than one molecule of a second polypeptide; (c) more than one molecule of a first polypeptide is linked to only one molecule of a second polypeptide; and (d) more than one molecule of a first polypeptide is linked to more than one molecule of a second polypeptide. In certain embodiments, when a linked molecule comprises more than one molecule of a first polypeptide and only one molecule of a second polypeptide, all or fewer than all of the molecules of the first polypeptide may be covalently or noncovalently linked to the second polypeptide. In certain embodiments, when a linked molecule comprises more than one molecule of a first polypeptide, one or more molecules of the first polypeptide may be covalently or noncovalently linked to other molecules of the first polypeptide.

As used herein, a "flexible linker" refers to any linker that is not predicted, according to its chemical structure, to be fixed in three-dimensional space. One skilled in the art can predict whether a particular linker is flexible in its intended context.

As used herein, the twenty conventional amino acids and their abbreviations follow conventional usage. See Immunology—A Synthesis, 2nd Edition, E. S. Golub and D. R. Gren, Eds., Sinauer Associates, Sunderland, Mass. (1991). In certain embodiments, one or more unconventional amino acids may be incorporated into a polypeptide. The term "unconventional amino acid" refers to any amino acid that is not one of the twenty conventional amino acids. The term "non-naturally occurring amino acids" refers to amino acids that are not found in nature. Non-naturally occurring amino acids are a subset of unconventional amino acids. Unconventional amino acids include, but are not limited to, stereoisomers (e.g., D-amino acids) of the twenty conventional amino acids, α-, α-disubstituted amino acids, N-alkyl amino acids, lactic acid, homoserine, homocysteine, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and any other unconventional amino acids and imino acids (e.g., 4-hydroxyproline) and known in the art. Unconventional amino acid residues include, but are not limited to, peptidomimetics and other reversed or inverted forms of amino acid moieties. In the polypeptide notation used herein, the left-hand direction is the amino terminal direction and the right-hand direction is the carboxy-terminal direction, in accordance with standard usage and convention.

In certain embodiments, conservative amino acid substitutions include substitution with one or more unconventional amino acid residues. In certain embodiments, unconventional amino acid residues are incorporated by chemical peptide synthesis rather than by synthesis in biological systems.

The term "acidic residue" refers to an amino acid residue in D- or L-form that comprises at least one acidic group when incorporated into a polypeptide between two other amino acid residues that are the same or different. In certain embodiments, an acidic residue comprises a side chain that comprises at least one acidic group. Exemplary acidic residues include, but are not limited to, aspartic acid (D) and glutamic acid (E). In certain embodiments, an acidic residue may be an unconventional amino acid.

The term "aromatic residue" refers to an amino acid residue in D- or L-form that comprises at least one aromatic group. In certain embodiments, an aromatic residue comprises a side chain that comprises at least one aromatic group. Exemplary aromatic residues include, but are not limited to, phenylalanine (F), tyrosine (Y), and tryptophan (W). In certain embodiments, an aromatic residue may be an unconventional amino acid.

The term "basic residue" refers to an amino acid residue in D- or L-form that may comprise at least one basic group when incorporated into a polypeptide between two amino acid residues that are the same or different. In certain embodiments, a basic residue comprises a side chain that comprises at least one basic group. Exemplary basic residues include, but are not limited to, histidine (H), lysine (K), and arginine (R). In certain embodiments, a basic residue may be an unconventional amino acid.

The terms "hydrophilic residue" and "Haa" refer to an amino acid residue in D- or L-form that comprises at least one hydrophilic group and/or polar group when incorporated into a polypeptide between two amino acid residues that are the same or different. In certain embodiments, a hydrophilic residue comprises a side chain that comprises at least one hydrophilic group and/or polar group. Exemplary hydrophilic residues include, but are not limited to, alanine (A) cysteine (C), aspartic acid (D), glutamic acid (E), histidine (H), lysine (K), asparagine (N), glutamine (Q), arginine (R), serine (S), and threonine (T). In certain embodiments, a hydrophilic residue may be an unconventional amino acid.

The term "neutral hydrophilic residue" refers to an amino acid residue in D- or L-form that comprises at least one hydrophilic and/or polar group, but does not comprise an acidic or basic group when incorporated into a polypeptide between two amino acid residues that are the same or different. Exemplary neutral hydrophilic residues include, but are not limited to, alanine (A), cysteine (C), serine (S), threonine (T), asparagine (N), and glutamine (Q). In certain embodiments, a neutral hydrophilic residue may be an unconventional amino acid.

The terms "lipophilic residue" and "Laa" refer to an amino acid residue in D- or L-form having at least one uncharged, aliphatic and/or aromatic group. In certain embodiments, a lipophilic residue comprises a side chain that comprises at least one uncharged, aliphatic and/or aromatic group. Exemplary lipophilic side chains include, but are not limited to, alanine (A), phenylalanine (F), isoleucine (I), leucine (L), norleucine (Nle), methionine (M), valine (V), tryptophan (W), and tyrosine (Y). In certain embodiments, a lipophilic residue may be an unconventional amino acid.

The term "amphiphilic residue" refers to an amino acid residue in D- or L-form that is capable of being either a hydrophilic or lipophilic residue. An exemplary amphiphilic residue includes, but is not limited to, alanine (A). In certain embodiments, an amphiphilic residue may be an unconventional amino acid.

The term "nonfunctional residue" refers to an amino acid residue in D- or L-form that lacks acidic, basic, and aromatic groups when incorporated into a polypeptide between two amino acid residues that are the same or different. Exemplary nonfunctional amino acid residues include, but are not limited to, methionine (M), glycine (G), alanine (A), valine (V), isoleucine (I), leucine (L), and norleucine (Nle). In certain embodiments, a nonfunctional residue may be an unconventional amino acid.

In certain embodiments, glycine (G) and proline (P) are considered amino acid residues that can influence polypeptide chain orientation.

In certain embodiments, a conservative substitution may involve replacing a member of one residue type with a member of the same residue type. As a non-limiting example, in certain embodiments, a conservative substitution may involve replacing an acidic residue, such as D, with a different acidic residue, such as E. In certain embodiments, a non-conservative substitution may involve replacing a member of one residue type with a member of a different residue type. As a non-limiting example, in certain embodiments, a non-conservative substitution may involve replacing an acidic residue, such as D, with a basic residue, such as K. In certain embodiments, a cysteine residue is substituted with another amino acid residue to prevent disulfide bond formation with that position in the polypeptide.

In making conservative or non-conservative substitutions, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a polypeptide is understood in the art. See, e.g., Kyte et al., *J. Mol. Biol.*, 157:105-131 (1982). It is known in certain instances that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional polypeptide thereby created is intended for use in immunological embodiments, as in the present case. In certain embodiments, the greatest local average hydrophilicity of a polypeptide, as governed by the hydrophilicity of its adjacent amino acids, correlates with its immunogenicity and antigenicity, i.e., with a biological property of the polypeptide.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. In certain instances, one may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | More Specific Exemplary Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

In certain embodiments, a skilled artisan will be able to determine suitable substitution variants of a reference polypeptide using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, areas that may be important for biological activity or for structure may be subject to conservative amino acid substitutions without destroying the biological activity or without adversely affecting the polypeptide structure.

Additionally, in certain embodiments, one skilled in the art can review structure-function studies identifying residues in similar polypeptides that are important for activity and/or structure. In view of such a comparison, in certain embodiments, one can predict the importance of amino acid residues in a polypeptide that correspond to amino acid residues which are important for activity or structure in similar polypeptides. In certain embodiments, one skilled in the art may opt for chemically similar amino acid substitutions for such predicted important amino acid residues.

In certain embodiments, one skilled in the art can also analyze the three-dimensional structure and amino acid sequence in relation to that structure in similar polypeptides. In view of such information, in certain embodiments, one skilled in the art may predict the alignment of amino acid residues of an antibody with respect to its three dimensional structure. In certain embodiments, one skilled in the art may choose not to make radical changes to amino acid residues predicted to be on the surface of the polypeptide, since such residues may be involved in important interactions with other molecules. Moreover, in certain embodiments, one skilled in the art may generate test variants containing a single amino acid substitution at each desired amino acid residue. In certain embodiments, the variants can then be screened using activity assays known to those skilled in the art. In certain embodiments, such variants could be used to gather information about suitable variants. For example, in certain embodiments, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See, e.g., Moult J., *Curr. Op. in Biotech.*, 7(4):422-427 (1996), Chou et al., *Biochemistry*, 13(2):222-245 (1974); Chou et al, *Biochemistry*, 113(2):211-222 (1974); Chou et al., *Adv. Enzymol. Relat. Areas Mol. Biol.*, 47:45-148 (1978); Chou et al., *Ann. Rev. Biochem.*, 47:251-276 and Chou et al., *Biophys. J.*, 26:367-384 (1979). Moreover, computer programs are currently available to assist with predicting secondary structure. One exemplary method of predicting secondary structure is based upon homology modeling. For example, in certain instances, two polypeptides that have a sequence identity of greater than 30%, or similarity greater than 40% may have similar structural topologies. The recent growth of the protein structural database (PDB) has provided enhanced predictability of secondary structure, including the potential number of folds within a polypeptide's structure. See, e.g., Holm et al., *Nucl. Acid. Res.*, 27(1):244-247 (1999). It has been suggested that there are a limited number of folds in a given polypeptide and that once a critical number of structures have been resolved, structural prediction will become dramatically more accurate. See, e.g., Brenner et al., *Curr. Op. Struct. Biol.*, 7(3): 369-376 (1997).

Additional exemplary methods of predicting secondary structure include, but are not limited to, "threading" (Jones, D., *Curr. Opin. Struct. Biol.*, 7(3):377-87 (1997); Sippl et al., *Structure*, 4(1):15-19 (1996).), "profile analysis" (Bowie et al., *Science*, 253:164-170 (1991); Gribskov et al., *Meth. Enzym.*, 183:146-159 (1990); Gribskov et al., *Proc. Nat. Acad. Sci.*, 84(13):4355-4358 (1987).), and "evolutionary linkage" (See Holm, supra (1999), and Brenner, supra (1997).).

In certain embodiments, identity and similarity of polypeptides can be readily calculated by known methods. Such methods include, but are not limited to, those described in Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., *SIAM J. Applied Math.*, 48:1073 (1988).

In certain embodiments, methods to determine identity are designed to give the largest match between the sequences tested. Certain exemplary methods to determine identity are described in publicly available computer programs. Exemplary computer program methods to determine identity between two sequences include, but are not limited to, the GCG program package, including GAP (Devereux et al., *Nucl. Acid. Res.*, 12:387 (1984); Genetics Computer Group, University of Wisconsin, Madison, Wis.), BLASTP, BLASTN, and FASTA (Altschul et al., *J. Mol. Biol.*, 215:403-410 (1990)). The BLASTX program is publicly available from the National Center for Biotechnology Information (NCBI) and other sources (*BLAST Manual, Altschul* et al. NCB/NLM/NIH Bethesda, Md. 20894; Altschul et al., supra (1990)). In certain embodiments, the Smith Waterman algorithm, which is known in the art, may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix is also used by the algorithm. See, e.g., Dayhoff et al., *Atlas of Protein Sequence and Structure*, 5(3) (1978) for the PAM 250 comparison matrix; Henikoff et al., *Proc. Natl. Acad. Sci* USA, 89:10915-10919 (1992) for the BLOSUM 62 comparison matrix.

In certain embodiments, the parameters for a polypeptide sequence comparison include the following:
Algorithm: Needleman et al., *J. Mol. Biol.*, 48:443-453 (1970);
Comparison matrix: BLOSUM 62 from Henikoff et al., supra (1992);
Gap Penalty: 12
Gap Length Penalty: 4
Threshold of Similarity: 0

In certain embodiments, the GAP program may be useful with the above parameters. In certain embodiments, the aforementioned parameters are the default parameters for polypeptide comparisons (along with no penalty for end gaps) using the GAP algorithm.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physicochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts).

In certain embodiments, a conservative amino acid substitution typically may not substantially change the structural characteristics of the parent sequence (e.g., in certain embodiments, a replacement amino acid should not tend to break a helix that occurs in the parent sequence, or disrupt other types of secondary structure that characterizes the parent sequence). Certain examples of art-recognized polypeptide secondary and tertiary structures are described, e.g., in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

In certain embodiments, a conservative amino acid substitution has little or no effect on the polarity of the charge at that position. In certain embodiments, any native residue in a polypeptide may be substituted with alanine, as has been previously described for "alanine scanning mutagenesis." See, e.g., See, e.g., MacLennan et al. Acta Physiol. Scand. Suppl. 643: 55-67 (1998); and Sasaki et al. Adv. Biophys. 35: 1-24 (1998).

The term "antibody" refers to an intact antibody, or a fragment of an antibody that competes with the intact antibody for antigen binding. In certain embodiments, antibody fragments are produced by recombinant DNA techniques. In certain embodiments, antibody fragments are produced by enzymatic or chemical cleavage of intact antibodies. Exemplary antibody fragments include, but are not limited to, Fab, Fab', F(ab')2, Fv, and scFv. Exemplary antibody fragments also include, but are not limited to, domain antibodies, nanobodies, minibodies ((scFv-$C_H3$)$_2$), maxibodies ((scFv-$C_H2$-$C_H3$)$_2$), diabodies (noncovalent dimer of scFv). An antibody fragment may, optionally, be linked to an immunoglobulin (Ig) heavy chain region comprising one or more of CH1, CH2 and CH3 regions. In certain embodiments, an antibody may comprise one or more heavy chains, one or more light chains, or one or more of both heavy and light chains, or fragments thereof which are capable of binding antigen.

Antibodies specific to an antigen may be produced in a number of ways. In certain embodiments, an antigen containing an epitope of interest may be introduced into an animal host (e.g., a mouse), thus producing antibodies specific to that epitope. In certain embodiments, antibodies specific to an epitope of interest may be obtained from biological samples taken from hosts that were naturally exposed to the epitope. In certain embodiments, introduction of human immunoglobulin (Ig) loci into mice in which the endogenous Ig genes have been inactivated offers the opportunity to obtain fully human monoclonal antibodies (MAbs).

Naturally occurring antibody structural units typically comprise a tetramer. A tetramer typically comprises two identical pairs of polypeptide chains, each pair having one light chain (in certain embodiments, about 25 kDa) and one heavy chain (in certain embodiments, about 50-70 kDa).

The term "heavy chain" refers to a heavy chain polypeptide having sufficient variable region sequence to confer specificity for a particular antigen. Thus, the term "heavy chain", as used herein, encompasses a full-length heavy chain and fragments thereof. A full-length heavy typically comprises a variable region domain, $V_H$, and three constant region domains, $C_H1$, $C_H2$, and $C_H3$. The $V_H$ domain is at the amino-terminus of the polypeptide, and the $C_H3$ domain is at the carboxy-terminus. A "heavy chain" may comprise a $V_H$ domain, or a portion of a $V_H$ domain comprising one or more of the complementarity determining regions (CDRs). A "heavy chain" may optionally include one or more constant region domains, $C_H1$, $C_H2$, and/or $C_H3$.

The term "light chain" refers to any polypeptide having sufficient light chain variable region sequence to confer specificity for a particular epitope. Thus, the term "light chain", as used herein, encompasses a full-length light chain and fragments thereof. A full-length light chain typically comprises a variable region domain, $V_L$, and a constant region domain, $C_L$. The variable region domain of the light chain is at the amino-terminus of the polypeptide. A "light chain" may comprise a $V_L$ domain, or a portion of a $V_L$ domain comprising one or more of the complementary determining regions (CDRs). A "light chain" may optionally include a constant region domain ($C_L$).

The amino-terminal portion of each chain typically includes a variable region ($V_H$ in the heavy chain and $V_L$ in the light chain) of about 100 to 110 or more amino acids. The variable regions of each light/heavy chain pair typically form the antigen binding site. The carboxy-terminal portion of each chain typically defines a constant region ($C_H$ domains in the heavy chain and $C_L$ in the light chain) that may be responsible for effector function. Exemplary antibody effector functions include activation of complement and stimulation of opsonophagocytosis. Naturally-occurring human light chains are typically classified as kappa and lambda light chains. Naturally-occurring human heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA has subclasses including, but not limited to, IgA1 and IgA2. Within naturally-occurring light and heavy chains, typically, the variable and constant regions are typically joined by a "J" region of about 12 or more amino acids, with the heavy chain also typically including a "D" region of about 10 more amino acids. See, e.g., Fundamental Immunology Ch. 7 (Paul, W., ed., 2nd ed. Raven Press, N.Y. (1989)).

In a naturally-occurring antibody, the variable regions typically exhibit the same general structure of relatively conserved framework regions (FR) joined by three hypervariable regions, also called complementarity determining regions or CDRs. The CDRs from the heavy and light chains of each pair typically are aligned by the framework regions, which may enable binding to a specific epitope. From N-terminal to C-terminal, both light and heavy chain variable regions typically comprise the domains FR1, CDR1, FR2, CDR2, FR3, CDR3, and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987); Chothia et al. Nature 342:878-883 (1989).

As discussed above, there are several types of antibody fragments. A Fab fragment is comprised of one light chain and the $C_H1$ and variable regions of one heavy chain. The heavy chain of a Fab molecule cannot form a disulfide bond with another heavy chain molecule. A Fab' fragment contains one light chain and one heavy chain that contains more of the constant region, between the $C_H1$ and $C_H2$ domains, such that an interchain disulfide bond can be formed between two heavy chains to form a F(ab')2 molecule. A Facb fragment is similar to a F(ab')2 molecule, except the constant region in the heavy chains of the molecule extends to the end of the CH2 domain.

An Fv fragment comprises the variable regions from both the heavy and light chains, but lacks the constant regions. A single-chain Fv (scFv) fragment comprises heavy and light chain variable regions connected by a flexible linker to form a single polypeptide chain which forms an antigen-binding region. Exemplary single chain antibodies are discussed in detail, e.g., in WO 88/01649 and U.S. Pat. Nos. 4,946,778 and 5,260,203.

A bivalent antibody is typically understood to have two identical antigen binding sites. However, a "bispecific" or "multispecific" or "bifunctional" or "multifunctional" antibody, in certain embodiments, is an artificial hybrid antibody having two different heavy/light chain pairs and two different antigen binding sites. Bispecific antibodies may be produced by a variety of methods including, but not limited to, fusion of hybridomas or linking of Fab' fragments. See, e.g., Songsivilai & Lachmann Clin. Exp. Immunol 79: 315-321 (1990), Kostelny et al. J. Immunol. 148:1547-1553 (1992).

The term "heavy chain" includes any heavy chain polypeptide having sufficient variable region sequence to confer specificity for a RANKL. In certain embodiments, a heavy chain comprises the amino acid sequence of SEQ ID NO: 2. In certain embodiments, a heavy chain comprises a fragment of the amino acid sequence of SEQ ID NO: 2 that includes at least one complementarity determining region (CDR) of SEQ ID NO: 2. In certain embodiments, a heavy chain comprises a fragment of the amino acid sequence of SEQ ID NO: 2 that includes at least two complementarity determining regions (CDRs) of SEQ ID NO: 2. In certain embodiments, a heavy chain comprises a fragment of the amino acid sequence of SEQ ID NO: 2 that includes at least three complementarity determining regions (CDRs) of SEQ ID NO: 2. In certain embodiments, a heavy chain comprises a fragment of the amino acid sequence of SEQ ID NO: 2 that contains the heavy chain portion of an antigen binding site.

In certain embodiments, a heavy chain variable region comprises the amino acid sequence of SEQ ID NO: 11. In certain embodiments, a heavy chain comprises a fragment of the amino acid sequence of SEQ ID NO: 11 that includes at least one complementarity determining region (CDR) of SEQ ID NO: 11. In certain embodiments, a heavy chain comprises a fragment of the amino acid sequence of SEQ ID NO: 11 that includes at least two complementarity determining regions (CDRs) of SEQ ID NO: 11. In certain embodiments, a heavy chain comprises a fragment of the amino acid sequence of SEQ ID NO: 11 that includes at least three complementarity determining regions (CDRs) of SEQ ID NO: 11. In certain embodiments, a heavy chain comprises a fragment of the amino acid sequence of SEQ ID NO: 11 that contains the heavy chain portion of an antigen binding site.

The term "light chain" includes any light chain polypeptide having sufficient variable region sequence to confer specificity for a RANKL. In certain embodiments, a light chain comprises the amino acid sequence of SEQ ID NO: 4. In certain embodiments, a light chain comprises a fragment of the amino acid sequence of SEQ ID NO: 4 that includes at least one complementarity determining region (CDR) of SEQ ID NO: 4. In certain embodiments, a light chain comprises a fragment of the amino acid sequence of SEQ ID NO: 4 that includes at least two complementarity determining regions (CDRs) of SEQ ID NO: 4. In certain embodiments, a light chain comprises a fragment of the amino acid sequence of SEQ ID NO: 4 that includes at least three complementarity determining regions (CDRs) of SEQ ID NO: 4. In certain embodiments, a light chain comprises a fragment of the amino acid sequence of SEQ ID NO: 4 that contains the light chain portion of an antigen binding site.

In certain embodiments, a light chain variable region comprises the amino acid sequence of SEQ ID NO: 12. In certain embodiments, a light chain comprises a fragment of the amino acid sequence of SEQ ID NO: 12 that includes at least one complementarity determining region (CDR) of SEQ ID NO: 12. In certain embodiments, a light chain comprises a fragment of the amino acid sequence of SEQ ID NO: 12 that includes at least two complementarity determining regions (CDRs) of SEQ ID NO: 12. In certain embodiments, a light chain comprises a fragment of the amino acid sequence of SEQ ID NO: 12 that includes at least three complementarity determining regions (CDRs) of SEQ ID NO: 12. In certain embodiments, a light chain comprises a fragment of the amino acid sequence of SEQ ID NO: 12 that contains the light chain portion of an antigen binding site.

An antibody substantially inhibits binding of RANKL to RANK when an excess of antibody reduces the quantity of RANKL bound to RANK by at least about 20%, 40%, 60%, 75%, 80%, 85%, 90%, 95%, or more (as measured by an in vitro competitive binding assay known in the art).

The term "epitope" refers to a polypeptide determinant capable of specific binding to an antibody. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of polypeptides and/or macromolecules. In certain embodiments, an antibody is said to specifically bind an antigen when the dissociation constant is ≤1 µM, in certain embodiments, when the dissociation constant is ≤100 nM, and in certain embodiments, when the dissociation constant is ≤10 nM.

The term "polynucleotide" refers to a polymeric form of nucleotides of at least 3 bases in length. In certain embodiments, a polynucleotide comprises deoxyribonucleotides. In certain embodiments, a polynucleotide comprises ribonucleotides. In certain embodiments, a polynucleotide comprises one or more deoxyribonucleotides and one or more ribonucleotides. In certain embodiments, a polynucleotide comprises one or more modified deoxyribonucleotides and/or modified ribonucleotides. The term "polynucleotide" includes single and double stranded forms of nucleic acids. In certain embodiments, a polynucleotide comprises at least one label for detection.

The term "isolated polynucleotide" refers to a polynucleotide of genomic, cDNA, or synthetic origin or some combination thereof. An "isolated polynucleotide" is either (1) not associated with all or a portion of a polynucleotide in which the "isolated polynucleotide" is found in nature, (2) is linked to a polynucleotide which it is not linked to in nature, or (3) does not occur in nature as part of a larger sequence.

Unless specified otherwise, the left-hand end of single-stranded polynucleotide sequences is the 5' end. Unless specified otherwise, the right-hand end of single-stranded polynucleotide sequences is the 3' end. Unless specified otherwise, the left-hand direction of double-stranded polynucleotide sequences is referred to as the 5' direction. Unless specified otherwise, the right-hand direction of double-stranded polynucleotide sequences is referred to as the 3' direction. The direction of 5' to 3' addition of nascent RNA transcripts is referred to as the transcription direction. In certain embodiments, "upstream sequences" on a DNA strand refer to sequences that are 5' of the polypeptide-encoding region of the DNA strand. In certain embodiments, "downstream sequences" on a DNA strand refer to sequences that are 3' of the polypeptide-encoding region of the DNA strand.

In certain embodiments, a polynucleotide comprises one or more naturally occurring nucleotides. In certain embodiments, a polynucleotide comprises one or more non-naturally occurring nucleotides. In certain embodiments, a polynucleotide comprises one or more naturally occurring nucleotides and one or more non-naturally occurring nucleotides.

The term "naturally occurring nucleotides" refers to nucleotides that can be found free and/or in polynucleotides in nature. Naturally occurring nucleotides include, but are not limited to, deoxyribonucleotides and ribonucleotides. Deoxyribonucleotides include, but are not limited to, adenosine, guanine, cytosine, and thymidine. Ribonucleotides include, but are not limited to, adenosine, cytosine, thymidine, and uricil. The term "non-naturally occurring nucleotides" or "modified nucleotides" refers to nucleotides that are not found free or in polynucleotides in nature. Non-naturally occurring nucleotides and modified nucleotides include, but are not limited to, nucleotides with modified or substituted sugar groups and nucleotides with modified or substitute nucleotide base groups.

The terms "polynucleotide linkage" and "oligonucleotide linkage" are used interchangeably and refer to a chemical moiety that links a first nucleotide to a second nucleotide. Polynucleotide linkages include, but are not limited to, phosphorothioate, phosphorodithioate, phosphoroselenoate, phosphorodiselenoate, phosphoroanilothioate, phoshoraniladate, and phosphoroamidate. See, e.g., LaPlanche et al. Nucl. Acids Res. 14:9081 (1986); Stec et al. J. Am. Chem. Soc. 106:6077 (1984); Stein et al. Nucl. Acids Res. 16:3209 (1988); Zon et al. Anti-Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990).

In certain embodiments, a polynucleotide is produced synthetically. In certain embodiments, a polynucleotide is produced enzymatically. Such enzymatic production of polynucleotides may occur in vivo, such as, for example, in a cell; or may occur in vitro, such as, for example, in a polymerase chain reaction (PCR). Exemplary methods of producing polynucleotides synthetically and enzymatically are known in the art. Exemplary methods of linking two or more polynucleotides chemically or enzymatically (e.g., using a ligase) are also know in the art.

In certain embodiments, polynucleotides of the present invention may be mutated in such a way that the sequence of the encoded polypeptide is not changed. As a non-limiting example, the polynucleotide sequence may be changed to codons more compatible with the chosen host cell. For certain bacterial, mammalian, and insect host cells, in certain embodiments, optimized codons are known in the art. Additionally, as a non-limiting example, codons may be substituted to eliminate restriction sites or to include silent restriction sites, which may aid in stability, expression, or processing of the polynucleotide in the selected host cell.

The term "agent" refers to a chemical compound, a mixture of chemical compounds, a biological molecule, or an extract made from biological materials.

As used herein, the term "label" refers to any molecule that can be detected. In certain embodiments, a polypeptide may be labeled by incorporation of a radiolabeled amino acid. In certain embodiments, biotin moieties that can be detected by marked avidin or streptavidin (e.g., streptavidin containing a fluorescent marker or enzymatic activity that can be detected by optical or colorimetric methods) may be attached to the polypeptide. In certain embodiments, a label may be incorporated into or attached to another reagent which in turn binds to the polypeptide of interest. For example, a label may be incorporated into or attached to an antibody that in turn specifically binds the polypeptide of interest. In certain embodiments, the label or marker can also be therapeutic. Various methods of labeling polypeptides and glycoproteins are known in the art and may be used. Certain general classes of labels include, but are not limited to, enzymatic, fluorescent, chemiluminescent, and radioactive labels. Examples of labels for polypeptides include, but are not limited to, the following: radioisotopes or radionucleotides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., fluorescein isothiocyanate (FITC), rhodamine, lanthanide phosphors, phycoerythrin (PE)), enzymatic labels (e.g., horseradish peroxidase, β-galactosidase, luciferase, alkaline phosphatase, glucose oxidase, glucose-6-phosphate dehydrogenase, alcohol dehydrogenase, malate dehydrogenase, penicillinase, luciferase), chemiluminescent, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

As used herein, the term "vehicle" refers to a molecule that has one or more properties selected from: reduces degradation of another molecule; increases the half-life of another molecule; reduces toxicity of another molecule; reduces immunogenicity of another molecule; and increases the biological activity of another molecule. Exemplary vehicles include, but are not limited to, an Fc domain, a linear polymer (including, but not limited to, polyethylene glycol (PEG), polylysine, and dextran), a branched-chain polymer (see, for example, U.S. Pat. Nos. 4,289,872; 5,229,490; and PCT Publication No. WO 93/21259), a lipid, a cholesterol group (such as a steroid), a carbohydrate or oligosaccharide, human serum albumin (HSA) and related molecules, transtheratin (TTR) and related molecules, and any natural or synthetic protein, polypeptide or peptide that binds to a salvage receptor. Certain exemplary vehicles are known in the art and/or are discussed herein.

The term "biological sample" includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "osteopenic disorder" refers to a condition which is characterized at least in part by an increase in bone resorption and/or a loss of bone mass or bone density. The term "osteopenic disorder" includes, but is not limited to, osteoporosis, osteopenia, Paget's disease, osteomyelitis, hypercalcemia, osteonecrosis, hyperparathyroidism, lytic bone metastases, periodontitis, rheumatoid arthritis, cachexia and anorexia, alopecia, and bone loss due to immobilization. The term "osteopenic disorder" also includes, but is not limited to, cancers that increase osteoclast activity, induce bone resorption, and/or result in a loss of bone mass or bone density, including, but not limited to, breast, prostate, and multiple myeloma, including certain cancers known to produce factors that result in over-expression of RANKL in the bone, and certain cancers that lead to increased osteoclast numbers and activity. The term "osteopenic disorder" also includes inflammatory or auto-immune disorders which are characterized at least in part by an increase in bone resorption and/or a loss of bone mass or bone density and includes, but is not limited to, rheumatoid arthritis, psoriatic arthritis, psoriasis, and inflammatory bowel disease.

The terms "pharmaceutical agent," "drug," or "therapeutic agent" as used herein refer to a chemical compound or composition capable of inducing a desired therapeutic effect when properly administered to a patient.

The term "modulator" refers to a compound that changes or alters the activity or function of a molecule. For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Certain exemplary activities and functions of a molecule include, but are not limited to, binding affinity, enzymatic activity, and signal transduction. Certain exemplary inhibitors include, but are not limited to, polypeptides, peptides, antibodies, peptibodies, carbohydrates and small organic molecules. Peptibodies are described, e.g., in WO01/83525.

As used herein, "substantially pure" means an object species is the predominant species present (i.e., on a molar basis it is more abundant than any other individual species in the composition). In certain embodiments, a substantially purified fraction is a composition wherein the object species comprises at least about 50 percent (on a molar basis) of all macromolecular species present. In certain embodiments, a substantially pure composition will comprise more than about 75%, 80%, 85%, 90%, 95%, or 99% of all macromolecular species present in the composition. In certain embodiments, the object species is purified to essential homogeneity (contaminant species cannot be detected in the composition by conventional detection methods) wherein the composition consists essentially of a single macromolecular species.

The term "patient" includes human and non-human subjects. In certain embodiments, a patient is a human or non-human subject that has low bone mass and/or is at risk for developing low bone mass and/or is experiencing one or more medical conditions that may increase the risk of loss of bone mass (e.g., cancer, an inflammatory disorder, an autoimmune disease). In certain embodiments, a patient with low bone mass will have a T-score of less than −1. A T-score is a measure of a patient's bone mineral density (BMD) in terms of standard deviations (SD) from the healthy young adult mean. Thus, in certain embodiments, a patient with low bone mass has a BMD that is more than 1 SD below the mean. In certain embodiments, a patient is a human or non-human subject that has weakened or structurally compromised bone, and/or that is at risk for developing weakened or structurally compromised bone. In certain embodiments, a patient is a human or non-human subject that has suffered a fracture and/or is identified as being at greater than normal risk for fractures

DETAILED DESCRIPTION OF CERTAIN EMBODIMENTS

RANKL Antibodies

Certain antibodies to receptor activator of NF-κB ligand (RANKL; also called osteoprotegerin ligand, or OPGL) are described, e.g., in U.S. Patent Publication No. U.S. 2004/0033535 A1 and in PCT Publication No. WO 2003/002713 A3.

In certain embodiments, fully human monoclonal antibodies against human RANKL are provided. In certain embodiments, polynucleotide sequences encoding heavy and/or light chain immunoglobulin molecules, particularly sequences encoding the heavy and/or light chain variable regions, are provided. In certain embodiments, polynucleotide sequences encoding one or more heavy and/or light chain complementarity determining regions (CDR's), particularly from CDR1 through CDR3, are provided. In certain embodiments, polypeptide sequences corresponding to heavy and/or light chain immunoglobulin molecules, particularly polypeptide sequences corresponding to the heavy and/or light chain variable regions, are provided. In certain embodiments, polypeptide sequences corresponding to one or more heavy and/or light chain complementarity determining regions (CDR's), particularly from CDR1 through CDR3, are provided. According to certain embodiments, a hybridoma cell line expressing a fully human monoclonal antibody against human RANKL is also provided. In certain embodiments, a purified fully human monoclonal antibody against human RANKL is provided.

In certain embodiments, an antibody comprises one or more constant regions from species other than human and one or more human variable regions. In certain embodiments, an antibody comprises one or more human complementarity determining regions (CDRs) and one or more framework regions and/or constant regions from species other than human. Such antibodies are referred to as "chimeric" antibodies. In certain embodiments, a RANKL antibody is a chimeric antibody. In certain embodiments, a RANKL antibody is a Fab fragment, a Fab' fragment, a F(ab')$_2$ fragment, an Fv fragment, or a single-chain Fv fragment.

Preparation of RANKL Antibodies

According to certain embodiments, antibodies that specifically bind RANKL are provided. In certain embodiments, antibodies may be produced by immunization with full-length RANKL, soluble forms of RANKL, or a fragment thereof. In certain embodiments, antibodies may be polyclonal or monoclonal, and/or may be recombinant antibodies. In certain embodiments, antibodies are human antibodies prepared, for example, by immunization of transgenic animals capable of producing human antibodies (see, for example, PCT Published Application No. WO 93/12227.).

In certain embodiments, the complementarity determining regions (CDRs) of the light and/or heavy chain variable regions of a RANKL antibody may be grafted to framework regions (FRs) from the same, or another, species. In certain embodiments, the CDRs of the light and/or heavy chain variable regions of a RANKL antibody may be grafted to consensus human FRs. To create consensus human FRs, in certain embodiments, FRs from several human heavy chain or light chain amino acid sequences are aligned to identify a consensus amino acid sequence. In certain embodiments, the FRs of a RANKL antibody heavy chain and/or light chain are replaced with the FRs from a different heavy chain and/or light chain. In certain embodiments, rare amino acids in the FRs of the heavy and light chains of a RANKL antibody are not replaced, while the rest of the FR amino acids are replaced. Rare amino acids are specific amino acids that are in positions in which they are not usually found in FRs. In certain embodiments, the grafted variable regions from a RANKL antibody may be used with a constant region that is different from the constant region of the RANKL antibody. In certain embodiments, the grafted variable regions are part of a single chain Fv antibody. Exemplary CDR grafting is described, e.g., in U.S. Pat. Nos. 6,180,370, 5,693,762, 5,693,761, 5,585,089, and 5,530,101.

According to certain embodiments, a RANKL antibody is prepared through the utilization of a transgenic mouse that has a substantial portion of the human antibody producing genome inserted but that is rendered deficient in the production of endogenous, murine, antibodies. Such mice, then, are capable of producing human immunoglobulin molecules and antibodies and are deficient in the production of murine immunoglobulin molecules and antibodies. Certain exemplary technologies utilized for achieving this result are disclosed in patents, applications, and documents disclosed in the specification, herein. In certain embodiments, one may employ methods such as those disclosed in PCT Published Application No. WO 98/24893. See also Mendez et al. Nature Genetics 15:146-156 (1997).

According to certain embodiments, fully human monoclonal RANKL antibodies are produced as follows. Transgenic mice containing human immunoglobulin genes are immunized with the antigen of interest (in this case, RANKL or a portion thereof). Lymphatic cells (such as B-cells) from the mice that express antibodies are obtained. Such recovered cells are fused with a myeloid-type cell line to prepare immortal hybridoma cell lines, and such hybridoma cell lines are screened and selected to identify hybridoma cell lines that produce antibodies specific to the antigen of interest. In certain embodiments, the production of a hybridoma cell line that produces RANKL antibodies is provided.

Exemplary RANKL antibodies are produced by certain hybridoma lines, including but not limited to, AMG 6.1, AMG 6.4, AMG 6.5, AMG 7.1, and AMG 7.2, which are described, e.g., in U.S. Patent Publication No. U.S. 2004/0033535 A1 and in PCT Publication No. WO 2003/002713 A3. In certain embodiments, RANKL antibodies are produced by at least one hybridoma line selected from AMG 6.1, AMG 6.4, and AMG 6.5. In certain embodiments, RANKL antibodies bind to RANKL with a dissociation constant (Kd) of between approximately 0.23 and 0.29 nM, including all points between those endpoints. In certain embodiments, RANKL antibodies bind to RANKL with a Kd of less than 0.23 nM.

In certain embodiments, a RANKL antibody is of the IgG2 isotype. In certain embodiments, a RANKL antibody comprises a human kappa light chain and a human IgG2 heavy chain. In certain embodiments, a RANKL antibody has been cloned for expression in mammalian cells. In certain embodiments, a variable region of a RANKL antibody is ligated to a constant region other than the constant region for the IgG2 isotype. Certain exemplary methods of cloning antibody sequences are known in the art. Certain exemplary methods of cloning a RANKL antibody are described, e.g., in U.S. Patent Publication No. U.S. 2004/0033535 A1 and in PCT Publication No. WO 2003/002713 A3.

In certain embodiments, a RANKL antibody is αRANKL-1 (also called αOPGL-1; see, e.g., U.S. Patent Publication No. U.S. 2004/0033535 A1 and PCT Publication No. WO 2003/002713 A3). The heavy chain of αRANKL-1 has the amino acid sequence shown in FIG. 2 (SEQ ID NO: 2) and can be encoded by the nucleotide sequence of FIG. 1 (SEQ ID NO: 1). The heavy chain variable region of αRANKL-1 has the amino acid sequence shown in FIG. 28 (SEQ ID NO: 11). The light chain of αRANKL-1 has the amino acid sequence shown in FIG. 4 (SEQ ID NO: 4) and can be encoded by the nucleotide sequence of FIG. 3 (SEQ ID NO: 3). The light chain variable region of αRANKL-1 has the amino acid sequence shown in FIG. 29 (SEQ ID NO: 12).

In certain embodiments, one or more conservative modifications to the heavy and light chains of αRANKL-1 (and corresponding modifications to the encoding nucleotides) will produce RANKL antibodies having functional and chemical characteristics similar to those of αRANKL-1. In certain embodiments, if alteration of the functional and/or chemical characteristics of αRANKL-1 is desired, non-conservative substitutions can be made in the heavy and/or light chain sequence. In certain embodiments, such non-conservative substitutions can be made by selecting, e.g., one or more replacement amino acids that differ from the replaced amino acids in their effect on maintaining (a) the structure of the peptide backbone in the area of the substitution, for example, as a sheet or helical conformation, (b) the charge or hydrophobicity of the molecule at the substitution site, and/or (c) the size of the molecule at the substitution site.

In certain embodiments, desired amino acid substitutions (whether conservative or non-conservative) can be determined by those skilled in the art at the time such substitutions are desired. In certain embodiments, amino acid substitutions can be used to identify important residues of αRANKL-1. In certain embodiments, amino acid substitutions can be used to increase or decrease the affinity of the RANKL antibodies.

In certain embodiments, antibodies are expressed in cell lines other than hybridoma cell lines. In certain embodiments, sequences encoding particular antibodies can be used for transformation of a suitable mammalian host cell. According to certain embodiments, transformation can be by any known method for introducing polynucleotides into a host cell. Exemplary transformation includes, but is not limited to, packaging the polynucleotide in a virus (or into a viral vector) and transducing a host cell with the virus (or vector); and transfection procedures known in the art, as exemplified, e.g., in U.S. Pat. Nos. 4,399,216; 4,912,040; 4,740,461; and 4,959,455. In certain embodiments, the transformation procedure used depends upon the host to be transformed. Certain exemplary methods for introduction of heterologous polynucleotides into mammalian cells are known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Certain exemplary mammalian cell lines available as hosts for expression are known in the art and include, but are not limited to, many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected by determining which cell lines show high expression levels and produce antibodies with acceptable RANKL binding properties.

PTH/PTHrP Peptides

A PTH/PTHrP peptide comprises a PTH/PTHrP modulating domain. In certain embodiments, a PTH/PTHrP peptide comprises a PTH/PTHrP modulating domain and a prepro domain. In certain embodiments, a PTH/PTHrP peptide comprises a PTH/PTHrP modulating domain and a portion of a prepro domain.

In certain embodiments, a PTH/PTHrP modulating domain is able to interact with a PTH-1 receptor. In certain embodiments, a PTH/PTHrP modulating domain is able to interact with a PTH-2 receptor. In certain embodiments, a PTH/PTHrP modulating domain is able to interact with both a PTH-1 receptor and a PTH-2 receptor. Certain exemplary PTH/PTHrP modulating domains are described, e.g., in U.S. Patent Publication No. 2003/0039654 and in PCT Publication No. WO 01/81415. Certain exemplary PTH and PTHrP modulating domains are shown in Tables 1A, 1B, and 2. In certain embodiments, a PTH/PTHrP peptide comprises a PTH/PTHrP modulating domain and does not comprise a functional prepro domain.

In certain embodiments, when a PTH/PTHrP peptide comprising a prepro domain is expressed in a cell, the prepro domain is cleaved from the PTH/PTHrP peptide during processing to form a mature PTH/PTHrP peptide. In certain embodiments, when a PTH/PTHrP peptide comprising a portion of a prepro domain is expressed in a cell, the portion of a prepro domain is cleaved from the PTH/PTHrP peptide during processing to form a mature PTH/PTHrP peptide. In certain embodiments, a portion of the prepro domain is cleaved from the PTH/PTHrP peptide during processing, to form a pro PTH/PTHrP peptide intermediate. In certain embodiments, the pro PTH/PTHrP peptide intermediate is further processed to form a mature PTH/PTHrP peptide.

In certain embodiments, additional exemplary PTH/PTHrP peptides may be created by randomizing a reference PTH/PTHrP peptide and selecting for PTH/PTHrP peptides having desired activity. Certain information about PTH and PTHrP can found, e.g., in Mannstadt et al. (1999), *Am. J. Physiol.* 277. 5Pt 2: F665-75; and Gardella (1996), *J. Biol. Chem.* 271 (33): 19888-93.

In various embodiments, a RANKL antibody-PTH/PTHrP chimeric molecule may comprise one or more of the following PTH/PTHrP peptides linked to one or more RANKL antibodies. In various embodiments, a RANKL antibody-PTH/PTHrP chimeric molecule may comprise any other peptides having PTH and/or PTHrP activity linked to one or more RANKL antibodies. In certain embodiments, a PTH/PTHrP peptide may comprise part of the sequence of a naturally occurring PTH or PTHrP. In certain embodiments, a peptide may comprise one or more randomized sequences. In certain embodiments, a PTH/PTHrP peptide having a desired activity may be selected from a pool of peptides having one or more randomized sequences using phage display and/or RNA-peptide screening. In certain embodiments, one skilled in the art can carry out phage display and/or RNA-peptide screening to select a peptide having a desired activity.

Certain Exemplary PTH/PTHrP Modulating Domains

Certain exemplary PTH/PTHrP modulating domains are selected from polypeptides of formula I:

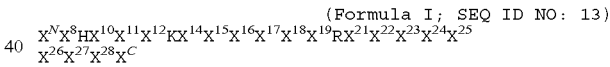
(Formula I; SEQ ID NO: 13)
$X^N X^8 H X^{10} X^{11} X^{12} K X^{14} X^{15} X^{16} X^{17} X^{18} X^{19} R X^{21} X^{22} X^{23} X^{24} X^{25} X^{26} X^{27} X^{28} X^C$ wherein:

$X^N$ is absent or is $X^3 X^4 X^5 X^6 X^7$, $X^2 X^3 X^4 X^5 X^6 X^7$, $YX^2 X^3 X^4 X^5 X^6 X^7$, or $YX^1 X^2 X^3 X^4 X^5 X^6 X^7$;

$X^1$ is an amino acid residue. In certain embodiments, $X^1$ is a nonfunctional residue, a hydrophilic residue, or an aromatic residue. In certain embodiments, $X^1$ is A, S or Y;

$X^2$ is an amino acid residue. In certain embodiments, $X^2$ is a nonfunctional residue. In certain embodiments, $X^2$ is V;

$X^3$ is an amino acid residue. In certain embodiments, $X^3$ is a hydrophilic residue. In certain embodiments, $X^3$ is S;

$X^4$ is an amino acid residue. In certain embodiments, $X^4$ is an acidic residue. In certain embodiments, $X^4$ is E;

$X^5$ is an amino acid residue. In certain embodiments, $X^5$ is a nonfunctional residue or a basic residue. In certain embodiments, $X^5$ is H or I;

$X^6$ is an amino acid residue. In certain embodiments, $X^6$ is an acidic residue or a hydrophilic residue. In certain embodiments, $X^6$ is Q or E;

$X^7$ is an amino acid residue. In certain embodiments, $X^7$ is a nonfunctional residue or an aromatic residue. In certain embodiments, $X^7$ is L or F;

$X^8$ is an amino acid residue. In certain embodiments, $X^8$ is a nonfunctional residue. In certain embodiments, $X^8$ is M or Nle;

$X^{10}$ is an amino acid residue. In certain embodiments, $X^{10}$ is an acidic residue or a hydrophilic residue. In certain embodiments, $X^{10}$ is N or D;

$X^{11}$ is an amino acid residue. In certain embodiments, $X^{11}$ is a nonfunctional residue or a basic residue. In certain embodiments, $X^{11}$ is L, R, or K;

$X^{12}$ is an amino acid residue. In certain embodiments, $X^{12}$ is a nonfunctional residue or an aromatic residue. In certain embodiments, $X^{12}$ is G, F, or W;

$X^{14}$ is an amino acid residue. In certain embodiments, $X^{14}$ is a basic residue or a hydrophilic residue. In certain embodiments, $X^{14}$ is H or S;

$X^{15}$ is an amino acid residue. In certain embodiments, $X^{15}$ is a nonfunctional residue. In certain embodiments, $X^{15}$ is L or I;

$X^{16}$ is an amino acid residue. In certain embodiments, $X^{16}$ is a nonfunctional residue or a hydrophilic residue. In certain embodiments, $X^{16}$ is Q, N, S, or A;

$X^{17}$ is an amino acid residue. In certain embodiments, $X^{17}$ is an acidic residue, a hydrophilic residue or a nonfunctional residue. In certain embodiments, $X^{17}$ is S, D, or L;

$X^{18}$ is an amino acid residue. In certain embodiments, $X^{18}$ is a nonfunctional residue. In certain embodiments, $X^{18}$ is M, L, V or Nle;

$X^{19}$ is an amino acid residue. In certain embodiments, $X^{19}$ is an acidic residue or a basic residue. In certain embodiments, $X^{19}$ is E or R;

$X^{21}$ is an amino acid residue. In certain embodiments, $X^{21}$ is a nonfunctional residue or basic residue. In certain embodiments, $X^{21}$ is V, M, R, or Nle;

$X^{22}$ is an amino acid residue. In certain embodiments, $X^{22}$ is a hydrophilic residue, an acidic residue, or an aromatic residue. In certain embodiments, $X^{22}$ is E or F;

$X^{23}$ is an amino acid residue. In certain embodiments, $X^{23}$ is an aromatic residue or lipophilic residue. In certain embodiments, $X^{23}$ is W or F;

$X^{24}$ is an amino acid residue. In certain embodiments, $X^{24}$ is a lipophilic residue. In certain embodiments, $X^{24}$ is L;

$X^{25}$ is an amino acid residue. In certain embodiments, $X^{25}$ is a hydrophilic residue or a basic residue. In certain embodiments, $X^{25}$ is R or H;

$X^{26}$ is an amino acid residue. In certain embodiments, $X^{26}$ is a hydrophilic residue or a basic residue. In certain embodiments, $X^{26}$ is K or H;

$X^{27}$ is an amino acid residue. In certain embodiments, $X^{27}$ is a lipophilic residue, a basic residue, or a nonfunctional residue. In certain embodiments, $X^{27}$ is K or L;

$X^{28}$ is an amino acid residue. In certain embodiments, $X^{28}$ is a lipophilic residue or a nonfunctional residue. In certain embodiments, $X^{28}$ is L or I;

$X^C$ is an amino acid residue. In certain embodiments, $X^C$ is absent. In certain embodiments, $X^C$ is $X^{29}$, $X^{29}X^{30}$, $X^{29}X^{30}X^{31}$, $X^{29}X^{30}X^{31}X^{32}$, $X^{29}X^{30}X^{31}X^{32}X^{33}$, $X^{29}X^{30}X^{31}X^{32}X^{33}X^{34}$, $X^{29}X^{30}X^{31}X^{32}X^{33}X^{34}X^{35}$, or $X^{29}X^{30}X^{31}X^{32}X^{33}X^{34}X^{35}X^{36}$;

$X^{29}$ is an amino acid residue. In certain embodiments, $X^{29}$ is a hydrophilic residue or a nonfunctional residue. In certain embodiments, $X^{29}$ is Q or A;

$X^{30}$ is an amino acid residue. In certain embodiments, $X^{30}$ is a hydrophilic residue or an acidic residue. In certain embodiments, $X^{30}$ is D or E;

$X^{31}$ is an amino acid residue. In certain embodiments, $X^{31}$ is a lipophilic residue or a nonfunctional residue. In certain embodiments, $X^{31}$ is V or I;

$X^{32}$ is an amino acid residue. In certain embodiments, $X^{32}$ is a basic residue. In certain embodiments, $X^{32}$ is H;

$X^{33}$ is an amino acid residue. In certain embodiments, $X^{33}$ is a hydrophilic residue. In certain embodiments, $X^{33}$ is N or T;

$X^{34}$ is an amino acid residue. In certain embodiments, $X^{34}$ is a nonfunctional residue or an aromatic residue. In certain embodiments, $X^{34}$ is A, F or Y;

$X^{35}$ is an amino acid residue. In certain embodiments, $X^{35}$ is an acidic residue. In certain embodiments, $X^{35}$ is E;

$X^{36}$ is an amino acid residue. In certain embodiments, $X^{36}$ is an aromatic residue. In certain embodiments, $X^{36}$ is Y;

In certain embodiments, one or more of $X^{14}$ through $X^{36}$ is a cysteine residue.

Certain exemplary PTH/PTHrP modulating domains selected from polypeptides of formula I (SEQ ID NO: 13) are shown in Tables 1A and 1B.

Certain exemplary PTH/PTHrP modulating domains are selected from polypeptides of formula II:

$$J^N J^7 J^8 HNL J^{12} KHL J^{16} SJ^{18} J^{19} RJ^{21} EWLRKKLJ^C \quad \text{(Formula II; SEQ ID NO: 14)}$$

wherein:

In certain embodiments, $J^N$ is absent. In certain embodiments, $J^N$ is $J^1J^2J^3J^4J^5J^6$, $J^2J^3J^4J^5J^6$, $J^3J^4J^5J^6$;

$J^1$ is an amino acid residue. In certain embodiments, $J^1$ is a nonfunctional residue, a hydrophilic residue, or an aromatic residue. In certain embodiments, $J^1$ is A, S or Y;

$J^2$ is an amino acid residue. In certain embodiments, $J^2$ is a nonfunctional residue. In certain embodiments, $J^2$ is V;

$J^3$ is an amino acid residue. In certain embodiments, $J^3$ is a hydrophilic residue. In certain embodiments, $J^3$ is S;

$J^4$ is an amino acid residue. In certain embodiments, $J^4$ is an acidic residue. In certain embodiments, $J^4$ is E;

$J^5$ is an amino acid residue. In certain embodiments, $J^5$ is a nonfunctional residue. In certain embodiments, $J^5$ is I;

$J^6$ is an amino acid residue. In certain embodiments, $J^6$ is a basic residue. In certain embodiments, $J^6$ is Q;

$J^7$ is an amino acid residue. In certain embodiments, $J^7$ is a nonfunctional residue or an aromatic residue. In certain embodiments, $J^7$ is L or F;

$J^8$ is an amino acid residue. In certain embodiments, $J^8$ is a nonfunctional residue. In certain embodiments, $J^8$ is M or Nle;

$J^{12}$ is an amino acid residue. In certain embodiments, $J^{12}$ is a nonfunctional residue or an aromatic residue. In certain embodiments, $J^{12}$ is G or W;

$J^{16}$ is an amino acid residue. In certain embodiments, $J^{16}$ is a nonfunctional residue or a hydrophilic residue. In certain embodiments, $J^{16}$ is N, S, or A;

$J^{18}$ is an amino acid residue. In certain embodiments, $J^{18}$ is a nonfunctional residue. In certain embodiments, $J^{18}$ is M, Nle, L, or V;

$J^{19}$ is an amino acid residue. In certain embodiments, $J^{19}$ is an acidic residue or a basic residue. In certain embodiments, $J^{19}$ is E or R;

$J^{21}$ is an amino acid residue. In certain embodiments, $J^{21}$ is a nonfunctional residue. In certain embodiments, $J^{21}$ is V, M, or Nle;

In certain embodiments, $J^C$ is absent. In certain embodiments, $J^C$ is $J^{29}$, $J^{29}J^{30}$, $J^{29}J^{30}J^{31}$, $J^{29}J^{30}J^{31}J^{32}$, $J^{29}J^{30}J^{31}J^{32}J^{33}$, or $J^{29}J^{30}J^{31}J^{32}J^{33}J^{34}$;

$J^{29}$ is an amino acid residue. In certain embodiments, $J^{29}$ is a hydrophilic residue or a nonfunctional residue. In certain embodiments, $J^{29}$ is Q or A;

$J^{30}$ is an amino acid residue. In certain embodiments, $J^{30}$ is a hydrophilic residue or an acidic residue. In certain embodiments, $J^{30}$ is D or E;

$J^{31}$ is an amino acid residue. In certain embodiments, $J^{31}$ is a lipophilic residue or a nonfunctional residue. In certain embodiments, $J^{31}$ is V or I;

$J^{32}$ is an amino acid residue. In certain embodiments, $J^{32}$ is a basic residue. In certain embodiments, $J^{32}$ is H;

$J^{33}$ is an amino acid residue. In certain embodiments, $J^{33}$ is an acidic residue. In certain embodiments, $J^{33}$ is N;

$J^{34}$ is an amino acid residue. In certain embodiments, $J^{34}$ is an aromatic residue. In certain embodiments, $J^{34}$ is F or Y;

In certain embodiments, one or more of $J^{14}$ through the C-terminal residue of a polypeptide of formula II is a cysteine residue.

Certain exemplary PTH/PTHrP modulating domains selected from polypeptides of formula II (SEQ ID NO: 14) are shown in Tables 1A and 1B below.

Certain exemplary PTH/PTHrP modulating domains are selected from polypeptides of formula III:

(Formula III; SEQ ID NO: 15)
$O^N LHO^{10}O^{11}O^{12}KSIO^{15}O^{16}LRRRFO^{23}LHHLIO^C$ wherein:

In certain embodiments, $O^N$ is absent. In certain embodiments, $O^N$ is $YO^1O^2O^3O^4O^5O^6O^7$, $O^1O^2O^3O^4O^5O^6O^7$, $O^2O^3O^4O^5O^6O^7$, $O^3O^4O^5O^6O^7$, $O^4O^5O^6O^7$, $O^5O^6O^7$, $O^6O^7$, or $O^7$;

$O^1$ is an amino acid residue. In certain embodiments, $O^1$ is a nonfunctional residue. In certain embodiments, $O^1$ is A;

$O_2$ is an amino acid residue. In certain embodiments, $O_2$ is a nonfunctional residue. In certain embodiments, $O_2$ is V;

$O_3$ is an amino acid residue. In certain embodiments, $O^3$ is a hydrophilic residue. In certain embodiments, $O^3$ is S;

$O_4$ is an amino acid residue. In certain embodiments, $O_4$ is an acidic residue. In certain embodiments, $O_4$ is E;

$O_5$ is an amino acid residue. In certain embodiments, $O_5$ is a basic residue or a nonfunctional residue. In certain embodiments, $O_5$ is H or I;

$O_6$ is an amino acid residue. In certain embodiments, $O^6$ is a hydrophilic residue. In certain embodiments, $O_6$ is Q;

$O_7$ is an amino acid residue. In certain embodiments, $O_7$ is a nonfunctional residue. In certain embodiments, $O_7$ is L;

$O_{10}$ is an amino acid residue. In certain embodiments, $O_{10}$ is an acidic residue or a hydrophilic residue. In certain embodiments, $O_{10}$ is N or D;

$O_{11}$ is an amino acid residue. In certain embodiments, $O_{11}$ is a basic residue or a nonfunctional residue. In certain embodiments, $O_{11}$ is K or L;

$O_{12}$ is an amino acid residue. In certain embodiments, $O_{12}$ is an aromatic residue or a nonfunctional residue. In certain embodiments, $O_{12}$ is G, F, or W;

$O_{15}$ is an amino acid residue. In certain embodiments, $O_{15}$ is a hydrophilic residue or a nonfunctional residue. In certain embodiments, $O_{15}$ is I or S;

$O_{16}$ is an amino acid residue. In certain embodiments, $O_{16}$ is a hydrophilic residue. In certain embodiments, $O_{16}$ is Q or N;

$O_{17}$ is an amino acid residue. In certain embodiments, $O_{17}$ is an acidic residue or a nonfunctional residue. In certain embodiments, $O_{17}$ is D or L;

$O_{23}$ is an amino acid residue. In certain embodiments, $O_{23}$ is an aromatic residue. In certain embodiments, $O_{23}$ is F or W;

In certain embodiments, $O^C$ is absent. In certain embodiments, $O^C$ is $O^{29}$, $O^{29}O^{30}$, $O^{29}O^{30}O^{31}$, $O^{29}O^{30}O^{31}O^{32}$, $O^{29}O^{30}O^{31}O^{32}O^{33}$, $O^{29}O^{30}O^{31}O^{32}O^{33}O^{34}$, $O^{29}O^{30}O^{31}O^{32}O^{33}O^{34}O^{35}$, or $O^{29}O^{30}O^{31}O^{32}O^{33}O^{34}O^{35}O^{36}$; wherein $O^{29}$ through $O^{36}$ are each independently selected amino acid residues;

In certain embodiments, one or more of $O^{14}$ through the C-terminal residue of a polypeptide of formula III is a cysteine residue.

Certain exemplary PTH/PTHrP modulating domains selected from polypeptides of formula III (SEQ ID NO: 15) are shown in Table 2 below.

Certain exemplary PTH/PTHrP modulating domain sequences are shown in Tables 1A, 1B and 2 below.

TABLE 1A

Exemplary PTH/PTHrP modulating domains based on naturally-occurring PTH polypeptides

| Description | Sequence | SEQ ID NO: |
|---|---|---|
| human PTH(1-84)[1] | SVSEIQLMHNLGKHLNSMERVEWLRKKLQDVHNFV ALGAPLAPRDAGSQRPRKKEDNVLVESHEKSLGEA DKADVNVLTKAKSQ | 16 |
| rat PTH(1-84)[2] | AVSEIQLMHNLGKHLASVERMQWLRKKLQDVHNFV SLGVQMAAREGSYQRPTKKEDNVLVDGNSKSLGEG DKADVDVLVKAKSQ | 17 |
| human PTH[3](7-84) | LMHNLGKHLNSMERVEWLRKKLQDVHNFVALGAPL APRDAGSQRPRKKEDNVLVESHEKSLGEADKADVN VLTKAKSQ | 18 |
| human PTH(1-44)[3] | SVSEIQLMHNLGKHLNSMERVEWLRKKLQDVHNFV ALGAPLAPR | 19 |
| human PTH(1-38)[3] | SVSEIQLMHNLGKHLNSMERVEWLRKKLQDVHNFV ALG | 20 |

TABLE 1A-continued

Exemplary PTH/PTHrP modulating domains based on naturally-occurring PTH polypeptides

| Description | Sequence | SEQ ID NO: |
|---|---|---|
| human PTH(2-38)[3] | VSEIQLMHNLGKHLNSMERVEWLRKKLQDVHNFVALG | 21 |
| human PTH(1-34)[4] | SVSEIQLMHNLGKHLNSMERVEWLRKKLQDVHNF | 22 |
| [Arg11]human PTH(1-34) | SVSEIQLMHNLGKHLNSMERVEWLRKKLQDVHNF | 23 |
| [Lys11] human PTH(1-34) | SVSEIQLMHNLGKHLNSMERVEWLRKKLQDVHNF | 24 |
| [Arg19] human PTH(1-34) | SVSEIQLMHNLGKHLNSMERVEWLRKKLQDVHNF | 25 |
| [Tyr1] human PTH (1-34)[3] | YVSEIQLMHNLGKHLNSMERVEWLRKKLQDVHNF | 26 |
| [Leu(8, 18), Tyr34] human PTH(1-34)[3] | SVSEIQLLHNLGKHLNSLERVEWLRKKLQDVHNY | 27 |
| bovine PTH(1-34)[5] | AVSEIQFMHNLGKHLSSMERVEWLRKKLQDVHNF | 28 |
| [Leu(8, 18), Tyr34] bovine PTH (1-34)[6] | AVSEIQFLHNLGKHLSSLERVEWLRKKLQDVHNY | 29 |
| porcine PTH (1-34)[3] | SVSEIQLMHNLGKHLSSLERVEWLRKKLQDVHNF | 30 |
| rat PTH (1-34)[3] | AVSEIQLMHNLGKHLASVERMQWLRKKLQDVHNF | 31 |
| [Leu (8, 21), Tyr34] rat PTH (1-34)[3] | AVSEIQLLHNLGKHLASVERLQWLRKKLQDVHNY | 32 |
| human PTH(1-31)[7] | SVSEIQLMHNLGKHLNSMERVEWLRKKLQDV | 33 |
| [Leu27] human PTH(1-31)[8] | SVSEIQLMHNLGKHLNSMERVEWLRKKLQDV | 34 |
| [Leu(8, 18) Tyr34] PTH (3-34)[9] | SEIQLLHNLGKHLNSLERVEWLRKKLQDVHNY | 35 |
| bovine PTH(3-34)[10] | SEIQFMHNLGKHLSSMERVEWLRKKLQDVHNF | 36 |
| [Leu(8, 18), Tyr34] bovine PTH(3-34)[11] | SEIQFLHNLGKHLSSLERVEWLRKKLQDVHNY | 37 |
| human PTH (7-34)[12] | LMHNLGKHLNSMERVEWLRKKLQDVHNF | 38 |
| [Leu(8, 18) Tyr34] human PTH(7-34)[9] | LLHNLGKHLNSLERVEWLRKKLQDVHNY | 39 |
| bovine PTH (7-34)[13] | FMHNLGKHLSSMERVEWLRKKLQDVHNF | 40 |
| [Tyr34] bovine PTH(7-34)[14] | FMHNLGKHLSSMERVEWLRKKLQDVHNY | 41 |
| [Leu(8, 18), Tyr34] bovine PTH(7-34)[15] | FLHNLGKHLSSLERVEWLRKKLQDVHNY | 42 |
| [Leu(8, 18), Trp12, Tyr34] bovine PTH(7-34)[16] | FLHNLWKHLSSLERVEWLRKKLQDVHNY | 43 |
| [D-Trp12, Tyr34] bovine PTH(7-34)[17] | FMHNL-D-Trp-KHLSSMERVEWLRKKLQDVHNY | 44 |
| human PTH (1-30) | SVSEIQLMHNLGKHLNSMERVEWLRKKLQD | 45 |
| [Arg11] human PTH(1-30) | SVSEIQLMHNRGKHLNSMERVEWLRKKLQD | 46 |

TABLE 1A-continued

Exemplary PTH/PTHrP modulating domains based on naturally-occurring PTH polypeptides

| Description | Sequence | SEQ ID NO: |
|---|---|---|
| [Lys11] human PTH(1-30) | SVSEIQLMHNKGKHLNSMERVEWLRKKLQD | 47 |
| [Arg19] human PTH(1-30) | SVSEIQLMHNLGKHLNSMRRVEWLRKKLQD | 48 |
| [Tyr1] human PTH(1-30) | YVSEIQLMHNLGKHLNSMERVEWLRKKLQD | 49 |
| [Leu(8, 18)] human PTH(1-30) | SVSEIQLLHNLGKHLNSLERVEWLRKKLQD | 50 |
| bovine PTH(1-30) | AVSEIQFMHNLGKHLSSMERVEWLRKKLQD | 51 |
| [Leu(8, 18)] bovine PTH (1-30) | AVSEIQFLHNLGKHLSSLERVEWLRKKLQD | 52 |
| porcine PTH(1-30) | SVSEIQLMHNLGKHLSSLERVEWLRKKLQD | 53 |
| rat PTH(1-30) | AVSEIQLMHNLGKHLASVERMQWLRKKLQD | 54 |
| [Leu(8, 21), Tyr34] rat PTH (1-30) | AVSEIQLLHNLGKHLASVERLQWLRKKLQD | 55 |
| [Leu27] human PTH(1-30) | SVSEIQLMHNLGKHLNSMERVEWLRKLLQD | 56 |
| human PTH(1-29) | SVSEIQLMHNLGKHLNSMERVEWLRKKLQ | 57 |
| human PTH(1-28) | SVSEIQLMHNLGKHLNSMERVEWLRKKL | 58 |
| [Leu(8, 18)] PTH(3-30) | SEIQLLHNLGKHLNSLERVEWLRKKLQD | 59 |
| bovine PTH (3-30) | SEIQFMHNLGKHLSSMERVEWLRKKLQD | 60 |
| [Leu(8, 18)] bovine PTH(3-30) | SEIQFLHNLGKHLSSLERVEWLRKKLQD | 61 |
| human PTH(7-30) | LMHNLGKHLNSMERVEWLRKKLQD | 62 |
| [Leu(8, 18)] human PTH(7-30) | LLHNLGKHLNSLERVEWLRKKLQD | 63 |
| bovine PTH (7-30) | FMHNLGKHLSSMERVEWLRKKLQD | 64 |
| [Leu(8, 18)] bovine PTH(7-30) | FLHNLGKHLSSLERVEWLRKKLQD | 65 |
| [Leu(8, 18), Trp12] bovine PTH(7-30) | FLHNLWKHLSSLERVEWLRKKLQD | 66 |
| [D-Trp12] bovine PTH(7-30) | FMHNL-D-Trp-KHLSSMERVEWLRKKLQD | 67 |

[1] Hendy et al. (1981), Proc. Natl. Acad. Sci USA 78: 7365; Kimura et al. (1983), Biochem. Biophys. Res. Commun. 114: 493; Zanelli et al. (1985), Endocrinology 117: 1962; Wingender et al. (1985), J. Biol. Chem. 264: 4367.
[2] Heinrich et al. (1984), J. Biol. Chem. 259: 3320.
[3] Bachem Catalogue (1999).
[4] Doppelt et al. (1981), Calcif. Tissue Int. 33: 649; Podbesek et al. (1983) Endocrinology 112: 1000; Kent et al. (1985), Clin. Sci. 68: 171; Mckee and Caulfield (1989), Peptide Res. 2: 161; Lee and Russell (1989); Biopolymers 28: 1115; Reeve et al. (1990), Br. Med. J. 301: 314; Neugebauer et al. (1994), Int. J. Peptide Protein Res. 43: 555.
[5] Nakamura et al. (1981); Proc. Soc. Exp. Biol. Med. 168: 168; Law et al. (1983), J. Clin. Endocrinol. Metab. 56: 1335; Wang et al. (1984), Eur. J. Pharmacol. 97, 209; Sham et al. (1986), Gen. Comp. Endocrinol. 61: 148; Smith et al. (1987), Arch. Biochem. Biophys. 253: 81.
[6] Based on Coltrera et al. (1981), J. Biol. Chem. 256: 10555; Bergeron et al. (1981), Endocrinology 109: 1552.
[7] Jouishomme et al. (1994), J. Bone Miner. Res. 9: 943; Whitfield and Morley; TIPS 16: 382.
[8] Barbier et al. (1997), J. Med. Chem. 40: 1373.
[9] Based on Schipani et al. (1993), Endocrinology 132: 2157-65.

TABLE 1A-continued

Exemplary PTH/PTHrP modulating domains based on naturally-occurring PTH polypeptides

[10]Scharla et al. (1991), Horm. Metab. Res. 23: 66-9; McGowan et al. (1983), Science 219: 67; Lowik et al. (1985), Cell Calcium 6: 311.
[11]Based on Jobert et al. (1997), Endocrinology 138: 5282; Schipani et al. (1993); Rosenblatt et al. (1977), J. Biol. Chem. 252: 5847; Segre et al. (1979), J. Biol. Chem. 254: 6980; Nussbaum et al. (1980), J. Biol. Chem. 225: 10183; Gray et al. (1980), Br. J. Pharmac. 76: 259.
[12]Nissenson et al. (1999), Endocrinology 140: 1294-1300.
[13]Jueppner et al. (1996), Endocrinology.
[14]Horiuchi et al. (1983), Science 220: 1053.
[15]Schipani et al. (1993); Holick et al. (1995), Bone 16: 140S (abstract 223, Conference, Melbourne, February 1995).
[16]Based on Dresner-Pollak et al. (1996), JBMR 11: 1061-5.
[17]Goldman et al. (1988), Endocrinology 123: 2597.

TABLE 1B

Exemplary PTH/PTHrP modulating domains based on Cys modifications of naturally-occurring PTH polypeptides

| Description | Sequence | SEQ ID NO: |
|---|---|---|
| Cys33 PTH(1-34) (Cys-33 insertion) | SVSEI QLMHN LGKHL NSMER VEWLR KKLQD VHCNF | 68 |
| Cys27, 33 PTH(1-34) (Cys-27 replacement, Cys-33 insertion) | SVSEI QLMHN LGKHL NSMER VEWLR KCLQD VHCNF | 69 |
| Cys-33 replacement | SVSEI QLMHN LGKHL NSMER VEWLR KKLQD VHCF | 70 |
| CGPTH 4 Cys-34 replacement | SVSEI QLMHN LGKHL NSMER VEWLR KKLQD VHNC | 71 |
| Cys14 PTH(1-34) | SVSEI QLMHN LGKCL NSMER VEWLR KKLQD VHNF | 72 |
| Cys15 PTH(1-34) | SMSEI QLMHN LGKHC NSMER VEWLR KKLQD VHNF | 73 |
| Cys16 PTH(1-34) | SVSEI QLMHN LGKHL CSMER VEWLR KKLQD VHNF | 74 |
| Cys17 PTH(1-34) | SVSEI QLMHN LGKHL NCMER VEWLR KKLQD VHNF | 75 |
| Cys18 PTH(1-34) | SVSEI QLMHN LGKHL NSCER VEWLR KKLQD VHNF | 76 |
| Cys19 PTH(1-34) | SVSEI QLMHN LGKHL NSMCR VEWLR KKLQD VHNF | 77 |
| Cys20PTH(1-34) | SVSEI QLMHN LGKHL NSMEC VEWLR KKLQD VHNF | 78 |
| Cys21PTH(1-34) | SVSEI QLMHN LGKHL NSMER CEWLR KKLQD VHNF | 79 |
| Cys22PTH(1-34) | SVSEI QLMHN LGKHL NSMER VCWLR KKLQD VHNF | 80 |
| Cys24PTH(1-34) | SVSEI QLMHN LGKHL NSMER VEWCR KKLQD VHNF | 81 |
| Cys25PTH(1-34) | SVSEI QLMHN LGKHL NSMER VEWLC KKLQD VHNF | 82 |
| Cys26PTH(1-34) | SVSEI QLMHN LGKHL NSMER VEWLR CKLQD VHNF | 83 |
| Cys27 PTH(1-34) | SVSEI QLMHN LGKHL MSMER VEWLR KCLQD VHNF | 84 |
| Cys28PTH(1-34) | SVSEI QLMHN LGKHL NSMER VEWLR KKCQD VHNF | 85 |
| Cys29PTH(1-34) | SVSEI QLMHN LGKHL NSMER VEWLR KKLCD VHNF | 86 |
| Cys30PTH(1-34) | SVSEI QLMHN LGKHL NSMER VEWLR KKLQC VHNF | 87 |
| Cys31PTH(1-34) | SVSEI QLMHN LGKHL NSMER VEWLR KKLQD CHNF | 88 |
| Cys32PTH(1-34) | SVSEI QLMHN LGKHL NSMER VEWLR KKLQD VCNF | 89 |

TABLE 2

Exemplary PTH/PTHrP modulating domains based on naturally-occurring PTHrP polypeptides

| Description | Sequence | SEQ ID NO: |
|---|---|---|
| human PTHrP (1-86)[3] | AVSEHQLLHDKGKSIQDLRRRFFLHHLIAEI HTAEIRATSEVSPNSKPSPNTKNHPVRFGSD KEGRYLTQETNKVETYKEQPLKTP | 90 |

TABLE 2-continued

Exemplary PTH/PTHrP modulating domains based on naturally-occurring PTHrP polypeptides

| Description | Sequence | SEQ ID NO: |
|---|---|---|
| human PTHrP (1-34)[18] | AVSEHQLLHDKGKSIQDLRRRFFLHHLIAEIHTA | 91 |
| [Tyr36] human PTHrP(1-36)[3] | AVSEHQLLHDKGKSIQDLRRRFFLHHLIAEIHTAEY | 92 |
| [Ile5, Trp23, Tyr36] human PTHrP (1-36)[3] | AVSEIQLLHDKGKSIQDLRRRFWLHHLIAEIHTAEY | 93 |
| Tyr-human PTHrP (1-34)[3] | YAVSEHQLLHDKGKSIQDLRRRFFLHHLIAEIHTA | 94 |
| [Asn10, Leu11, D-Phe12] human PTHrP(1-34)[19] | AVSEHQLLHNL-D-Phe-KSIQDLRRRFFLHHLIAEIHTA | 95 |
| PTHrP (7-34)[20] | LLHDKGKSIQDLRRRFFLHHLIAEIHTA | 96 |
| [Asn10, Leu11] human PTHrP (7-34) | LLHNLGKSIQDLRRRFFLHHLIAEIHTA | 97 |
| [Asn16, Leu17] PTHrP (7-34)[21] | LLHDKGKSINLLRRRFFLHHLIAEIHTA | 98 |
| [Leu11, D-Trp12] human PTHrP(7-34)[22] | LLHDL-D-Trp-KSIQDLRRRFFLHHLIAEIHTA | 99 |
| [Asn10, Leu11, D-Trp12] PTHrP(7-34)[23] | LLHNL-D-Trp-KSIQDLRRRFFLHHLIAEIHTA | 100 |
| [D-Trp 12] PTH rP(8-34) | LHNL-D-Trp-KSIQDLRRRFFLHHLIAEIHTA | 101 |
| [D-Phe12] PTHrP(8-34) | LHNL-D-Phe-KSIQDLRRRFFLHHLIAEIHTA | 102 |
| [Asn10, Leu11, D-Trp12] human PTHrP(7-34)[20] | LLHNL-D-Trp-KSIQDLRRRFFLHHLIAEIHTA | 103 |
| human PTHrP(1-30) | AVSEHQLLHDKGKSIQDLRRRFFLHHLIAE | 104 |
| [Ile5, Trp23] human PTHrP(1-30) | AVSEIQLLHDKGKSIQDLRRRFWLHHLIAE | 105 |
| Tyr-human PTHrP(1-30) | YAVSEHQLLHDKGKSIQDLRRRFFLHHLIAE | 106 |
| [Asn10, Leu11, D-Phe12] human PTHrP(1-30) | AVSEHQLLHNL-D-Phe-KSIQDLRRRFFLHHLIAE | 107 |
| PTHrP (7-30) | LLHDKGKSIQDLRRRFFLHHLIAE | 108 |
| [Asn10, Leu11] human PTHrP(7-30) | LLHNLGKSIQDLRRRFFLHHLIAE | 109 |
| [Asn16, Leu17] PTHrP(7-30) | LLHDKGKSINLLRRRFFLHHLIAE | 110 |
| [Leu11, D-Trp12] human PTHrP(7-30) | LLHDL-D-Trp-KSIQDLRRRFFLHHLIAE | 111 |
| [Asn10, Leu11, D-Trp12] PTHrP(7-30) | LLHNL-D-Trp-KSIQDLRRRFFLHHLIAE | 112 |
| [D-Trp12] PTHrP(8-30) | LHNL-D-Trp-KSIQDLRRRFFLHHLIAE | 113 |
| [D-Phe12] PTHrP(8-30) | LHNL-D-Phe-KSIQDLRRRFFLHHLIAE | 114 |
| [Asn10, Leu11, D-Trp12] human PTHrP(7-30) | LLHNL-D-Trp-KSIQDLRRRFFLHHLIAE | 115 |

TABLE 2-continued

Exemplary PTH/PTHrP modulating domains based on naturally-occurring PTHrP polypeptides

| Description | Sequence | SEQ ID NO: |
|---|---|---|
| [Haa(Laa Laa Haa Haa)2 Laa22-31] human PTH (1-34)[24] | SVSEIQLMHNLGKHLNSMERVELLEKLLEKLHNF | 116 |
| [Haa(Laa Laa Haa Haa)2 Laa 22-31] human PTH (1-34)[24] | SVSEIQLMHNLGKHLNSMERVELLEKLLKKLHNF | 117 |
| [Haa(Laa Laa Haa Haa)2 Laa 22-31] human PTH (1-34)[25] | SVSEIQLMHNLGKHLNSMERVALAEALAEALHNF | 118 |
| [Haa(Laa Laa Haa Haa)2 Laa22-31] human PTH (1-34)[26] | SVSEIQLMHNLGKHLNSMERVSLLSSLLSSLHNF | 119 |
| [Haa(Laa Laa Haa Haa)2 Laa22-31] human PTH (1-34)[27] | SVSEIQLMHNLGKHLNSMERVAFYDKVAEKLHNF | 120 |
| [Haa(Laa Laa Haa Haa)2 Laa 22-31] human PTH (7-34)[24] | LMHNLGKHLNSMERVELLEKLLKKLHNF | 121 |
| [Haa(Laa Laa Haa Haa)2 Laa 22-31] human PTH (7-34)[24] | LMHNLGKHLNSMERVELLEKLLKKLHNF | 122 |
| [Haa(Laa Laa Haa Haa)2 Laa 22-31] human PTH (7-34)[25] | LMHNLGKHLNSMERVALAEALAEALHNF | 123 |
| [Haa(Laa Laa Haa Haa)2 Laa 22-31] human PTH (7-34)[26] | LMHNLGKHLNSMERVSLLSSLLSSLHNF | 124 |
| [Haa(Laa Laa Haa Haa)2 Laa 22-31] human PTH (7-34)[27] | LMHNLGKHLNSMERVAFYDKVAEKLHNF | 125 |
| [Haa(Laa Laa Haa Haa)2 Laa22-31] human PTHrP (1-34)[24] | AVSEHQLLHDKGKSIQDLRRRELLEKLLEKLHTA | 126 |
| [Haa(Laa Laa Haa Haa)2 Laa22-31] human PTHrP (1-34)[24] | AVSEHQLLHDKGKSIQDLRRRELLEKLLKKLHTA | 127 |
| [Haa(Laa Laa Haa Haa)2 Laa22-31] human PTHrP (1-34)[25] | AVSEHQLLHDKGKSIQDLRRRALAEALAEALHTA | 128 |
| [Haa(Laa Laa Haa Haa)2 Laa22-31] human PTHrP (1-34)[26] | AVSEHQLLHDKGKSIQDLRRRSLLSSLLSSLHTA | 129 |
| [Haa(Laa Laa Haa Haa)2 Laa22-31] human PTHrP (1-34)[27] | AVSEHQLLHDKGKSIQDLRRRAFYDKVAEKLHTA | 130 |
| [Haa(Laa Laa Haa Haa)2 Laa 22-31] human PTHrP (7-34)[28] | LLHDKGKSIQDLRRRELLEKLLEKLHTA | 131 |
| [Haa(Laa Laa Haa Haa)2 Laa22-31] human PTHrP (7-34)[24] | LLHDKGKSIQDLRRRELLEKLLKKLHTA | 132 |
| [Haa(Laa Laa Haa Haa)2 Laa 22-31] human PTHrP (7-34)[25] | LLHDKGKSIQDLRRRALAEALAEALHTA | 133 |

TABLE 2-continued

Exemplary PTH/PTHrP modulating domains based on naturally-occurring PTHrP polypeptides

| Description | Sequence | SEQ ID NO: |
|---|---|---|
| [Haa(Laa Laa Haa Haa)2 Laa22-31] human PTHrP (7-34)[26] | LLHDKGKSIQDLRRRSLLSSLLSSLHTA | 134 |
| [Haa(Laa Laa Haa Haa)2 Laa 22-31] human PTHrP (7-34)[27] | LLHDKGKSIQDLRRRAFYDKVAEKLHTA | 135 |
| [Lys11, Lys13; Arg19, Arg21; Haa(Laa Laa Haa Haa)2 Laa 22-31] human PTHrP (1-34)[29] | AVSEHQLLHDKGKSIQDLRRRELLEKLLRKLHTA | 136 |
| [Lys11, Lys13; Arg19, Arg21; Haa(Laa Laa Haa Haa)2 Laa 22-31] human PTHrP (1-34)[30] | AVSEHQLLHDKGKSIQDLRRRELLEKLLEKLHTS | 137 |
| [Lys11, Lys13; Arg19, Arg21; Haa(Laa Laa Haa Haa)2 Laa 22-31] human PTHrP (1-34)[31] | AVSEHQLLHDKGKSIQDLRRRELLEKLLKLHTAGRR | 138 |
| [Lys11, Lys13; Arg19, Arg21; Haa(Laa Laa Haa Haa)2 Laa 22-31] human PTHrP (1-34)[32] | AVSEHQLLHDKGKSIQDLRRRELLEKLLEKLKEL | 139 |
| [Lys11, Lys13, Ala19, Arg21, Haa(Laa Laa Haa Haa)2 Laa 22-31] human PTHrP (1-34)[33] | AVSEHQLLHDKGKSIQDLARRELLEKLLKLHTA | 140 |
| [Lys11, Lys13, Arg19, Ala21, Haa(Laa Laa Haa Haa)2 Laa 22-31] human PTHrP (1-34)[34] | AVSEHQLLHDKGKSIQDLRRAELLEKLLEKLHTA | 141 |
| [Leu11, Lys13, Arg19, Arg21, Haa(Laa Laa Haa Haa)2 Laa 22-31] human PTHrP (1-34)[35] | AVSEAQLLHDLGKSIQDLRRRELLEKLLEKLHAL | 142 |
| [Lys11, Lys13, Arg19, Arg21, Haa(Laa Laa Haa Haa)2 Laa 22-31] human PTHrP (1-34)[36] | AVSEHQLLHDKGKSIQDLRRRELLERLLERLHTA | 143 |
| [Arg11, Arg13, Arg19, Arg21, Haa(Laa Laa Haa Haa)2 Laa 22-31] human PTHrP (1-34)[37] | AVSEHQLLHDRGRSIQDRRRELLERLLERHLTA | 144 |
| [Arg11, Lys13, Arg19, Arg21, Haa(Laa Laa Haa Haa)2 Laa 22-31] human PTHrP (1-34)[38] | AVSEHQLLHDRGKSIQDLRRRELLERLLKRLHTA | 145 |
| [Arg11, Arg13, Arg19, Arg21, Haa(Laa Laa Haa Haa)2 Laa 22-31] human PTHrP (1-34)[39] | AVSEHQLLHDRGRSIQDLRRRELLERLLKRLHTA | 146 |
| Haa(Laa Laa Haa Haa)2 Laa 22-31] human PTHrP (1-34)[40] | AVSEHQLLHDKGKSIQDLRRRALAEALAEALHTA | 147 |
| Haa(Laa Laa Haa Haa)2 Laa 22-31] human PTHrP (1-34)[41] | AVSEHQLLHDKGKSIQDLRRRSLLSSLLSSLHTA | 148 |

TABLE 2-continued

Exemplary PTH/PTHrP modulating domains based on naturally-occurring PTHrP polypeptides

| Description | Sequence | SEQ ID NO: |
|---|---|---|
| Haa(Laa Laa Haa Haa)2 Laa 22-31] human PTHrP (1-34)<sup>42</sup> | AVSEHQLLHDKGKSIQDLRRRAFYDKVAEKLHTA | 149 |
| Haa(Laa Laa Haa Haa)2 Laa 22-31] human PTHrP (1-34)<sup>43</sup> | AVSEIQFMHNLGKHLSSMERVELLEKLLEKLHNY | 150 |
| Haa(Laa Laa Haa Haa)2 Laa 22-31] human PTHrP (1-34)<sup>44</sup> | AVSEIQFMHNLGKHLSSMRRRELLEKLLEKLHNY | 151 |
| [Haa(Laa Laa Haa Haa)2 Laa 22-30] human PTH (1-30) | SVSEIQLMHNLGKHLNSMERVELLEKLLEK | 152 |
| [Haa(Laa Laa Haa Haa)2 Laa 22-30] human PTH (1-30) | SVSEIQLMHNLGKHLNSMERVELLEKLLKK | 153 |
| [Haa(Laa Laa Haa Haa)2 Laa 22-30] human PTH (1-30) | SVSEIQLMHNLGKHLNSMERVALAEALAEA | 154 |
| [Haa(Laa Laa Haa Haa)2 Laa 22-30] human PTH (1-30) | SVSEIQLMHNLGKHLNSMERVSLLSSLLSS | 155 |
| [Haa(Laa Laa Haa Haa)2 Laa 22-30] human PTH (1-34)<sup>27</sup> | SVSEIQLMHNLGKHLNSMERVAFYDKVAEKLHNF | 156 |
| [Haa(Laa Laa Haa Haa)2 Laa 22-30] human PTH (7-30) | LMHNLGKHLNSMERVELLEKLLEK | 157 |
| [Haa(Laa Laa Haa Haa)2 Laa 22-30] human PTH (7-30) | LMHNLGKHLNSMERVELLEKLLKK | 158 |
| [Haa(Laa Laa Haa Haa)2 Laa 22-30] human PTH (7-30) | LMHNLGKHLNSMERVALAEALAEA | 159 |
| [Haa(Laa Laa Haa Haa)2 Laa 22-30] human PTH (7-30) | LMHNLGKHLNSMERVSLLSSLLSS | 160 |
| [Haa(Laa Laa Haa Haa)2 Laa 22-30] human PTH (7-30) | LMHNLGKHLNSMERVAFYDKVAEK | 161 |
| [Haa(Laa Laa Haa Haa)2 Laa 22-30] human PTHrP (1-30) | AVSEHQLLHDKGKSIQDLRRRELLEKLLEK | 162 |
| [Haa(Laa Laa Haa Haa)2 Laa 22-30] human PTHrP (1-30) | AVSEHQLLHDKGKSIQDLRRRELLEKLLKK | 163 |
| [Haa(Laa Laa Haa Haa)2 Laa22-30] human PTHrP (1-30) | AVSEHQLLHDKGKSIQDLRRRALAEALAEA | 164 |
| [Haa(Laa Laa Haa Haa)2 Laa22-30] human PTHrP (1-30) | AVSEHQLLHDKGKSIQDLRRRSLLSSLLSS | 165 |
| [Haa(Laa Laa Haa Haa)2 Laa22-30] human PTHrP (1-30) | AVSEHQLLHDKGKSIQDLRRRAFYDKVAEK | 166 |

TABLE 2-continued

Exemplary PTH/PTHrP modulating domains based on naturally-occurring PTHrP polypeptides

| Description | Sequence | SEQ ID NO: |
|---|---|---|
| [Haa(Laa Laa Haa Haa)2 Laa22-30] human PTHrP (7-30) | LLHDKGKSIQDLRRRELLEKLLEK | 167 |
| [Haa(Laa Laa Haa Haa)2 Laa 22-30] human PTHrP (7-30) | LLHDKGKSIQDLRRRELLEKLLKK | 168 |
| [Haa(Laa Laa Haa Haa)2 Laa22-30] human PTHrP (7-30) | LLHDKGKSIQDLRRRALAEALAEA | 169 |
| [Haa(Laa Laa Haa Haa)2 Laa 22-30] human PTHrP (7-30) | LLHDKGKSIQDLRRRSLLSSLLSS | 170 |
| [Haa(Laa Laa Haa Haa)2 Laa22-30] human PTHrP (7-30) | LLHDKGKSIQDLRRRAFYDKVAEK | 171 |
| [Lys11, Lys13; Arg19, Arg21; Haa(Laa Laa Haa Haa)2 Laa 22-30] human PTHrP (1-30) | AVSEHQLLHDKGKSIQDLRRRELLEKLLRK | 172 |
| [Lys11, Lys13; Arg19, Arg21; Haa(Laa Laa Haa Haa)2 Laa 22-30] human PTHrP (1-30) | AVSEHQLLHDKGKSIQDLRRRELLEKLLEK | 173 |
| [Lys11, Lys13; Arg19, Arg21; Haa(Laa Laa Haa Haa)2 Laa 22-30] human PTHrP (1-30) | AVSEHQLLHDKGKSIQDLRRRELLEKLLEKL | 174 |
| [Lys11, Lys13; Arg19, Arg21; Haa(Laa Laa Haa Haa)2 Laa 22-30] human PTHrP (1-30) | AVSEHQLLHDKGKSIQDLRRRELLEKLLEK | 175 |
| [Lys11, Lys13, Ala19, Arg21, Haa(Laa Laa Haa Haa)2 Laa 22-30] human PTHrP (1-30) | AVSEHQLLHDKGKSIQDLARRELLEKLLEK | 176 |
| [Lys11, Lys13, Arg19, Ala21, Haa(Laa Laa Haa Haa)2 Laa 22-30] human PTHrP (1-30) | AVSEHQLLHDKGKSIQDLRRAELLEKLLEK | 177 |
| [Leu11, Lys13, Arg19, Arg21, Haa(Laa Laa Haa Haa)2 Laa 22-30] human PTHrP (1-30) | AVSEAQLLHDLGKSIQDLRRRELLEKLLEK | 178 |
| [Lys11, Lys13, Arg19, Arg21, Haa(Laa Laa Haa Haa)2 Laa 22-30] human PTHrP (1-30) | AVSEHQLLHDKGKSIQDLRRRELLERLLER | 179 |
| [Arg11, Arg13, Arg19, Arg21, Haa(Laa Laa Haa Haa)2 Laa 22-30] human PTHrP (1-30) | AVSEHQLLHDRGRSIQDRRRELLERLLER | 180 |
| [Arg11, Lys13, Arg19, Arg21, Haa(Laa Laa Haa Haa)2 Laa 22-30] human PTHrP (1-30) | AVSEHQLLHDRGKSIQDLRRRELLERLLKR | 181 |

TABLE 2-continued

Exemplary PTH/PTHrP modulating domains based on naturally-occurring PTHrP polypeptides

| Description | Sequence | SEQ ID NO: |
|---|---|---|
| [Arg11, Arg13, Arg19, Arg21, Haa(Laa Laa Haa Haa)2 Laa 22-30] human PTHrP (1-30) | AVSEHQLLHDRGRSIQDLRRRELLERLLKR | 182 |
| Haa(Laa Laa Haa Haa)2 Laa 22-30] human PTHrP (1-30) | AVSEHQLLHDKGKSIQDLRRRALAEALAEA | 183 |
| Haa(Laa Laa Haa Haa)2 Laa 22-30] human PTHrP (1-30) | AVSEHQLLHDKGKSIQDLRRRSLLSSLLSS | 184 |
| Haa(Laa Laa Haa Haa)2 Laa 22-30] human PTHrP (1-30) | AVSEHQLLHDKGKSIQDLRRRAFYDKVAEK | 185 |
| Haa(Laa Laa Haa Haa)2 Laa 22-30] human PTHrP (1-30) | AVSEIQFMHNLGKHLSSMERVELLEKLLEK | 186 |
| Haa(Laa Laa Haa Haa)2 Laa 22-30] human PTHrP (1-30) | AVSEIQFMHNLGKHLSSMRRRELLEKLLEK | 187 |

[18] Moseley et al. (1987), Proc. Natl. Acad. Sci. USA 84: 5048; Suva et al. (1987), Science 237: 893; Kemp et al. (1987), Science 238: 1568; Paspaliaris et al. (1995), Bone 16: 141S abstract 225, Conference, Melbourne 1995).
[19] Based on JP 07316195, May 25, 1994 (Nippon Kayaku).
[20] Nagasaki et al. (1989), Biochem. Biophys. Res. Commun. 158: 1036; Nutt et al.; Endocrinology 127, 491 (1990).
[21] Williams et al. (1998), J. Reproduction & Fertility 112: 59-67.
[22] Gardella et al. (1996), Endocrinol. 137: 3936-41; Fukayama et al. (1998), Am. J. Physiol. 274:E297-E303.
[23] Li et al. (1996), Endocrinology.
[24] Incorporating SEQ ID NO: 26 from U.S. Pat. No. 6,051,686.
[25] Incorporating SEQ ID NO: 28 from U.S. Pat. No. 6,051,686.
[26] Incorporating SEQ ID NO: 29 from U.S. Pat. No. 6,051,686.
[27] Incorporating SEQ ID NO: 30 from U.S. Pat. No. 6,051,686.
[28] Incorporating SEQ ID NO: 26 from U.S. Pat. No. 6,051,686
[29] Incorporating SEQ ID NO: 5 from U.S. Pat. No. 6,051,686.
[30] Based on SEQ ID NOS: 8, 9 from U.S. Pat. No. 6,051,686
[31] Incorporating SEQ ID NO: 10 from U.S. Pat. No. 6,051,686
[32] Incorporating SEQ ID NO: 11 from U.S. Pat. No. 6,051,686
[33] Incorporating SEQ ID NO: 12 from U.S. Pat. No. 6,051,686
[34] Incorporating SEQ ID NO: 12 from U.S. Pat. No. 6,051,686
[35] Incorporating SEQ ID NO: 14 from U.S. Pat. No. 6,051,686
[36] Incorporating SEQ ID NO: 15 from U.S. Pat. No. 6,051,686
[37] Incorporating SEQ ID NO: 16 from U.S. Pat. No. 6,051,686
[38] Incorporating SEQ ID NO: 17 and 18 from U.S. Pat. No. 6,051,686
[39] Incorporating SEQ ID NO: 19 from U.S. Pat. No. 6,051,686
[40] Incorporating SEQ ID NO: 20 from U.S. Pat. No. 6,051,686
[41] Incorporating SEQ ID NO: 21 from U.S. Pat. No. 6,051,686
[42] Incorporating SEQ ID NO: 22 from U.S. Pat. No. 6,051,686
[43] Modified from SEQ ID NO: 23 from U.S. Pat. No. 6,051,686
[44] Modified from SEQ ID NO: 24 from U.S. Pat. No. 6,051,686

In certain embodiments, a PTH/PTHrP modulating domain comprises the sequence of the peptide known as TIP39:

```
                                        (SEQ ID NO: 245)
SLALADDAAFRERARLLAALERRHWLNSYMHKLLVLDAP
```

TIP39 is described by Usdin et al. (1999), Nature Neurosci. 2(11): 941-3; Usdin et al. (1996), Endocrinology 137(10): 4285-97; Usdin et al. (1995), J. Biol. Chem. 270(26): 15455-8; Usdin et al. (1999), Endocrinol. 140(7): 3363-71.

In certain embodiments, a PTH/PTHrP modulating domain comprises a polypeptide selected from the polypeptides of formula I (SEQ ID NO: 13). In certain embodiments, a PTH/PTHrP modulating domain comprises a polypeptide selected from the polypeptides of formula II (SEQ ID NO: 14). In certain embodiments, a PTH/PTHrP modulating domain comprises a polypeptide selected from the polypeptides of formula III (SEQ ID NO: 15). In certain embodiments, a PTH/PTHrP modulating domain comprises a polypeptide selected from the polypeptides of formula I (SEQ ID NO: 13), except the polypeptide comprises one or more conservative amino acid substitutions and/or one or more nonconservative substitutions. In certain embodiments, a PTH/PTHrP modulating domain comprises a polypeptide selected from the polypeptides of formula II (SEQ ID NO: 14), except the polypeptide comprises one or more conservative amino acid substitutions and/or one or more nonconservative substitutions. In certain embodiments, a PTH/PTHrP modulating domain comprises a polypeptide selected from the polypeptides of formula III (SEQ ID NO: 15), except the polypeptide comprises one or more conservative amino acid substitutions and/or one or more nonconservative substitutions. In certain embodiments, a PTH/PTHrP modulating domain comprises a polypeptide selected from polypeptides of formula I (SEQ ID NO: 13), wherein one or more residues between position 14 and the C-terminal amino acid of the polypeptide is substituted with a cysteine residue. In certain embodiments, a PTH/PTHrP modulating domain comprises a polypeptide selected from polypeptides of formula II (SEQ ID NO: 14), wherein one or more residues between position 14 and the C-terminal amino acid of the polypeptide is substituted with a cysteine residue. In certain embodiments, a PTH/PTHrP modulating domain comprises a polypeptide selected from polypeptides of formula III (SEQ ID NO: 15), wherein one or more residues between position 14 and the C-terminal amino acid of the polypeptide is substituted with a cysteine residue.

In certain embodiments, a PTH/PTHrP modulating domain comprises a polypeptide (i) having the amino acid sequence of TIP39 (SEQ ID NO: 160), or (ii) selected from the polypeptides of Table 1A, or (iii) selected from the polypeptides of Table 1B, or (iv) selected from the polypeptides of Table 2. In certain embodiments, a PTH/PTHrP modulating domain comprises a polypeptide (i) having the amino acid sequence of TIP39 (SEQ ID NO: 160), except the polypeptide comprises one or more conservative amino acid substitutions and/or one or more nonconservative substitutions, or (ii) selected from the polypeptides of Table 1A, except the polypeptide comprises one or more conservative amino acid substitutions and/or one or more nonconservative substitutions, or (iii) selected from the polypeptides of Table 1B, except the polypeptide comprises one or more conservative amino acid substitutions and/or one or more nonconservative substitutions, or (iv) selected from the polypeptides of Table 2, except the polypeptide comprises one or more conservative amino acid substitutions and/or one or more nonconservative substitutions. In certain embodiments, a PTH/PTHrP modulating domain comprises a polypeptide (i) having the amino acid sequence of TIP39 (SEQ ID NO: 160), except one or more residues between position 14 and the C-terminal amino acid of the polypeptide is substituted with a cysteine residue, or (ii) selected from the polypeptides of Table 1A, except one or more residues between position 14 and the C-terminal amino acid of the polypeptide is substituted with a cysteine residue, or (iii) selected from the polypeptides of Table 1B, except one or more residues between position 14 and the C-terminal amino acid of the polypeptide is substituted with a cysteine residue, or (iv) selected from the polypeptides of Table 2, except one or more residues between position 14 and the C-terminal amino acid of the polypeptide is substituted with a cysteine residue.

In certain embodiments, one or more residues between position 27 and the C-terminus of the PTH/PTHrP modulating domain is a cysteine residue.

Certain Exemplary Prepro Domains

In certain embodiments, a PTH/PTHrP peptide comprises a prepro domain and a modulating domain. In certain embodiments, the prepro domain is N-terminal to the modulating domain. In certain embodiments, the prepro domain and the modulating domain are separated by 0 to 30 amino acids. In certain embodiments, the prepro domain and the modulating domain are separated by 0 to 10 amino acids. In certain embodiments, the prepro domain and the modulating domain are separated by 0, 1, 2, 3, 4, or 5 amino acids. Certain exemplary prepro domains are shown in Tables 3 and 4.

TABLE 3

Exemplary prepro domains based on naturally-occurring PTH polypeptides

| Description | Sequence | Acc. No. | SEQ ID NO: |
|---|---|---|---|
| human | MIPAKDMAKVMIVMLAICFLT KSDGKSVKKR | NP_000306 | 188 |
| rattus norvegicus | MMSASTMAKVMILMLAVCLLT QADGKPVKKR | NP_058740 | 189 |
| sus scrofa | MMSAKDTVKVMVVMLAICFLA RSDGKPIKKR | P01269 | 190 |
| gallus gallus | MTSTKNLAKAIVILYAICFFT NSDGRPMMKR | P15743 | 191 |
| bos taurus | MMSAKDMVKVMIVMLAICFLA RSDGKSVKKR | P01268 | 192 |
| felis cattus | MMSAKDMVKVMVVMFAICFLA KSDGKPVKKR | AAG30545 | 193 |
| canis familiaris | MMSAKDMVKVMIVMFAICFLA KSDGKPVKKR | NP_001003302 | 194 |
| mus musculus | MMSANTVAKVMIIMLAVCLLT QTDGKPVRKR | NP_065648 | 195 |

TABLE 4

Exemplary prepro domains based on naturally-occurring PTHrP polypeptides

| Description | Sequence | Acc. No. | SEQ ID NO: |
|---|---|---|---|
| human | MQRRLVQQWSVAVFLLSYA VPSCGRSVEGLSRRLKR | NP_945317 | 196 |
| rattus norvegicus | MLRRLVQQWSVLVFLLSYS VPSRGRSVEGLGRRLKR | NP_036768 | 197 |
| sus scrofa | MLWRLVQQWSVAVFLLSYS VPSCGRSVEELGRRLKR | NP_999081 | 198 |
| gallus gallus | MMFTKLFQQWSFAVFLLSY SVPSYGRSVEGISRRLKR | NP_990669 | 199 |
| bos taurus | MLWRLVQQWSVAVFLLSYS VPSCGRSVEELGRRLKR | P58073 | 200 |
| felis cattus (partial) | LLSYSVPSCGRSVEELGRR LKR | AAL13054 | 201 |
| canis familiaris | MLRRLVQQWGAVAVFLLSY SVPSCGRSVEELGRRLKR | NP_001003303 | 202 |
| mus musculus | MLRRLVQQWSVLVFLLSYS VPSRGRSVEGLGRRLKR | CAC39218 | 203 |
| oryctolagus cuniculus | MLRRLVQQWSVAVFLLSYS VPSCGRSVEGPGRRLKR | AAG13414 | 204 |
| Phoca vitulina | MLRRLVQQWSVAVFLLSYS VPSCGRSVEELGRRLKR | CAH39862 | 205 |
| Cervus elaphus (partial) | QWSVXVFLXSYSVPSCGRS VEELGRRLKR | AAP93209 | 206 |
| ovis aries (partial) | VGVFLLSYSVPSCGRSVEEL GRRLKR | AAG48348 | 207 |

Certain Exemplary PTH/PTHrP Peptides

In certain embodiments, PTH/PTHrP peptides may be prepared by methods known in the art, including, but not limited to, methods described, e.g., in U.S. Pat. Nos. 4,423,037; 4,968,669; 5,001,223; or 6,051,686. In certain embodiments, two or more PTH/PTHrP peptides may be linked in tandem (i.e., multiple peptides linked sequentially), with or without linkers. In certain embodiments, a PTH/PTHrP peptide containing a cysteinyl residue may be cross-linked with another cysteine-containing polypeptide. In certain embodiments, a PTH/PTHrP peptide having more than one cysteine residue may form an intrapeptide disulfide bond. In certain embodiments, a PTH/PTHrP peptide may be derivatized, as discussed below.

In certain embodiments, conservative amino acid substitutions will produce peptides having functional and chemical characteristics similar to those of the PTH/PTHrP peptide prior to making the substitutions. In certain embodiments, if alteration of the functional and/or chemical characteristics of a PTH/PTHrP peptide is desired, non-conservative substitutions can be made in the peptide sequence. In certain embodiments, such non-conservative substitutions can be made by selecting, e.g., one or more replacement amino acids that differ from the replaced amino acids in their effect on maintaining (a) the structure of the peptide backbone in the area of the substitution, for example, as a sheet or helical conformation, (b) the charge or hydrophobicity of the molecule at the substitution site, and/or (c) the size of the molecule at the substitution site.

Certain exemplary desired amino acid substitutions (whether conservative or non-conservative) can be determined by those skilled in the art at the time such substitutions are desired. In certain embodiments, amino acid substitutions can be used to identify important residues of a PTH/PTHrP peptide, or to increase or decrease the affinity of the PTH/PTHrP peptide for the PTH-1 receptor and/or the PTH-2 receptor.

Certain Exemplary Methods of Preparing of PTH/PTHrP Peptides

In certain embodiments, a PTH/PTHrP peptide can be made in transformed host cells using recombinant DNA techniques. Thus, in certain embodiments, a recombinant DNA molecule coding for the peptide is prepared. Certain exemplary methods of preparing such DNA molecules are known in the art. In certain embodiments, a sequence coding for a peptide can be excised from DNA using a suitable restriction enzyme or enzymes. In certain embodiments, a DNA molecule can be synthesized using chemical synthesis techniques, including, but not limited to, the phosphoramidite method. In certain embodiments, a combination of these techniques, and other techniques known in the art, can be used.

In certain embodiments, a vector capable of expressing a PTH/PTHrP peptide in an appropriate host cell is provided. In certain embodiments, the vector comprises the DNA molecule that codes for the peptide operably linked to one or more appropriate expression control sequences. Certain exemplary methods of operably linking a coding DNA to one or more expression control sequences are known in the art. Certain exemplary expression control sequences include, but are not limited to, promoters, activators, enhancers, operators, ribosomal binding sites, start signals, stop signals, cap signals, polyadenylation signals, and other signals involved with the control of transcription and/or translation. In certain embodiments, the resulting vector having the coding DNA is used to transform an appropriate host. In various embodiments, one skilled in the art can select an appropriate transformation method according to the selected host cell.

In various embodiments, one of the large number of available and well-known host cells may be used to express a PTH/PTHrP peptide. In certain embodiments, a particular host cell is selected based on a number of factors known in the art, including but not limited to, compatibility with the chosen expression vector, toxicity of the peptide encoded by the DNA molecule in that particular cell type, rate of transformation, ease of recovery of the expressed peptide, expression characteristics, bio-safety, and costs. In certain embodiments, consideration of these factors is made with the understanding that not all host cells may be equally effective for the expression of a particular DNA sequence. Exemplary useful hosts include, but are not limited to, bacteria (such as *E. coli* sp.), yeast (such as *Saccharomyces* sp. and *Pichia pastoris*) and other fungi, insect cells, plants and plant cells, mammalian (including human) cells in culture, certain mammals (including sheep, goats, cows, and pigs), and other host cells and organisms known in the art. Mammalian cell lines available as hosts for expression include, but are not limited to, certain immortalized cell lines available from the American Type Culture Collection (ATCC), including but not limited to, Chinese Hamster Ovary (CHO) cells, HeLa cells, baby hamster kidney (BHK) cells, monkey kidney cells (COS), human hepatocellular carcinoma cells (e.g. Hep G2) and the like, which may optionally be adapted for growth in serum-free culture medium. Certain exemplary host cells include, but are not limited to, 293T cells and CHO AM-1/D cells.

In certain embodiments, the transformed host is cultured and the peptide purified. In certain embodiments, host cells are cultured according to methods known in the art, including conventional fermentation conditions, to express the desired peptide. In certain embodiments, the peptide is purified from the culture according to methods known in the art.

In certain embodiments, a PTH/PTHrP peptide may be made by synthetic methods. For example, in certain embodiments, solid phase synthesis techniques may be used. Certain exemplary solid phase synthesis techniques are known in the art, including but not limited to, those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. In certain embodiments, solid phase synthesis may be the most cost-effective method of making certain small peptides.

In certain embodiments, derivatized peptides may be made using known organic chemistry techniques. In certain embodiments, the un-derivatized peptide is first made using either biochemical or synthetic methods, and is then derivatized using organic chemistry techniques.

Certain Exemplary Linkers

If a polypeptide is described as being "linked" to another polypeptide, the linked molecule may or may not include a linker. In certain embodiments, if a linker serves primarily as a spacer between two molecules, its precise chemical structure is not critical. In certain embodiments, a linker comprises amino acid residues linked together by peptide bonds, i.e., a linker comprises a peptide. Thus, in certain embodiments, a linker is a peptide having between 1 and 20 amino acids residues, including all numbers between those endpoints. The amino acid residues used in linkers may be conventional or unconventional amino acid residues. In certain embodiments, amino acid residues in a linker may be glycosylated and/or derivatized in another manner. In certain embodiments, the amino acid residues in a linker are selected from glycine, alanine, proline, asparagine, glutamine, and lysine. In certain embodiments, a linker comprises a majority of amino acid residues that are sterically unhindered, such as glycine and/or alanine. Thus, in certain embodiments, a linker is selected from a polyglycine (e.g., (Gly)$_4$ (SEQ ID NO: 246), (Gly)$_5$ (SEQ ID NO: 247)), a poly(Gly-Ala), and a polyalanine. Certain exemplary linkers include, but are not limited to:

| | |
|---|---|
| (Gly)$_3$Lys(Gly)$_4$; | (SEQ ID NO: 208) |
| (Gly)$_3$AsnGlySer(Gly)$_2$; | (SEQ ID NO: 209) |
| (Gly)$_3$Cys(Gly)$_4$; | (SEQ ID NO: 210) |
| GlyProAsnGlyGly; and | (SEQ ID NO: 211) |
| GlyGlyGlyAlaPro. | (SEQ ID NO: 212) |

To explain the above nomenclature, for example, (Gly)$_3$Lys (Gly)$_4$(SEQ ID NO: 208) means Gly-Gly-Gly-Lys-Gly-Gly-Gly-Gly (SEQ ID NO: 208). In certain embodiments, a linker comprises a combination of Gly and Ala residues. In certain embodiments, a linker comprises 10 or fewer amino acid residues. In certain embodiments, a linker comprises 1, 2, 3, 4, 5, 6, 7, 8, 9, or 10 amino acid residues. In certain embodiments, a linker comprises 11-30 amino acid residues, including all numbers between those endpoints.

In certain embodiments, a peptide linker may result from the restriction enzyme sites used to clone two polypeptides into a single coding sequence. In certain embodiments, the restriction enzyme sites are added to the coding sequence of one or both of the polypeptides. In certain embodiments, the amino acid sequence of such linkers is dictated, at least in part, by the restriction enzyme sites selected for the cloning procedures.

In certain embodiments, non-peptide linkers are provided. Certain exemplary non-peptide linkers include, but are not limited to, alkyl linkers such as —NH—(CH$_2$)$_s$—C(O)—, wherein s=2-20. Such alkyl linkers may, in certain embodiments, further comprise substitutions including, but not limited to, non-sterically hindering group such as lower alkyl (e.g., C$_1$-C$_6$) lower acyl, halogen (e.g., Cl, Br), CN, NH$_2$, phenyl, etc. A non-limiting exemplary non-peptide linker is a PEG linker,

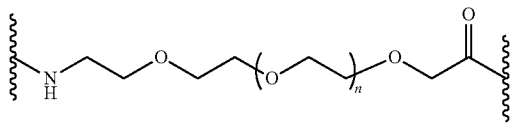

wherein n is a number such that the linker has a molecular weight of 100 to 5000 kD. In certain embodiments, n is a number such that the linker has a molecular weight of 100 to 500 kD, including all points between those endpoints.

In certain embodiments, a linker may result from a chemical and/or enzymatic process used to connect two polypeptides to one another. Certain exemplary chemical and/or enzymatic processes for connecting polypeptides are described, e.g., in the Pierce Applications Handbook and Catalog (2003/2004) (Pierce Biotechnology, Inc., Rockford, Ill.).

Certain Exemplary RANKL Antibody-PTH/PTHrP Chimeric Molecules

In certain embodiments, a RANKL antibody-PTH/PTHrP chimeric molecule comprises at least one RANKL antibody, at least one linker, and at least one PTH/PTHrP peptide. Exemplary linkers include, but are not limited to, a peptide linker, an alkyl linker, a PEG linker, and a linker that that results from a chemical or enzymatic process used to connect two polypeptides. In certain embodiments, at least one PTH/PTHrP peptide comprises a PTH/PTHrP modulating domain and a prepro domain. In certain embodiments, at least one PTH/PTHrP peptide comprises a PTH/PTHrP modulating domain but not a prepro domain. In certain embodiments, at least one RANKL antibody comprises two full-length heavy chains and two full-length light chains. In certain embodiments, at least one RANKL antibody comprises at least one truncated heavy chain and/or at least one truncated light chain. In certain embodiments, at least one RANKL antibody is an antibody fragment. Certain exemplary antibody fragments include, but are not limited to, a Fab, a Fab', a F(ab')$_2$, an Fv, and a single-chain Fv (scFv).

In certain embodiments, at least one PTH/PTHrP peptide may be linked to another molecule through the PTH/PTHrP peptide's C-terminus. In certain embodiments, a PTH/PTHrP peptide may be linked to another molecule through the PTH/PTHrP peptide's N-terminus. In certain embodiments, a PTH/PTHrP peptide is linked to a C-terminus of another molecule. In certain embodiments, a PTH/PTHrP peptide is linked to an N-terminus of another molecule.

In certain embodiments, a PTH/PTHrP peptide is linked to either the N-terminus or the C-terminus of the heavy chain of a RANKL antibody. In certain embodiments, a PTH/PTHrP peptide is linked to either the N-terminus or the C-terminus of the light chain of a RANKL antibody. In certain embodiments, a first PTH/PTHrP peptide is linked to the heavy chain of a RANKL antibody and a second PTH/PTHrP peptide having the same or different amino acid sequence as the first PTH/PTHrP peptide is linked to the light chain of the RANKL antibody. In certain embodiments, a RANKL antibody-PTH/PTHrP chimeric molecule comprises a linker between two components of the chimeric molecule.

In certain embodiments, at least one PTH/PTHrP peptide is fused to the heavy chain of a RANKL antibody. In certain embodiments, at least one PTH/PTHrP peptide is fused to the light chain of a RANKL antibody. In certain embodiments, a first PTH/PTHrP peptide is fused to the heavy chain of a RANKL antibody and a second PTH/PTHrP peptide having the same or different amino acid sequence as the first PTH/PTHrP peptide is fused to the light chain of the RANKL antibody. In certain embodiments, the heavy chain of a RANKL antibody is fused to at least two PTH/PTHrP peptides having the same or different sequence. In certain embodiments, the light chain of a RANKL antibody is fused to at least two PTH/PTHrP peptides having the same or different sequence. In certain embodiments, the heavy chain of a RANKL antibody is fused to at least two first PTH/PTHrP peptides having the same or different sequence and the light chain of a RANKL antibody is fused to at least two second PTH/PTHrP peptides having the same or different sequence.

In certain embodiments, a chimeric molecule comprises a ratio of two PTH/PTHrP peptides per one RANKL antibody. In certain embodiments, such a chimeric molecule comprises a first PTH/PTHrP peptide linked to a first heavy chain of a RANKL antibody and a second PTH/PTHrP peptide linked to a second heavy chain of the RANKL antibody. In certain embodiments, such a chimeric molecule comprises a first PTH/PTHrP peptide linked to a first light chain of a RANKL antibody and a second PTH/PTHrP peptide linked to a second light chain of the RANKL antibody. One skilled in the art can design additional chimeric molecules comprising a ratio of two PTH/PTHrP peptides per one RANKL antibody.

In certain embodiments, a chimeric molecule comprises four PTH/PTHrP peptides per one RANKL antibody. In certain embodiments, such a chimeric molecule comprises a first PTH/PTHrP peptide linked to a first heavy chain of RANKL, a second PTH/PTHrP peptide linked to a second heavy chain of RANKL, a third PTH/PTHrP peptide linked to a first light chain of RANKL, a fourth PTH/PTHrP peptide linked to a second light chain of RANKL. In certain embodiments, such a chimeric molecule comprises a first PTH/PTHrP peptide linked to the N-terminus of a first heavy chain of RANKL, a second PTH/PTHrP peptide linked to the C-terminus of the first heavy chain of RANKL, a third PTH/PTHrP peptide linked to the N-terminus of a second heavy chain of RANKL, and a fourth PTH/PTHrP peptide linked to the C-terminus of the second heavy chain of RANKL. In certain embodiments, such a chimeric molecule comprises a first PTH/PTHrP peptide linked to the N-terminus of a first light chain of RANKL, a second PTH/PTHrP peptide linked to the C-terminus of the first light chain of RANKL, a third PTH/PTHrP peptide linked to the N-terminus of a second light chain of RANKL, and a fourth PTH/PTHrP peptide linked to the C-terminus of the second light chain of RANKL. In certain embodiments, such a chimeric molecule comprises a first PTH/PTHrP peptide and a second PTH/PTHrP peptide linked to the N-terminus of a first heavy chain of RANKL, and a third PTH/PTHrP peptide and a fourth PTH/PTHrP peptide linked to the N-terminus of a second heavy chain of RANKL. One skilled in the art can design additional chimeric molecules comprising a ratio of four PTH/PTHrP peptides per one RANKL antibody.

In certain embodiments, a chimeric molecule comprises eight PTH/PTHrP peptides per one RANKL antibody. In certain embodiments, such a chimeric molecule comprises a first PTH/PTHrP peptide linked to the N-terminus of a first heavy chain of RANKL, a second PTH/PTHrP peptide linked to the C-terminus of the first heavy chain of RANKL, a third PTH/PTHrP peptide linked to the N-terminus of a second heavy chain of RANKL, a fourth PTH/PTHrP peptide linked to the C-terminus of the second heavy chain of RANKL, a fifth PTH/PTHrP peptide linked to the N-terminus of a first light chain, a sixth PTH/PTHrP peptide linked to the C-terminus of a first light chain, a seventh PTH/PTHrP peptide linked to the N-terminus of a second light chain, and an eighth PTH/PTHrP peptide linked to the C-terminus of a second light chain. In certain embodiments, such a chimeric molecule comprises a first PTH/PTHrP peptide and a second PTH/PTHrP peptide linked to the N-terminus of a first heavy chain of RANKL, a third PTH/PTHrP peptide and a fourth PTH/PTHrP peptide linked to the N-terminus of a second heavy chain of RANKL, a fifth PTH/PTHrP peptide and a sixth PTH/PTHrP peptide linked to the N-terminus of a first light chain of RANKL, and a seventh PTH/PTHrP peptide and an eighth PTH/PTHrP peptide linked to the N-terminus of a second light chain of RANKL. One skilled in the art can design additional chimeric molecules comprising a ratio of eight PTH/PTHrP peptides per one RANKL antibody.

In certain embodiments, at least one RANKL antibody in a RANKL antibody-PTH/PTHrP chimeric molecule is selected from a Fab, Fab', F(ab')2, Fv, and scFv. In certain embodiments, a RANKL antibody-PTH/PTHrP chimeric molecule comprises a peptide linker between at least two of the components.

In various embodiments, a RANKL antibody-PTH/PTHrP chimeric molecule comprises at least one PTH/PTHrP modulating domain selected from the amino acid sequences of Tables 1A, 1B and 2 (SEQ ID NOs: 16 to 187). In certain embodiments, a RANKL antibody-PTH/PTHrP chimeric molecule comprises at least one PTH/PTHrP prepro domain selected from the amino acid sequences of Tables 3 and 4 (SEQ ID NOs: 188 to 207). In certain embodiments, a RANKL antibody-PTH/PTHrP chimeric molecule comprises at least one PTH/PTHrP peptide having the sequence shown in FIG. 8 (SEQ ID NO: 6).

In certain embodiments, a RANKL antibody-PTH/PTHrP chimeric molecule comprises at least one heavy chain having the amino acid sequence shown in FIG. 2 (SEQ ID NO: 2). In certain embodiments, a RANKL antibody-PTH/PTHrP chimeric molecule comprises at least one heavy chain comprising a variable region having the amino acid sequence shown in FIG. 28 (SEQ ID NO: 11). In certain embodiments, a RANKL antibody-PTH/PTHrP chimeric molecule comprises at least one heavy chain comprising a variable region that is at least about 85%, at least about 90%, at least about 91%, at least about 92%, at least about 93%, at least about 94%, at least about 95%, at least about 96%, at least about 97%, at least about 98% or at least about 99% identical to the amino acid sequence shown in FIG. 28 (SEQ ID NO: 11). In certain embodiments, a RANKL antibody-PTH/PTHrP chimeric molecule comprises at least one light chain having the amino acid sequence shown in FIG. 4 (SEQ ID NO: 4). In certain embodiments, a RANKL antibody-PTH/PTHrP chimeric molecule comprises at least one light chain comprising a variable region having the amino acid sequence shown in FIG. 29 (SEQ ID NO: 12). In certain embodiments, a RANKL antibody-PTH/PTHrP chimeric molecule comprises at least one light chain comprising a variable region that is at least about 85%, at least about 90%, at least about 91%, at least about 92%, at least about 93%, at least about 94%, at least about 95%, at least about 96%, at least about 97%, at least about 98%, or at least about 99% identical to the amino acid sequence shown in FIG. 29 (SEQ ID NO: 12).

In certain embodiments, a RANKL antibody-PTH/PTHrP chimeric molecule comprises one RANKL antibody and one PTH/PTHrP peptide. In certain embodiments, a RANKL antibody-PTH/PTHrP chimeric molecule comprises one RANKL antibody and two PTH/PTHrP peptides. In certain embodiments, a RANKL antibody-PTH/PTHrP chimeric molecule comprises one RANKL antibody and more than two PTH/PTHrP peptides. In certain embodiments, a RANKL antibody-PTH/PTHrP chimeric molecule comprises more than one RANKL antibody and one PTH/PTHrP peptide. In certain embodiments, a RANKL antibody-PTH/PTHrP chimeric molecule comprises more than one RANKL antibody and more than one PTH/PTHrP peptide.

In certain embodiments, a polypeptide comprising a light chain of a RANKL antibody and a PTH/PTHrP peptide fused to a heavy chain of a RANKL antibody is referred to as "PTH/PTHrP-αRANKL heavy chain fusion." In certain embodiments, a polypeptide comprising a heavy chain of a RANKL antibody and a PTH/PTHrP peptide fused to a light chain of a RANKL antibody is referred to as "PTH/PTHrP-αRANKL light chain fusion." In certain embodiments, a polypeptide comprising a first PTH/PTHrP peptide fused to a heavy chain of a RANKL antibody and a second PTH/PTHrP peptide fused to a light chain of a RANKL antibody, wherein the first PTH/PTHrP peptide and the second PTH/PTHrP peptide are the same or different, is referred to as "PTH/PTHrP-αRANKL heavy+light chain fusion."

In certain embodiments, a PTH/PTHrP peptide fused to the heavy chain of a RANKL antibody has the amino acid sequence shown in FIG. 12 (SEQ ID NO: 10, called synPTH-αRANKL-1 heavy chain or synPTH-αRANKL-1 IgG2). That polypeptide, along with a light chain having the sequence shown in FIG. 4 (SEQ ID NO: 4), is referred to as "synPTH-αRANKL-1 heavy chain fusion" or "synPTH- αRANKL-1 HCF". In certain embodiments, a PTH/PTHrP peptide fused to the light chain of a RANKL antibody has the amino acid sequence shown in FIG. 10 (SEQ ID NO: 8, called synPTH-αRANKL-1 light chain or synPTH-αRANKL-1 kappa). That polypeptide, along with a heavy chain having the sequence shown in FIG. 2 (SEQ ID NO: 2), is referred to as "synPTH-αRANKL-1 light chain fusion" or "synPTH-αRANKL-1 LCF". A polypeptide comprising a PTH/PTHrP peptide fused to the heavy chain of a RANKL antibody having the amino acid sequence shown in FIG. 12 (SEQ ID NO: 10, called synPTH-αRANKL-1 heavy chain or synPTH-αRANKL-1 IgG2) and a PTH/PTHrP peptide fused to the light chain of a RANKL antibody having the amino acid sequence shown in FIG. 10 (SEQ ID NO: 8, called synPTH-αRANKL-1 light chain or synPTH-αRANKL-1 kappa) is referred to as "synPTH-αRANKL-1 heavy+light chain fusion" or "synPTH-αRANKL-1 HC+LCF".

Certain Exemplary Derivatives

In certain embodiments, a RANKL antibody-PTH/PTHrP chimeric molecule is derivatized. In certain embodiments, the RANKL antibody-PTH/PTHrP chimeric molecule is derivatized after the linked molecule is produced. In certain embodiments, one or more components of the RANKL antibody-PTH/PTHrP chimeric molecule are derivatized prior to forming the RANKL antibody-PTH/PTHrP chimeric molecule. For example, in certain embodiments, a RANKL antibody and/or a linker and/or a PTH/PTHrP peptide may be derivatized before forming the chimeric molecule.

In certain embodiments, by derivatizing a reference polypeptide, the solubility, absorption, stability, and/or biological half-life of the reference polypeptide is improved. In certain embodiments, derivatizing a reference polypeptide may reduce or eliminate one or more undesirable side-effects of the reference polypeptide in vivo.

A derivative of a reference RANKL antibody-PTH/PTHrP chimeric molecule has one or more modifications of one or more amino acid residues of the reference RANKL antibody-PTH/PTHrP chimeric molecule. Certain exemplary modifications include, but are not limited to, acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

In certain embodiments, lysinyl residues and/or N-terminal amine groups may be derivatized by reaction with, e.g., succinic and/or other carboxylic acid anhydrides, which may reverse the charge of the lysinyl residues. Certain other reagents that may derivatize primary amine groups include, but are not limited to, imidoesters, including methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

In certain embodiments, an arginyl residue may be derivatized by reaction with, e.g., phenylglyoxal, 2,3-butanedione, 1,2-cyclohexanedione, and/or ninhydrin. In certain embodiments, derivatization of arginyl residues is carried out under alkaline conditions. In certain embodiments, reagents that are capable of derivatizing arginyl residues are also capable of derivatizing lysine, an N-terminal amine group, and/or the arginine epsilon-amino group.

In certain embodiments, tyrosyl residues may be derivatized by reaction with, e.g., aromatic diazonium compounds and/or tetranitromethane. In certain embodiments, tyrosyl residues may be derivatized to introduce one or more spectral labels. In certain embodiments, N-acetylimidizole and tetranitromethane may be used to form O-acetyl tyrosyl species and 3-nitro derivatives, respectively.

In certain embodiments, carboxyl side chain groups (e.g., aspartyl or glutamyl) may be selectively modified by reaction with carbodiimides (R'—N=C=N—R') such as 1-cyclohexyl-3-(2-morpholinyl-(4-ethyl) carbodiimide and/or 1-ethyl-3-(4-azonia-4,4-dimethylpentyl) carbodiimide. In certain embodiments, aspartyl and/or glutamyl residues may be converted to asparaginyl and glutaminyl residues by reaction with ammonium ions.

In certain embodiments, glutaminyl residues may be deamidated to glutamyl residues. In certain embodiments, asparaginyl residues may be deamidated to aspartyl residues. In certain embodiments, Alternatively, glutaminyl and/or asparaginyl residues may be deamidated, e.g., under mildly acidic conditions.

In certain embodiments, a cysteinyl residue can be replaced by another moiety to either eliminate disulfide bond formation with that location in the polypeptide and/or to stabilize cross-linking with another location in the polypeptide. See, e.g., Bhatnagar et al. (1996), J. Med. Chem. 39: 3814-9.

In certain embodiments, derivatization with bifunctional agents can be used to cross-link a polypeptide to another polypeptide, and/or to another molecule, moiety, surface, support matrix, and/or molecule. Certain exemplary cross-linking agents include, but are not limited to, 1,1-bis(diazoacetyl)-2-phenylethane; glutaraldehyde; N-hydroxysuccinimide esters, including esters with 4-azidosalicylic acid; homobifunctional imidoesters, including disuccinimidyl esters such as 3,3'-dithiobis(succinimidylpropionate); and bifunctional maleimides, including bis-N-maleimido-1,8-octane. In certain embodiments, a derivatizing agent may yield photoactivatable intermediates that are capable of forming crosslinks in the presence of light. Certain such derivatizing agents include, but are not limited to, methyl-3-[(p-azidophenyl)dithio]propioimidate. In certain embodiments, materials are employed fro polypeptide immobilization. Certain such materials include, but are not limited to, reactive water-insoluble matrices, including cyanogen bromide-activated carbohydrates and the reactive substrates described in U.S. Pat. Nos. 3,969,287; 3,691,016; 4,195,128; 4,247,642; 4,229,537; and 4,330,440.

In certain embodiments, carbohydrate (oligosaccharide) groups may be attached to certain sites in reference polypeptides. In certain embodiments, those sites are known to be glycosylation sites. In certain embodiments, O-linked oligosaccharides are attached to serine (Ser) and/or threonine (Thr) residues. In certain embodiments, N-linked oligosaccharides are attached to asparagine (Asn) residues. In certain embodiments, N-linked oligosaccharides are attached to asparagine (Asn) residues when they are part of the sequence Asn-X-Ser/Thr, where X is any amino acid except proline. In various embodiments, the structures of N-linked and/or O-linked oligosaccharides and the sugar residues found in each type may be the same or different. In certain embodiments, N-acetylneuraminic acid (also referred to as sialic acid) may be found both N-linked and O-linked oligosaccharides. In certain embodiments, sialic acid is the terminal residue of an N-linked and/or O-linked oligosaccharide and, by virtue of its negative charge, may confer acidic properties to the glycosylated polypeptide. In certain embodiments, a polypeptide is glycosylated at one or more locations during recombinant production (e.g., in mammalian cells such as CHO, BHK, COS). In certain embodiments, a polypeptide is glycosylated at one or more locations by synthetic or semi-synthetic procedures known in the art.

Certain exemplary modifications of a reference polypeptide include, but are not limited to, hydroxylation of proline and/or lysine, phosphorylation of a hydroxyl group of serine and/or threonine, oxidation of the sulfur atom of cysteine, methylation of the alpha-amino group of the lysine, arginine, and/or histidine side chains. See, e.g., Creighton, Proteins: Structure and Molecule Properties (W. H. Freeman & Co., San Francisco), pp. 79-86 (1983).

In certain embodiments, derivatives of reference polypeptides are prepared for pharmaceutical use. In certain embodiments, derivatives of reference polypeptides retain certain properties analogous to those of the starting polypeptide. In certain embodiments, reference polypeptides are derivatized using "peptide mimetics" or "peptidomimetics". See, e.g., Fauchere, J. Adv. Drug Res. 15:29 (1986); Veber and Freidinger TINS p. 392 (1985); and Evans et al. J. Med. Chem. 30:1229 (1987). In certain embodiments, such derivatives of reference polypeptides are developed with the aid of computerized molecular modeling. Peptide mimetics that are structurally similar to therapeutically useful peptides may, in certain embodiments, be used to produce a similar therapeutic or prophylactic effect. In certain embodiments, a derivatives of a reference polypeptide made using peptidomimetics is structurally similar to the reference polypeptide, but has one or more peptide linkages replaced by at least one linkage selected from: —$CH_2$NH—, —$CH_2$S—, —$CH_2$—$CH_2$—, —CH=CH-(cis and trans), —$COCH_2$—, —CH(OH) $CH_2$—, and —$CH_2$SO—, by methods known in the art. Substitution of one or more amino acids with a D-amino acid of the same type (e.g., D-lysine in place of L-lysine) may be used in certain embodiments to generate more stable polypeptides. In certain embodiments, a constrained derivative of a reference polypeptide may be generated by methods known in the art (see, e.g., Rizo and Gierasch Ann. Rev. Biochem. 61:387 (1992)); for example, by adding internal cysteine residues capable of forming intramolecular disulfide bonds and/or by cross-linking the reference polypeptide by other methods, which cyclizes the polypeptide.

Certain exemplary derivatives of a reference RANKL antibody-PTH/PTHrP chimeric molecule include, but are not limited to:

1. A RANKL antibody-PTH/PTHrP chimeric molecule that is cyclic. As a non-limiting example, a RANKL antibody-PTH/PTHrP chimeric molecule may be cyclized by cross-linking two cysteine residues to form an intra-molecular disulfide bond.
2. A RANKL antibody-PTH/PTHrP chimeric molecule that is cross-linked to at least one other molecule, which is the same or different. As a non-limiting example, the RANKL antibody-PTH/PTHrP chimeric molecule may be cross-linked to at least one other molecule through one or more cysteine residues. As another non-limiting example, the RANKL antibody-PTH/PTHrP chimeric molecule may be cross-linked to at least one other molecule through at least one C-terminus.
3. A RANKL antibody-PTH/PTHrP chimeric molecule that has one or more peptidyl [—C(O)NR—] linkages replaced by one or more non-peptidyl linkage. Non-limiting exemplary non-peptidyl linkages include, but are not limited to, —$CH_2$-carbamate [—$CH_2$—OC(O) NR—], phosphonate, —$CH_2$-sulfonamide [—$CH_2$—S (O)$_2$NR—], urea [—NHC(O)NH—], —$CH_2$-secondary amine, and alkylated peptide [—C(O)NR$^6$— wherein R$^6$ is lower alkyl].
4. A RANKL antibody-PTH/PTHrP chimeric molecule having at least one derivatized N-terminus. In certain embodiments, an N-terminus may be acylated or modified to a substituted amine. Non-limiting exemplary N-terminal derivative groups include, but are not limited to, —NRR$^1$ (other than —NH$_2$), —NRC(O)R$^1$, —NRC (O)OR$^1$, —NRS(O)$_2$R$^1$, —NHC(O)NHR$^1$, succinimide, and benzyloxycarbonyl-NH— (CBZ-NH—), wherein R and R$^1$ are each independently hydrogen or lower alkyl and wherein the phenyl ring may be substituted with 1 to 3 substituents selected from $C_1$-$C_4$ alkyl, $C_1$-$C_4$ alkoxy, chloro, and bromo.
5. A RANKL antibody-PTH/PTHrP chimeric molecule having at least one derivatized C-terminus. In certain embodiments, a C-terminus may be esterified or amidated. Non-limiting exemplary C-terminal derivative groups include, but are not limited to, —C(O)R$^2$ wherein R$^2$ is lower alkoxy or —NR$^3$R$^4$ wherein R$^3$ and R$^4$ are independently hydrogen or $C_1$-$C_8$ alkyl (preferably $C_1$-$C_4$ alkyl).
6. A RANKL antibody-PTH/PTHrP chimeric molecule in which at least one disulfide bond has been replaced with at least one cross-linking moiety that is not a disulfide bond (e.g., an alkylene). See, e.g., Bhatnagar et al. (1996), J. Med. Chem. 39: 3814-9; Alberts et al. (1993) Thirteenth Am. Pep. Symp., 357-9. In certain embodiments, the cross-linking moiety is more stable than the disulfide bond.
7. A RANKL antibody-PTH/PTHrP chimeric molecule in which one or more amino acid residues has been modified chemically or enzymatically. In certain embodiments, a derivatizing agent modifies one or more particular amino acid side chains.

Certain Exemplary Vehicles

In certain embodiments, a RANKL antibody-PTH/PTHrP chimeric molecule is attached, either covalently or non-covalently, to at least one vehicle. In certain embodiments, one or more vehicles are attached, either covalently or non-covalently, to a RANKL antibody-PTH/PTHrP chimeric molecule after the chimeric molecule has been produced. In certain embodiments, one or more vehicles are attached, either covalently or non-covalently, to one or more components of a RANKL antibody-PTH/PTHrP chimeric molecule prior to assembling the chimeric molecule. As a non-limiting example, one or more vehicles may be attached to a PTH/PTHrP peptide and then one or more vehicle-PTH/PTHrP peptides may be linked to a RANKL antibody to form a RANKL antibody-PTH/PTHrP chimeric molecule having one or more vehicles attached. In certain embodiments, additional vehicles may then be attached to the RANKL antibody-PTH/PTHrP chimeric molecule (which already has one or more vehicles attached).

Certain exemplary vehicles include, but are not limited to, polypeptides and small molecules (including, but not limited to, peptidomimetic compounds). In certain embodiments, a polypeptide or small molecule vehicle is capable of binding to a salvage receptor. Certain such vehicles are described, e.g., in U.S. Pat. No. 5,739,277. Certain polypeptide vehicles could be selected, e.g., by phage display or RNA-peptide screening for the ability to bind a salvage receptor (such as the FcRn salvage receptor). Such salvage-receptor binding vehicles can, in certain embodiments, be selected for longer half-lives (e.g., by avoiding sequences recognized by proteases) and/or decreased immunogenicity (e.g., by favoring non-immunogenic sequences).

Certain exemplary vehicles include, but are not limited to, polymer vehicles. Certain methods of attaching polymer vehicles to polypeptides are described, e.g., in PCT Publication No. WO 96/11953. Exemplary polymer vehicles include, but are not limited to, polyethylene glycol (PEG). In certain embodiments, modifying a therapeutic polypeptide with PEG improves the in vivo efficacy of the polypeptide. In certain embodiments, modifying a therapeutic polypeptide with PEG extends the polypeptide's circulating half-life. In certain embodiments, modifying a therapeutic polypeptide with PEG increases the polypeptide's solubility. In certain embodiments, modifying a therapeutic polypeptide with PEG reduces the polypeptide's toxicity and/or immunogenicity.

In certain embodiments, PEG may be attached to more than one therapeutic molecule, for example, in a polypeptide-PEG-polypeptide configuration. In certain embodiments, two PEG molecules are attached to a therapeutic molecule. When two PEG molecules are attached to a therapeutic molecule, in certain embodiments, the first PEG molecule may be attached to the second PEG molecule, which is then attached to the therapeutic molecule, or both the first and second PEG molecules may be attached to separate locations on the therapeutic molecule. In certain embodiments, a PEG is attached to a cysteine side chain of a polypeptide.

Certain conjugation chemistries for attaching a PEG vehicle to a polypeptide are known in the art. Certain exemplary conjugation chemistries are described, e.g., in Zalipsky, *Advanced Drug Delivery Reviews* 16:157-182 (1995). In certain embodiments, a PEG can be attached to a molecule via acylation or reductive alkylation through a reactive group on the PEG moiety (e.g., an aldehyde, amino, thiol, or ester group) to a reactive group on the molecule (e.g., an aldehyde, amino, or ester group).

In certain embodiments, a method of attaching a PEG to a polypeptide comprises combining a polypeptide and a PEG molecule, where each bears a functionality that is reactive toward the other. In certain embodiments, a polypeptide can be prepared by solid phase synthesis and "preactivated" with an appropriate functional group at a particular site. In certain embodiments, a polypeptide bearing a first functional group can be purified and/or characterized prior to reacting the polypeptide with a PEG molecule bearing a second functional group that is capable of reacting with the first functional group. In certain embodiments, the reaction of the first and second functional groups occurs in an aqueous solution. In certain embodiments, the reaction is monitored by reverse phase analytical HPLC. In certain embodiments, the reacted PEG-polypeptide molecule can be purified, e.g., by preparative HPLC, and/or characterized, e.g., by analytical HPLC, amino acid analysis and/or laser desorption mass spectrometry.

In certain embodiments, a polypeptide may be prepared by solid phase synthesis in which an orthogonal protection strategy is used to allow for attachment of one or more PEG vehicles to one or more particular amino groups. In certain embodiments, a polypeptide is synthesized with removable protecting groups on amino groups and other reactive groups that are not selected for attachment of PEG. PEG molecules are then attached to the protected polypeptide through the unprotected amino groups and/or other reactive groups. Following attachment of PEG, in certain embodiments, the protecting groups may be removed. In certain embodiments, the aforementioned method of selective attachment of PEG is useful for attaching PEG to only one of the lysine residues present in a PTH/PTHrP peptide. Thus, as a non-limiting example, for PTH(1-34), the side chain of one of the lysine residues at positions 13, 26, or 27 may be left unprotected while the other lysine residues are protected with, e.g., a Dde protecting group. After attaching PEG, the Dde groups may, in certain embodiments, be selectively removed using 2% hydrazine in water for 5 to 30 minutes at room temperature. In certain embodiments, the lysine at position 27 is selected for attachment of PEG.

In certain embodiments, solid phase synthesis may be used to prepare a polypeptide having PEG at its C-terminus. In certain such embodiments, PEG may link the polypeptide to the solid phase synthesis resin. Following synthesis of the polypeptide, the polypeptide and PEG may be cleaved from the resin such that the PEG is retained with the polypeptide.

In certain embodiments, site-directed attachment of PEG maximizes retention of biological activity while minimizing conjugate heterogeneity. In certain embodiments, site-directed attachment of PEG is achieved through recombinant protein techniques and/or selective conjugation chemistries. As a non-limiting example, site-directed mutagenesis may be used to incorporate one or more amino acids having reactive functional groups into a polypeptide at one or more positions predicted to have minimal impact on protein activity. Certain such site-directed mutagenesis is described, e.g., in Goodson, et al, *Bio/Technology* 8:343-346 (1990) and Tsutsumi, et al., *Proc. Natl. Acad. Sci.* 97:8548-8553 (2000). Exemplary amino acids having reactive functional groups include, but are not limited to, cysteine. In certain embodiments, an activated monofunctional PEG polymer may be prepared and/or obtained commercially. Certain exemplary activated PEG polymers that react with cysteine thiols include, but are not limited to, PEG-maleimide, PEG-vinylsulfone, PEG-iodoacetamide, PEG-orthopyridyl-disulphide and PEG-epoxides. In certain embodiments, a PEG-maleimide is selected for conjugating with the mutagenized polypeptide. The mutagenized polypeptide may then be combined with the activated PEG under appropriate reaction conditions to promote formation of a PEG-polypeptide conjugate. In certain embodiments, the PEG-polypeptide is purified and/or characterized.

In various embodiments, the PEG vehicle may be of any molecular weight and may be linear or branched. The average molecular weight of the PEG, in certain embodiments, ranges from about 2 kDa to about 100 kDa. In certain embodiments, the average molecular weight of the PEG is between about 5 kDa and about 50 kDa. In certain embodiments, the average molecular weight of the PEG is about 5 kDa, about 20 kDa, or about 30 kDa. In certain embodiments, the average molecular weight of linear monomethoxy PEG-maleimides are between about 5 kDa and about 30 kDa, or between about 20 kDa and about 30 kDa. In certain embodiments, the average molecular weight of a branched PEG-maleimide is about 40 kDa. In certain embodiments, a 40 kDa branched PEG-maleimide may comprise two 20 kDa polymer "arms" joined through a linker, which also serves as the polypeptide attachment site. In certain embodiments, an 8 kDa bis-functional PEG-(maleimide)$_2$ is used for a polypeptide-PEG-polypeptide conjugate.

Exemplary polymer vehicles include, but are not limited to, polysaccharide polymers. Dextrans are polysaccharide polymers comprised of individual subunits of glucose predominantly linked by α1-6 linkages. Dextran is available in many molecular weights, including, but not limited to molecular weights of about 1 kDa to about 70 kDa. In certain embodiments, dextran has a molecular weight of between about 1 kDa and about 20 kDa. In certain embodiments, dextran may be used as a vehicle by itself or in combination with another vehicle. See, e.g., PCT Publication Nos. WO 96/11953 and WO 96/05309. Exemplary use of dextran conjugated to therapeutic molecules is described, e.g., in European Patent Publication No. 0 315 456.

Certain Exemplary Uses for a RANKL Antibody-PTH/PTHrP Chimeric Molecule

In certain embodiments, methods of treating a bone disorder comprising administering a therapeutically effective amount of a RANKL antibody-PTH/PTHrP chimeric molecule are provided. In certain embodiments, methods of treating a bone disorder comprising administering a therapeutically effective amount of a RANKL antibody-PTH/PTHrP chimeric molecule and at least one additional therapeutic agent are provided. In certain such embodiments, one or more of the at least one additional therapeutic agents is administered in a therapeutically effective amount. In certain embodiments, the bone disorder is a disorder characterized at least in part by an increase in bone resorption and/or a net bone loss. In certain embodiments, treatment with a RANKL antibody-PTH/PTHrP chimeric molecule is used to suppress the rate of bone resorption. In certain embodiments, treatment may be used to reduce the rate of bone resorption in patients in which the resorption rate is above normal. In certain embodiments, treatment may be used to reduce the rate of bone resorption to below normal levels in order to compensate for below normal levels of bone formation in a patient. In certain embodiments, treatment with a RANKL antibody-PTH/PTHrP chimeric molecule is used to increase the rate of bone formation. In certain embodiments, treatment may be used to increase the rate of bone formation in patients in which the formation rate is below normal. In certain embodiments, treatment may be used to increase the rate of bone formation to above normal levels in order to compensate for above normal levels of bone resorption in a patient.

Certain exemplary conditions that may be treated include, but are not limited to, the following:

Primary and secondary hyperparathyroidism;

Tumor metastases, including metastases to bone (including metastases to bone that are related to breast and prostate cancer);

Cachexia and anorexia, including cachexia and anorexia associated with cancer;

Osteopenia, including osteopenia following surgery, osteopenia induced by steroid administration, osteopenia associated with disorders of the small and large intestine, osteopenia associated with chronic hepatic and renal diseases, and osteopenia related to or aggravated by aberrant PTH receptor signaling, including certain forms of osteoporosis;

Osteoporosis, including primary osteoporosis, post-menopausal and age-related osteoporosis, endocrine osteoporosis (including hyperthyroidism, hyperparathyroidism, Cushing's syndrome, and acromegaly), hereditary and congenital forms of osteoporosis (including osteogenesis imperfecta, homocystinuria, Menkes' syndrome, Riley-Day syndrome), and osteoporosis due to immobilization of extremities;

Osteoporosis that is secondary to other disorders, including hemochromatosis, hyperprolactinemia, anorexia nervosa, thyrotoxicosis, diabetes mellitus, celiac disease, inflammatory bowel disease, primary biliary cirrhosis, rheumatoid arthritis, ankylosing spondylitis, multiple myeloma, lymphoproliferative diseases, and systemic mastocytosis;

Osteoporosis secondary to surgery (e.g., gastrectomy) or to drug therapy, including chemotherapy, anticonvulsant therapy, immunosuppressive therapy, and anticoagulant therapy;

Osteoporosis secondary to glucocorticosteroid treatment for certain diseases, including rheumatoid arthritis (RA), systemic lupus erythematosus (SLE), asthma, temporal arthritis, vasculitis, chronic obstructive pulmonary disease, polymyalgia rheumatica, polymyositis, and chronic interstitial lung disease;

Osteoporosis secondary to glucocorticosteroid and/or immunomodulatory treatment to prevent organ rejection following organ transplant such as kidney, liver, lung, and heart transplants;

Osteoporosis due to submission to microgravity, such as observed during space travel;

Osteoporosis associated with malignant disease, such as breast cancer, prostate cancer;

Paget's disease of bone (osteitis deformans) in adults and juveniles;

Osteomyelitis, in other words, an infectious lesion in bone, leading to bone loss;

Hypercalcemia, including hypercalcemia resulting from solid tumors (including breast, lung and kidney) and hematologic malignacies (including multiple myeloma, lymphoma and leukemia), idiopathic hypercalcemia, and hypercalcemia associated with hyperthyroidism and renal function disorders;

Osteonecrosis, in other words, bone cell death, including osteonecrosis associated with traumatic injury, osteonecrosis associated with Gaucher's disease, osteonecrosis associated with sickle cell anemia, osteonecrosis associated with systemic lupus erythematosus, osteonecrosis associated with rheumatoid arthritis, osteonecrosis associated with periodontal disease, osteonecrosis associated with osteolytic metastasis, and osteonecrosis associated with other conditions; and Loss of cartilage and joint erosion associated with rheumatoid arthritis.

Certain Exemplary Uses of a RANKL Antibody-PTH/PTHrP Chimeric Molecule

In certain embodiments, a RANKL antibody-PTH/PTHrP chimeric molecule may be used alone or with at least one additional therapeutic agent for the treatment of bone disorders. In certain embodiments, a RANKL antibody-PTH/PTHrP chimeric molecule is used in conjunction with a therapeutically effective amount of an additional therapeutic agent. Certain exemplary therapeutic agents that may be administered with a RANKL antibody-PTH/PTHrP chimeric molecule include, but are not limited to, bone anti-resorptive agents, bone anabolic agents, anti-inflammatory agents, immune suppressant agents, and cancer therapy agents. Certain exemplary therapeutic agents also include, but are not limited to, bone morphogenic factors, including but not limited to BMP-1 through BMP-12; transforming growth factor-β, (TGF-β) and TGF-β family members; interleukin-1 (IL-1) inhibitors, including but not limited to, IL-1 ra and derivatives thereof, Kineret™, and anakinra; TNFα inhibitors, including but not limited to, soluble TNFα receptors, Enbrel™, etanercept, anti-TNFα antibodies, Remicade™, infliximab, Humira, adalimumab, parathyroid hormone and analogs thereof; parathyroid related protein and analogs thereof; E series prostaglandins; bisphosphonate, including but not limited to alendronate and others; bone-enhancing minerals, including but not limited to fluoride and calcium; modulators of sclerostin; non-steroidal anti-inflammatory drugs (NSAIDs), including but not limited to, COX-2 inhibitors, including but not limited to Celebrex™, celecoxib, Vioxx™, and rofecoxib; immunosuppressants, including but not limited to methotrexate and leflunomide; serine protease inhibitors, including but not limited to, secretory leukocyte protease inhibitors (SLPIs); IL-6 inhibitors (including but not limited to, antibodies to IL-6), IL-8 inhibitors (including but not limited to, antibodies to IL-8); IL-18 inhibitors (including but not limited to, IL-18 binding proteins and IL-18 antibodies); interleukin-1 converting enzyme (ICE) modulators; fibroblast growth factors, including but not limited to, FGF-1 to FGF-10, and FGF modulators; PAF antagonists; keratinocyte growth factors (KGFs), KGF-related molecules, and KGF modulators; matrix metalloproteinase (MMP) modulators; nitric oxide synthase (NOS) modulators, including but not limited to, modulators of inducible NOS; modulators of glucocorticoid receptors; modulators of glutamate receptors; modulators of lipopolysaccharide (LPS) levels; and noradrenaline and modulators and mimetics thereof.

In certain embodiments, a RANKL antibody-PTH/PTHrP chimeric molecule and particular therapeutic agents are used to treat various inflammatory conditions, autoimmune conditions, cancer, metabolic disorders, and/or other conditions with attendant bone loss. In certain embodiments, in view of the condition and the desired level of treatment, two, three, or more agents may be administered. In certain embodiments, such agents may be provided together by inclusion in the same formulation. In certain embodiments, such agents and a RANKL antibody-PTH/PTHrP chimeric molecule may be provided together by inclusion in the same formulation. In certain embodiments, such agents may be provided together by inclusion in a treatment kit. In certain embodiments, such agents and a RANKL antibody-PTH/PTHrP chimeric molecule may be provided together by inclusion in a treatment kit. In certain embodiments, such agents may be provided separately. In certain embodiments, when administered by gene therapy, the genes encoding polypeptide agents and/or a RANKL antibody-PTH/PTHrP chimeric molecule may be included in the same vector. In certain embodiments, the genes encoding polypeptide agents and/or a RANKL antibody-PTH/PTHrP chimeric molecule may be under the control of the same promoter region. In certain embodiments, the genes encoding polypeptide agents and/or a RANKL antibody-PTH/PTHrP chimeric molecule may be in separate vectors.

In certain embodiments, methods of treating bone loss associated with an IL-1 mediated disease comprise administering a RANKL antibody-PTH/PTHrP chimeric molecule and at least one interleukin-1 (IL-1) inhibitor. In certain embodiments, a RANKL antibody-PTH/PTHrP chimeric molecule may be administered prior to, concurrent with, and/or subsequent to administering at least one IL-1 inhibitor. In certain embodiments, a composition comprises a RANKL antibody-PTH/PTHrP chimeric molecule, at least one IL-1 inhibitor, and at least one additional molecule described herein. In certain embodiments, methods of treatment use at least one IL-1 inhibitor and/or at least one TNF-α inhibitor in conjunction with a RANKL antibody-PTH/PTHrP chimeric molecule. In certain embodiments, a RANKL antibody-PTH/PTHrP chimeric molecule in combination with at least one IL-1 inhibitor and/or at least one TNFα inhibitor may be used for treatment of bone loss associated with an IL-1 and/or TNFα mediated disease.

Acute and chronic interleukin-1 (IL-1)-mediated diseases include, but are not limited to, the following: acute pancreatitis; amyotrophic lateral sclerosis (ALS, or Lou Gehrig's disease); Alzheimer's disease; cachexia/anorexia, including AIDS-induced cachexia; asthma and other pulmonary diseases; atherosclerosis; autoimmune vasculitis; chronic fatigue syndrome; *Clostridium* associated illnesses, including *Clostridium*-associated diarrhea; coronary conditions and indications, including congestive heart failure, coronary restenosis, myocardial infarction, myocardial dysfunction (e.g., related to sepsis), and coronary artery bypass graft; cancer, including, but not limited to, leukemias, including multiple myeloma leukemia and myelogenous (e.g., AML and CML), and tumor metastasis; diabetes (including insulin-dependent diabetes); endometriosis; fever; fibromyalgia; glomerulonephritis; graft versus host disease and/or transplant rejection; hemorrhagic shock; hyperalgesia; inflammatory bowel disease; inflammatory conditions of a joint, including osteoarthritis, psoriatic arthritis, and rheumatoid arthritis; inflammatory eye disease, including those associated with, for example, corneal transplant; ischemia, including cerebral ischemia (including brain injury as a result of, e.g., trauma, epilepsy, hemorrhage or stroke, each of which may lead to neurodegeneration); Kawasaki's disease; learning impairment; lung diseases (including acute respiratory distress syndrome, or ARDS); multiple sclerosis; myopathies (e.g., muscle protein metabolism, including muscle protein metabolism in sepsis); neurotoxicity (including such condition induced by HIV); osteoporosis; pain, including cancer-related pain; Parkinson's disease; periodontal disease; preterm labor; psoriasis; reperfusion injury; septic shock; side effects from radiation therapy; temporal mandibular joint disease; sleep disturbance; uveitis; and an inflammatory condition resulting from, e.g., strain, sprain, cartilage damage, trauma, orthopedic surgery, infection, or other disease processes.

In various embodiments, an IL-1 inhibitor may be any polypeptide or molecule capable of specifically preventing activation of cellular receptors to IL-1, which may result from any number of mechanisms. Exemplary mechanisms include, but are not limited to, downregulating IL-1 production, binding free IL-1, interfering with IL-1 binding to its receptor, interfering with formation of the IL-1 receptor complex (i.e., association of IL-1 receptor with IL-1 receptor accessory protein), and interfering with modulation of IL-1 signaling after binding to its receptor.

Certain interleukin-1 inhibitors include, but are not limited to, IL-1 receptor antagonists, including Kineret™ and anakinra, IL-1 ra, IL-1 ra variants, and IL-1 ra derivatives, which are collectively termed "IL-1 ra proteins;" anti-IL-1 receptor monoclonal antibodies (see, e.g., EP 623674, which is hereby incorporated by reference for any purpose); IL-1 binding proteins, including soluble IL-1 receptors (see, e.g., U.S. Pat. Nos. 5,492,888, 5,488,032, and 5,464,937, 5,319,071, and 5,180,812); anti-IL-1 monoclonal antibodies (see, e.g., WO 9501997, WO 9402627, WO 9006371, U.S. Pat. No. 4,935,343, EP 364778, EP 267611 and EP 220063); IL-1 receptor accessory proteins and antibodies thereto (see, e.g., WO 96/23067 and WO 99/37773); inhibitors of interleukin-1 beta converting enzyme (ICE) or caspase I (see, e.g., WO 99/46248, WO 99/47545, and WO 99/47154), which may be used to inhibit IL-1 beta production and secretion; interleukin-1 beta protease inhibitors; and other compounds and polypeptides that block in vivo synthesis or extracellular release of IL-1.

Interleukin-1 receptor antagonist (IL-1 ra) is a human polypeptide that acts as a natural inhibitor of interleukin-1 and is a member of the IL-1 family, which includes IL-1α and IL-1β. Certain exemplary receptor antagonists, including IL-1 ra and variants and derivatives thereof, as well as methods of making and using them, are described, e.g., in U.S. Pat. No. 5,075,222; WO 91/08285; WO 91/17184; AU 9173636;

WO 92/16221; WO 93/21946; WO 94/06457; WO 94/21275; FR 2706772; WO 94/21235; DE 4219626, WO 94/20517; WO 96/22793; WO 97/28828; and WO 99/36541. In certain embodiments, an IL-1 receptor antagonist may be glycosylated. In certain embodiments, an IL-1 receptor antagonist may be non-glycosylated.

In certain embodiments, methods of treating bone loss associated with a TNFα-mediated disease comprise administering a RANKL antibody-PTH/PTHrP chimeric molecule and at least one TNFα inhibitor. In certain embodiments, a RANKL antibody-PTH/PTHrP chimeric molecule may be administered prior to, concurrent with, and/or subsequent to administering at least one TNFα inhibitor. In certain embodiments, a composition comprising a RANKL antibody-PTH/PTHrP chimeric molecule, at least one TNFα inhibitor, and at least one additional molecule described herein, may be administered.

Certain acute and chronic TNF-mediated diseases include, but are not limited to: cachexia and anorexia; cancer, including, but not limited to, leukemia; chronic fatigue syndrome; coronary conditions and/or indications, including, but not limited to, congestive heart failure, coronary restenosis, myocardial infarction, myocardial dysfunction (including but not limited to, such condition related to sepsis), and coronary artery bypass graft; depression; diabetes, including, but not limited to, juvenile onset Type 1 diabetes, diabetes mellitus, and insulin resistance (including, but not limited to, insulin resistance associated with obesity); endometriosis, endometritis, and related conditions; fibromyalgia and analgesia; graft versus host rejection; hyperalgesia; inflammatory bowel diseases, including, but not limited to, Crohn's disease and *Clostridium difficile*-associated diarrhea; ischemia, including, but not limited to, cerebral ischemia, which includes, but is not limited to, brain injury as a result of trauma, epilepsy, hemorrhage, and/or stroke; lung disease, including, but not limited to, adult respiratory distress syndrome, asthma, and pulmonary fibrosis; multiple sclerosis; neuroinflammatory diseases; ocular diseases and conditions, including, but not limited to, corneal transplant, ocular degeneration and uveitis; pain, including, but not limited to, cancer-related pain; pancreatitis; periodontal diseases; Pityriasis rubra pilaris (PRP); prostatitis, including bacterial and non-bacterial prostatitis, and related conditions; psoriasis and related conditions; pulmonary fibrosis; reperfusion injury; rheumatic diseases, including, but not limited to, rheumatoid arthritis, osteoarthritis, juvenile arthritis (including, but not limited to, juvenile rheumatoid arthritis), seronegative polyarthritis, ankylosing spondylitis, Reiter's syndrome and reactive arthritis, Still's disease, psoriatic arthritis, enteropathic arthritis, polymyositis, dermatomyositis, scleroderma, systemic sclerosis, vasculitis (e.g., Kawasaki's disease), cerebral vasculitis, Lyme disease, staphylococcal-induced ("septic") arthritis, Sjögren's syndrome, rheumatic fever, polychondritis and polymyalgia rheumatica and giant cell arteritis); septic shock; side effects from radiation therapy; systemic lupus erythematosus (SLE); temporal mandibular joint disease; thyroiditis; and tissue transplantation and/or an inflammatory condition, e.g., resulting from strain, sprain, cartilage damage, trauma, orthopedic surgery, infection (e.g., HIV, *Clostridium difficile* and related species) or other disease process.

Certain exemplary activities of TNF inhibitors include, but are not limited to, downregulating or inhibiting TNF production, binding free TNF, interfering with TNF binding to its receptor, and interfering with modulation of TNF signaling after binding to its receptor. The term "TNF inhibitor" includes, but is not limited to, solubilized TNF receptors, including soluble tumor necrosis factor receptor type I (sTNF-RI; also called the p55 receptor), soluble tumor necrosis factor receptor type II (also called the p75 receptor), Enbrel™, etanercept; antibodies to TNF, including Remicade™, infliximab, Humira™, adalimumab (see, e.g., U.S. Pat. Nos. 6,090,382 and 6,258,562); antibodies to TNF receptor; sTNF-RI (see, e.g., WO 98/24463), Avakine™; inhibitors of TNF-α converting enzyme (TACE); and other molecules that affect TNF activity.

EP 393 438 and EP 422 339, describe the amino acid and nucleic acid sequences of a soluble TNF receptor type I (also known as sTNFR-I or 30 kDa TNF inhibitor) and a soluble TNF receptor type II (also known as sTNFR-II or 40 kDa TNF inhibitor), which are collectively termed "sTNFRs". EP 393 438 and EP 422 339 also describe modified forms of sTNFR-I and sTNFR-II, including, but not limited to fragments, functional derivatives, and variants. Furthermore, EP 393 438 and EP 422 339 describe methods for isolating genes that code for the inhibitors, cloning the genes into suitable vectors, transforming or transfecting the genes into certain cell types, and expressing the genes to produce the inhibitors.

Published PCT Application No. WO 98/01555, describes truncated forms of sTNFR-I and sTNFR-II. Certain exemplary truncated sTNFR-I's include, but are not limited to, sTNFR-I 2.6D/C105, sTNFR-I 2.6D/C106, sTNFR-I 2.6D/N105, sTNFR-I 2.3D/d8, sTNFR-I 2.3D/d18, sTNFR-I 2.3D/d15, either methionylated or nonmethionylated, and variants and derivatives thereof.

In certain embodiments, methods of treating bone loss associated with inflammatory and/or autoimmune diseases comprise administering a RANKL antibody-PTH/PTHrP chimeric molecule and at least one serine protease inhibitor. In certain embodiments, a RANKL antibody-PTH/PTHrP chimeric molecule may be administered prior to, concurrent with, and/or subsequent to administering at least one serine protease inhibitor. In certain embodiments, a composition comprising a RANKL antibody-PTH/PTHrP chimeric molecule, at least one serine protease inhibitor, and at least one additional molecule described herein, may be administered.

An exemplary serine protease inhibitor is secretory leukocyte protease inhibitor (SLPI) and fragments and analogs thereof. Exemplary serine protease inhibitors also include, but are not limited to, anti-leukoprotease (ALP), mucous protease inhibitor (MPI), human seminal plasma inhibitor-I (HUSI-I), bronchial mucus inhibitor (BMI), and cervical mucus inhibitor (CUSI). In certain embodiments, a serine protease inhibitor also may be LPS modulator. See, e.g., Jin et al. (1997), Cell 88(3): 417-26. In certain embodiments, these molecules are well-suited for use in conditions leading to bone loss because they are preferentially directed to the cartilage.

Certain exemplary serine protease inhibitors are described, e.g., in U.S. Pat. Nos. 4,760,130; 5,900,400; and 5,633,227. The molecules disclosed in the foregoing references as well as any variants or analogues thereof are collectively termed "serine protease inhibitors."

In certain embodiments, a method of treating bone loss comprises administering a RANKL antibody-PTH/PTHrP chimeric molecule and at least one IL-18 inhibitor. In certain embodiments, a RANKL antibody-PTH/PTHrP chimeric molecule may be administered prior to, concurrent with, and/or subsequent to administering at least one IL-18 inhibitor. In certain embodiments, a composition comprising a RANKL antibody-PTH/PTHrP chimeric molecule, at least one IL-18 inhibitor, and at least one additional molecule described herein, is administered.

Certain exemplary conditions that may be treated include, but are not limited to, inflammation, autoimmune diseases, IL-1 mediated diseases, and TNF-mediated diseases. Certain exemplary conditions that may be treated with a RANKL antibody-PTH/PTHrP chimeric molecule and at least one IL-18 inhibitor include, but are not limited to, arthritis, including rheumatoid arthritis; systemic lupus erythematosus (SLE); graft versus host disease (GvHD); hepatitis; sepsis; and the loss of bone and cartilage accompanying these diseases.

Certain exemplary IL-18 inhibitors include, but are not limited to, antibodies that bind to IL-18; antibodies that bind to IL-18R; antibodies that bind to IL-18RAcP; IL-18 bp; IL-18R fragments (e.g., a solubilized extracellular domain of the IL-18 receptor); peptides that bind to IL-18 and reduce or prevent its interaction with IL-18R; peptides that bind to IL-18R and reduce or prevent its interaction with IL-18 or with IL-18RAcP; peptides that bind to IL-18RAcP and reduce or prevent its interaction with IL-18R; and small molecules that reduce or prevent IL-18 production or the interaction between any of IL-18, IL-18R, and IL-18RAcP.

In certain embodiments, a RANKL antibody-PTH/PTHrP chimeric molecule may be used with at least one therapeutic agent for treating bone loss associated with inflammation. In certain embodiments, a RANKL antibody-PTH/PTHrP chimeric molecule may be used with at least one therapeutic agent for treating bone loss associated with an immune disorder. Certain exemplary therapeutic agents for inflammation and immune disorders include, but are not limited to, corticosteroids, including, but not limited to, prednisolone; non-steroidal anti-inflammatory drugs (NSAIDs), including, but not limited to, cyclooxygenase type 1 (COX-1) and cyclooxygenase type 2 (COX-2) inhibitors; disease modifying anti-rheumatic drugs (DMARDs), including, but not limited to, methotrexate, hydroxychloroquine, chloroquine, cyclosporine, gold compounds (including auranofin, aurothiomalate and aurothioglucose), and leflunomide; type IV phosphodiesterase inhibitors, including, but not limited to, Rolipram and Pentoxifylline; Tacrolimus (FK-506); Sirolimus (rapamycin); mycophenolic acid; 5-lipoxygenase inhibitors, including, but not limited to, Zileuton; modulators of interleukin-6 (IL-6); small molecule modulators of 38 kDa mitogen-activated protein kinase (p38-MAPK); small molecule modulators of intracellular molecules involved in inflammation pathways, wherein such intracellular molecules include, but are not limited to, jnk, IKK, NF-κB, ZAP70, and lck. Certain exemplary therapeutic agents for inflammation are described, e.g., in C. A. Dinarello and L. L. Moldawer Proinflammatory and Anti-Inflammatory Cytokines in Rheumatoid Arthritis: A Primer for Clinicians Third Edition (2001) Amgen Inc. Thousand Oaks, Calif. Certain exemplary therapeutic agents for inflammation and autoimmune diseases include, but are not limited to, interferon gamma (IFN-γ) modulators; modulators of OX40/OX40L (including soluble forms of OX40); modulators of 4-1 BB/4-1 BB ligand (including soluble forms of 4-1 BB); and modulators of B cell-T cell costimulatory pathways, including, but not limited to, modulators of the receptor ligand pairs CD28/B7, CD40/CD40L, ICOS/B7RP1, and AGP-3/TACI/BAFFR (AGP-3 binds to both TACI and BAFFR receptors). Certain exemplary modulators of B cell-T cell costimulatory pathways include, but are not limited to, inhibitors of CD28, B7.1, and B7.2 (including soluble forms of B7.1 or B7.2 and soluble forms of CTLA4, both of which may be fused to a heterologous peptide or polypeptide which reduces or prevents degradation and/or increases half-life, reduces toxicity, reduces immunogenicity, or increases biological activity of a therapeutic polypeptide by increasing solubility or circulating half-life); inhibitors of CD40 and CD40L (including soluble forms of CD40 which may be fused to a heterologous peptide or polypeptide); inhibitors of ICOS and B7RP1 (including soluble forms of ICOS which may be fused to a heterologous peptide or polypeptide) and inhibitors of AGP-3, TACI and BAFFR (including soluble forms of TACI and BAFFR). ICOS, B7RP1 and inhibitors thereof are described, e.g., in WO00/46240. AGP-3, TACI and BAFFR and inhibitors thereof are described, e.g., in WO0/47740, WO01/85872, WO02/15273, WO98/39361, and von Bulow and Bram (1997) *Science* 278:138-140.

In certain embodiments, a RANKL antibody-PTH/PTHrP chimeric molecule may be used to treat bone loss associated with cancer. In certain embodiments, a RANKL antibody-PTH/PTHrP chimeric molecule may be used to treat bone loss associated with cancer where malignant and/or metastatic tumors have promoted the spread of cancer to bone. Certain exemplary cancers include, but are not limited to, breast, prostate, thyroid, kidney, lung, esophageal, rectal, bladder, cervical, ovarian, and liver cancers, as well as cancer of the gastrointestinal tract. In certain embodiments, a RANKL antibody-PTH/PTHrP chimeric molecule may be used to treat bone loss associated with, e.g., certain hematological malignancies. Certain hematological malignancies include, but are not limited to, multiple myeloma and lymphoma, including Hodgkin's Disease. In certain embodiments, a RANKL antibody-PTH/PTHrP chimeric molecule may be used to treat bone loss associated with hormone ablative therapy. For example, such therapy may be employed in the treatment of hormone-responsive cancer, such as breast and prostate cancer, In certain embodiments, a RANKL antibody-PTH/PTHrP chimeric molecule is administered alone. In certain embodiments, a RANKL antibody-PTH/PTHrP chimeric molecule is administered with at least one other therapeutic agent, including, but not limited to, at least one other cancer therapy agent. Certain exemplary cancer therapy agents include, but are not limited to, radiation therapy and chemotherapy. Certain exemplary chemotherapy may involve treatment with one or more of the following: anthracyclines, taxol, tamoxifene, doxorubicin, 5-fluorouracil, and other drugs known in the art. In certain embodiments, a cancer therapy agent is a luteinizing hormone-releasing hormone (LHRH) antagonist. In certain embodiments, a LHRH antagonist is a peptide antagonist.

In certain embodiments, the cancer therapy agent is an inhibitor of one or more of an epidermal growth factor receptor (EGFR), HER2, vegF, a vegF receptor, hepatocyte growth factor (HGF)/scatter factor (SF), c-Met, angiopoietin, Tie2, a platelet derived growth factor receptor (PDGFR), an insulin-like growth factor receptor (IGFR), mucin-like glycoprotein, CDC20, and CDC33, An inhibitor may be a polypeptide, antibody, peptide, peptide-Fc chimeric molecule, carbohydrate, lipid, or small molecule, In certain embodiments, the cancer therapy agent is an antibody. Certain exemplary therapeutic antibodies include, but are not limited to, mouse, mouse-human chimeric, CDR-grafted, humanized and fully human antibodies, and synthetic antibodies, including those selected by screening antibody libraries. Certain exemplary antibodies include, but are not limited to, those which bind to Her2, CDC20, CDC33, mucin-like glycoproteins, epidermal growth factor receptors (EGFRs), vegF, vegF receptors, hepatocyte growth factors (HGFs)/scatter factors (SFs), insulin-like growth factor receptors (IFGRs) and optionally induce a cytostatic and/or cytotoxic effect on tumor cells. Certain exemplary antibodies include, but are not limited to, HERCEPTIN™, trastuzumab, RITUXAN™, rituximab, AVASTIN™, bevacizumab, ZEVALIN™, ibritumomab tiuxetan, LYMPHOCIDE™, epratuzumab ERBITUX™, cetuximab, IMC-C225, BEXXAR™ tositumomab, iodine 131 tositumomab, panitumumab, and Campath.

In certain embodiments, cancer therapy agents are polypeptides which selectively induce apoptosis in tumor cells, including, but not limited to, the TNF-related polypeptide TRAIL and agonists of a TRAIL receptor. In certain embodiments, a RANKL antibody-PTH/PTHrP chimeric molecule may be administered at least one of prior to, concurrent with, and subsequent to treatment with a cancer therapy agent. In certain embodiments, a RANKL antibody-PTH/PTHrP chimeric molecule may be administered prophylactically to prevent or mitigate the onset of bone loss by metastatic cancer. In certain embodiments, a RANKL antibody-PTH/PTHrP chimeric molecule may be administered for the treatment of an existing condition of bone loss due to metastasis.

In certain embodiments, a RANKL antibody-PTH/PTHrP chimeric molecule may be used to prevent and/or treat bone loss associated with multiple myeloma and/or to prevent and/or treat the disease itself. Multiple myeloma is a B cell derived tumor that may result in significant morbidity and/or mortality. In certain instances, a clinical manifestation of multiple myeloma is focal bone loss, which may be due to increased osteoclast activation in localized regions. Many myeloma patients present with bone lesions visible by radiological analysis and suffer from skeletal pain. In certain instances, patients with myeloma are susceptible to pathological fractures of involved bone, which may occur either spontaneously or due to injury. In certain instances, the skeletal lesions that occur during myeloma not only lead to bone fractures, but also deformity and occasionally nerve compression, particularly in the vertebral spine. In some patients, a pathological increase in serum calcium (hypercalcemia) occurs, and may cause significant problems during disease treatment. In certain embodiments, a RANKL antibody-PTH/PTHrP chimeric molecule may be administered to patients to reduce or block bone resorption and release of calcium, which may reduce the risk of fractures and spinal deformity.

In certain instances, myeloma cells do not directly participate in bone destruction, but instead produce extracellular signals that lead to osteoclast differentiation and activation. In certain instances, osteoclasts produce high levels of the cytokine IL-6, particularly when they become activated. IL-6 is a B-cell growth factor, and contributes to the growth of both murine and human myeloma cells in vitro. In certain instances, myeloma cells may also either directly or indirectly produce RANKL, which may result in local bone lysis surrounding the myeloma cells embedded in bone marrow spaces. In certain instances, the normal osteoclasts adjacent to the myeloma cell in turn produce IL-6, which may lead to local expansion of the tumor cells. In certain instances, myeloma cells expand in a clonal fashion and may occupy bone spaces that are created by inappropriate bone resorption.

It has been observed that OPG administration in rodents induces rapid death of the osteoclast population. See, e.g., Lacey et al. (2000) Am. J. Pathol. 157:435-448. In certain instances, a reduction in the number of osteoclasts may counteract the effect of increased IL-6 production by those cells and may therefore affect the growth and survival of myeloma cells within trabecular bone. Thus, in certain embodiments, administration of a RANKL antibody-PTH/PTHrP chimeric molecule to a myeloma patient may not only reduce bone resorption, but may also affect the expansion and survival of the tumor itself.

B-cells express the receptor for RANKL, RANK. Myeloma cells also express RANK, and in addition may produce RANKL. In certain instances, the expression of both RANKL and RANK in the same cell population may create an autocrine stimulus that affects survival of the myeloma cell. Thus, in certain embodiments, administration of a RANKL antibody-PTH/PTHrP chimeric molecule may reduce tumor cell survival, thereby decreasing or eliminating the tumor burden seen in myeloma patients.

Certain Exemplary Pharmaceutical Compositions Comprising a RANKL Antibody-PTH/PTHrP Chimeric Molecule In certain embodiments, pharmaceutical compositions are provided comprising a therapeutically effective amount of a RANKL antibody-PTH/PTHrP chimeric molecule and a pharmaceutically acceptable diluent, carrier, solubilizer, emulsifier, preservative and/or adjuvant.

In certain embodiments, pharmaceutical compositions are provided comprising a therapeutically effective amount of a RANKL antibody-PTH/PTHrP chimeric molecule; a therapeutically effective amount of at least one additional therapeutic agent; and a pharmaceutically acceptable diluent, carrier, solubilizer, emulsifier, preservative and/or adjuvant. Exemplary additional therapeutic agents include, but are not limited to, bone morphogenic factors, including but not limited to BMP-1 through BMP-12; transforming growth factor-$\beta$ (TGF-$\beta$) and TGF-$\beta$ family members; interleukin-1 (IL-1) inhibitors, including but not limited to IL-1 ra and derivatives thereof, Kineret™, and anakinra; TNF$\alpha$ inhibitors, including but not limited to a soluble TNF$\alpha$ receptor, Enbrel™, etanercept, anti-TNF$\alpha$ antibodies, Remicade™, infliximab, Humira™, and adalimumab; parathyroid hormone and analogs thereof, parathyroid related protein and analogs thereof; E series prostaglandins; bisphosphonates (including alendronate and others); bone-enhancing minerals, including but not limited to fluoride and calcium; modulators of sclerostin; non-steroidal anti-inflammatory drugs (NSAIDs), including but not limited to COX-2 inhibitors such as Celebrex™, celecoxib, Vioxx™, and rofecoxib; immunosuppressants, including but not limited to methotrexate or leflunomide; serine protease inhibitors, including but not limited to, secretory leukocyte protease inhibitor (SLPI); IL-6 inhibitors (e.g., antibodies to IL-6), IL-8 inhibitors (e.g., antibodies to IL-8); IL-18 inhibitors (e.g., IL-18 binding protein or IL-18 antibodies); Interleukin-1 converting enzyme (ICE) modulators; fibroblast growth factors, including but not limited to FGF-1 to FGF-10 and FGF modulators; PAF antagonists; a keratinocyte growth factor (KGF), KGF-related molecules, or KGF modulators; matrix metalloproteinase (MMP) modulators; Nitric oxide synthase (NOS) modulators, including modulators of inducible NOS; modulators of glucocorticoid receptor; modulators of glutamate receptor; modulators of lipopolysaccharide (LPS) levels; and noradrenaline and modulators and mimetics thereof.

Certain exemplary pharmaceutical compositions may be for administration by injection, oral administration, pulmonary administration, nasal administration, transdermal administration, and/or other forms of administration. In certain embodiments, acceptable formulation materials are nontoxic to recipients at the dosages and concentrations employed.

In certain embodiments, the pharmaceutical composition may contain one or more formulation materials for modifying, maintaining, and/or preserving, for example, the pH, osmolarity, viscosity, clarity, color, isotonicity, odor, sterility, stability, rate of dissolution or release, rate of clearance of a compound and/or its derivatives, adsorption, and/or penetration of the composition. Certain exemplary suitable formulation materials include, but are not limited to, amino acids (including glycine, glutamine, asparagine, arginine, and lysine); antimicrobials; antioxidants (including ascorbic acid, sodium sulfite, sodium metabisulfite, and sodium hydrogensulfite); buffers (including borate, bicarbonate, acetate, Tris-HCl, citrates, phosphates, and other organic acids); bulking agents (including mannitol, lactose, and glycine); chelating agents (including ethylenediamine tetraacetic acid (EDTA)); complexing agents (including caffeine, polyvinylpyrrolidone, beta-cyclodextrin. and hydroxypropyl-beta-cyclodextrin); fillers; monosaccharides; disaccharides; and other carbohydrates (including glucose, mannose, and dextrins); polypeptides (including serum albumin, gelatin or immunoglobulins); coloring, flavoring and diluting agents; emulsifying agents; hydrophilic polymers (including polyvinylpyrrolidone); low molecular weight polypeptides; salt-forming counterions (including sodium); preservatives (including benzalkonium chloride, benzoic acid, benzyl alcohol, salicylic acid, thimerosal, phenethyl alcohol, methylparaben, propylparaben, chlorhexidine, sorbic acid, and hydrogen peroxide); solvents (including glycerin, propylene glycol, and polyethylene glycol); sugar alcohols (including mannitol and sorbitol); suspending agents; additives, including surfactants, wetting agents, detergents, and solubilizing agents (including pluronics, PEG, sorbitan esters, Tween 20, Tween 80, polysorbates such as polysorbate 20, polysorbate 80, triton, tromethamine, lecithin, cholesterol, tyloxapal); stability enhancing agents (including sucrose and sorbitol); tonicity enhancing agents (including alkali metal halides, sodium or potassium chloride, mannitol sorbitol); delivery vehicles; diluents of various buffer content, pH, and ionic strength; polymeric compounds (including polylactic acid and polyglycolic acid); excipients and/or pharmaceutical adjuvants. See, e.g., Remington's Pharmaceutical Sciences, 18$^{th}$ Edition, A. R. Gennaro, ed., Mack Publishing Company (1990).

In certain embodiments, physiologically acceptable salts of certain molecules are provided. Physiologically acceptable salts include any salts that are known or later discovered to be appropriate for one or more pharmaceutical applications. Certain exemplary physiologically acceptable salts include, but are not limited to, acetate, trifluoroacetate, hydrohalide (including hydrochloride and hydrobromide), sulfate, citrate, tartrate, glycolate, and oxylate.

In various embodiments, the compositions may be prepared in liquid form, or may be in dried form (including a powder or tablet). In certain embodiments, the compositions may be in a transdermal formulation. In certain embodiments, the compositions may be designed for sustained release.

In certain embodiments, the therapeutic agents may be diluted using an inert material. An inert material may also be used, in certain embodiments, to increase the volume of a pharmaceutical composition. Exemplary such inert materials include, but are not limited to, carbohydrates (including, e.g., mannitol, α-lactose, anhydrous lactose, cellulose, sucrose, modified dextrans, and starch). Exemplary such inert materials also include, but are not limited to, certain inorganic salts (including, e.g., calcium triphosphate, magnesium carbonate, and sodium chloride). Exemplary such inert materials also include, but are not limited to, certain commercially available diluents, including Fast-Flo, Emdex, STA-Rx 1500, Emcompress, and Avicell.

In certain embodiments, a RANKL antibody-PTH/PTHrP chimeric molecule is linked to a half-life extending vehicle known in the art. In certain embodiments, another therapeutic agent is linked to a half-life extending vehicle known in the art. Exemplary such vehicles include, but are not limited to, the Fc domain, polyethylene glycol, and dextran. Such vehicles are described, e.g., in U.S. application Ser. No. 09/428,082 and published PCT Application No. WO 99/25044.

In certain embodiments, an optimal pharmaceutical composition will be determined by one skilled in the art depending upon, for example, the intended route of administration, delivery format, and/or desired dosage. See, for example, Remington's Pharmaceutical Sciences, supra. In certain embodiments, such compositions may influence the physical state, stability, rate of in vivo release and/or rate of in vivo clearance of a RANKL antibody-PTH/PTHrP chimeric molecule.

In certain embodiments, the primary vehicle or carrier in a pharmaceutical composition may be either aqueous or non-aqueous in nature. Certain exemplary vehicles or carriers include, but are not limited to, water for injection, physiological saline solution or artificial cerebrospinal fluid, possibly supplemented with other materials common in compositions for parenteral administration. Certain exemplary vehicles or carriers include, but are not limited to, neutral buffered saline and saline mixed with serum albumin. In certain embodiments, pharmaceutical compositions comprise Tris buffer of about pH 7.0-8.5, which may further include sorbitol or a suitable substitute therefore. In certain embodiments, pharmaceutical compositions comprise acetate buffer of about pH 4.0-5.5, which may further include sorbitol or a suitable substitute therefore. In certain embodiments, a composition comprising a RANKL antibody-PTH/PTHrP chimeric molecule, with or without at least one additional therapeutic agent, may be prepared for storage by mixing the selected composition having the desired degree of purity with optional formulation agents (Remington's Pharmaceutical Sciences, supra) in the form of a lyophilized cake or an aqueous solution. In certain embodiments, a composition comprising a RANKL antibody-PTH/PTHrP chimeric molecule, with or without at least one additional therapeutic agent, may be formulated as a lyophilizate using appropriate excipients, including sucrose.

In certain embodiments, a pharmaceutical composition can be selected for parenteral delivery. In certain embodiments, the composition may be selected for inhalation or for delivery through the digestive tract, such as orally. The preparation of certain such pharmaceutically acceptable compositions is within the skill of the art.

In certain embodiments, formulation components are present in concentrations that are acceptable to the site of administration. In certain embodiments, buffers are used to maintain the composition at physiological pH or at a slightly lower pH, typically within a pH range of from about 5 to about 8, including all points between the endpoints.

In certain embodiments, when parenteral administration is contemplated, a therapeutic composition may be in the form of a pyrogen-free, parenterally acceptable aqueous solution comprising the desired RANKL antibody-PTH/PTHrP chimeric molecule, with or without additional therapeutic agents, in a pharmaceutically acceptable vehicle. In certain embodiments, a vehicle for parenteral injection is sterile distilled water in which the RANKL antibody-PTH/PTHrP chimeric molecule, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads, or liposomes, that may provide for the controlled or sustained release of the product which may then be delivered via a depot injection. In certain embodiments, hyaluronic acid may be used, and may have the effect of promoting sustained duration in the circulation. In certain embodiments, implantable drug delivery devices may be used to introduce the desired molecule.

In certain embodiments, a pharmaceutical composition may be formulated for inhalation. In certain embodiments, a RANKL antibody-PTH/PTHrP chimeric molecule, with or without at least one additional therapeutic agent, may be formulated as a dry powder for inhalation. In certain embodiments, an inhalation solution comprising a RANKL antibody-PTH/PTHrP chimeric molecule, with or without at least one additional therapeutic agent, may be formulated with a propellant for aerosol delivery. In certain embodiments, solutions may be nebulized. Certain exemplary pulmonary administration is described in PCT application no. PCT/US94/001875, which describes pulmonary delivery of chemically modified polypeptides. Certain exemplary of pulmonary administration of various polypeptides are described, e.g., in Adjei et al., Pharma. Res. (1990) 7: 565-9; Adjei et al. (1990), Internatl. J. Pharmaceutics 63: 135-44 (leuprolide acetate); Braquet et al. (1989), J. Cardiovasc. Pharmacol. 13 (suppl. 5): s.143-146 (endothelin-1); Hubbard et al. (1989), Annals Int. Med. 3: 206-12 ($\alpha$1-antitrypsin); Smith et al. (1989), J. Clin. Invest. 84: 1145-6 ($\alpha$1-proteinase); Oswein et al. (March 1990), "Aerosolization of Proteins", Proc. Symp. Resp. Drug Delivery II, Keystone, Colorado (recombinant human growth hormone); Debs et al. (1988), J. Immunol. 140: 3482-8 (interferon-$\gamma$ and tumor necrosis factor $\alpha$); and Platz et al., U.S. Pat. No. 5,284,656 (granulocyte colony stimulating factor).

In certain embodiments, a mechanical device is used for pulmonary administration of a pharmaceutical composition. Certain exemplary mechanical devices include, but are not limited to nebulizers, metered dose inhalers, and powder inhalers, certain of which are known to those skilled in the art. Certain exemplary commercially available mechanical devices include, but are not limited to, the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass. In certain embodiments, a mechanical device is used with a pharmaceutical composition formulation particularly suited for dispensing with that device. In certain embodiments, such formulations include an appropriate propellant material for use in that device.

In certain embodiments, the therapeutic agent or agents are prepared in a particulate form for most effective delivery to the distal lung. In certain embodiments, such a particulate form has an average particle size of less than 10 μm. In certain embodiments, such a particulate form has an average particle size of about 0.5 to 5 μm, including all points between the endpoints.

In certain embodiments, a pharmaceutical composition for pulmonary administration comprises a pharmaceutically acceptable carrier. Certain such carriers include, but are not limited to, carbohydrates, including trehalose, mannitol, xylitol, sucrose, lactose, and sorbitol. Certain exemplary carriers that may be included in a pharmaceutical composition for pulmonary administration include, but are not limited to, DPPC, DOPE, DSPC, and DOPC; natural and synthetic surfactants; PEG; dextrans, including cyclodextran; bile salts and other related enhancers; cellulose and cellulose derivatives; amino acids; liposomes; microcapsules and microspheres; and inclusion complexes.

In certain embodiments, a formulation for use with a nebulizer (either jet or ultrasonic), comprises the therapeutic agent or agents dissolved in water. In certain embodiments, the therapeutic agent or agents is dissolved at a concentration of about 0.1 to 25 mg/ml, including all points between the endpoints. Certain such formulations include, but are not limited to, one or more buffers and/or one or more simple sugars. In certain embodiments, addition of buffers and/or simple sugars enhances polypeptide stabilization and regulation of osmotic pressure. In certain embodiments, a nebulizer formulation contains one or more surfactants. In certain embodiments, a surfactant may reduce or prevent surface-induced aggregation of the therapeutic agent or agents caused by atomization of the solution to form the aerosol.

In certain embodiments, a formulation for use with a metered-dose inhaler device comprises a finely divided powder containing the therapeutic agent or agents suspended in a propellant with the aid of a surfactant. In certain embodiments, the propellant may be any conventional material employed for this purpose. Certain exemplary materials include, but are not limited to, chlorofluorocarbons, hydrochlorofluorocarbons, hydrofluorocarbons, and hydrocarbons, including trichlorofluoromethane, dichlorodifluoromethane, dichlorotetrafluoroethanol, and 1,1,1,2-tetrafluoroethane, and combinations thereof. Certain exemplary surfactants include, but are not limited to, sorbitan trioleate, oleic acid, and soya lecithin. In certain embodiments, a formulation for use with an inhaler device will comprise one or more bulking agents. Bulking agents include, but are not limited to, lactose, sorbitol, sucrose, mannitol, trehalose, and xylitol. Certain such bulking agents may, in certain embodiments, comprise 50 to 90% by weight (including all points between the endpoints) of the formulation and may, in certain embodiments, facilitate dispersal of the powder from the device.

In certain embodiments, a pharmaceutical composition may be formulated for nasal administration. In certain embodiments, such formulations include dextran and/or cyclodextran. In certain embodiments, delivery via transport across other mucous membranes is also contemplated.

In certain embodiments, it is contemplated that formulations may be administered orally. In certain embodiments, a RANKL antibody-PTH/PTHrP chimeric molecule, with or without at least one additional therapeutic agent, that is administered in this fashion may be formulated with or without carriers customarily used in the compounding of solid dosage forms, including tablets, capsules, pills, troches, and lozenges, cachets, or pellets. In certain embodiments, liposomal or proteinoid encapsulation may be used to formulate the compositions (as, for example, proteinoid microspheres, described, e.g., in U.S. Pat. No. 4,925,673). In certain embodiments, a capsule may be designed to release the active portion of the formulation at the point in the gastrointestinal tract when bioavailability is maximized and/or pre-systemic degradation is minimized. In certain embodiments, at least one additional agent can be included to facilitate absorption of a RANKL antibody-PTH/PTHrP chimeric molecule. In certain embodiments, at least one additional agent can be included to facilitate absorption of one or more additional therapeutic agents. In certain embodiments, additional components may be used. Certain additional components include, but are not limited to, diluents, flavorings, low melting point waxes, vegetable oils, lubricants, suspending agents, tablet disintegrating agents, and binders. In certain embodiments, liposomal encapsulation may be used. In certain embodiments, the liposomes may be derivatized with various polymers (see, e.g., U.S. Pat. No. 5,013,556). A description of certain exemplary solid dosage forms for the therapeutic can be found, e.g., in Chapter 10 of Marshall, K., Modern Pharmaceutics (1979), edited by G. S. Banker and C. T. Rhodes.

In certain embodiments, a pharmaceutical composition may comprise an effective quantity of a RANKL antibody-PTH/PTHrP chimeric molecule, with or without at least one additional therapeutic agent, in a mixture with non-toxic excipients which are suitable for the manufacture of tablets. In certain embodiments, by dissolving the tablets in sterile water, or another appropriate vehicle, solutions may be prepared in unit-dose form. Certain exemplary excipients include, but are not limited to, inert diluents, including calcium carbonate, sodium carbonate and bicarbonate, lactose, and calcium phosphate; and binding agents, including starch, gelatin, and acacia; and lubricating agents, including magnesium stearate, stearic acid, talc.

Certain exemplary additional pharmaceutical compositions will be evident to those skilled in the art, including formulations involving a RANKL antibody-PTH/PTHrP peptide chimeric molecule, with or without at least one additional therapeutic agents, in sustained- or controlled-delivery formulations. Certain exemplary techniques for formulating sustained- or controlled-delivery vehicles include, but are not limited to, liposome carriers, bio-erodible microparticles and porous beads, and depot injections. Certain techniques for formulating such sustained- or controlled-delivery vehicles are known in the art. In certain embodiments, a RANKL antibody-PTH/PTHrP chimeric molecule, with or without at least one additional therapeutic agent, can be incorporated into an inert matrix which permits release by diffusion and/or leaching mechanisms. In certain embodiments, slowly degenerating matrices may also be incorporated into the formulation, e.g., alginates and/or polysaccharides. Certain enteric coatings may have a delayed release effect. Also, PCT Application No. PCT/US93/00829 describes the controlled release of porous polymeric microparticles for the delivery of pharmaceutical compositions. In certain embodiments, sustained-release preparations may include semipermeable polymer matrices. In certain embodiments, such semipermeable polymer matrices allow water to enter and push drug out through a single small opening due to osmotic effects. See, e.g., the Oros therapeutic system (Alza Corp.). In certain embodiments, such semipermeable polymer matrices are in the form of shaped articles, e.g. films, or microcapsules. Certain exemplary sustained release matrices may include, but are not limited to, polyesters, hydrogels, polylactides (U.S. Pat. No. 3,773,919 and EP 058,481), copolymers of L-glutamic acid and gamma ethyl-L-glutamate (Sidman et al., *Biopolymers*, 22:547-556 (1983)), poly(2-hydroxyethyl-methacrylate) (Langer et al., *J. Biomed. Mater. Res.*, 15:167-277 (1981) and Langer, *Chem. Tech.*, 12:98-105 (1982)), ethylene vinyl acetate (Langer et al., supra), and poly-D(−)-3-hydroxybutyric acid (EP 133,988). In certain embodiments, sustained release compositions may include liposomes, which can be prepared by any of several methods known in the art. See e.g., Eppstein et al., *Proc. Natl. Acad. Sci. USA*, 82:3688-3692 (1985); EP 036,676; EP 088,046 and EP 143,949.

In certain embodiments, a RANKL antibody-PTH/PTHrP chimeric molecule may be chemically modified to make oral delivery efficacious. In certain embodiments, one or more additional therapeutic agents may be chemically modified to make oral delivery efficacious. In certain embodiments, the chemical modification involves attachment of a vehicle to the therapeutic agent that permits (a) inhibition of proteolysis; and/or (b) uptake into the blood stream from the stomach or intestine; and/or (c) an increase in stability of the agent; and/or (d) an increase in circulation time of the agent in the body. Certain such vehicles include, but are not limited to, PEG, copolymers of ethylene glycol and propylene glycol, poly-1,3-dioxolane, poly-1,3,6-tioxocane, carboxymethyl cellulose, dextran, polyvinyl alcohol, polyvinyl pyrrolidone, and polyproline. See, e.g., Abuchowski and Davis, Soluble Polymer-Enzyme Adducts, Enzymes as Drugs (1981), Hocenberg and Roberts, eds., Wiley-Interscience, New York, N.Y., pp. 367-83; and Newmark, et al. (1982), J. Appl. Biochem. 4:185-9.

In certain embodiments, a salt of a modified aliphatic amino acid, such as sodium N-(8-[2-hydroxybenzoyl]amino) caprylate (SNAC), may be used as a carrier to enhance absorption of a therapeutic agent. See, e.g., U.S. Pat. No. 5,792,451.

In certain embodiments, therapeutic agents may be formulated as fine multiparticulates, such as granules or pellets. In certain embodiments, such granules or pellets have a particle size of about 1 mm. In certain embodiments, for capsule administration, therapeutic agents may be formulated as a powder, lightly compressed plug, or a tablet. In certain embodiments, compression may be used to create a formulation.

In certain embodiments, a pharmaceutical composition may contain one or more colorants and/or flavoring agents. In certain embodiments, the pharmaceutical composition may take the form of a beverage containing the therapeutic agent or agents. In certain embodiments, the therapeutic agent or agents may be formulated, e.g., by liposome or microsphere encapsulation, and then included in the beverage.

In certain embodiments, one or more disintegrate may be included in a pharmaceutical composition. Certain exemplary disintegrants include, but are not limited to, starch, including commercial disintegrants that are based on starch, including Explotab. Certain exemplary disintegrants include, but are not limited to, sodium starch glycolate, Amberlite, sodium carboxymethylcellulose, ultramylopectin, sodium alginate, gelatin, orange peel, acid carboxymethyl cellulose, natural sponge, alginic acid and its sodium salt, and bentonite. Certain exemplary disintegrants include, but are not limited to, insoluble cationic exchange resins. Powdered gums, including agar, Karaya, and/or tragacanth may also be used as disintegrants and/or binders (discussed below) in certain embodiments.

In certain embodiments, one or more binders may be used to hold the therapeutic agent or agents together in, e.g., a tablet form. In certain embodiments, binders include materials from natural products, including, e.g., acacia, tragacanth, starch and/or gelatin. Certain exemplary binders include, but are not limited to, methyl cellulose (MC), ethyl cellulose (EC), and carboxymethyl cellulose (CMC). In certain embodiments, polyvinyl pyrrolidone (PVP) and/or hydroxypropylmethyl cellulose (HPMC) may be used in alcoholic solutions to granulate the therapeutic agent or agents.

In certain embodiments, an antifrictional agent may be included in a formulation of the therapeutic agent or agents to prevent sticking during the formulation process. Certain exemplary antifriction agents include, but are not limited to, lubricants, which include, but are not limited to, stearic acid (including its magnesium and calcium salts), polytetrafluoroethylene (PTFE), liquid paraffin, vegetable oils, and waxes. Certain exemplary antifriction agents include, but are not limited to, soluble lubricants, including sodium lauryl sulfate, magnesium lauryl sulfate, polyethylene glycol of various molecular weights, and Carbowax 4000 and 6000.

In certain embodiments, a glidant may improve the flow properties of the therapeutic agent or agents and/or of the pharmaceutical composition during formulation. Glidants may also aid rearrangement during compression in certain embodiments. Certain exemplary glidants include, but are not limited to, starch, talc, pyrogenic silica, and hydrated silicoaluminate.

In certain embodiments, a pharmaceutical composition comprises one or more surfactants. In certain embodiments, a surfactant may act as a wetting agent and aid dissolution of the pharmaceutical composition into an aqueous environment. Certain exemplary surfactants include, but are not limited to, anionic detergents, which include sodium lauryl sulfate, dioctyl sodium sulfosuccinate, and dioctyl sodium sulfonate; cationic detergents, which include benzalkonium chloride and benzethonium chloride; nonionic detergents, including lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose.

In certain embodiments, one or more additives are also included in the compositions to enhance uptake of the compound. Certain such additives include, but are not limited to, fatty acids, including oleic acid, linoleic acid, and linolenic acid.

In certain embodiments, one or more coatings may be included in the pharmaceutical composition. Certain exemplary coatings include, but are not limited to, sugars, nonenteric materials, including methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols; and enteric materials, including esters of phthalic acid. In certain embodiments, a mixture of materials may provide an optimum film coating. In various embodiments, film coating may be carried out in a pan coater, in a fluidized bed, and/or by compression coating.

In certain embodiments, a pharmaceutical composition to be used for in vivo administration is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, a composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it may be stored in sterile vials as a solution, suspension, gel, emulsion, solid, or as a dehydrated or lyophilized powder. In certain embodiments, such formulations may be stored either in a ready-to-use form or in a form (e.g., lyophilized) that is reconstituted prior to administration.

In certain embodiments, kits are provided for producing a single-dose administration unit. In certain embodiments, the kits may each contain both a first container having a dried polypeptide and a second container having an aqueous formulation. In certain embodiments, kits containing single and multi-chambered pre-filled syringes (e.g., liquid syringes and lyosyringes) are provided.

In certain embodiments, the effective amount of a pharmaceutical composition comprising a RANKL antibody-PTH/PTHrP chimeric molecule, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered; the indication for which the RANKL antibody-PTH/PTHrP chimeric molecule, with or without at least one additional therapeutic agent, is being used; the route of administration; and/or the size (body weight, body surface or organ size) of the patient; and/or the condition (the age and general health) of the patient. In certain embodiments, the clinician may consider the sex and/or diet of the patient and/or the severity of any infections. In certain embodiments, the clinician may titer the dosage and modify the route of administration to obtain the optimal therapeutic effect.

In certain embodiments, the frequency of dosing will take into account the pharmacokinetic parameters of the RANKL antibody-PTH/PTHrP chimeric molecule in the formulation used. In certain embodiments, the frequency of dosing will take into account the pharmacokinetic parameters of one or more additional therapeutic agents in the formulation used. In certain embodiments, a clinician will administer the composition until a dosage is reached that achieves the desired effect. In certain embodiments, the composition may therefore be administered as a single dose, or as two or more doses (which may or may not contain the same amount of the desired molecule) over time, or as a continuous infusion via an implantation device, a catheter, or other way. In certain embodiments, further refinement of the appropriate dosage is routinely made by those of ordinary skill in the art and is within the ambit of tasks routinely performed by them. In certain embodiments, appropriate dosages may be ascertained through use of appropriate dose-response data.

In certain embodiments, RANKL antibody-PTH/PTHrP chimeric molecule therapy allows for less frequent dosing than administration of PTH alone. Forteo® (teraparatide) comprises PTH[1-34] and is administered as a 20 µg dose once daily. Preos® comprises PTH[1-84] and is administered as a 100 µg dose once daily. In certain embodiments, a RANKL antibody-PTH/PTHrP chimeric molecule is administered once per week to achieve a similar effect to PTH[1-34] or PTH[1-84] administered once per day. In certain embodiments, a RANKL antibody-PTH/PTHrP chimeric molecule is administered once every two weeks, once every three weeks, or once every four weeks to achieve a similar effect to PTH[1-34] or PTH[1-84] administered once per day. In certain embodiments, a RANKL antibody-PTH/PTHrP chimeric molecule is administered once per month, once every two months, once every three months, once every six months, or once per year to achieve a similar effect to PTH[1-34] or PTH[1-84] administered once per day.

In certain embodiments, a typical dosage may range from about 0.1 µg/kg to up to about 100 mg/kg (including all points between the endpoints) or more, depending on the factors mentioned above. In certain embodiments, the dosage may range from about 0.1 µg/kg up to about 100 mg/kg; or about 1 µg/kg up to about 100 mg/kg; or about 5 µg/kg up to about 100 mg/kg; or about 0.5 mg/kg to about 20 mg/kg; or about 0.5 mg/kg to about 10 mg/kg; or about 0.5 mg/kg to about 5 mg/kg.

In certain embodiments, the route of administration of the pharmaceutical composition is in accord with certain known methods. Certain exemplary routes of administration include, but are not limited to, oral, through injection by intravenous, intraperitoneal, intracerebral (intra-parenchymal), intracerebroventricular, intramuscular, intra-ocular, intraarterial, intraportal, and/or intralesional routes; by sustained release systems and/or by implantation devices. In certain embodiments, the compositions may be administered by bolus injection, continuously by infusion, and/or by implantation device.

In certain embodiments, the composition may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, and/or continuous administration.

In certain embodiments, it may be desirable to use a pharmaceutical composition comprising a RANKL antibody-PTH/PTHrP chimeric molecule, with or without at least one additional therapeutic agent, in an ex vivo manner. In such instances, cells, tissues, and/or organs that have been removed from the patient are exposed to a pharmaceutical composition comprising a RANKL antibody-PTH/PTHrP chimeric molecule, with or without at least one additional therapeutic agent, after which the cells, tissues, and/or organs are subsequently implanted back into the patient.

In certain embodiments, a RANKL antibody-PTH/PTHrP chimeric molecule can be delivered by implanting certain cells that have been genetically engineered. In certain embodiments, one or more additional therapeutic agents can be delivered by implanting certain cells that have been genetically engineered. Methods of implantation include, but are not limited to, methods described herein and other methods known in the art. In certain embodiments, implanted genetically engineered cells express and secrete a particular molecule. In certain embodiments, such cells may be animal or human cells, and may be autologous, heterologous, or xenogeneic. In certain embodiments, the cells may be immortalized. In certain embodiments, in order to decrease the chance of an immunological response, the cells may be encapsulated to avoid infiltration of surrounding tissues. In certain embodiments, the encapsulation materials are typically biocompatible, semipermeable polymeric enclosures or membranes that allow the release of the polypeptide product(s) but prevent the destruction of the cells by the patient's immune system or by other detrimental factors from the surrounding tissues.

EXAMPLES

The following examples, including the experiments conducted and results achieved are provided for illustrative purposes only and are not to be construed as limiting the present invention.

Example 1

Preparing synPTH-αRANKL-1 Light Chain Expression Plasmid

A synthetic oligonucleotide having the sequence shown in FIG. 7 (SEQ ID NO: 5) was obtained from Picoscript (Houston, TX). That oligonucleotide sequence contains a 5' XbaI restriction site (TCTAGA) followed by a Kozak sequence (CCACC), which are shown in bold in FIG. 7. The oligonucleotide sequence also contains a synthetic coding sequence for the first 65 amino acids of human preproparathyroid protein (preproPTH). See, e.g., Genbank accession no. CAA23843. The first 65 amino acids of human prepro-PTH contains a prepro domain and amino acids 1-34 of the human PTH modulating domain. The oligonucleotide sequence also contains a coding sequence for a helical linker sequence, GGGAP (SEQ ID NO: 212). That linker coding sequence also contains a BSSHII restriction site (GCGCGC).

The synthetic oligonucleotide was cloned into plasmid pCR4.0-TOPO by Picoscript prior to delivery (oligo-pCR4.0 TOPO). Oligo-pCR4.0 TOPO was digested with XbaI and BssHII restriction endonucleases to release the synPTH coding sequence. The synPTH coding sequence was separated by agarose gel electrophoresis and purified using a QIAquick® Gel Extraction Kit (Qiagen).

The αRANKL-1 (also called αOPGL-1) light chain was amplified from αRANKL-1-kappa/pDSRα19 plasmid (also called αOPGL-1-kappa/pDSRα19, described in PCT Publication No. WO 03/002713), as follows. Ten ng of αRANKL-1-kappa/pDSRα19 plasmid DNA was used in a PCR reaction using Pfu polymerase (Stratagene). The following primers were included in the reaction:

```
5'αRANKL-1 Kappa BssHI-     (SEQ ID NO: 214):
I Primer
           BssHII
    G  A  P  E  I  V  L  T  Q  (SEQ ID NO: 240)
5'-AA CTT GGC GCG CCC GAA ATT GTG TTG ACG CAG-3';

3'Human Kappa Constant Region (SEQ ID NO: 215):
Primer
5'-CTT GTC GAC TCA ACA CTC TCC CCT GTT GAA GCT C-3'
SalI  *  C  E  G  R  N  F  S   (SEQ ID NO: 241)
```

The PCR reaction generated a 671 base pair PCR product, which encodes the amino acid sequence of αRANKL-1 light chain with 3 amino acids (GAP) of the linker sequence on the N-terminus. The 671 base pair PCR product was separated by agarose gel electrophoresis and purified using a QIAquick® Gel Extraction Kit (Qiagen). After purification, the 671 base pair PCR product was digested with BssHII and SalI, separated by agarose gel electrophoresis, and then purified using a QIAquick® Gel Extraction Kit (Qiagen). The purified fragment is referred to herein as αRANKL-1 kappa+linker coding sequence.

The purified synPTH coding sequence and the purified αRANKL-1 kappa+linker coding sequence were ligated overnight at 4° C. using T4 ligase (New England Biolabs) in the manufacturer's recommended buffer into plasmid pDSRα20 that had been previously digested with XbaI and SalI. pDSRα20 was produced from pDSRα19 (see PCT Publication No. WO 90/14363) by mutating a guanosine at position 2563 to an adenosine by site-directed mutagenesis. The ligation products were transformed into competent TOP10 cells (Invitrogen) and the cells were selected for ampicillin resistance. Plasmid from positive clones was isolated and the insert verified by DNA sequencing. The sequence of the insert is shown in FIG. 9 (SEQ ID NO: 7). That sequence encodes a polypeptide having the amino acid sequence shown in FIG. 10 (SEQ ID NO: 8), which is referred to as "synPTH-αRANKL-1 kappa" or "synPTH-αRANKL-1 light chain." That polypeptide with a polypeptide having the amino acid sequence of FIG. 2 (SEQ ID NO: 2) are together referred to as "synPTH-αRANKL-1 light chain fusion" or "synPTH-αRANKL-1 LCF".

Figure 13:
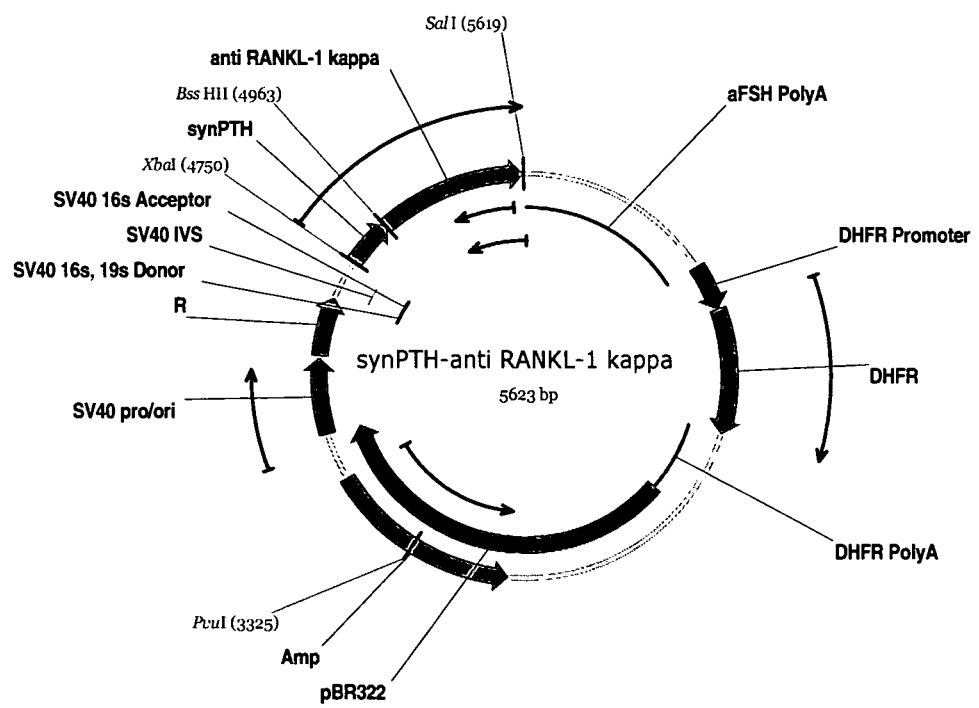
FIG. 13 shows a schematic diagram of the synPTH-αRANKL-1 (kappa) light chain expression plasmid synPTH-αRANKL-1-kappa/pDSRa20.

A schematic diagram of expression vector synPTH-αRANKL-1-kappa pDSRα20 is shown in FIG. 13. The expression vector has 5326 base pairs and contains the functional regions shown in Table 5.

TABLE 5

Features of synPTH-αRANKL-1-kappa/pDSRα20

| Plasmid location (base pairs) | Region Description |
|---|---|
| 2 to 886 | A transcription termination/polyadenylation signal from the α-subunit of the bovine pituitary glycoprotein hormone (α-FSH) (Goodwin, et al., 1983, *Nucleic Acids Res*. 11: 6873-82; Genbank Accession Number X00004) |
| 887 to 2027 | A mouse dihydrofolate reductase (DHFR) minigene containing the endogenous mouse DHFR promoter, the cDNA coding sequences, and the DHFR transcription termination/polyadenylation signals (Gasser et al, 1982, *Proc. Natl. Acad. Sci. U.S.A.* 79: 6522-6; Nunberg et al., 1980, *Cell* 19:v355-64; Setzer et al., 1982, *J. Biol. Chem.* 257: 5143-7; McGrogan et al., 1985, *J. Biol. Chem.* 260: 2307-14) |
| 2036 to 3952 | pBR322 sequences containing the ampicillin resistance marker gene and the origin for replication of the plasmid in *E. coli* (Genbank Accession Number J01749) |
| 3954 to 4297 | An SV40 early promoter, enhancer and origin of replication (Takebe et al., 1988, *Mol. Cell Biol.* 8: 466-72, Genbank Accession Number J02400) |
| 4305 to 4570 | A translational enhancer element from the HTLV-1 LTR domain (Seiki et al., 1983, *Proc. Natl. Acad. Sci. U.S.A.* 80: 3618-22, Genbank Accession Number J02029) |
| 4579 to 4735 | An intron from the SV40 16S, 19S splice donor/acceptor signals (Okayama and Berg, 1983. *Mol. Cell Biol.* 3: 280-9, Genbank Accession Number J02400) |
| 4750 to 5619 | The synPTH-αRANKL-1-kappa cDNA between the XbaI and SalI sites |

Example 2

Preparing synPTH-αRANKL-1 Heavy Chain Expression Plasmid

The synPTH coding sequence was prepared as described above in Example 1.

The αRANKL-1 (also called αOPGL-1) heavy chain was amplified from αRANKL-1-IgG2/pDSRα19 plasmid (also called αOPGL-1-IgG2/pDSRα19, described in PCT Publication No. WO 03/002713) as follows. Ten ng of αRANKL-1-IgG2/pDSRα19 plasmid DNA was used in a PCR reaction using Pfu polymerase (Stratagene). The following primers were included in the reaction:

```
5'αRANKL-1 IgG2 BssHII Primer (SEQ ID NO: 216):
    BssHII
  G  A  P  E  V  Q  L  L  E  (SEQ ID NO: 242)
5'-AA CTT GGC GCG CCC GAG GTG CAG CTG TTG GAG-3'
3' human IgG2 constant region primer
(SEQ ID NO: 217):

5'-G CAT GTC GAC TCA TTT ACC CGG AGA CAG GGA GAG-
3'
SalI  *  K  G  P  S  L  S  L  (SEQ ID NO: 243)
```

The PCR reaction generated a 1372 base pair PCR product, which encodes the amino acid sequence of αRANKL-1 heavy chain with 3 amino acids (GAP) of the linker sequence on the N-terminus. The 1372 base pair PCR product was separated by agarose gel electrophoresis and purified using a QIAquick® Gel Extraction Kit (Qiagen). After purification, the 1372 base pair PCR product was digested with BssHII and SalI, separated by agarose gel electrophoresis, and then purified using a QIAquick® Gel Extraction Kit (Qiagen). The purified fragment is referred to herein as αRANKL-1 IgG2+ linker coding sequence.

The purified synPTH coding sequence and the purified αRANKL-1 IgG2+linker coding sequence were ligated overnight at 4° C. using T4 ligase (New England Biolabs) in the manufacturer's recommended buffer into plasmid pDSRα20 that had been previously digested with XbaI and SalI. The ligation products were transformed into competent TOP10 cells (Invitrogen) and the cells were selected for ampicillin resistance. Plasmid from positive clones was isolated and the insert verified by DNA sequencing. The DNA sequence of the insert is shown in FIG. 11 (SEQ ID NO: 9) and the polypeptide encoded by the DNA sequence of FIG. 11 has the amino acid sequence shown in FIG. 12 (SEQ ID NO: 10). The polypeptide is referred to as "synPTH-αRANKL-1 IgG2" or "synPTH-αRANKL-1 heavy chain." That polypeptide, along with a polypeptide having the amino acid sequence of FIG. 4 (SEQ ID NO: 4) are together referred to as "synPTH-αRANKL-1 heavy chain fusion" or "synPTH-αRANKL-1 HCF."

Figure 14:
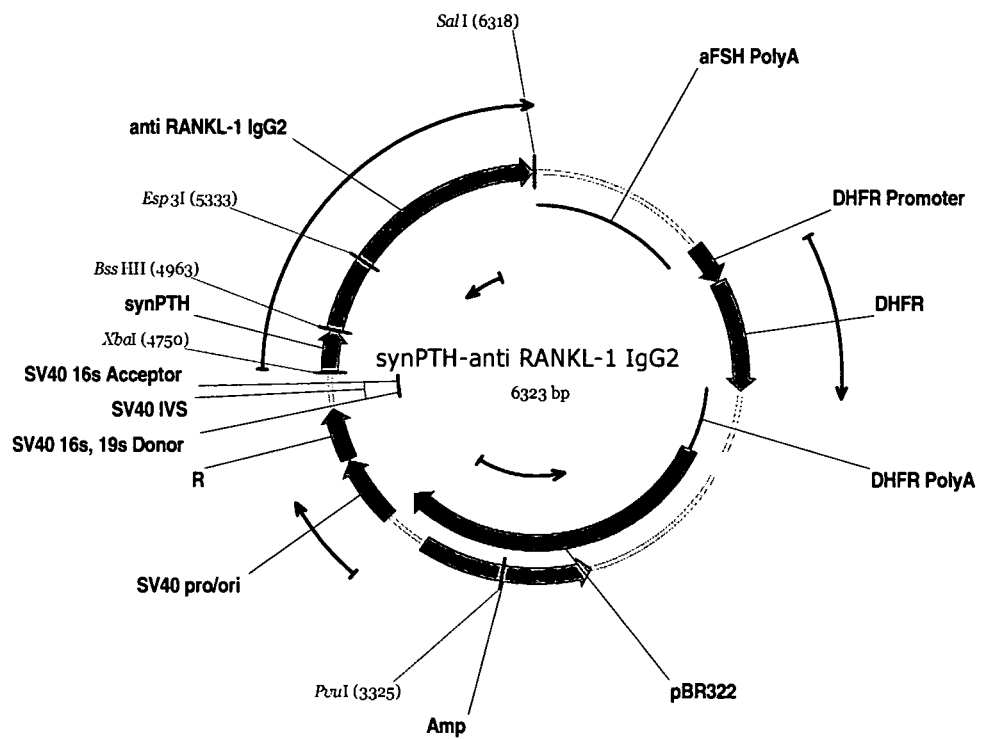
FIG. 14 shows a schematic diagram of the synPTH-αRANKL-1 (IgG2) heavy chain expression plasmid, synPTH-αRANKL-1-IgG2/pDSRa20.

A schematic diagram of expression vector synPTH-αRANKL-1-IgG2 pDSRα20 is shown in FIG. 14. The expression vector has 6323 base pairs and contains the functional regions shown in Table 6.

TABLE 6

Features of synPTH-aRANKL-1-IgG2/pDSRα20

| Plasmid location (base pairs) | Region Description |
|---|---|
| 2 to 886 | A transcription termination/polyadenylation signal from the α-subunit of the bovine pituitary glycoprotein hormone (α-FSH) (Goodwin, et al., 1983, *Nucleic Acids Res*. 11: 6873-82; Genbank Accession Number X00004) |
| 887 to 2027 | A mouse dihydrofolate reductase (DHFR) minigene containing the endogenous mouse DHFR promoter, the cDNA coding sequences, and the DHFR transcription termination/polyadenylation signals (Gasser et al, 1982, *Proc. Natl. Acad. Sci.* U.S.A. 79: 6522-6; Nunberg et al., 1980, *Cell* 19: 355-64; Setzer et al., 1982, *J. Biol. Chem.* 257: 5143-7; McGrogan et al., 1985, *J. Biol. Chem.* 260: 2307-14) |
| 2036 to 3952 | pBR322 sequences containing the ampicillin resistance marker gene and the origin for replication of the plasmid in *E. coli* (Genbank Accession Number J01749) |
| 3954 to 4297 | An SV40 early promoter, enhancer and origin of replication (Takebe et al., 1988, *Mol. Cell Biol.* 8: 466-72, Genbank Accession Number J02400) |
| 4305 to 4570 | A translational enhancer element from the HTLV-1 LTR domain (Seiki et al., 1983, *Proc. Natl. Acad. Sci. U.S.A.* 80: 3618-22, Genbank Accession Number J02029) |
| 4579 to 4735 | An intron from the SV40 16S, 19S splice donor/acceptor signals (Okayama and Berg, 1983. *Mol. Cell Biol.* 3: 280-9, Genbank Accession Number J02400) |
| 4750 to 6318 | The synPTH-αRANKL-1-IgG2 cDNA between the XbaI and SalI sites |

Example 3

Expression of synPTH-αRANKL-1

Expression in Chinese Hamster Ovary (CHO) Cells

For expression of synPTH-αRANKL-1 heavy chain fusion, dihydrofolate reductase deficient (DHFR-) serum-free adapted CHO AM-1/D (described in U.S. Pat. No. 6,210, 924) cells were co-transfected with synPTH-αRANKL-1-IgG2 pDSRα20 and αRANKL-1-kappa/pDSRα19 (also called αOPGL-1-kappa/pDSRα19; see PCT Publication No. WO 03/002713) using the calcium phosphate method. For expression of synPTH-αRANKL-1 light chain fusion, dihydrofolate reductase deficient (DHFR-) serum-free adapted CHO AM-1/D cells were co-transfected with synPTH-αRANKL-1-kappa pDSRα20 and αRANKL-1-IgG2/pDSRα19 (also called αOPGL-1-IgG2/pDSRα19; see PCT Publication No. WO 03/002713) using the calcium phosphate method.

Expression of each of the synPTH-αRANKL-1 heavy chain fusion and the synPTH-αRANKL-1 light chain fusion was carried out as follows. Transfected cells were plated in 10 cm plates and selected in DMEM media supplemented with 1× non-essential amino acids, 1× penicillin, streptomycin, glutamine, and 1× sodium pyruvate (Invitrogen) and containing dialyzed fetal bovine serum (Invitrogen) and lacking hypoxanthine-thymidine to select for cells expressing the DHFR enzyme. After two weeks of selection with media changes every three to four days, surviving colonies were combined into a master pool of transfected clones. An aliquot of the conditioned media from the master pool of transfected cells was screened by western blot to confirm expression of the secreted synPTH-αRANKL-1 light chain chimeric molecule and/or the secreted synPTH-αRANKL-1 heavy chain chimeric molecule. The master pool of transfected cells was grown for two to three weeks, with splitting and media changes, in T175 flasks and used to seed 800 cm$^2$ roller bottles at 2×107 cells per roller bottle. After two days, the cells were washed with 1×PBS and transferred to serum-free media. The cells were grown for one week to condition the media. Two to three harvests of serum-free medium conditioned for seven days were combined and used for purification of recombinant protein.

Expression in 293T Cells

For expression of synPTH-αRANKL-1 heavy+light chain fusion (also called synPTH-αRANKL-1 HC+LCF), 293T cells that had been adapted to growth in serum-free media were co-transfected with synPTH-αRANKL-1-IgG2 pDSRα20 and synPTH-αRANKL-1-kappa pDSRα20. Transfections were carried out in 500 mL or 1 L cultures as follows. The cell inoculum (5×105 cells/mL× culture volume) was centrifuged at 2500 rpm for 10 minutes at 4° C. to remove conditioned medium. The cells were resuspended in serum-free DMEM (Invitrogen) and centrifuged again at 2500 rpm for 10 minutes at 4° C. After aspirating the wash solution, the cells were resuspended in growth medium (DMEM/F12 at a ratio of 3:1, supplemented with 1× Insulin-Transferrin-Selenium Supplement, 1× Penicillin, Streptomycin, Glutamine, 2 mM L-Glutamine, 20 mM HEPES, 0.01% Pluronic F68) in a 1 L or 3 L spinner flask. The spinner flask culture was maintained with 125 rpm stirring in a humidified incubator at 37° C. and 5% CO2.

Plasmid DNA was complexed with the transfection reagent (X-TremeGene RO-1539; Roche) in a 50 mL conical tube as follows. One μg of plasmid DNA per mL culture was added to 5% of the final culture volume of serum-free DMEM, followed by 1 μL X-TremeGene RO-1539 (Roche) per mL of culture. The DNA/transfection reagent complex was incubated at room temperature for approximately 30 minutes and then added to the cells in the spinner flask. The transfection/expression was performed over seven days, after which the conditioned medium was harvested by centrifugation at 4000 rpm for 60 minutes at 4° C.

Example 4

Purification of synPTH-αRANKL-1

SynPTH-αRANKL-1 heavy chain fusion (comprising synPTH fused to a αRANKL-1 heavy chain (SEQ ID NO: 10) and αRANKL-1 light chain (SEQ ID NO: 4)), synPTH-αRANKL-1 light chain fusion (comprising synPTH fused to a αRANKL-1 light chain (SEQ ID NO: 8) and αRANKL-1 heavy chain (SEQ ID NO: 2)), or synPTH-αRANKL-1 heavy+light chain fusion (comprising synPTH fused to a αRANKL-1 heavy chain (SEQ ID NO: 10) and synPTH fused to a αRANKL-1 light chain (SEQ ID NO: 8)) were purified from the host cells as follows. All purification processes were carried out at room temperature.

Purification of synPTH-αRANKL-1 Heavy Chain Fusion and synPTH-αRANKL-1 Light Chain Fusion The host cell culture fluid (CCF) from CHO cell expression of synPTH-αRANKL-1 heavy chain fusion and synPTH-αRANKL-1 light chain fusion were separately centrifuged in a Beckman JS-4.2 rotor at 3500 rpm for 1 hour at 4° C. to remove cell debris. The CCF supernatant was then filtered through a sterile 0.2 μm filter. In some instances, the filtered CCF supernatant was then concentrated by tangential flow ultrafiltration using a 10 kD or a 30 kD molecular weight cut-off membrane. The CCF supernatant was then loaded onto a Protein A column (Amersham/Pharmacia) equilibrated in PBS. After loading, the column was washed with PBS until the absorbance at 280 nm of the flow-through returned to baseline. The synPTH-αRANKL-1 was eluted from the column using 20 mM acetic acid, 10 mM sodium chloride, pH 3.2. The absorbance at 280 nm of the eluate was monitored and fractions containing protein were collected. The fractionation tubes contained 20 μl of 1 M Tris base, pH 11 per 1 ml of eluate.

The synPTH-αRANKL-1 eluted from the Protein A column was adjusted to pH 5.0 with 50% acetic acid and then loaded directly onto a cation exchange column (SPHP chromatography resin, Amersham/Pharmacia) that was equilibrated with 20 mM acetate, pH 5.0. After loading, the column was washed with 20 mM acetate, pH 5.0. The synPTH-αRANKL-1 was then eluted using a linear gradient of 0 M sodium chloride to 0.5 M sodium chloride in 20 mM acetate, pH 5.0. The absorbance at 280 nm of the eluate was monitored and the eluted synPTH-αRANKL-1 was collected in fractions. The fractions were assayed by Coomassie-stained SDS-PAGE to identify fractions containing a polypeptide that migrated at the predicted size of the synPTH-αRANKL-1.

The fractions containing synPTH-αRANKL-1 heavy chain fusion or synPTH-αRANKL-1 light chain fusion were pooled separately, filtered through a 0.2μ Posidyne filter, aliquoted, and then stored at 4° C. in 20 mM sodium acetate, 350 mM sodium chloride, pH 5.0.

Purification of synPTH-αRANKL-1 Heavy+Light Chain Fusion

The host cell culture fluid (CCF) from 293T cell expression of synPTH-αRANKL-1 heavy+light chain fusion was centrifuged in a Beckman JS-4.2 rotor at 3500 rpm for 1 hour at 4° C. to remove cell debris. The CCF supernatant was then filtered through a sterile 0.2 μm filter. In some instances, the filtered CCF supernatant was concentrated by tangential flow ultrafiltration using a 10 kD or a 30 kD molecular weight cut-off membrane. The CCF supernatant was then loaded onto a Protein A column (Amersham/Pharmacia) equilibrated in PBS. After loading, the column was washed with PBS until the absorbance at 280 nm of the flow-through returned to baseline. The synPTH-αRANKL-1 heavy+light chain fusion was eluted from the column using 20 mM acetic acid, 10 mM sodium chloride, pH 3.2. The absorbance at 280 nm of the eluate was monitored and fractions containing protein were collected.

The fractions containing synPTH-αRANKL-1 heavy+ light chain fusion were pooled, adjusted to pH 5.0 with 1 M Tris base pH 11, filtered through a 0.2μ Posidyne filter, aliquoted, and stored at 4° C. in 20 mM sodium acetate, 10 mM sodium chloride, pH 5.0.

Example 5 synPTH-αRANKL-1 Heavy Chain Fusion Activity

Human RANKL "knockin" mice (huRANKL mice) were generated as described below.
Identification of Murine BAC Clone Containing RANKL Oligo Primer Analysis Software, Version 5.0 (Wojciech & Piotr Rychlik, Plymouth, Minn.) was used to generate 2 sets of primer pairs to exon 5 of murine RANKL(Primer Sets A & B) as well as one set of primer pairs spanning exons 3 and 4 of murine RANKL (Primer Set C). Primer Set A (2699-81 and 2699-82) generates a 259 base pair PCR product. Primer Set B (2699-83 and 2699-84) generates a 326 base pair PCR product while Primer Set C (2699-86 and 2699-87) generates a 273 base pair product.

```
Primer Set A:
2699-81:
GCA TCA TGA AAC ATC GGG AAG C    (SEQ ID NO: 218)

2699-82:
CCC AAA GTA CGT CGC ATC TTG A    (SEQ ID NO: 219)

Primer Set B:
2699-83:
GTT AAG CAA CGG AAA ACT AAG G    (SEQ ID NO: 220)

2699-84:
CAA AGT ACG TCG CAT CTT GAT      (SEQ ID NO: 221)

Primer Set C:
2699-86:
GCA AGG TAG GGT TCA ACT GA       (SEQ ID NO: 222)

2699-87:
GTC CTG TAT GGG TGG TAG TCT T    (SEQ ID NO: 223)
```

Primers were tested using ES cell DNA to confirm that each primer pair amplified a band of the predicted size. Primer Set A was used to screen the Down-to-the-Well Mouse ES BAC DNA Pools-Release I (Genome Systems, Inc., St. Louis, Mo.), a library that represents three genomic equivalents. This library is contained in 240 microtiter dishes and the clones in these dishes have been pooled to allow for identification of an individual clone by performing three sequential rounds of PCR. Initially, the 24 "upper pools", each consisting of DNA from 10 microtiter plates, as well as negative controls (water and irrelevant DNA) were amplified using Primer Sets A, B, and C. PCR and thermocycling was performed using standard recombinant DNA technology. An aliquot of each PCR reaction was run on a 2% Agarose/TAE gel. Pool 18, corresponding to microtiter plates 171-180, was identified as being strongly positive with all 3 primer sets. Individual plate pools for microtiter plates 171-180 were then amplified, identifying plate pool 172 as the positive plate. Down-to-the-Well pools amplified using Primer Set A identified well G10 as the location on plate 172 for the BAC clone desired. Clone Mu ES BAC DNA 172G10 was obtained from Genome Systems. PCR reactions with Primer Sets A, B and C gave distinct bands confirming that this clone contained the desired region of murine RANKL.
RANKL Knock-in Vector A 1.4 kb DNA fragment with homology to the 3' region of exon 5 of the mouse RANKL genomic locus was generated by PCR amplification using Pfu Turbo Hotstart DNA Polymerase (Stratagene), the Mu ES BAC DNA 172G10 and the following primers:

```
2796-94:
ATTGCGATCGCGTTACTGGGAGAAGTGCAGATTT (SEQ ID NO: 224)

2796-95:
AATGGCGCGCCCATAGCGTAGCGTTCATTATCCT (SEQ ID NO: 225)
```

The resulting PCR fragment contained an SgfI restriction enzyme site at the 5' end and an AscI restriction enzyme site at the 3' end. The PCR fragment was digested with SgfI and AscI. Vector pAMGENKO3 (Amgen proprietary vector) was also digested with SgfI and AscI. The digested PCR fragment and the large fragment of the digested pAMGENKO3 vector were gel purified using Gel Purification Kit (Qiagen). The purified PCR fragment was ligated into the purified large fragment of pAMGENKO3 and transformed into Electro Max DH10B competent E. coli cells (Invitrogen). Ten colonies were picked and grown for 4 hours on LB plates containing ampicillin. The bacteria were directly screened by PCR analysis for short arm positive colonies using the 2796-94 and 2796-95 primers and Taq polymerase (PerkinElmer). Plasmid DNA from short arm positive colonies was prepared using a Spin Miniprep Kit (Qiagen). Diagnostic restriction enzyme analysis was conducted on prepared plasmid DNA using SgfI and AscI enzymes. A plasmid that was positive in both the short arm PCR analysis and the diagnostic restriction enzyme analysis was selected and labeled pAMGENKO3-OPGL-SA.

A 4.9 kb DNA fragment with homology to the intron between exon 4 and exon 5 of the mouse RANKL genomic locus was generated by PCR amplification using Advantage HF 2 PCR kit (BD Biosciences Clontech), clone Mu ES BAC DNA 172G10, and primers:

```
2802-13:   ATTGCGGCCGCAGTGGACTTACTCAAACCTTCT
           (SEQ ID NO: 244)

2802-12:   ACCCGCTCGAGGATACTAGTGATGGAGCAACATG
           (SEQ ID NO: 213)
```

The resulting PCR fragment contained a NotI restriction enzyme site at the 5' end and an XhoI restriction enzyme site at the 3' end. The PCR fragment and pAMGENKO3-OPGL-SA were separately digested with NotI and XhoI. The digested PCR fragment and the large fragment of the digested pAMGENKO3-OPGL-SA were then separately gel purified using Qiagen Gel Purification Kit. The purified PCR fragment was ligated into the purified large fragment of pAMGENKO3-OPGL-SA and transformed into Electro Max DH10B competent E. coli cells. Sixty-four colonies were picked and grown for 4 hours on LB plates containing ampicillin. The bacteria were directly screened for the presence of the long arm by PCR analysis using Taq polymerase with primers:

```
2797-56: TGCAATCTGCGCCTCAGTCTTC    (SEQ ID NO: 226)

2797-57: ATTTCTCACCGTCGGCATCTCC    (SEQ ID NO: 227)
```

Plasmid DNA from long arm positive colonies was prepared using a Spin Miniprep Kit (Qiagen). Diagnostic restriction enzyme analysis on the prepared plasmid DNA was then conducted using NotI and XhoI enzymes. A plasmid that was positive in both the long arm PCR analysis and the diagnostic restriction enzyme analysis was selected and labeled pAMGENKO3-OPGL-SA-LA.

The 0.25 kb mouse RANKL fragment with a BstZ17I restriction site (engineered in the 5' end for long arm screening) was generated by PCR amplification using Pfu Turbo Hotstart DNA Polymerase, clone Mu ES BAC DNA 172G10, and primers:

2796-88: ATTCTCGAGGTATACCTATAGCTTAAGGGCAGGATAGA (SEQ ID NO:228)

2796-89: CTTTATGGGAACCTAGAGAGAAAC (SEQ ID NO:229)

The 0.41 kb coding region of exon 5 of human RANKL was generated by PCR amplification from human cDNA using Pfu Turbo Hotstart DNA Polymerase and primers:

2796-90: TCTAGGTTCCCATAAAGTGAGTCTGT (SEQ ID NO:230)

2796-91: TTCCACGAAATGAGTCTCAATCTATATCTCGAACTTTAAAA (SEQ ID NO:231)

Since the 0.25 kb mouse RANKL fragment overlaps with the 0.41 kb human RANKL exon 5 fragment, a larger 0.66 kb fragment was generated using primers (2796-88 and 2796-91) and Pfu Turbo Hotstart DNA Polymerase. A 1.24 kb mouse 3' untranslated region of exon 5 of RANKL was generated by PCR amplification using Pfu Turbo Hotstart DNA Polymerase, clone Mu ES BAC DNA 172G10, and primers:

2796-92: GTTCGAGATATAGATTGAGACTCATTTCGTGGAACATTA (SEQ ID NO:232)

2796-93: ATTGGCCGGCCCTTTGGAGAAAGATAGAAGCCAC (SEQ ID NO:233)

Since the 1.24 kb PCR fragment overlaps with the 0.66 kb PCR fragment, a larger 1.9 kb chimeric knock-in fragment was generated by PCR with Pfu Turbo Hotstart DNA Polymerase and the primers 2796-88 and 2796-93. The amplified PCR fragment contained an XhoI restriction enzyme site at the 5' end and an FseI restriction enzyme site at the 3' end. The PCR fragment and pAMGENKO3-OPGL-SA-LA were separately digested with NotI and XhoI. The digested PCR fragment and the large fragment of the digested pAMGENKO3-OPGL-SA-LA were separately gel purified using Qiagen Gel Purification Kit. The purified PCR fragment was ligated to the purified large fragment and transformed into Electro Max DH10B competent *E. coli* cells (Invitrogen). Twenty colonies were picked from the ligation reaction and grown for 4 hours on LB plates containing ampicillin. The bacteria were directly screened by PCR with primers.

2796-92: GTTCGAGATATAGATTGAGACT-
CATTTCTGGAACATTA (SEQ ID NO: 232)

2796-93: ATTGGCCGGCCCTTTGGAGAAAGATA-
GAAGCCAC (SEQ ID NO: 233)

Plasmids from PCR positive colonies were prepared using Miniprep Kit (Qiagen). Restriction enzyme digestion with XhoI and FseI followed by electrophoresis on a 1% agarose gel was used to confirm the presence of the insert. Positive DNAs were confirmed by sequencing. The final knock-in targeting vector was called pAMGENKO3-OPGL-KI.

A large plasmid preparation of the pAMGENKO3-OPGL-KI targeting construct was prepared using Qiagen plasmid Mega kit. Two hundred micrograms of pAMGENKO3-OPGL-KI was linearized with NotI and then purified by adding half a volume of 7.5 M ammonium acetate and one volume of phenol/chloroform (GIBCO BRL), vortexing to mix, and centrifuging for 5 minutes at 10,000 rpm. The aqueous layer was transferred to a clean tube and one volume of chloroform (GIBCO BRL) was added. The mixture was then vortexed to mix and centrifuged for 2 minutes at 10,000 rpm. The aqueous layer was transferred to a clean tube and 2.5 volumes of 100% ethanol was added. The solution was then mixed by inverting the tube several times and centrifuging for 10 minutes at 10,000 rpm. The supernatant was removed and the pelleted DNA at the bottom of the tube was washed with 70% ethanol and resuspended in 10 mM Tris-HCL and 1 mM EDTA, pH 8.0 buffer.

Embryonic Stem Cell Targeting and Generation of Knockin Mice

GS-1 Embryonic Stem (ES) cells (129SvJ; Genome Systems) were grown in Dulbecco's modified Eagle medium (DMEM) (Invitrogen) supplemented with 15% Fetal Bovine Serum (FBS) (Hyclone), 100 µg/ml penicillin/streptomycin (Invitrogen), 2 mM glutamine (Invitrogen), 103 units/ml leukemia inhibitory factor (LIF) (Chemicon), 0.1 mM NEAA (Life Technologies), and 0.1 µM 2-mercaptoethanol (Life Technologies). Mouse embryonic fibroblast (MEF) feeder cells were grown in Dulbecco's modified Eagle medium (DMEM) (Invitrogen) supplemented with 10% Fetal Bovine Serum (FBS) (Hyclone), 100 µg/ml penicillin/streptomycin (Invitrogen), and 2 mM glutamine (Invitrogen). MEFs were derived from explanted day 13-14 fetuses of neomycin-resistant mice. Prior to use as feeder layers for ES cells, MEFs were inactivated by treatment with 10 µg/ml mitomycin C (Roche) for 2-3 hours. Both MEFs and ES cells were grown at 37° C., 5% $CO_2$.

For targeting, $10^7$ GS-1 ES cells (129SvJ; Genome Systems) were mixed with 25 µg of linearized pAMGENKO3-OPGL-KI and electroporated at 250 V, 500 µF with a Bio-Rad Gene Pulser. Transfected clones were selected in G418 (210 µg/ml active ingredient) (Invitrogen) and FIAU (0.2 µM final concentration) (Moravek) on neomycin-resistant MEF feeder cells. After 7 days of selection, clones were picked, trypsinized, and plated in 96 wells in triplicate. Two sets of plates were frozen in freezing medium consisting of 10% DMSO (Sigma), 10% FBS, and DMEM. The wells were then covered with a layer of sterile mineral oil (Sigma) and the sealed plates were placed in Styrofoam boxes for freezing at −80° C. The third set of plates was used for PCR and Southern analyses. The cells were rinsed with PBS and incubated at 60° C. overnight in lysis buffer (10 mM Tris, 10 mM EDTA, 10 mM NaCl, 0.5% sarcosyl, and 1 mg/ml proteinase K). DNA was precipitated from the plates using 7.5 M $NH_4OAc$, followed by 70% ethanol washes, and finally resuspended in TE pH 8.0.

To screen for homologous recombination in the short arm side, DNAs from ES cell clones were screened using Expand High Fidelity PCR Kit (Roche) with one PCR primer annealing in the neomycin resistance cassette and one PCR primer annealing in the genomic region outside the short arm:

2818-35: GATCTCTCGTGGGATCATTGTT (SEQ ID NO:236)

-continued

```
                                              (SEQ ID NO:237)
    2818-36: AACCCACTTAGAAGATGCTGCT
```

In addition, the presence of the human RANKL exon 5 was assessed by PCR using primers 2817-87 and 2797-55. For PCR positive DNAs, Southern Blot analysis was used to confirm homologous recombination on the long arm side as follows. Genomic DNAs were digested with BstZ171 (New England Biolabs) overnight and resolved by electrophoresis on a 0.9% agarose gel in 1×TAE buffer overnight (the wild type allele produces a 16 kb fragment versus a 12 kb fragment for the targeted allele). The gel was denatured twice by treatment with 0.5 M NaOH/1.5 M NaCl for 15 minutes and then neutralized twice by treatment with 0.5 M Tris-HCl pH 7.0/1.5 M NaCl for 15 minutes. Digested DNAs were then transferred to a Nytran SuperCharge Nylon membrane (Schleicher & Schuell) in 20×SSC overnight using a Rapid Downward Transfer Systems (Schleicher & Schuell) and then crosslinked using a UV Stratalinker 2400 (Stratagene). The membrane was prehybridized with Express Hybridization Solution (Clontech) at 60° C. for 3 hours and transferred to Express Hybridization buffer containing $1.5 \times 10^6$ cpm/ml radiolabeled long arm probe at 60° C. for 3 hours. The probe was labeled with $\alpha^{32}P$ dCTP (3000 Ci/mmol, Amersham) using a random primer labeling kit (Amersham) and purified with a Sephadex G-50 Quick Spin Column (cat. #1273965, Roche). The hybridization membrane was washed once with 2×SSC and 0.1% SDS, at room temperature for 15 minutes, then washed once with 0.1×SSC and 0.1% SDS at 60° C. for 20 minutes. The hybridization membrane was then exposed to imaging film for several days (depending on the strength of the signal). Wild type allele was represented as a 16 kb band on a Southern Blot, while the targeted allele was a 12 kb band.

After ES clones that had undergone homologous recombination were identified by PCR and Southern blot analyses, previously frozen stocks (described above) were thawed and injected into 2.5 day C57Bl/6 (Taconic) blastocysts. The injected blastocysts were then introduced into pseudopregnant females and germ line transmitting chimeras were identified. Offspring of these chimeras were genotyped by PCR to identify mice that were heterozygous for the targeting event and these heterozygous mice were subsequently bred to each other to obtain homozygous knock-in mice.

Screening for Heterozygous and Homozygous Knock-in Mice

Tail DNAs from the mice were isolated using DNeasy Kit (Qiagen) and screened by PCR using puRetaq Ready-to-Go PCR Beads (Amersham) using the following primers:

```
                                              (SEQ ID NO:238)
    3151-52: CATGGAACTTGGGAGTGACTTT (SEQ ID NO:239)
    3151-53: TCAAGGTTCTCAGTGGCACAT
```

The PCR product was purified using Qiaquick PCR Purification (Qiagen) and cut with BstZ171. The resulting fragments were resolved on a 1% percent agarose gel with the wild type allele represented as 1.5 kb band and the targeted allele represented as 0.9 kb and 0.6 kb bands. Therefore, a 1.5 kb band only represents a wild type mouse, a mixture of 0.9 kb and 0.6 kb bands represents a homozygous knock-in mouse, and a mixture of 1.5 kb, 0.9 kb, and 0.6 kb bands represents a heterozygous mouse.

Biological Activity of synPTH-αRANKL-1 Heavy Chain Fusion

The activity of synPTH-αRANKL-1 heavy chain fusion was determined in mice as follows.

Protocol

Ten month old female human RANKL knock-in mice (huRANKL mice) and wild-type mice were used for the study (n=6 per group). The huRANKL mice were injected subcutaneously (SC) at the neck with vehicle (PBS), human PTH (1-34) (100 µg/kg, 5 days/week), αRANKL-1 (2 or 10 mg/kg, once/week; αRANKL-1 comprises a heavy chain having the amino acid sequence of SEQ ID NO: 2 and a light chain having the amino acid sequence of SEQ ID NO: 4; also called αOPGL-1, see PCT Publication No. WO 03/002713), or synPTH-αRANKL-1 heavy chain fusion (2 or 10 mg/kg, once/week). Wild-type mice were treated with vehicle (PBS) or with synPTH-αRANKL-1 heavy chain fusion (2 mg/kg, once/week). PTH(1-34) was diluted into 0.001N HCl, 0.15M NaCl and 2% bovine serum albumin, and αRANKL-1 and synPTH-αRANKL-1 were diluted into PBS.

Bone mineral density was analyzed at baseline (prior to initiation of treatment) and then at weeks 1, 2, and 3 after the treatment. Blood samples were also collected at baseline, and at 2, 6, 24, 48, and 72 hours, and then weekly thereafter. The blood samples were used for whole blood ionized calcium analysis, osteocalcin analysis, and TRAP-5b analysis. At the end of the study, tibiae were collected for dynamic and static histomorphometry. All animals were housed in filter-top cages with food and water ad libitum on a 12-hour light dark cycle.

Biochemical Markers of Bone Turnover

Blood ionized calcium was determined at baseline, and at 2 hours, 6 hours, 24 hours, 48 hours, and 72 hours after treatment as follows. Mice were anesthetized with isofulrane (Abbott Laboratories, North Chicago, Ill.) and blood samples were collected retro-orbitally into heparinized capillary tubes (Fisher Scientific). Whole blood ionized calcium levels were determined using a Model 634 $Ca^{++}$/pH Analyzer (Chiron Diagnostics, Norwood, Mass.) before treatment (baseline) and on days 3 and 5. The measured calcium levels were adjusted to account for the variations in pH from pH 7.1.

Figure 15:
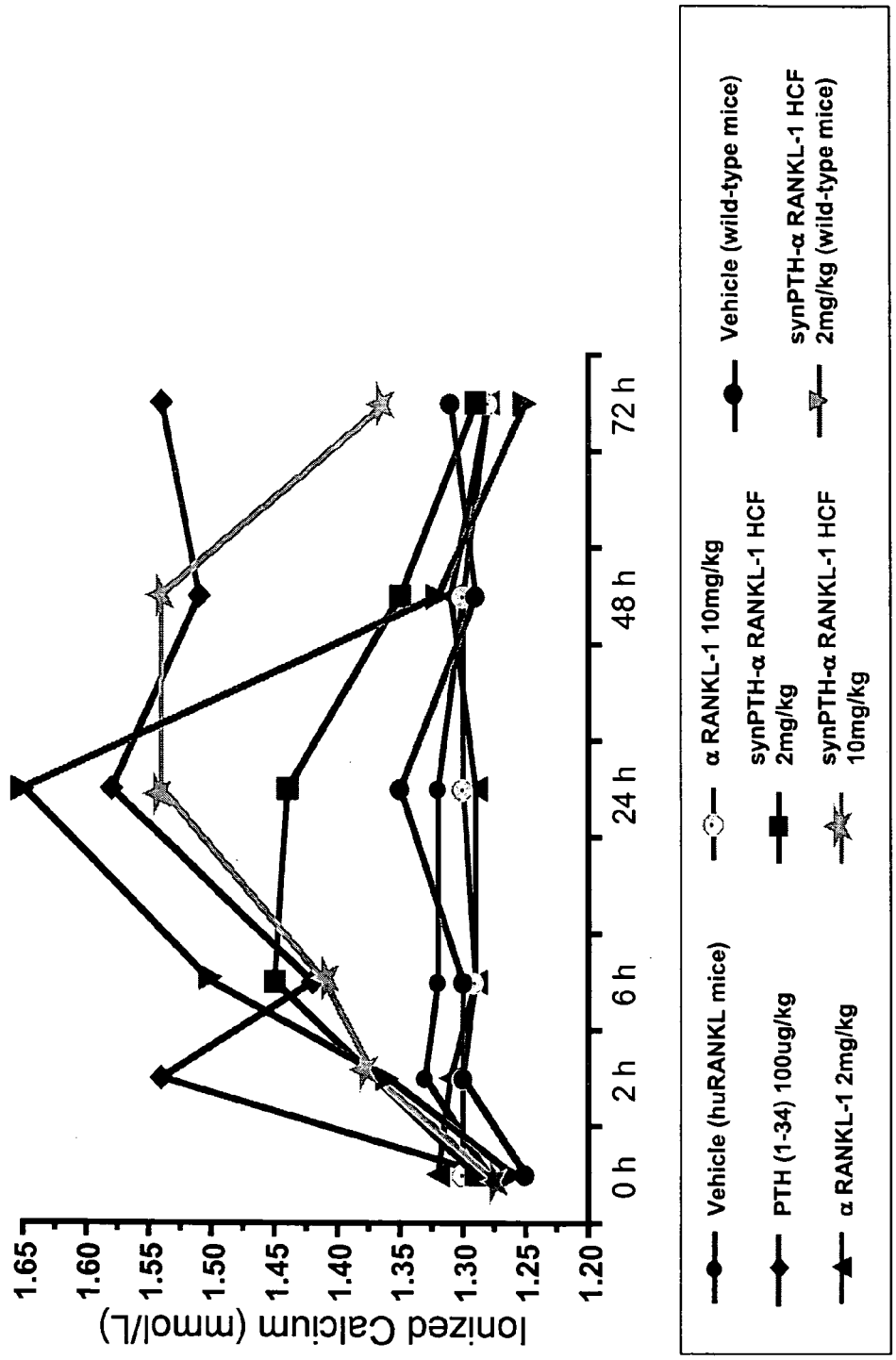
FIG. 15 shows blood ionized calcium levels in aged huRANKL mice and in aged wild-type mice according to the work in Example 5. HuRANKL mice were treated with vehicle, 100 μg/kg human PTH(1-34), 2 mg/kg αRANKL-1, 10 mg/kg αRANKL-1, 2 mg/kg synPTH-αRANKL-1 heavy chain fusion (synPTH-αRANKL-1 HCF), or 10 mg/kg synPTH-αRANKL-1 heavy chain fusion (synPTH-αRANKL-1 HCF). Wild type mice were treated with vehicle or with 2 mg/kg synPTH-αRANKL-1 heavy chain fusion (synPTH-αRANKL-1 HCF). Blood ionized calcium levels were measured before treatment, and at 2, 6, 24, 48, and 72 hours post-treatment.

FIG. 15 shows ionized calcium levels (mmol/L) in huRANKL mice treated with vehicle (PBS), 100 µg/kg human PTH(1-34) 5× per week, 2 mg/kg αRANKL-1 weekly, 10 mg/kg αRANKL-1 weekly, 2 mg/kg synPTH-αRANKL-1 heavy chain fusion weekly, or 10 mg/kg synPTH-αRANKL-1 heavy chain fusion weekly. In that experiment, blood ionized calcium levels in huRANKL mice increased significantly in response to 5× per week PTH(1-34) injections. Weekly injections of either 2 mg/kg or 10 mg/kg αRANKL-1 caused a slight reduction in blood ionized calcium levels in huRANKL mice, which is consistent with an antiresorptive effect of αRANKL-1. Weekly injections of 2 mg/kg synPTH-αRANKL-1 heavy chain fusion caused modest hypercalcemia. Weekly injections of 10 mg/kg synPTH-αRANKL-1 heavy chain fusion caused slightly greater hypercalcemia, but not greater that the hypercalcemia observed with 5× per week human PTH(1-34) injections.

FIG. 15 also shows ionized calcium levels in wild type mice treated with vehicle or with 2 mg/kg synPTH-αRANKL-1 heavy chain fusion weekly. αRANKL-1 antibody does not neutralize murine RANKL, so synPTH-αRANKL-1 heavy chain fusion is expected to behave like PTH alone. Indeed, in that experiment, 2 mg/kg synPTH-αRANKL-1 heavy chain fusion caused significantly greater hypercalcemia in wild type mice compared to a similar dose in huRANKL mice. Those results suggest that the RANKLneutralizing effects of αRANKL-1 were important for controlling bone catabolism and reducing hypercalcemia in synPTH-αRANKL-1 heavy chain fusion treated mice Serum TRAP-5b levels were measured at baseline, 1 week, 2 weeks, and 3 weeks to assess the effect of the various treatments on bone resorption, as follows. Blood was collected at each time point from isofulrane anesthetized mice retro-orbitally into Microtainer® serum separator tubes (Becton Dickinson, Franklin Lakes, N.J.). The blood was allowed to sit at room temperature for about 30 minutes and then spun at 14,000 rpm at 4° C. for 10 minutes in a TOMY high speed microcentrifuge MRX-152 with a TOMY TMA-6 24-well rotor. Serum was then transferred to a separate eppendorf tube and stored in a −80° C. freezer until analyzed. Serum TRAP-5b levels were measured using a solid phase immunofixed enzyme activity assay specific for mouse TRAP5b (SBA Sciences, Turku, Finland). Serum samples were assayed in duplicate, according to the manufacturer's protocol.

Figure 16:
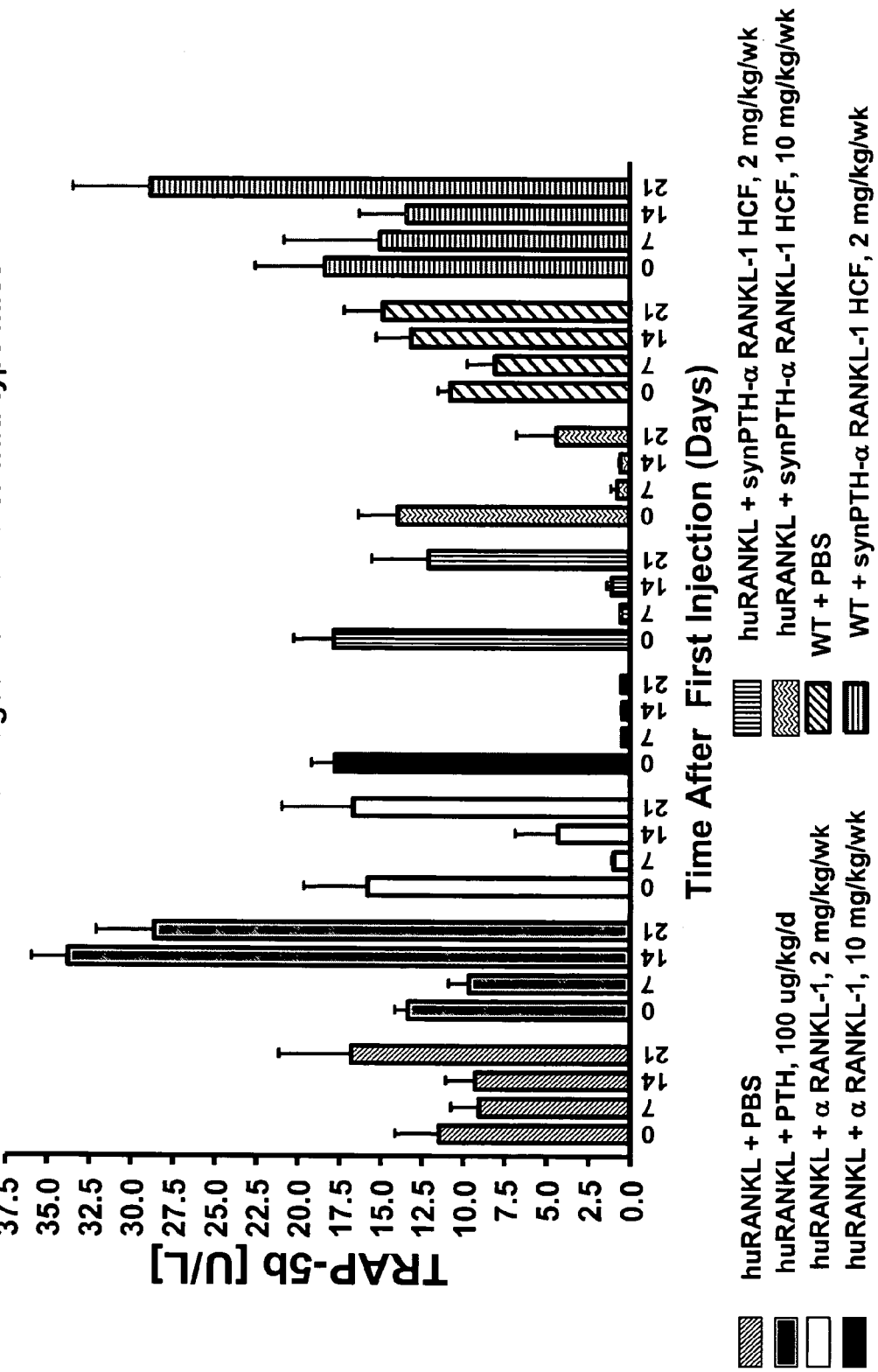
FIG. 16 shows serum TRAP-5b levels in aged huRANKL mice treated with vehicle (PBS), human PTH(1-34), αRANKL-1, or synPTH-αRANKL-1 heavy chain fusion (synPTH-αRANKL-1 HCF); and in aged wild-type mice treated with vehicle (PBS) or synPTH-αRANKL-1 heavy chain fusion (synPTH-αRANKL-1 HCF) according to the work in Example 5.

FIG. 16 shows serum TRAP-5b levels in huRANKL mice treated with vehicle (PBS), 100 μg/kg human PTH(1-34) 5× per week, 2 mg/kg αRANKL-1 weekly, 10 mg/kg αRANKL-1 weekly, 2 mg/kg synPTH-αRANKL-1 heavy chain fusion weekly, or 10 mg/kg synPTH-αRANKL-1 heavy chain fusion weekly. FIG. 16 also shows serum TRAP-5b levels in wild type mice treated with vehicle (PBS) or with 2 mg/kg synPTH-αRANKL-1 heavy chain fusion weekly. That experiment shows that 5× per week injections of human PTH(1-34) caused a significant increase in TRAP-5b levels in huRANKL mice. Similarly, weekly injection of 2 mg/kg synPTH-αRANKL-1 heavy chain fusion caused a significant increase in TRAP-5b levels in wild type mice having only murine RANKL, which is not neutralized by αRANKL-1 antibody, as discussed above.

In contrast, as shown in FIG. 16, weekly injections of αRANKL-1 caused a rapid and significant decrease in TRAP-5b levels in huRANKL mice. Similarly, weekly injections of synPTH-αRANKL-1 heavy chain fusion also caused a rapid and significant decrease in serum TRAP-5b levels, suggesting that the αRANKL-1 portion of the chimeric molecule is able to counter the effects of synPTH on TRAP-5b levels.

Serum osteocalcin levels were measured at baseline, 1 week, 2 weeks, and 3 weeks to assess the effect of each treatment on bone formation, as follows. Blood was collected and serum isolated as discussed above for measurement of TRAP-5b levels. Serum osteocalcin levels were determined using an immunoradiometric assay (IRMA) specific for mouse intact osteocalcin (Immunotopics, Inc. San Clemente, Calif.). The analyses were performed according to the manufacturer's protocol.

Figure 17:
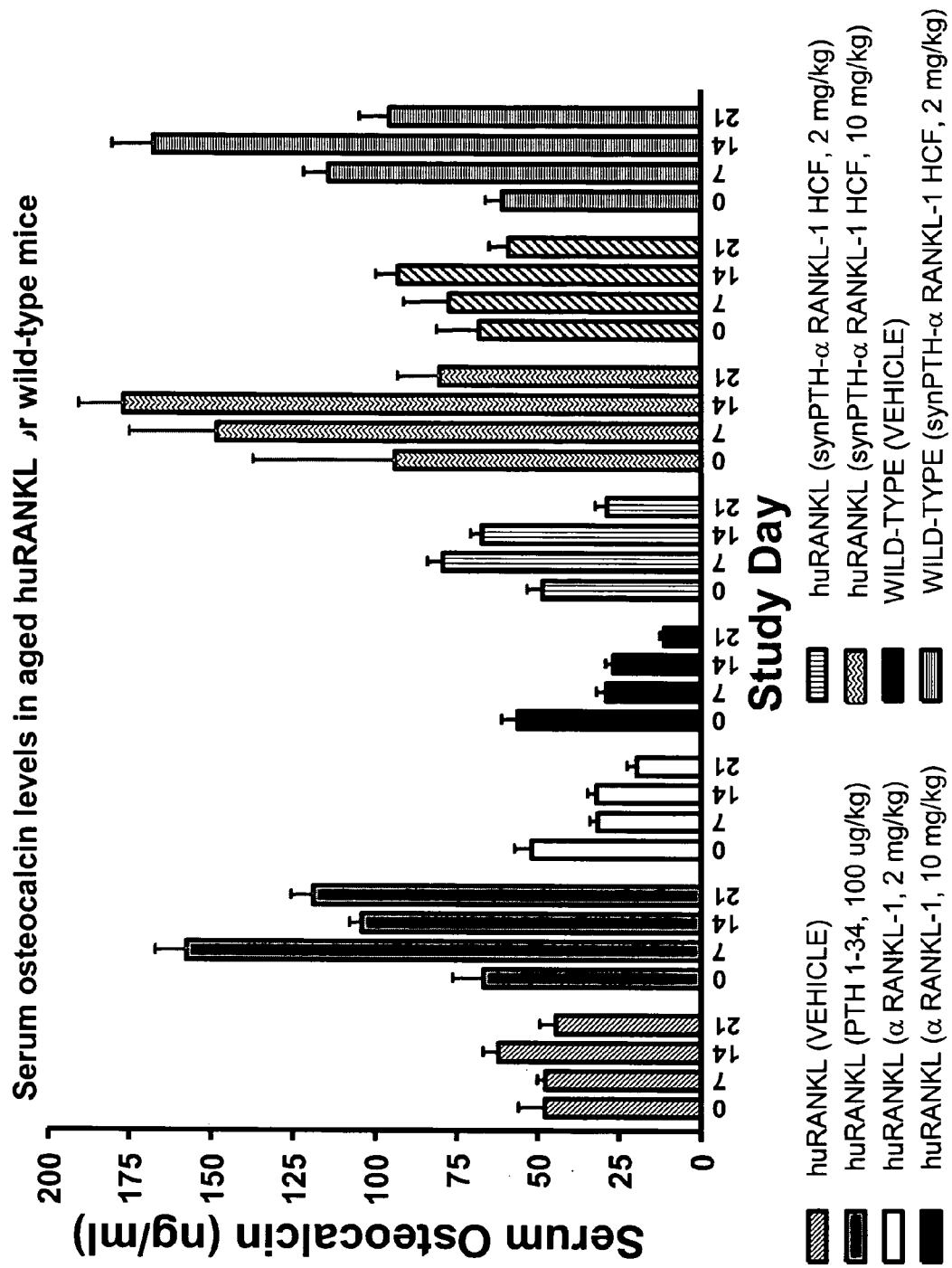
FIG. 17 shows serum osteocalcin levels in aged huRANKL mice treated with vehicle (PBS), human PTH(1-34), αRANKL-1, or synPTH-αRANKL-1 heavy chain fusion (synPTH-αRANKL-1 HCF); and in aged wild-type mice treated with vehicle (PBS) or synPTH-αRANKL-1 heavy chain fusion (synPTH-αRANKL-1 HCF) according to the work in Example 5.

FIG. 17 shows serum osteocalcin levels in huRANKL mice treated with vehicle (PBS), 100 μg/kg human PTH(1-34) 5× per week, 2 mg/kg αRANKL-1 weekly, 10 mg/kg αRANKL-1 weekly, 2 mg/kg synPTH-αRANKL-1 heavy chain fusion weekly, or 10 mg/kg synPTH-αRANKL-1 heavy chain fusion weekly. FIG. 17 also shows serum osteocalcin levels in wild type mice treated with vehicle (PBS) or with 2 mg/kg synPTH-αRANKL-1 heavy chain fusion weekly.

In that experiment, 5× per week injections of 100 μg/kg human PTH(1-34) caused a modest but significant increase in osteocalcin in huRANKL mice. Weekly αRANKL-1 injections caused a modest but significant decline in serum osteocalcin in huRANKL mice, which is probably due to feedback suppression secondary to the inhibition of bone resorption. Weekly injections of 2 mg/kg synPTH-αRANKL-1 heavy chain fusion caused little or no increase in serum osteocalcin levels in huRANKL mice, while weekly injections of 10 mg/kg synPTH-αRANKL-1 heavy chain fusion caused the greatest increase in serum osteocalcin in huRANKL mice. That increase was greater than the increase resulting from injection of 100 μg/kg human PTH(1-34) in huRANKL mice.

Bone Mineral Density

The bone mineral density (BMD) of the lumbar vertebrae (L1-L5), the femur/tibia (entire femur and the proximal half of the tibia), and the proximal tibia was measured in the huRANKL and wild type mice at baseline and at weeks 1, 2, and 3 after treatment. BMD was measured in mice anesthetized with isoflurane using dual-energy X-ray absorptiometry (DXA) (GE Lunar Piximusll, GE Lunar, Madison, Wis.).

The data from the experiment are presented as mean±standard error (SEM). One-way analysis of variance followed by Dunnett's comparison was used to determine the effect of treatment by comparing PBS-treated mice to synPTH-αRANKL-1 treated mice. Percent changes in BMD from baseline were calculated for both the PBS and synPTH-αRANKL-1 treated mice, and the percent changes in the synPTH-αRANKL-1 treated mice were compared to the percent changes in the PBS treated mice. Probability values<0.05 were considered significant.

Figure 18:
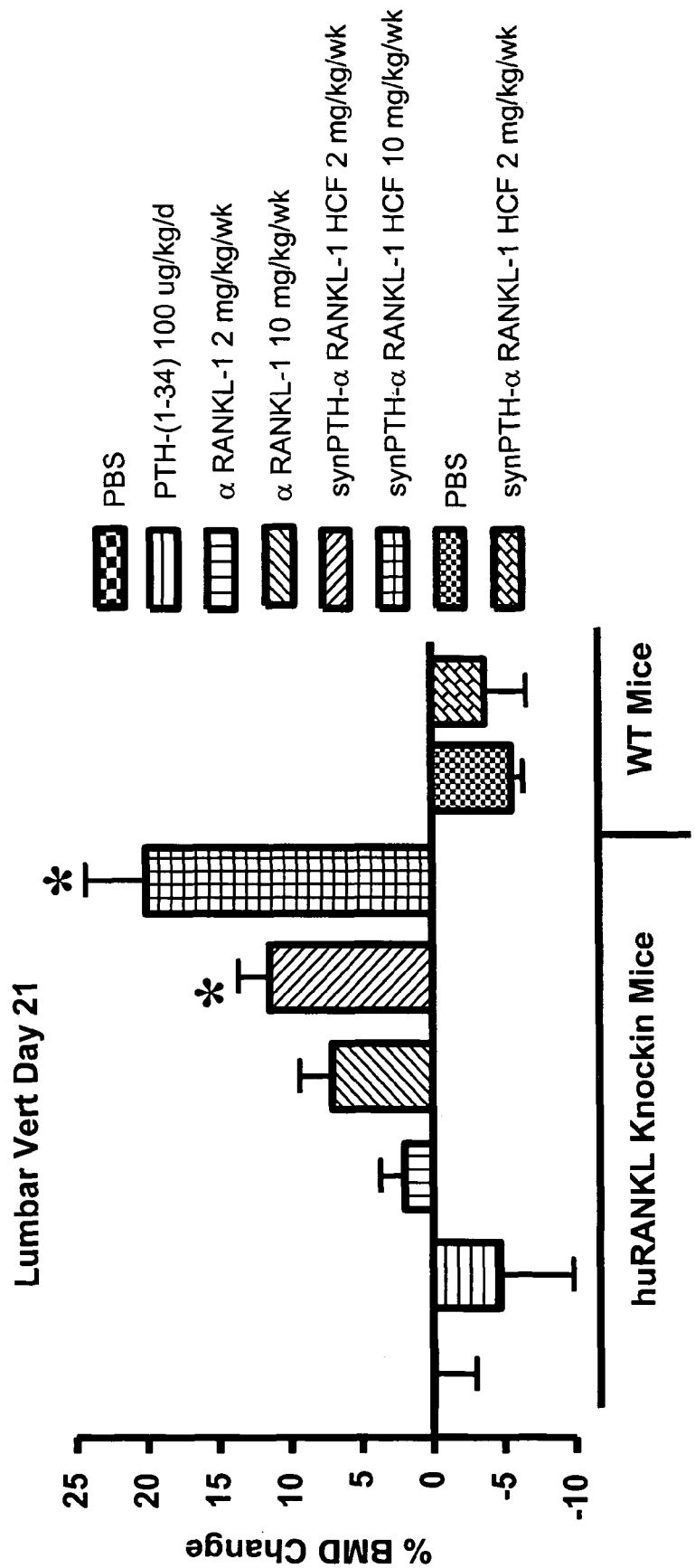
FIG. 18 shows the change in bone mineral density (BMD) of lumbar vertebrae in huRANKL mice treated with vehicle (PBS), human PTH(1-34), αRANKL-1, or synPTH-αRANKL-1 heavy chain fusion (synPTH-αRANKL-1 HCF); and in aged wild-type mice treated with vehicle (PBS) or synPTH-αRANKL-1 heavy chain fusion (synPTH-αRANKL-1 HCF) according to the work in Example 5.

FIG. 18 shows the percent BMD change of the lumbar vertebrae in huRANKL mice treated with vehicle (PBS), 100 μg/kg human PTH(1-34) 5× per week, 2 mg/kg αRANKL-1 weekly, 10 mg/kg αRANKL-1 weekly, 2 mg/kg synPTH-αRANKL-1 heavy chain fusion weekly, or 10 mg/kg synPTH-αRANKL-1 heavy chain fusion weekly. FIG. 18 also shows the percent BMD change of the lumbar vertebrae in wild type mice treated with vehicle (PBS) or with 2 mg/kg synPTH-αRANKL-1 heavy chain fusion weekly. The data are expressed as a percent change in BMD at 3 weeks relative to the baseline BMD (prior to treatment). There was no statistically significant change in BMD in huRANKL mice treated with vehicle (PBS) or 5× per week human PTH(1-34) or either weekly dose of αRANKL-1. In contrast, the increase in BMD found in huRANKL mice treated with weekly synPTH-αRANKL-1 heavy chain fusion was statistically significant. As expected, wild type mice treated with weekly synPTH-αRANKL-1 heavy chain fusion showed no increase in BMD in that experiment, likely because the murine RANKL is not neutralized by αRANKL-1.

Figure 19:
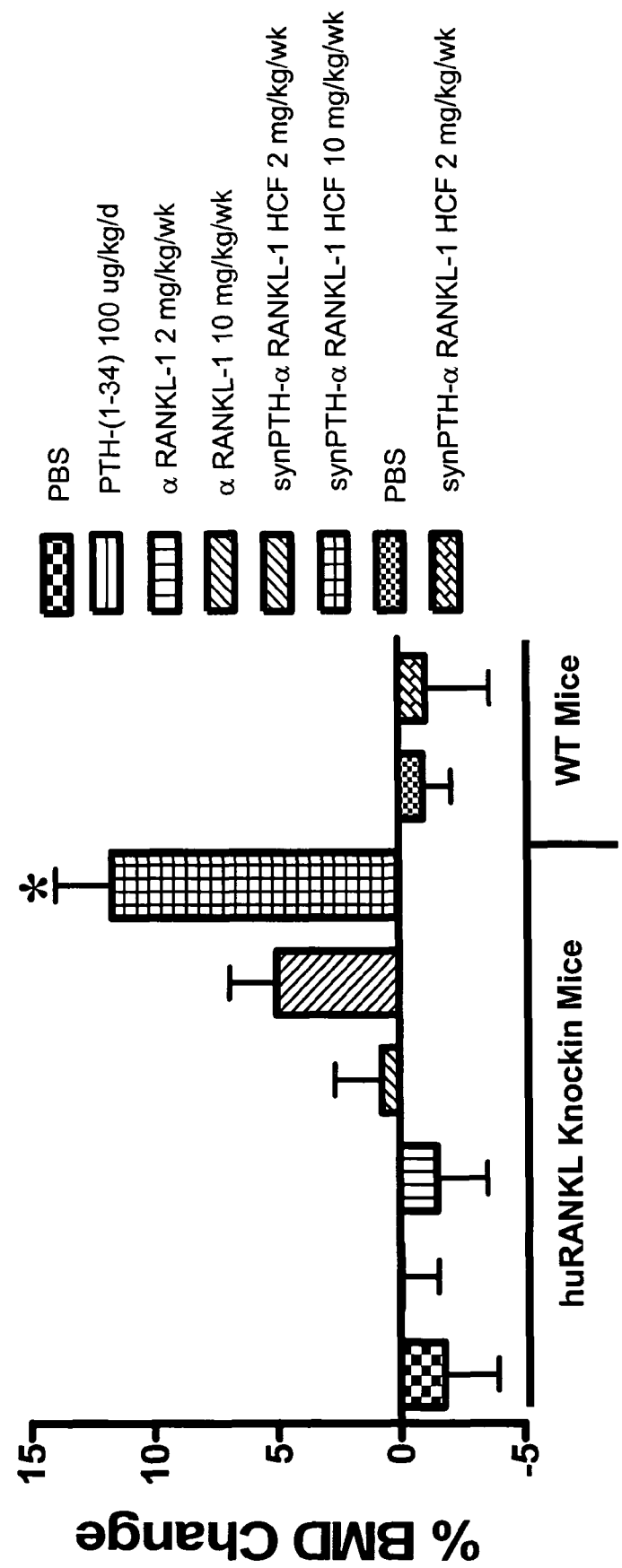
FIG. 19 shows the change in bone mineral density (BMD) of whole leg in huRANKL mice treated with vehicle (PBS), human PTH(1-34), αRANKL-1, or synPTH-αRANKL-1 heavy chain fusion (synPTH-αRANKL-1 HCF); and in aged wild-type mice treated with vehicle (PBS) or synPTH-αRANKL-1 heavy chain fusion (synPTH-αRANKL-1 HCF) according to the work in Example 5.

FIG. 19 shows the BMD of whole leg in huRANKL mice treated with vehicle (PBS), 100 μg/kg human PTH(1-34) 5× per week, 2 mg/kg αRANKL-1 weekly, 10 mg/kg αRANKL-1 weekly, 2 mg/kg synPTH-αRANKL-1 heavy chain fusion weekly, or 10 mg/kg synPTH-αRANKL-1 heavy chain fusion weekly. FIG. 18 also shows the percent BMD change of whole leg in wild type mice treated with vehicle (PBS) or with 2 mg/kg synPTH-αRANKL-1 heavy chain fusion weekly. The data are expressed as a percent change in BMD at 3 weeks relative to the baseline BMD (prior to treatment). There was no statistically significant change in BMD in huRANKL mice treated with vehicle (PBS) or 5× per week human PTH(1-34) or either weekly dose of αRANKL-1. The increase shown for weekly administration of 2 mg/kg synPTH-αRANKL-1 heavy chain fusion was not statistically significant in that experiment. In contrast, the increase in BMD found in huRANKL mice treated with 10 mg/kg synPTH-αRANKL-1 heavy chain fusion weekly was statistically significant. As expected, wild type mice treated with weekly synPTH-αRANKL-1 heavy chain fusion showed no increase in BMD in that experiment, likely because the murine RANKL is not neutralized by αRANKL-1.

The data shown in FIGS. 18 and 19 suggest that BMD in aged mice does not show a statistically significant increase in response to either daily administration of 100 µg/kg PTH(1-34) or weekly administration of 2 or 10 mg/kg αRANKL-1 alone. However, weekly administration of 10 mg/kg synPTH-αRANKL-1 heavy chain fusion results in a statistically significant increase in BMD of both lumbar vertebrae and whole leg. Weekly administration of 2 mg/kg synPTH-αRANKL-1 heavy chain fusion may increase BMD as well.

Bone Histomorphometry

At the end of the three week study, huRANKL mice treated with vehicle (PBS), 100 µg/kg human PTH(1-34) 5× per week, 2 mg/kg αRANKL-1 weekly, 10 mg/kg αRANKL-1 weekly, 2 mg/kg synPTH-αRANKL-1 heavy chain fusion weekly, or 10 mg/kg synPTH-αRANKL-1 heavy chain fusion weekly; and wild type mice treated with vehicle (PBS) or with 2 mg/kg synPTH-αRANKL-1 heavy chain fusion weekly were sacrificed and tibiae collected for static and dynamic histomorphometry.

Tibiae were fixed in 70% ethanol and cleaned of muscle and soft tissue. The front part of each tibia was trimmed longitudinally, and tibiae were dehydrated in ascending ethanol concentrations and then embedded in methyl methacrylate. Frontal sections (4 µm and 8 µm) were cut using a Leica Model 2065 microtome (Leica Instruments GmbH). Histomorphometric analyses were conducted using OsteoMeasure™ bone analysis software (Osteometrics, Inc., Decatur, Ga.). Proximal metaphysis sections of the tibiae were analyzed. Four fields were analyzed from each tibia under 20× magnification, using a field size of 350×350 µm (0.1225 $mm^2$/field). Total area of analysis was therefore 0.49 $mm^2$ on each section.

Masson's trichrome-stained sections of tibiae were used for static analysis. Trabecular bone volume was measured and then normalized to total tissue volume by the method described in Kostenuik et al. *Bone* 34: 656 (2004). Osteoclast number and osteoblast number were counted under the microscope and normalized to trabecular bone surface by the method described in Kostenuik et al. Bone 34: 656 (2004).

Figure 20:
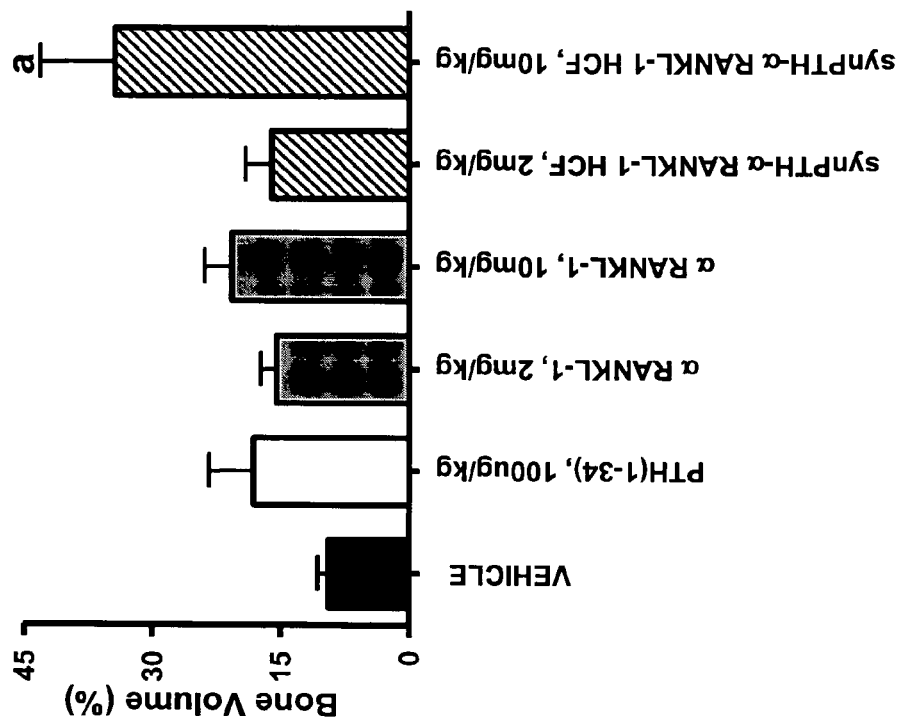
FIG. 20 shows the change in bone volume of proximal tibial metaphysis in huRANKL mice treated with vehicle (PBS), human PTH(1-34), αRANKL-1, or synPTH-αRANKL-1 heavy chain fusion (synPTH-αRANKL-1 HCF); and in aged wild-type mice treated with vehicle (PBS) or synPTH-αRANKL-1 heavy chain fusion (synPTH-αRANKL-1 HCF) according to the work in Example 5.

FIG. 20 shows the trabecular bone volume measurements of the proximal tibial metaphysis in huRANKL mice. The huRANKL mice treated with 10 mg/kg synPTH-αRANKL-1 heavy chain fusion weekly showed a statistically significant increase in trabecular bone volume in that experiment.

Figure 21:
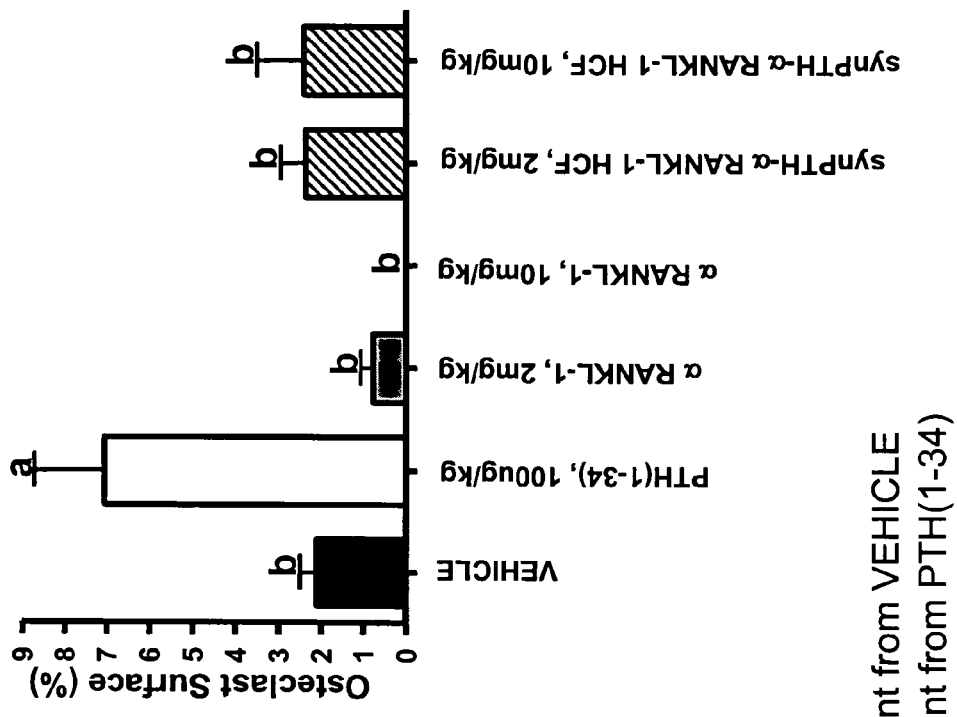
FIG. 21 shows the change in osteoclast surface percentage in huRANKL mice treated with vehicle (PBS), human PTH (1-34), αRANKL-1, or synPTH-αRANKL-1 heavy chain fusion (synPTH-αRANKL-1 HCF); and in aged wild-type mice treated with vehicle (PBS) or synPTH-αRANKL-1 heavy chain fusion (synPTH-αRANKL-1 HCF) according to the work in Example 5.

FIG. 21 shows the osteoclast surface measurements of the proximal tibial metaphysis in huRANKL mice. HuRANKL mice treated with 100 µg/kg human PTH(1-34) 5× per week showed a statistically significant increase in osteoclast surface percentage over huRANKL mice treated with vehicle (PBS). HuRANKL mice treated with synPTH-αRANKL-1 heavy chain fusion showed a statistically significant decrease in osteoclast surface percentage relative to PTH(1-34)-treated mice, suggesting that αRANKL-1 is able to counter the osteoclast stimulating effects of PTH(1-34). HuRANKL mice treated with either 10 mg/kg αRANKL-1 or synPTH-αRANKL-1 heavy chain fusion did not show a statistically significant decrease in osteoclast surface percentage relative to vehicle (PBS) alone as determined by Tukey Kramer or Dunnett's test.

Figure 22:
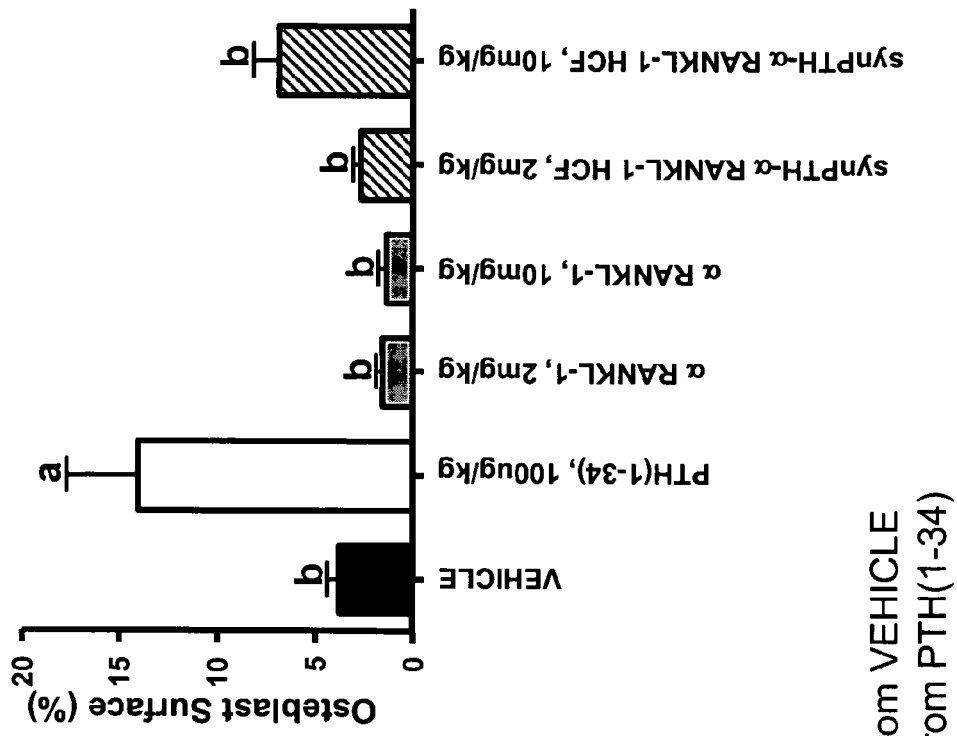
FIG. 22 shows the change in osteoblast surface percentage in huRANKL mice treated with vehicle (PBS), human PTH (1-34), αRANKL-1, or synPTH-αRANKL-1 heavy chain fusion (synPTH-αRANKL-1 HCF); and in aged wild-type mice treated with vehicle (PBS) or synPTH-αRANKL-1 heavy chain fusion (synPTH-αRANKL-1 HCF) according to the work in Example 5.

FIG. 22 shows the osteoblast surface measurements of the proximal tibial metaphysis in huRANKL mice. HuRANKL mice treated with 100 µg/kg human PTH(1-34) 5× per week showed a statistically significant increase in osteoblast surface percentage over huRANKL mice treated with vehicle (PBS), αRANKL-1, or synPTH-αRANKL-1 heavy chain fusion.

Unstained sections of tibiae were used for dynamic analysis. Tetracycline and calcin label length and interval were measured. The rate of bone formation was calculated from the tetracycline and calcin label length and interval measurements using the method described in Parfitt et al. *J. Bone Mineral Res.* 2: 595-610 (1987).

Figure 23:
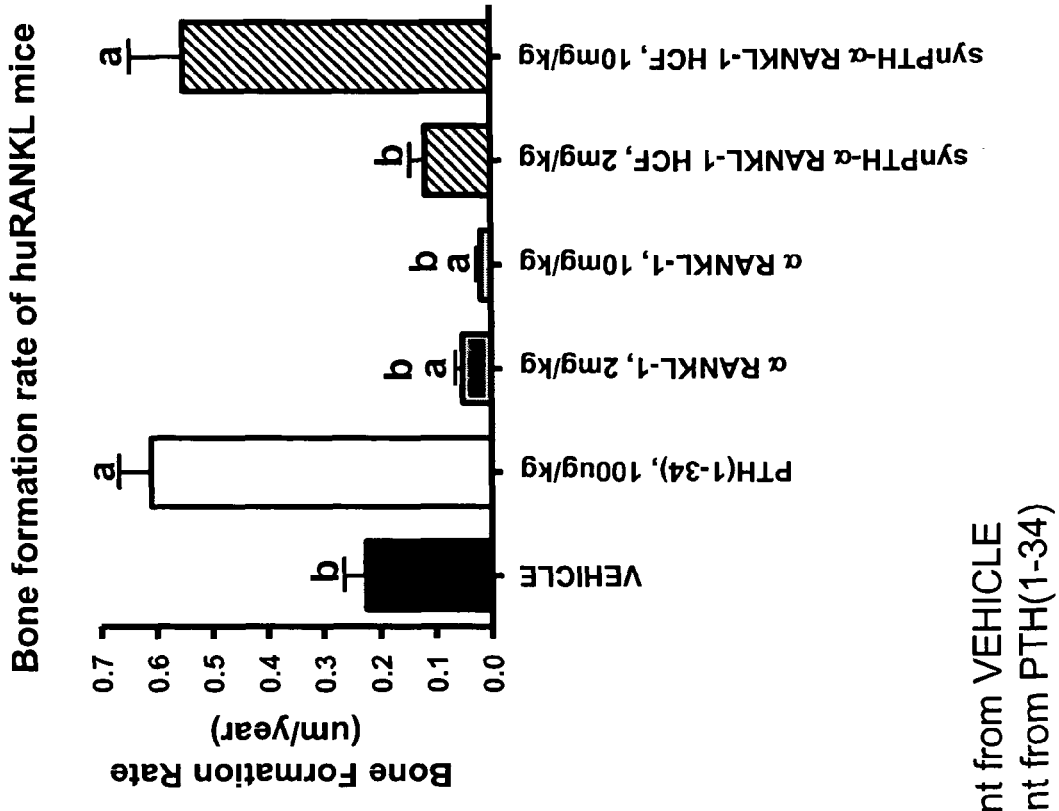
FIG. 23 shows the rate of bone formation in huRANKL mice treated with vehicle (PBS), human PTH(1-34), αRANKL-1, or synPTH-αRANKL-1 heavy chain fusion (synPTH-αRANKL-1 HCF); and in aged wild-type mice treated with vehicle (PBS) or synPTH-αRANKL-1 heavy chain fusion (synPTH-αRANKL-1 HCF) according to the work in Example 5.

FIG. 23 shows the bone formation rate of huRANKL mice. HuRANKL mice treated with either 100 µg/kg human PTH(1-34) 5× per week or 10 mg/kg synPTH-αRANKL-1 heavy chain fusion weekly showed a statistically significant increase in the rate of bone formation relative to huRANKL mice treated only with vehicle (PBS). HuRANKL mice treated with 2 mg/kg or 10 mg/kg αRANKL-1 weekly showed a decrease in bone formation rate relative to vehicle, while mice treated with 2 mg/kg synPTH-αRANKL-1 heavy chain fusion weekly showed neither a statistically significant increase nor decrease in bone formation rate relative to vehicle. These results suggest that weekly treatment with 10 mg/kg synPTH-αRANKL-1 heavy chain fusion results in a comparable increase in bone formation as treatment with 100 µg/kg human PTH(1-34) 5× per week. However, treatment with 10 mg/kg synPTH-αRANKL-1 heavy chain fusion does not significantly increase osteoclast or osteoblast surface percentage, unlike treatment with 100 µg/kg human PTH(1-34) 5× per week. See FIGS. 21 and 22.

Micro-Computed Tomography (microCT)

Figure 24:
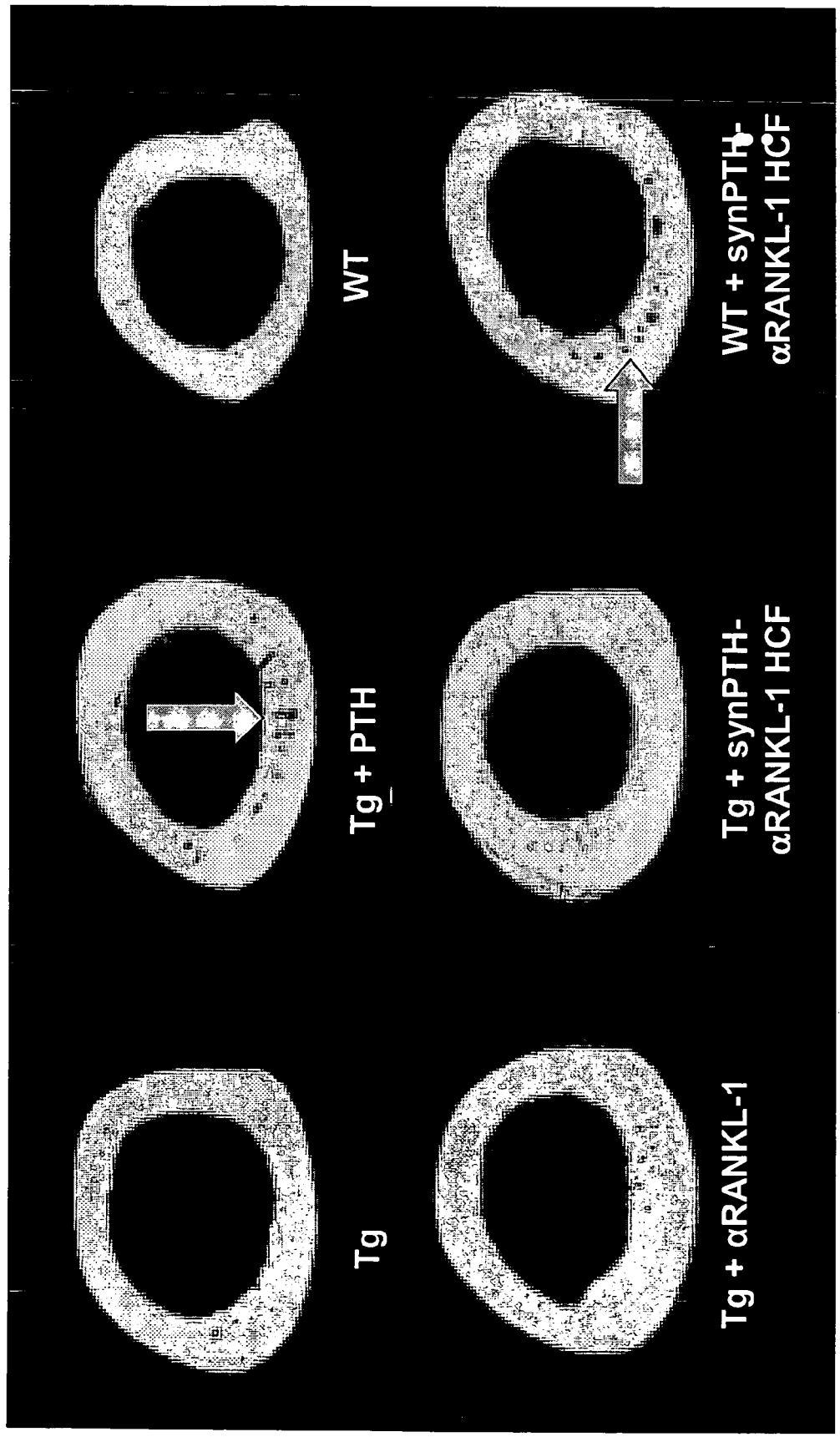
FIG. 24 shows micro-computed tomography (microCT) of femoral shafts from huRANKL mice treated with vehicle (PBS), human PTH(1-34), αRANKL-1, or synPTH-αRANKL-1 heavy chain fusion (synPTH-αRANKL-1 HCF); and from aged wild-type mice treated with vehicle (PBS) or synPTH-αRANKL-1 heavy chain fusion (synPTH-αRANKL-1 HCF) according to the work in Example 5.

Cortical porosity was analyzed in cross-sections of the femoral midshaft in huRANKL and wild type mice. FIG. 24 shows the microCT of the femoral shaft of huRANKL mice treated with vehicle (PBS), 100 µg/kg human PTH(1-34) 5× per week, 10 mg/kg αRANKL-1 weekly, or 10 mg/kg synPTH-αRANKL-1 heavy chain fusion weekly; and wild type mice treated with vehicle (PBS) or 2 mg/kg synPTH-αRANKL-1 heavy chain fusion weekly. Administration of human PTH(1-34) resulted in the appearance of endocortical porosity in huRANKL mice (indicated by an arrow in the left panel of FIG. 24), while neither weekly administration of αRANKL-1 or synPTH-αRANKL-1 heavy chain fusion resulted in endocortical porosity in huRANKL mice. In contrast, weekly administration of synPTH-αRANKL-1 heavy chain fusion in wild type mice resulted in endocortical porosity (indicated by an arrow in the right panel of FIG. 24). That result is likely due to the inability of αRANKL-1 to neutralize murine RANKL, so synPTH-αRANKL-1 heavy chain fusion acts like human PTH(1-34) alone. These results suggest that PTH alone results in cortical porosity, which may be associated with reduced bone strength. These results also suggest that αRANKL-1 reduces or prevents the cortical porosity caused by PTH.

L6 vertebrae, left tibiae, and left femurs were examined with an eXplore MS Micro-CT System (GE Healthcare, Waukesha, Wis., USA). Bones were placed in 2 ml cryo-tubes with a density phantom (SB3; provided with eXplore MS Micro-CT System), the tubes were filled with PBS, and the bones stabilized in the tubes with gauze. The bones were scanned with an eXplore MS Micro-CT System, which uses Volumetric Conebeam technology, at 0.5° rotations for 200° at 80 kVp and 80 µA, calibrated with the density phantom. The data were reconstructed to yield images with a voxel size of 18 µm×18 µm×18 µm.

Regions of interest were analyzed for cortical and trabecular morphometric and density parameters using analysis software (GEMS MicroView). The central 10% (in length) of the femur diaphysis was analyzed for cortical bone matrix mineral density (BMMD) and average cortical area. Endosteal and periosteal perimeters were generated at the midsection using Image-J (NIH). Regions of trabecular bone from the L6 vertebrae, proximal tibia, and distal femur were isolated and analyzed for BMD and stereology parameters, including bone volume fraction (BV/TV).

Images for all scans were generated using 3-D surface rendering with a threshold based on the density phantom for each scan (30% of the bone mimetic density for trabecular bone (320 mg/ml), 60% of the bone mimetic density for cortical bone (640 mg/ml)). These threshold levels were determined using histomorphometric techniques within the software (GEMS MicroView), and eliminated bias from the individual scans.

Figure 25:
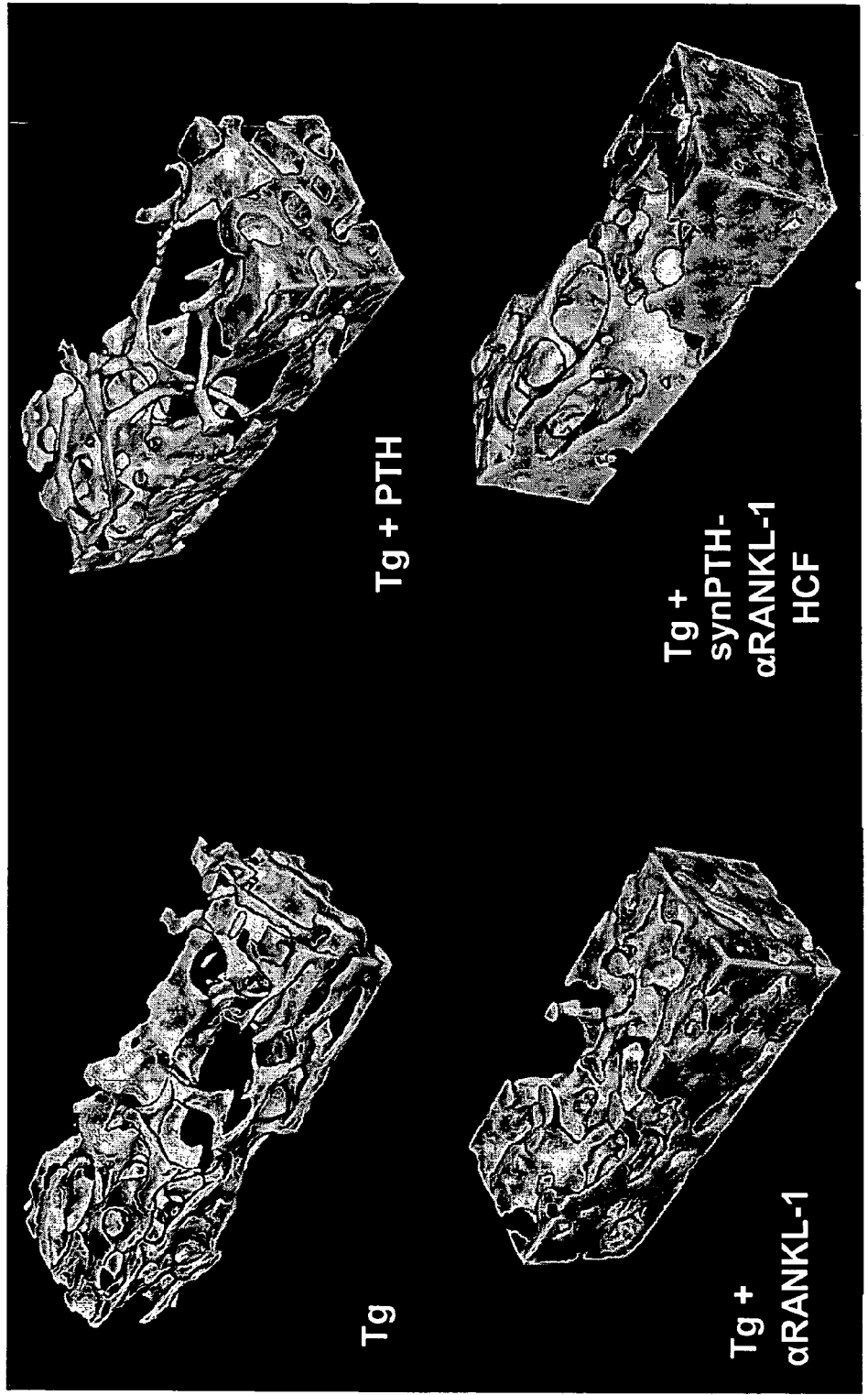
FIG. 25 shows micro-computed tomography (microCT) of L6 vertebrae from huRANKL mice treated with vehicle (PBS), human PTH(1-34), αRANKL-1, or synPTH-αRANKL-1 heavy chain fusion (synPTH-αRANKL-1 HCF).

FIG. 25 shows microCT results for the L6 vertebrae from huRANKL mice treated with vehicle (PBS), 100 µg/kg human PTH(1-34) 5× per week, 10 mg/kg αRANKL-1 weekly, or 10 mg/kg synPTH-αRANKL-1 heavy chain fusion weekly. huRANKL mice treated with either 10 mg/kg αRANKL-1 weekly or 10 mg/kg synPTH-αRANKL-1 heavy chain fusion weekly show an increase in trabecular bone mass as compared to huRANKL mice treated with vehicle (PBS).

Figure 26:
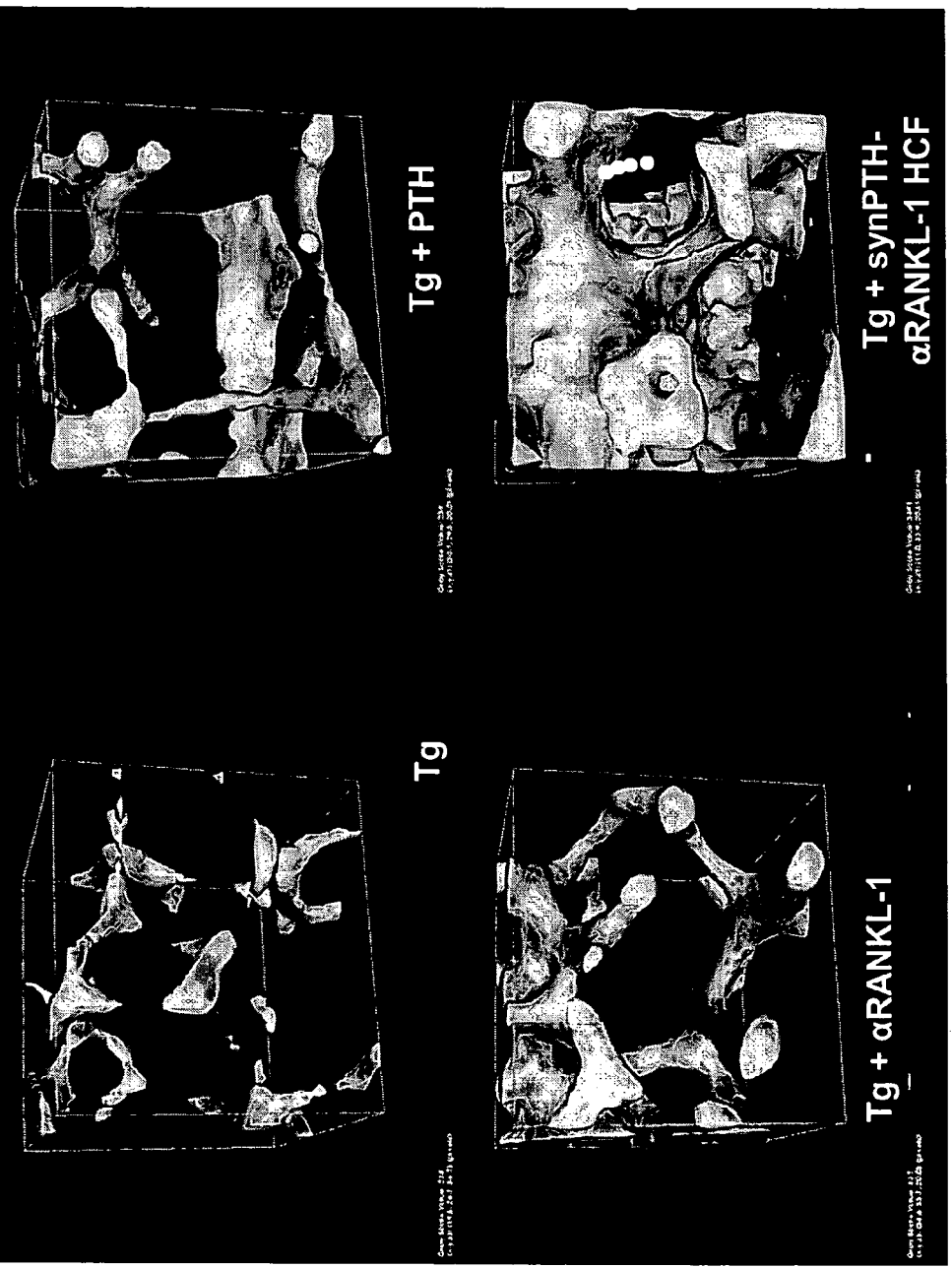
FIG. 26 shows micro-computed tomography (microCT) of left tibiae from huRANKL mice treated with vehicle (PBS), human PTH(1-34), αRANKL-1, or synPTH-αRANKL-1 heavy chain fusion (synPTH-αRANKL-1 HCF).

FIG. 26 shows microCT results for the left proximal tibiae from huRANKL mice treated with vehicle (PBS), 100 µg/kg human PTH(1-34) 5× per week, 10 mg/kg αRANKL-1 weekly, or 10 mg/kg synPTH-αRANKL-1 heavy chain fusion weekly. huRANKL mice treated with 10 mg/kg synPTH-αRANKL-1 heavy chain fusion weekly showed a significant increase in bone density as compared to huRANKL mice treated with vehicle (PBS). huRANKL mice treated with 100 µg/kg human PTH(1-34) 5× per week or 10 mg/kg αRANKL-1 weekly showed a moderate increase in trabecular bone mass as compared to huRANKL mice treated with vehicle (PBS).

Figure 27:
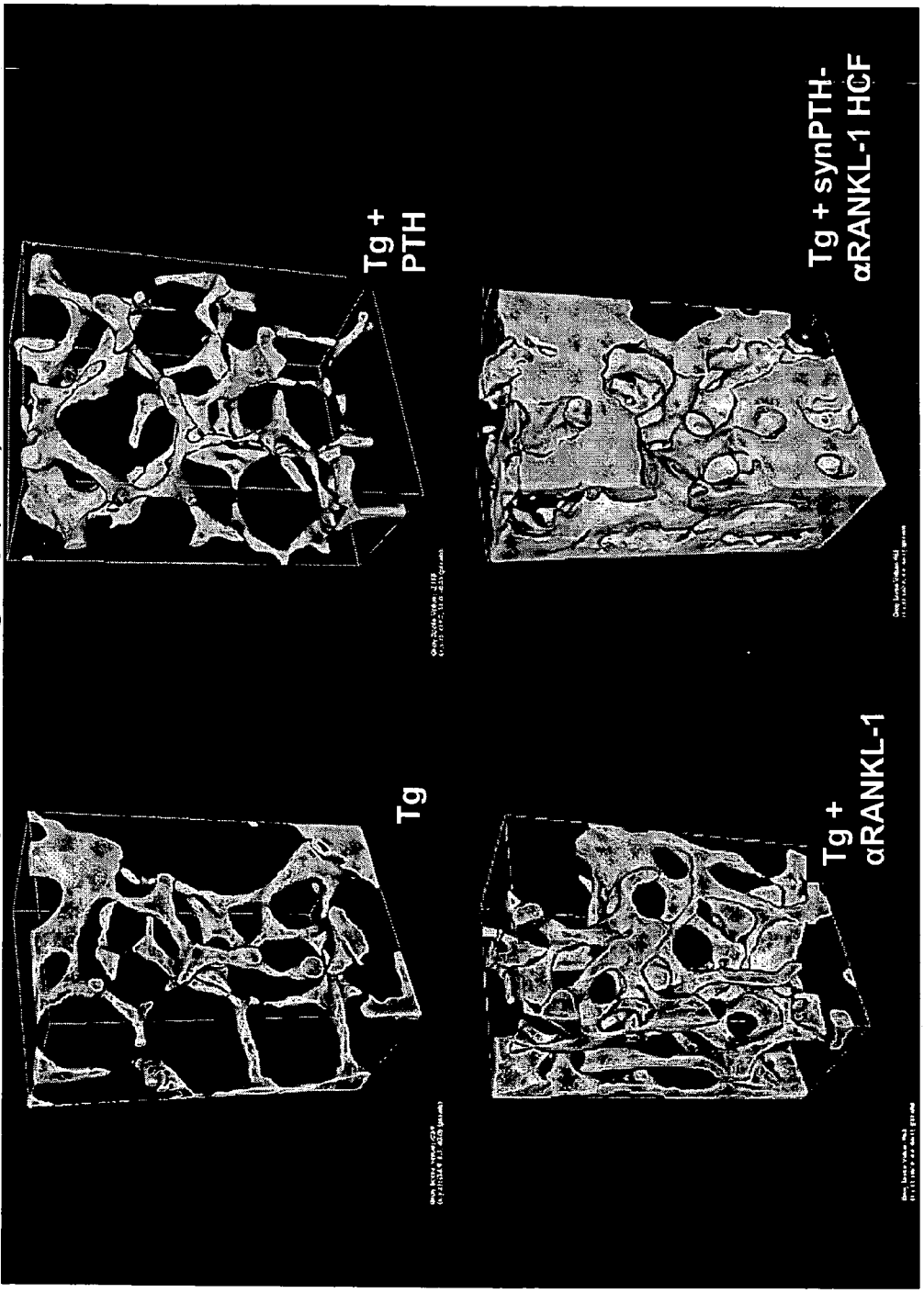
FIG. 27 shows micro-computed tomography (microCT) of left femurs from huRANKL mice treated with vehicle (PBS), human PTH(1-34), αRANKL-1, or synPTH-αRANKL-1 heavy chain fusion (synPTH-αRANKL-1 HCF).

FIG. 27 shows microCT results for the left distal femurs from huRANKL mice treated with vehicle (PBS), 100 µg/kg human PTH(1-34) 5× per week, 10 mg/kg αRANKL-1 weekly, or 10 mg/kg synPTH-αRANKL-1 heavy chain fusion weekly. huRANKL mice treated with 10 mg/kg synPTH-αRANKL-1 heavy chain fusion weekly showed a significant increase in bone density as compared to huRANKL mice treated with vehicle (PBS). huRANKL mice treated with 10 mg/kg αRANKL-1 weekly showed a moderate increase in trabecular bone mass as compared to huRANKL mice treated with vehicle (PBS).

We claim:

1. A receptor activator of NF-κB ligand (RANKL) antibody-parathyroid hormone/parathyroid hormone related protein (PTH/PTHrP) chimeric molecule, comprising:
   (a) an antibody that binds to RANKL; and
   (b) a PTH/PTHrP peptide comprising a PTH/PTHrP modulating domain;
   wherein the PTH/PTHrP peptide is operably linked to the antibody.

2. The RANKL antibody-PTH/PTHrP chimeric molecule of claim 1, wherein the PTH/PTHrP peptide is operably linked to a heavy chain.

3. The RANKL antibody-PTH/PTHrP chimeric molecule of claim 1, wherein the PTH/PTHrP peptide is operably linked to a light chain.

4. The RANKL antibody-PTH/PTHrP chimeric molecule of claim 2, wherein the PTH/PTHrP peptide is operably linked to the N-terminus of the heavy chain.

5. The RANKL antibody-PTH/PTHrP chimeric molecule of claim 3, wherein the PTH/PTHrP peptide is operably linked to the N-terminus of the light chain.

6. The RANKL antibody-PTH/PTHrP chimeric molecule of claim 4, wherein the PTH/PTHrP peptide is fused to the N-terminus of the heavy chain.

7. The RANKL antibody-PTH/PTHrP chimeric molecule of claim 5, wherein the PTH/PTHrP peptide is fused to the N-terminus of the light chain.

8. The RANKL antibody-PTH/PTHrP chimeric molecule of claim 1 wherein the antibody comprises a heavy chain comprising CDR1, CDR2, and CDR3 as set forth in SEQ ID NO:11.

9. The RANKL antibody-PTH/PTHrP chimeric molecule of claim 1 wherein the antibody comprises a light chain comprising CDR1, CDR2, and CDR3 as set forth in SEQ ID NO:12.

10. The RANKL antibody-PTH/PTHrP chimeric molecule of claim 1 wherein the antibody comprises a heavy chain and a light chain, and wherein the heavy chain comprises CDR1, CDR2, and CDR3 as set forth in SEQ ID NO:11, and the light chain comprises CDR1, CDR2, and CDR3 as set forth in SEQ ID NO:12.

11. The RANKL antibody-PTH/PTHrP chimeric molecule of claim 1, wherein the antibody is selected from a single-chain Fv antibody (scFv), a Fab antibody, a Fab' antibody, a (Fab')2 antibody, a domain antibody, a nanobody, a minibody, a maxibody, and a diabody.

12. A RANKL antibody-PTH/PTHrP chimeric molecule, comprising:
   (a) an antibody comprising a heavy chain and a light chain, wherein the antibody binds to RANKL;
   (b) a first PTH/PTHrP peptide comprising a PTH/PTHrP modulating domain; and
   (c) a second PTH/PTHrP peptide;
   wherein the first PTH/PTHrP peptide is operably linked to the light chain and the second PTH/PTHrP peptide is operably linked to the heavy chain, and wherein the first and second PTH/PTHrP peptides are the same or different.

13. The RANKL antibody-PTH/PTHrP chimeric molecule of claim 12, wherein the first PTH/PTHrP peptide is operably linked to the N-terminus of the light chain and the second PTH/PTHrP peptide is operably linked to the N-terminus of the heavy chain.

14. The RANKL antibody-PTH/PTHrP chimeric molecule of claim 12, wherein the first PTH/PTHrP peptide is fused to the N-terminus of the light chain and the second PTH/PTHrP peptide is fused to the N-terminus of the heavy chain.

15. The RANKL antibody-PTH/PTHrP chimeric molecule of claim 1, wherein:
   (a) the antibody comprises a heavy chain and a light chain, wherein the heavy chain comprises a first variable region comprising the amino acid sequence as set forth in SEQ ID NO: 11, and wherein the light chain comprises a second variable region comprising the amino acid sequence as set forth in SEQ ID NO: 12; and
   (b) wherein the PTH/PTHrP peptide is operably linked to the heavy chain or the light chain.

16. The RANKL antibody-PTH/PTHrP chimeric molecule of claim 15, wherein the PTH/PTHrP peptide is operably linked to the heavy chain.

17. The RANKL antibody-PTH/PTHrP chimeric molecule of claim 15, wherein the PTH/PTHrP peptide is operably linked to the light chain.

18. The RANKL antibody-PTH/PTHrP chimeric molecule of claim 16, wherein the PTH/PTHrP peptide is operably linked to the N-terminus of the heavy chain.

19. The RANKL antibody-PTH/PTHrP chimeric molecule of claim 17, wherein the PTH/PTHrP peptide is operably linked to the N-terminus of the light chain.

20. The RANKL antibody-PTH/PTHrP chimeric molecule of claim 18, wherein the PTH/PTHrP peptide is fused to the N-terminus of the heavy chain.

21. The RANKL antibody-PTH/PTHrP chimeric molecule of claim 19, wherein the PTH/PTHrP peptide is fused to the N-terminus of the light chain.

22. The RANKL antibody-PTH/PTHrP chimeric molecule of claim 15, wherein the heavy chain and the light chain are connected by a flexible linker to form a single-chain antibody.

23. The RANKL antibody-PTH/PTHrP chimeric molecule of claim 22, wherein the single-chain antibody is a single-chain Fv antibody.

24. The RANKL antibody-PTH/PTHrP chimeric molecule of claim 15, wherein the antibody is a Fab antibody.

25. The RANKL antibody-PTH/PTHrP chimeric molecule of claim 15, wherein the antibody is a Fab' antibody.

26. The RANKL antibody-PTH/PTHrP chimeric molecule of claim 15, wherein the antibody is a (Fab')2 antibody.

27. The RANKL antibody-PTH/PTHrP chimeric molecule of claim 15, wherein the antibody is fully human.

28. The RANKL antibody-PTH/PTHrP chimeric molecule of claim 15, wherein the RANKL antibody-PTH/PTHrP chimeric molecule inhibits binding of RANKL to a receptor activator of NF-κB (RANK).

29. A RANKL antibody-PTH/PTHrP chimeric molecule, comprising:
   (a) an antibody comprising a heavy chain and a light chain, wherein the heavy chain comprises a first variable region comprising CDR1, CDR2, and CDR3 as set forth in SEQ ID NO: 11, and wherein the light chain comprises a variable region comprising CDR1, CDR2, and CDR3 as set forth in SEQ ID NO: 12, and wherein the antibody binds to RANKL;
   (b) a first PTH/PTHrP comprising a PTH/PTHrP modulating domain; and
   (c) a second PTH/PTHrP peptide;
   wherein the first PTH/PTHrP peptide is operably linked to the light chain and the second PTH/PTHrP peptide is operably linked to the heavy chain, and wherein the first and second PTH/PTHrP peptides are the same or different.

30. The RANKL antibody-PTH/PTHrP chimeric molecule of claim 29, wherein the first PTH/PTHrP peptide is operably linked to the N-terminus of the light chain and the second PTH/PTHrP peptide is operably linked to the N-terminus of the heavy chain.

31. The RANKL antibody-PTH/PTHrP chimeric molecule of claim 30, wherein the first PTH/PTHrP peptide is fused to the N-terminus of the light chain and the second PTH/PTHrP peptide is fused to the N-terminus of the heavy chain.

32. A RANKL antibody-PTH/PTHrP chimeric molecule, comprising
(a) an antibody comprising a heavy chain and a light chain, wherein:
   (i) the heavy chain comprises a first variable region, wherein the first variable region comprises a sequence that has at least 92% identity to the amino acid sequence set forth in SEQ ID NO: 11, and
   (ii) the light chain comprises a second variable region, wherein the second variable region comprises a sequence that has at least 90% identity to the amino acid sequence set forth in SEQ ID NO: 12,
wherein the antibody binds to RANKL; and
(b) a PTH/PTHrP comprising a PTH/PTHrP modulating domain;
wherein the PTH/PTHrP peptide is operably linked to the heavy chain or the light chain.

33. The RANKL antibody-PTH/PTHrP chimeric molecule of claim 32, wherein the first variable region comprises a sequence that has at least 95% identity to the amino acid sequence set forth in SEQ ID NO: 11, and wherein the second variable region comprises a sequence that has at least 95% identity to the amino acid sequence set forth in SEQ ID NO: 12.

34. The RANKL antibody-PTH/PTHrP chimeric molecule of claim 32, wherein the first variable region comprises a sequence that has at least 99% identity to the amino acid sequence set forth in SEQ ID NO: 11, and wherein the second variable region comprises a sequence that has at least 99% identity to the amino acid sequence set forth in SEQ ID NO: 12.

35. The RANKL antibody-PTH/PTHrP chimeric molecule of claim 1, wherein the PTH/PTHrP peptide comprises a PTH/PTHrP modulating domain comprising the amino acid sequence selected from at least one of SEQ ID NOs: 16 to 67.

36. The RANKL antibody-PTH/PTHrP chimeric molecule of claim 35, wherein the PTH/PTHrP modulating domain comprises the amino acid sequence of SEQ ID NO: 22.

37. The RANKL antibody-PTH/PTHrP chimeric molecule of claim 1, wherein the PTH/PTHrP peptide comprises the amino acid sequence of SEQ ID NO: 6 from residue 32 to residue 70.

38. A RANKL antibody-PTH/PTHrP chimeric molecule selected from:
(a) a RANKL antibody-PTH/PTHrP chimeric molecule comprising a first polypeptide having the amino acid sequence of SEQ ID NO: 2 from residue 20 to residue 467 and a second polypeptide having the amino acid sequence of SEQ ID NO: 8 from residue 32 to residue 285;
(b) a RANKL antibody-PTH/PTHrP chimeric molecule comprising a first polypeptide having the amino acid sequence of SEQ ID NO: 10 from residue 32 to residue 518 and a second polypeptide having the amino acid sequence of SEQ ID NO: 4 from residue 21 to residue 235; and
(c) a RANKL antibody-PTH/PTHrP chimeric molecule comprising a first polypeptide having the amino acid sequence of SEQ ID NO: 10 from residue 32 to residue 518 and a second polypeptide having the amino acid sequence of SEQ ID NO: 8 from residue 32 to residue 285.

39. The RANKL antibody-PTH/PTHrP chimeric molecule of claim 1, wherein the PTH/PTHrP peptide comprises a PTH/PTHrP modulating domain comprising the amino acid sequence of at least one of SEQ ID NOs: 68 to 89.

40. The RANKL antibody-PTH/PTHrP chimeric molecule of claim 1, wherein the PTH/PTHrP peptide comprises a PTH/PTHrP modulating domain comprising the amino acid sequence of at least one of SEQ ID NOs: 90 to 107 except that one or more residues at position 14 through the C-terminus of the PTH/PTHrP modulating domain is substituted with a cysteine residue.

41. A method of treating bone loss in a patient, comprising administering the RANKL antibody-PTH/PTHrP chimeric molecule of any one of claims 1, 12, 15, 29, 32, and 38.

42. A method of treating bone loss in a patient, comprising administering the RANKL antibody-PTH/PTHrP chimeric molecule of any one of claims 1, 12, 15, 29, 32, and 38 and at least one agent selected from a bone anti-resorptive agent, a bone anabolic agent, an anti-inflammatory agent, an immune suppressing agent, and a cancer therapy agent.

43. The method of claim 41 further comprising administering at least one therapeutic agent selected from a bone morphogenic factor, transforming growth factor-62 (TGF-β), an interleukin-1 (IL-1) inhibitor, IL-1ra, anakinra, a TNFα inhibitor, a soluble TNFα receptor, etanercept, an anti-TNFα antibody, infliximab, adalimumab, a prostaglandin, a bisphosphonate, alendronate, fluoride, calcium, a non-steroidal anti-inflammatory drug (NSAID), a COX-2 inhibitor, celecoxib, rofecoxib, an immunosuppressant, methotrexate, leflunomide, a serine protease inhibitor, a secretory leukocyte protease inhibitor (SLPI), an IL-6 inhibitor, an IL-6 antibody, an IL-8 inhibitor, an IL-8 antibody, an IL-18 inhibitor, an IL-18 binding protein, an IL-18 antibody, an Interleukin-1 converting enzyme (ICE) modulator, a fibroblast growth factor (FGF), an FGF modulator, a PAF antagonist, a keratinocyte growth factor (KGF), a KGF-related molecule, a KGF modulator; a matrix metalloproteinase (MMP) modulator, a nitric oxide synthase (NOS) modulator, a modulator of glucocorticoid receptor, a modulator of glutamate receptor, a modulator of lipopolysaccharide (LPS) levels, a noradrenaline, a noradrenaline mimetic, and a noradrenaline modulator.

44. A method of treating bone loss associated with an inflammatory condition in a patient, comprising administering the RANKL antibody-PTH/PTHrP chimeric molecule of any one of claims 1, 12, 15, 29, 32, and 38.

45. A method of treating bone loss associated with an autoimmune condition in a patient, comprising administering the RANKL antibody-PTH/PTHrP chimeric molecule of any one of claims 1, 12, 15, 29, 32, and 38.

46. A method of treating bone loss associated with rheumatoid arthritis in a patient, comprising administering the RANKL antibody-PTH/PTHrP chimeric molecule of any one of claims 1, 12, 15, 29, 32, and 38.

47. A method of treating bone loss associated with cancer comprising administering the RANKL antibody-PTH/PTHrP chimeric molecule of any one of claims 1, 12, 15, 29, 32, and 38.

48. A method of treating bone loss associated with cancer comprising administering the RANKL antibody-PTH/PTHrP chimeric molecule of any one of claims 1, 12, 15, 29, 32, and 38 and at least one therapeutic agent selected from an epidermal growth factor receptor (EGFR) inhibitor, a HER2 inhibitor, a vegF inhibitor, a vegF receptor inhibitor, a hepatocyte growth factor (HGF)/scatter factor (SF) inhibitor, a c-Met inhibitor, an angiopoietin inhibitor, a Tie2 inhibitor, a platelet derived growth factor receptor (PDGFR) inhibitor, an insulin-like growth factor receptor (IGFR) inhibitor, a mucin-like glycoprotein inhibitor, a CDC20 inhibitor, and a CDC33 inhibitor.

49. A method of treating bone loss associated with cancer comprising administering the RANKL antibody-PTH/PTHrP chimeric molecule of any one of claims 1, 12, 15, 29, 32, and 38 and at least one antibody selected from a Her2 antibody, a CDC20 antibody, an EGFR antibody, a vegF antibody, a vegF receptor antibody, a hepatocyte growth factor (HGF)/scatter factor (SF) antibody, an insulin-like growth factor receptor (IFGR) antibody, and a CDC33 antibody.

50. The RANKL antibody-PTH/PTHrP chimeric molecule of claim 1, wherein the antibody comprises a heavy chain comprising the amino acid sequence as set forth in SEQ ID NO: 11.

51. The RANKL antibody-PTH/PTHrP chimeric molecule of claim 1, wherein the antibody comprises a light chain comprising the amino acid sequence as set forth in SEQ ID NO: 12.

52. The RANKL antibody-PTH/PTHrP chimeric molecule of claim 1 wherein the antibody comprises a heavy chain comprising the amino acid sequence as set forth in SEQ ID NO: 2 from residue 20 to residue 467.

53. The RANKL antibody-PTH/PTHrP chimeric molecule of claim 1 wherein the antibody comprises a light chain comprising the amino acid sequence as set forth in SEQ ID NO: 4 from residue 21 to residue 235.

54. The RANKL antibody-PTH/PTHrP chimeric molecule of claim 1 wherein the antibody comprises a heavy chain and a light chain, and wherein the heavy chain comprises the amino acid sequence as set forth in SEQ ID NO: 2 from residue 20 to residue 467 and the light chain comprises the amino acid sequence as set forth in SEQ ID NO: 4 from residue 21 to residue 235.

55. A RANKL antibody-PTH/PTHrP chimeric molecule, comprising:

(a) an antibody that binds to RANKL; and
(b) a PTH/PTHrP peptide comprising a PTH/PTHrP modulating domain, wherein the PTH/PTHrP modulating domain comprises the amino acid sequence of SEQ ID NO: 22;

and wherein the PTH/PTHrP peptide is operably linked to the N-terminus of a heavy chain of the antibody.

56. The RANKL antibody-PTH/PTHrP chimeric molecule of claim 55 wherein the antibody comprises a heavy chain comprising CDR1, CDR2 and CDR3 as set forth in SEQ ID NO: 11.

57. The RANKL antibody-PTH/PTHrP chimeric molecule of claim 55 wherein the antibody comprises a light chain comprising CDR1, CDR2 and CDR3 as set forth in SEQ ID NO: 12.

58. The RANKL antibody-PTH/PTHrP chimeric molecule of claim 55 wherein the antibody comprises a heavy chain comprising CDR1, CDR2 and CDR3 as set forth in SEQ ID NO: 11 and a light chain comprising CDR1, CDR2 and CDR3 as set forth in SEQ ID NO: 12.

59. The RANKL antibody-PTH/PTHrP chimeric molecule of claim 55 wherein the antibody comprises a heavy chain comprising the amino acid sequence as set forth in SEQ ID NO: 11.

60. The RANKL antibody-PTH/PTHrP chimeric molecule of claim 55 wherein the antibody comprises a light chain comprising the amino acid sequence as set forth in SEQ ID NO: 12.

61. The RANKL antibody-PTH/PTHrP chimeric molecule of claim 55 wherein the antibody comprises a heavy chain comprising a first variable region comprising the amino acid sequence as set forth in SEQ ID NO: 11 and a light chain comprising a second variable region comprising the amino acid sequence as set forth in SEQ ID NO: 12.

62. A pharmaceutical composition comprising the RANKL antibody-PTH/PTHrP chimeric molecule of any one of claims 1, 12, 15, 29, 32, 38 and 55.

* * * * *

SEQUENCE LISTING

```
<160> NUMBER OF SEQ ID NOS: 247

<210> SEQ ID NO 1
<211> LENGTH: 1426
<212> TYPE: DNA
<213> ORGANISM: Artificial Sequence
<220> FEATURE:
<223> OTHER INFORMATION: Description of Artificial Sequence: Synthetic
      alpha-RANKL-1 heavy chain

<400> SEQUENCE: 1
aagcttgacc accatggagt ttgggctgag ctggcttttt cttgtggcta tttaaaagg      60 tgtccagtgt gaggtgcagc tgttggagtc tgggggaggc ttggtacagc ctggggggtc    120
cctgagactc tcctgtgcag cctctggatt caccttagc agctatgcca tgagctgggt    180
ccgccaggct ccagggaagg ggctgagtg ggtctcaggt attactggga gtggtggtag    240
tacatactac gcagactccg tgaagggccg gttcaccatc tccagagaca attccaagaa    300
cacgctgtat ctgcaaatga acagcctgag agccgaggac acggccgtat attactgtgc    360
gaaagatcca gggactacgg tgattatgag ttggttcgac ccctggggcc agggaaccct    420
ggtcaccgtc tcctcagcct ccaccaaggg cccatcggtc ttccccctgg cgccctgctc    480
caggagcacc tccgagagca gcggccct gggctgcctg gtcaaggact acttccccga    540
accggtgacg gtgtcgtgga actcaggcgc tctgaccagc ggcgtgcaca ccttcccagc    600
tgtcctacag tcctcaggac tctactccct cagcagcgtg gtgaccgtgc cctccagcaa    660
cttcggcacc cagacctaca cctgcaacgt agatcacaag cccagcaaca caaggtgga    720 caagacagtt gagcgcaaat gttgtgtcga gtgcccaccg tgcccagcac cacctgtggc    780
aggaccgtca gtcttcctct tccccccaaa acccaaggac accctcatga tctcccggac    840
ccctgaggtc acgtgcgtgg tggtggacgt gagccacgaa gaccccgagg tccagttcaa    900
ctggtacgtg gacggcgtgg aggtgcataa tgccaagaca aagccacggg aggagcagtt    960
caacagcacg ttccgtgtgg tcagcgtcct caccgttgtg caccaggact ggctgaacgg   1020
caaggagtac aagtgcaagg tctccaacaa aggcctccca gcccccatcg agaaaaccat   1080
ctccaaaacc aaagggcagc cccgagaacc acaggtgtac accctgcccc catcccggga   1140
ggagatgacc aagaaccagg tcagcctgac ctgcctggtc aaaggcttct accccagcga   1200
```

-continued

```
catcgccgtg gagtgggaga gcaatgggca gccggagaac aactacaaga ccacacctcc    1260
catgctggac tccgacggct ccttcttcct ctacagcaag ctcaccgtgg acaagagcag    1320
gtggcagcag gggaacgtct tctcatgctc cgtgatgcat gaggctctgc acaaccacta    1380
cacgcagaag agcctctccc tgtctccggg taaatgataa gtcgac                  1426
```

<210> SEQ ID NO 2
<211> LENGTH: 467
<212> TYPE: PRT
<213> ORGANISM: Artificial Sequence
<220> FEATURE:
<223> OTHER INFORMATION: Description of Artificial Sequence: Synthetic
      alpha-RANKL-1 heavy chain

<400> SEQUENCE: 2

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Gly Ile Thr Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Asp Pro Gly Thr Thr Val Ile Met Ser Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320
```

Arg Val Val Ser Val Leu Thr Val Val His Gln Asp Trp Leu Asn Gly
              325                 330                 335

Lys Glu Tyr Lys Cys Lys Val Ser Asn Lys Gly Leu Pro Ala Pro Ile
          340                 345                 350

Glu Lys Thr Ile Ser Lys Thr Lys Gly Gln Pro Arg Glu Pro Gln Val
      355                 360                 365

Tyr Thr Leu Pro Pro Ser Arg Glu Glu Met Thr Lys Asn Gln Val Ser
  370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
              405                 410                 415

Met Leu Asp Ser Asp Gly Ser Phe Phe Leu Tyr Ser Lys Leu Thr Val
          420                 425                 430

Asp Lys Ser Arg Trp Gln Gln Gly Asn Val Phe Ser Cys Ser Val Met
      435                 440                 445

His Glu Ala Leu His Asn His Tyr Thr Gln Lys Ser Leu Ser Leu Ser
  450                 455                 460

Pro Gly Lys
465

<210> SEQ ID NO 3
<211> LENGTH: 728
<212> TYPE: DNA
<213> ORGANISM: Artificial Sequence
<220> FEATURE:
<223> OTHER INFORMATION: Description of Artificial Sequence: Synthetic
      alpha-RANKL-1 light chain

<400> SEQUENCE: 3
tctagaccac catggaaacc ccagcgcagc ttctcttcct cctgctactc tggctcccag      60
ataccaccgg agaaattgtg ttgacgcagt ctccaggcac cctgtctttg tctccagggg    120
aaagagccac cctctcctgt agggccagtc agagtgttcg cggcaggtac ttagcctggt    180
accagcagaa acctggccag gctcccaggc tcctcatcta tggtgcatcc agcagggcca    240
ctggcatccc agacaggttc agtggcagtg gtctgggac agacttcact ctcaccatca     300
gcagactgga gcctgaagat tttgcagtgt tttactgtca gcagtatggt agttcacctc    360
ggacgttcgg ccaagggacc aaggtggaaa tcaaacgaac tgtggctgca ccatctgtct    420
tcatcttccc gccatctgat gagcagttga aatctggaac tgcctctgtt gtgtgcctgc    480
tgaataactt ctatcccaga gaggccaaag tacagtggaa ggtggataac gccctccaat    540
cgggtaactc ccaggagagt gtcacagagc aggacagcaa ggacagcacc tacagcctca    600
gcagcaccct gacgctgagc aaagcagact acgagaaaca caaagtctac gcctgcgaag    660
tcacccatca gggcctgagc tcgcccgtca caaagagctt caacagggga gagtgttgat    720
aagtcgac                                                             728

<210> SEQ ID NO 4
<211> LENGTH: 235
<212> TYPE: PRT
<213> ORGANISM: Artificial Sequence
<220> FEATURE:
<223> OTHER INFORMATION: Description of Artificial Sequence: Synthetic
      alpha-RANKL-1 light chain

<400> SEQUENCE: 4

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Arg Gly Arg Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Phe Tyr Cys Gln Gln Tyr
            100                 105                 110

Gly Ser Ser Pro Arg Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 5
<211> LENGTH: 221
<212> TYPE: DNA
<213> ORGANISM: Artificial Sequence
<220> FEATURE:
<223> OTHER INFORMATION: Description of Artificial Sequence: Synthetic
      synPTH cDNA sequence

<400> SEQUENCE: 5
tctagaccac catgatcccc gccaaggaca tggccaaggt gatgatcgtg atgctggcca      60
tttgtttcct gaccaagagc gatggcaagt ccgtgaagaa gagatccgtg agcgagatcc     120
agctgatgca caacctgggc aagcacctga actccatgga gagtggag tggctgcgca      180 agaagctgca ggacgtgcac aacttcggcg cggcgcgcc c                         221

<210> SEQ ID NO 6
<211> LENGTH: 70
<212> TYPE: PRT
<213> ORGANISM: Artificial Sequence
<220> FEATURE:
<223> OTHER INFORMATION: Description of Artificial Sequence: Synthetic
      synPTH amino acid sequence

<400> SEQUENCE: 6

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser

```
                   20                  25                  30

Val Ser Glu Ile Gln Leu Met His Asn Leu Gly Lys His Leu Asn Ser
            35                  40                  45

Met Glu Arg Val Glu Trp Leu Arg Lys Lys Leu Gln Asp Val His Asn
        50                  55                  60

Phe Gly Gly Gly Ala Pro
65                  70

<210> SEQ ID NO 7
<211> LENGTH: 875
<212> TYPE: DNA
<213> ORGANISM: Artificial Sequence
<220> FEATURE:
<223> OTHER INFORMATION: Description of Artificial Sequence: Synthetic
      synPTH alpha-RANKL-1 light chain

<400> SEQUENCE: 7
tctagaccac catgatcccc gccaaggaca tggccaaggt gatgatcgtg atgctggcca      60
tttgtttcct gaccaagagc gatggcaagt ccgtgaagaa gagatccgtg agcgagatcc     120
agctgatgca caacctgggc aagcacctga actccatgga gagagtggag tggctgcgca     180
agaagctgca ggacgtgcac aacttcggcg gcggcgcgcc cgaaattgtg ttgacgcagt     240
ctccaggcac cctgtctttg tctccagggg aaagagccac cctctcctgt agggccagtc     300
agagtgttcg cggcaggtac ttagcctggt accagcagaa acctggccag ctcccaggc     360 tcctcatcta tggtgcatcc agcagggcca ctggcatccc agacaggttc agtggcagtg     420
ggtctgggac agacttcact ctcaccatca gcagactgga gcctgaagat tttgcagtgt     480
tttactgtca gcagtatggt agttcacctc ggacgttcgg ccaagggacc aaggtggaaa     540
tcaaacgaac tgtggctgca ccatctgtct tcatcttccc gccatctgat gagcagttga     600
aatctggaac tgcctctgtt gtgtgcctgc tgaataactt ctatcccaga gaggccaaag     660
tacagtggaa ggtggataac gccctccaat cgggtaactc ccaggagagt gtcacagagc     720
aggacagcaa ggacagcacc tacagcctca gcagcaccct gacgctgagc aaagcagact     780
acgagaaaca caaagtctac gcctgcgaag tcacccatca gggcctgagc tcgcccgtca     840
caaagagctt caacagggga gagtgttgag tcgac                                 875

<210> SEQ ID NO 8
<211> LENGTH: 285
<212> TYPE: PRT
<213> ORGANISM: Artificial Sequence
<220> FEATURE:
<223> OTHER INFORMATION: Description of Artificial Sequence: Synthetic
      synPTH alpha-RANKL-1 light chain

<400> SEQUENCE: 8

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
            20                  25                  30

Val Ser Glu Ile Gln Leu Met His Asn Leu Gly Lys His Leu Asn Ser
        35                  40                  45

Met Glu Arg Val Glu Trp Leu Arg Lys Lys Leu Gln Asp Val His Asn
    50                  55                  60

Phe Gly Gly Gly Ala Pro Glu Ile Val Leu Thr Gln Ser Pro Gly Thr
65                  70                  75                  80

Leu Ser Leu Ser Pro Gly Glu Arg Ala Thr Leu Ser Cys Arg Ala Ser
```

|    |    |    |    |    | 85  |    |    |    |    | 90  |    |    |    |    | 95  |    |    |
|----|----|----|----|----|-----|----|----|----|----|-----|----|----|----|----|-----|----|----|

Gln Ser Val Arg Gly Arg Tyr Leu Ala Trp Tyr Gln Gln Lys Pro Gly
                100                 105                 110

Gln Ala Pro Arg Leu Leu Ile Tyr Gly Ala Ser Ser Arg Ala Thr Gly
            115                 120                 125

Ile Pro Asp Arg Phe Ser Gly Ser Gly Ser Gly Thr Asp Phe Thr Leu
    130                 135                 140

Thr Ile Ser Arg Leu Glu Pro Glu Asp Phe Ala Val Phe Tyr Cys Gln
145                 150                 155                 160

Gln Tyr Gly Ser Ser Pro Arg Thr Phe Gly Gln Gly Thr Lys Val Glu
                165                 170                 175

Ile Lys Arg Thr Val Ala Ala Pro Ser Val Phe Ile Phe Pro Pro Ser
            180                 185                 190

Asp Glu Gln Leu Lys Ser Gly Thr Ala Ser Val Val Cys Leu Leu Asn
    195                 200                 205

Asn Phe Tyr Pro Arg Glu Ala Lys Val Gln Trp Lys Val Asp Asn Ala
210                 215                 220

Leu Gln Ser Gly Asn Ser Gln Glu Ser Val Thr Glu Gln Asp Ser Lys
225                 230                 235                 240

Asp Ser Thr Tyr Ser Leu Ser Ser Thr Leu Thr Leu Ser Lys Ala Asp
                245                 250                 255

Tyr Glu Lys His Lys Val Tyr Ala Cys Glu Val Thr His Gln Gly Leu
            260                 265                 270

Ser Ser Pro Val Thr Lys Ser Phe Asn Arg Gly Glu Cys
    275                 280                 285

<210> SEQ ID NO 9
<211> LENGTH: 1574
<212> TYPE: DNA
<213> ORGANISM: Artificial Sequence
<220> FEATURE:
<223> OTHER INFORMATION: Description of Artificial Sequence: Synthetic
      synPTH alpha-RANKL-1 heavy chain

<400> SEQUENCE: 9
tctagaccac catgatcccc gccaaggaca tggccaaggt gatgatcgtg atgctggcca      60
tttgtttcct gaccaagagc gatggcaagt ccgtgaagaa gagatccgtg agcgagatcc     120
agctgatgca caacctgggc aagcacctga actccatgga gagagtggag tggctgcgca     180
agaagctgca ggacgtgcac aacttcggcg gcggcgcgcc cgaggtgcag ctgttggagt     240
ctgggggagg cttggtacag cctgggggtc cctgagact  ctcctgtgca gcctctggat     300
tcacctttag cagctatgcc atgagctggg tccgccaggc tccagggaag gggctggagt     360
gggtctcagg tattactggg agtggtggta gtacatacta cgcagactcc gtgaagggcc     420
ggttcaccat ctccagagac aattccaaga acacgctgta tctgcaaatg aacagcctga     480
gagccgagga cacggccgta tattactgtg cgaaagatcc aggactacg  gtgattatga     540 gttggttcga cccctggggc cagggaaccc tggtcaccgt ctcctcagcc tccaccaagg     600
gcccatcggt cttccccctg gcgccctgct ccaggagcac ctccgagagc acagcggccc     660
tgggctgcct ggtcaaggac tacttccccg aaccggtgac ggtgtcgtgg aactcaggcg     720
ctctgaccag cggcgtgcac accttcccag ctgtcctaca gtcctcagga ctctactccc     780
tcagcagcgt ggtgaccgtg ccctccagca cttcggcac  ccagacctac acctgcaacg     840
tagatcacaa gcccagcaac accaaggtgg acaagacagt tgagcgcaaa tgttgtgtcg     900

```
agtgcccacc gtgcccagca ccacctgtgg caggaccgtc agtcttcctc ttccccccaa    960
aacccaagga caccctcatg atctcccgga cccctgaggt cacgtgcgtg gtggtggacg   1020
tgagccacga agaccccgag gtccagttca actggtacgt ggacggcgtg gaggtgcata   1080
atgccaagac aaagccacgg gaggagcagt tcaacagcac gttccgtgtg gtcagcgtcc   1140
tcaccgttgt gcaccaggac tggctgaacg gcaaggagta caagtgcaag gtctccaaca   1200
aaggcctccc agcccccatc gagaaaacca tctccaaaac caaagggcag ccccgagaac   1260
cacaggtgta caccctgccc ccatcccggg aggagatgac caagaaccag gtcagcctga   1320
cctgcctggt caaaggcttc taccccagcg acatcgccgt ggagtgggag agcaatgggc   1380
agccggagaa caactacaag accacacctc ccatgctgga ctccgacggc tccttcttcc   1440
tctacagcaa gctcaccgtg gacaagagca ggtggcagca ggggaacgtc ttctcatgct   1500
ccgtgatgca tgaggctctg cacaaccact acacgcagaa gagcctctcc ctgtctccgg   1560
gtaaatgagt cgac                                                     1574
```

<210> SEQ ID NO 10
<211> LENGTH: 518
<212> TYPE: PRT
<213> ORGANISM: Artificial Sequence
<220> FEATURE:
<223> OTHER INFORMATION: Description of Artificial Sequence: Synthetic synPTH alpha-RANKL-1 heavy chain

<400> SEQUENCE: 10

```
Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
                20                  25                  30

Val Ser Glu Ile Gln Leu Met His Asn Leu Gly Lys His Leu Asn Ser
            35                  40                  45

Met Glu Arg Val Glu Trp Leu Arg Lys Lys Leu Gln Asp Val His Asn
        50                  55                  60

Phe Gly Gly Gly Ala Pro Glu Val Gln Leu Leu Glu Ser Gly Gly Gly
65                  70                  75                  80

Leu Val Gln Pro Gly Gly Ser Leu Arg Leu Ser Cys Ala Ala Ser Gly
                85                  90                  95

Phe Thr Phe Ser Ser Tyr Ala Met Ser Trp Val Arg Gln Ala Pro Gly
            100                 105                 110

Lys Gly Leu Glu Trp Val Ser Gly Ile Thr Gly Ser Gly Gly Ser Thr
        115                 120                 125

Tyr Tyr Ala Asp Ser Val Lys Gly Arg Phe Thr Ile Ser Arg Asp Asn
    130                 135                 140

Ser Lys Asn Thr Leu Tyr Leu Gln Met Asn Ser Leu Arg Ala Glu Asp
145                 150                 155                 160

Thr Ala Val Tyr Tyr Cys Ala Lys Asp Pro Gly Thr Thr Val Ile Met
                165                 170                 175

Ser Trp Phe Asp Pro Trp Gly Gln Gly Thr Leu Val Thr Val Ser Ser
            180                 185                 190

Ala Ser Thr Lys Gly Pro Ser Val Phe Pro Leu Ala Pro Cys Ser Arg
        195                 200                 205

Ser Thr Ser Glu Ser Thr Ala Ala Leu Gly Cys Leu Val Lys Asp Tyr
    210                 215                 220

Phe Pro Glu Pro Val Thr Val Ser Trp Asn Ser Gly Ala Leu Thr Ser
225                 230                 235                 240
```

```
Gly Val His Thr Phe Pro Ala Val Leu Gln Ser Ser Gly Leu Tyr Ser
                245                 250                 255

Leu Ser Ser Val Val Thr Val Pro Ser Ser Asn Phe Gly Thr Gln Thr
            260                 265                 270

Tyr Thr Cys Asn Val Asp His Lys Pro Ser Asn Thr Lys Val Asp Lys
        275                 280                 285

Thr Val Glu Arg Lys Cys Cys Val Glu Cys Pro Pro Cys Pro Ala Pro
    290                 295                 300

Pro Val Ala Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
                325                 330                 335

Val Ser His Glu Asp Pro Glu Val Gln Phe Asn Trp Tyr Val Asp Gly
            340                 345                 350

Val Glu Val His Asn Ala Lys Thr Lys Pro Arg Glu Glu Gln Phe Asn
        355                 360                 365

Ser Thr Phe Arg Val Val Ser Val Leu Thr Val Val His Gln Asp Trp
    370                 375                 380

Leu Asn Gly Lys Glu Tyr Lys Cys Lys Val Ser Asn Lys Gly Leu Pro
385                 390                 395                 400

Ala Pro Ile Glu Lys Thr Ile Ser Lys Thr Lys Gly Gln Pro Arg Glu
                405                 410                 415

Pro Gln Val Tyr Thr Leu Pro Pro Ser Arg Glu Glu Met Thr Lys Asn
            420                 425                 430

Gln Val Ser Leu Thr Cys Leu Val Lys Gly Phe Tyr Pro Ser Asp Ile
        435                 440                 445

Ala Val Glu Trp Glu Ser Asn Gly Gln Pro Glu Asn Asn Tyr Lys Thr
    450                 455                 460

Thr Pro Pro Met Leu Asp Ser Asp Gly Ser Phe Phe Leu Tyr Ser Lys
465                 470                 475                 480

Leu Thr Val Asp Lys Ser Arg Trp Gln Gln Gly Asn Val Phe Ser Cys
                485                 490                 495

Ser Val Met His Glu Ala Leu His Asn His Tyr Thr Gln Lys Ser Leu
            500                 505                 510

Ser Leu Ser Pro Gly Lys
        515

<210> SEQ ID NO 11
<211> LENGTH: 122
<212> TYPE: PRT
<213> ORGANISM: Artificial Sequence
<220> FEATURE:
<223> OTHER INFORMATION: Description of Artificial Sequence: Synthetic
      alpha-RANKL-1 heavy chain variable region

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                        85                  90                  95
Ala Lys Asp Pro Gly Thr Thr Val Ile Met Ser Trp Phe Asp Pro Trp
                100                 105                 110
Gly Gln Gly Thr Leu Val Thr Val Ser Ser
        115                 120

<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      alpha-RANKL-1 light chain variable region

<400> SEQUENCE: 12

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Arg Gly Arg
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Ile Pro Asp Arg Phe Ser
50                  55                  60
Gly Ser Gly Ser Gly Thr Asp Phe Thr Leu Thr Ile Ser Arg Leu Glu
65                  70                  75                  80
Pro Glu Asp Phe Ala Val Phe Tyr Cys Gln Gln Tyr Gly Ser Ser Pro
                85                  90                  95
Arg Thr Phe Gly Gln Gly Thr Lys Val Glu Ile Lys
            100                 105

<210> SEQ ID NO 13
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: may or may not be present
<220> FEATURE:
<221> NAME/KEY: MOD_RES
<222> LOCATION: (2)..(8)
<223> OTHER INFORMATION: region may encompass 1-7 variable amino acids
      or not present
<220> FEATURE:
<221> NAME/KEY: MOD_RES
<222> LOCATION: (10)..(12)
<223> OTHER INFORMATION: Variable amino acid
<220> FEATURE:
<221> NAME/KEY: MOD_RES
<222> LOCATION: (14)..(19)
<223> OTHER INFORMATION: Variable amino acid
<220> FEATURE:
<221> NAME/KEY: MOD_RES
<222> LOCATION: (21)..(28)
<223> OTHER INFORMATION: Variable amino acid
<220> FEATURE:
<221> NAME/KEY: MOD_RES
<222> LOCATION: (29)..(36)
<223> OTHER INFORMATION: region may encompass 1-8 variable amino acids
      or is not present
<220> FEATURE:
<223> OTHER INFORMATION: see specification as filed for detailed
``` description of preferred embodiments

<400> SEQUENCE: 13

Tyr Xaa Xaa Xaa Xaa Xaa Xaa Xaa His Xaa Xaa Xaa Lys Xaa Xaa Xaa
1               5                   10                  15

Xaa Xaa Xaa Arg Xaa Xaa Xaa Xaa Xaa Xaa Xaa Xaa Xaa Xaa
            20                  25                  30

Xaa Xaa Xaa Xaa
        35

<210> SEQ ID NO 14
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: region may encompass 1-6 variable amino acids
      or not present
<220> FEATURE:
<221> NAME/KEY: MOD_RES
<222> LOCATION: (7)..(8)
<223> OTHER INFORMATION: Variable amino acid
<220> FEATURE:
<221> NAME/KEY: MOD_RES
<222> LOCATION: (11)
<223> OTHER INFORMATION: nonfunctional or basic amino acid
<220> FEATURE:
<221> NAME/KEY: MOD_RES
<222> LOCATION: (12)
<223> OTHER INFORMATION: Variable amino acid
<220> FEATURE:
<221> NAME/KEY: MOD_RES
<222> LOCATION: (16)
<223> OTHER INFORMATION: Variable amino acid
<220> FEATURE:
<221> NAME/KEY: MOD_RES
<222> LOCATION: (18)
<223> OTHER INFORMATION: Variable amino acid
<220> FEATURE:
<221> NAME/KEY: MOD_RES
<222> LOCATION: (19)
<223> OTHER INFORMATION: acidic or basic amino acid
<220> FEATURE:
<221> NAME/KEY: MOD_RES
<222> LOCATION: (21)
<223> OTHER INFORMATION: Variable amino acid
<220> FEATURE:
<221> NAME/KEY: MOD_RES
<222> LOCATION: (29)..(34)
<223> OTHER INFORMATION: region may encompass 1-6 variable amino acids
      or is not present
<220> FEATURE:
<223> OTHER INFORMATION: see specification as filed for detailed
      description of preferred embodiments

<400> SEQUENCE: 14

Xaa Xaa Xaa Xaa Xaa Xaa Xaa Xaa His Asn Xaa Xaa Lys His Leu Xaa
1               5                   10                  15

Ser Xaa Xaa Arg Xaa Glu Trp Leu Arg Lys Lys Leu Xaa Xaa Xaa Xaa
            20                  25                  30

Xaa Xaa

<210> SEQ ID NO 15
<211> LENGTH: 38
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: may or may not be present
<220> FEATURE:
<221> NAME/KEY: MOD_RES
<222> LOCATION: (2)..(8)
<223> OTHER INFORMATION: region may encompass 1-7 amino acids or is
      not present
<220> FEATURE:
<221> NAME/KEY: MOD_RES
<222> LOCATION: (11)..(13)
<223> OTHER INFORMATION: Variable amino acid
<220> FEATURE:
<221> NAME/KEY: MOD_RES
<222> LOCATION: (17)..(19)
<223> OTHER INFORMATION: Variable amino acid
<220> FEATURE:
<221> NAME/KEY: MOD_RES
<222> LOCATION: (25)
<223> OTHER INFORMATION: Variable amino acid
<220> FEATURE:
<221> NAME/KEY: MOD_RES
<222> LOCATION: (31)..(38)
<223> OTHER INFORMATION: region may encompass 1-8 variable amino acids
      or is not present
<220> FEATURE:
<223> OTHER INFORMATION: see specification as filed for detailed
      description of preferred embodiments

<400> SEQUENCE: 15

Tyr Xaa Xaa Xaa Xaa Xaa Xaa Xaa Leu His Xaa Xaa Xaa Lys Ser Ile
1               5                   10                  15

Xaa Xaa Xaa Leu Arg Arg Arg Phe Xaa Leu His His Leu Ile Xaa Xaa
            20                  25                  30

Xaa Xaa Xaa Xaa Xaa Xaa
        35

<210> SEQ ID NO 16
<211> LENGTH: 84
<212> TYPE: PRT
<213> ORGANISM: Homo sapiens

<400> SEQUENCE: 16

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 17
<211> LENGTH: 84
<212> TYPE: PRT
<213> ORGANISM: Rattus sp.

<400> SEQUENCE: 17

Ala Val Ser Glu Ile Gln Leu Met His Asn Leu Gly Lys His Leu Ala
1               5                   10                  15
```

```
Ser Val Glu Arg Met Gln Trp Leu Arg Lys Lys Leu Gln Asp Val His
             20                  25                  30

Asn Phe Val Ser Leu Gly Val Gln Met Ala Ala Arg Glu Gly Ser Tyr
         35                  40                  45

Gln Arg Pro Thr Lys Lys Glu Asp Asn Val Leu Val Asp Gly Asn Ser
     50                  55                  60

Lys Ser Leu Gly Glu Gly Asp Lys Ala Asp Val Asp Val Leu Val Lys
 65                  70                  75                  80

Ala Lys Ser Gln

<210> SEQ ID NO 18
<211> LENGTH: 78
<212> TYPE: PRT
<213> ORGANISM: Homo sapiens

<400> SEQUENCE: 18

Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
             20                  25                  30

Ala Pro Leu Ala Pro Arg Asp Ala Gly Ser Gln Arg Pro Arg Lys Lys
         35                  40                  45

Glu Asp Asn Val Leu Val Glu Ser His Glu Lys Ser Leu Gly Glu Ala
     50                  55                  60

Asp Lys Ala Asp Val Asn Val Leu Thr Lys Ala Lys Ser Gln
 65                  70                  75

<210> SEQ ID NO 19
<211> LENGTH: 44
<212> TYPE: PRT
<213> ORGANISM: Homo sapiens

<400> SEQUENCE: 19

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
             20                  25                  30

Asn Phe Val Ala Leu Gly Ala Pro Leu Ala Pro Arg
         35                  40

<210> SEQ ID NO 20
<211> LENGTH: 38
<212> TYPE: PRT
<213> ORGANISM: Homo sapiens

<400> SEQUENCE: 20

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
             20                  25                  30

Asn Phe Val Ala Leu Gly
         35

<210> SEQ ID NO 21
<211> LENGTH: 37
<212> TYPE: PRT
<213> ORGANISM: Homo sapiens

<400> SEQUENCE: 21
```

```
Val Ser Glu Ile Gln Leu Met His Asn Leu Gly Lys His Leu Asn Ser
1               5                   10                  15

Met Glu Arg Val Glu Trp Leu Arg Lys Leu Gln Asp Val His Asn
            20                  25                  30

Phe Val Ala Leu Gly
            35
```

<210> SEQ ID NO 22
<211> LENGTH: 34
<212> TYPE: PRT
<213> ORGANISM: Homo sapiens

<400> SEQUENCE: 22

```
Ser Val Ser Glu Ile Gln Leu Met His Asn Leu Gly Lys His Leu Asn
1               5                   10                  15

Ser Met Glu Arg Val Glu Trp Leu Arg Lys Leu Gln Asp Val His
            20                  25                  30

Asn Phe
```

<210> SEQ ID NO 23
<211> LENGTH: 34
<212> TYPE: PRT
<213> ORGANISM: Homo sapiens

<400> SEQUENCE: 23

```
Ser Val Ser Glu Ile Gln Leu Met His Asn Arg Gly Lys His Leu Asn
1               5                   10                  15

Ser Met Glu Arg Val Glu Trp Leu Arg Lys Lys Leu Gln Asp Val His
            20                  25                  30

Asn Phe
```

<210> SEQ ID NO 24
<211> LENGTH: 34
<212> TYPE: PRT
<213> ORGANISM: Homo sapiens

<400> SEQUENCE: 24

```
Ser Val Ser Glu Ile Gln Leu Met His Asn Lys Gly Lys His Leu Asn
1               5                   10                  15

Ser Met Glu Arg Val Glu Trp Leu Arg Lys Lys Leu Gln Asp Val His
            20                  25                  30

Asn Phe
```

<210> SEQ ID NO 25
<211> LENGTH: 34
<212> TYPE: PRT
<213> ORGANISM: Homo sapiens

<400> SEQUENCE: 25

```
Ser Val Ser Glu Ile Gln Leu Met His Asn Leu Gly Lys His Leu Asn
1               5                   10                  15

Ser Met Arg Arg Val Glu Trp Leu Arg Lys Lys Leu Gln Asp Val His
            20                  25                  30

Asn Phe
```

<210> SEQ ID NO 26
<211> LENGTH: 34
<212> TYPE: PRT
<213> ORGANISM: Homo sapiens

```
<400> SEQUENCE: 26

Tyr Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 27
<211> LENGTH: 34
<212> TYPE: PRT
<213> ORGANISM: Homo sapiens

<400> SEQUENCE: 27

Ser Val Ser Glu Ile Gln Leu Leu His Asn Leu Gly Lys His Leu Asn
1               5                   10                  15

Ser Leu Glu Arg Val Glu Trp Leu Arg Lys Lys Leu Gln Asp Val His
            20                  25                  30

Asn Tyr

<210> SEQ ID NO 28
<211> LENGTH: 34
<212> TYPE: PRT
<213> ORGANISM: Bos taurus

<400> SEQUENCE: 28

Ala Val Ser Glu Ile Gln Phe Met His Asn Leu Gly Lys His Leu Ser
1               5                   10                  15

Ser Met Glu Arg Val Glu Trp Leu Arg Lys Lys Leu Gln Asp Val His
            20                  25                  30

Asn Phe

<210> SEQ ID NO 29
<211> LENGTH: 34
<212> TYPE: PRT
<213> ORGANISM: Bos taurus

<400> SEQUENCE: 29

Ala Val Ser Glu Ile Gln Phe Leu His Asn Leu Gly Lys His Leu Ser
1               5                   10                  15

Ser Leu Glu Arg Val Glu Trp Leu Arg Lys Lys Leu Gln Asp Val His
            20                  25                  30

Asn Tyr

<210> SEQ ID NO 30
<211> LENGTH: 34
<212> TYPE: PRT
<213> ORGANISM: Sus scrofa

<400> SEQUENCE: 30

Ser Val Ser Glu Ile Gln Leu Met His Asn Leu Gly Lys His Leu Ser
1               5                   10                  15

Ser Leu Glu Arg Val Glu Trp Leu Arg Lys Lys Leu Gln Asp Val His
            20                  25                  30

Asn Phe

<210> SEQ ID NO 31
<211> LENGTH: 34
<212> TYPE: PRT
<213> ORGANISM: Rattus sp.
```

<400> SEQUENCE: 31

Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp Val His
                20                  25                  30

Asn Phe

<210> SEQ ID NO 32
<211> LENGTH: 34
<212> TYPE: PRT
<213> ORGANISM: Rattus sp.

<400> SEQUENCE: 32

Ala Val Ser Glu Ile Gln Leu Leu His Asn Leu Gly Lys His Leu Ala
1               5                   10                  15

Ser Val Glu Arg Leu Gln Trp Leu Arg Lys Lys Leu Gln Asp Val His
                20                  25                  30

Asn Tyr

<210> SEQ ID NO 33
<211> LENGTH: 31
<212> TYPE: PRT
<213> ORGANISM: Homo sapiens

<400> SEQUENCE: 33

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
                20                  25                  30

<210> SEQ ID NO 34
<211> LENGTH: 31
<212> TYPE: PRT
<213> ORGANISM: Homo sapiens

<400> SEQUENCE: 34

Ser Val Ser Glu Ile Gln Leu Met His Asn Leu Gly Lys His Leu Asn
1               5                   10                  15

Ser Met Glu Arg Val Gly Trp Leu Arg Lys Leu Leu Gln Asp Val
                20                  25                  30

<210> SEQ ID NO 35
<211> LENGTH: 32
<212> TYPE: PRT
<213> ORGANISM: Homo sapiens

<400> SEQUENCE: 35

Ser Glu Ile Gln Leu Leu His Asn Leu Gly Lys His Leu Asn Ser Leu
1               5                   10                  15

Glu Arg Val Glu Trp Leu Arg Lys Lys Leu Gln Asp Val His Asn Tyr
                20                  25                  30

<210> SEQ ID NO 36
<211> LENGTH: 32
<212> TYPE: PRT
<213> ORGANISM: Bos taurus

<400> SEQUENCE: 36

Ser Glu Ile Gln Phe Met His Asn Leu Gly Lys His Leu Ser Ser Met
1               5                   10                  15

Glu Arg Val Glu Trp Leu Arg Lys Lys Leu Gln Asp Val His Asn Phe
            20                  25                  30

<210> SEQ ID NO 37
<211> LENGTH: 32
<212> TYPE: PRT
<213> ORGANISM: Bos taurus

<400> SEQUENCE: 37

Ser Glu Ile Gln Phe Leu His Asn Leu Gly Lys His Leu Ser Ser Leu
1               5                   10                  15

Glu Arg Val Glu Trp Leu Arg Lys Lys Leu Gln Asp Val His Asn Tyr
            20                  25                  30

<210> SEQ ID NO 38
<211> LENGTH: 28
<212> TYPE: PRT
<213> ORGANISM: Homo sapiens

<400> SEQUENCE: 38

Leu Met His Asn Leu Gly Lys His Leu Asn Ser Met Glu Arg Val Glu
1               5                   10                  15

Trp Leu Arg Lys Lys Leu Gln Asp Val His Asn Phe
            20                  25

<210> SEQ ID NO 39
<211> LENGTH: 28
<212> TYPE: PRT
<213> ORGANISM: Homo sapiens

<400> SEQUENCE: 39

Leu Leu His Asn Leu Gly Lys His Leu Asn Ser Leu Glu Arg Val Glu
1               5                   10                  15

Trp Leu Arg Lys Lys Leu Gln Asp Val His Asn Tyr
            20                  25

<210> SEQ ID NO 40
<211> LENGTH: 28
<212> TYPE: PRT
<213> ORGANISM: Bos taurus

<400> SEQUENCE: 40

Phe Met His Asn Leu Gly Lys His Leu Ser Ser Met Glu Arg Val Glu
1               5                   10                  15

Trp Leu Arg Lys Lys Leu Gln Asp Val His Asn Phe
            20                  25

<210> SEQ ID NO 41
<211> LENGTH: 28
<212> TYPE: PRT
<213> ORGANISM: Bos taurus

<400> SEQUENCE: 41

Phe Met His Asn Leu Gly Lys His Leu Ser Ser Met Glu Arg Val Glu
1               5                   10                  15

Trp Leu Arg Lys Lys Leu Gln Asp Val His Asn Tyr
            20                  25

<210> SEQ ID NO 42
<211> LENGTH: 28
<212> TYPE: PRT
<213> ORGANISM: Bos taurus

<400> SEQUENCE: 42

Phe Leu His Asn Leu Gly Lys His Leu Ser Ser Leu Glu Arg Val Glu
1               5                   10                  15

Trp Leu Arg Lys Lys Leu Gln Asp Val His Asn Tyr
            20                  25

<210> SEQ ID NO 43
<211> LENGTH: 28
<212> TYPE: PRT
<213> ORGANISM: Bos taurus

<400> SEQUENCE: 43

Phe Leu His Asn Leu Trp Lys His Leu Ser Ser Leu Glu Arg Val Glu
1               5                   10                  15

Trp Leu Arg Lys Lys Leu Gln Asp Val His Asn Tyr
            20                  25

<210> SEQ ID NO 44
<211> LENGTH: 28
<212> TYPE: PRT
<213> ORGANISM: Bos taurus
<220> FEATURE:
<221> NAME/KEY: MOD_RES
<222> LOCATION: (6)
<223> OTHER INFORMATION: D-Trp

<400> SEQUENCE: 44

Phe Met His Asn Leu Trp Lys His Leu Ser Ser Met Glu Arg Val Glu
1               5                   10                  15

Trp Leu Arg Lys Lys Leu Gln Asp Val His Asn Tyr
            20                  25

<210> SEQ ID NO 45
<211> LENGTH: 30
<212> TYPE: PRT
<213> ORGANISM: Homo sapiens

<400> SEQUENCE: 45

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp
            20                  25                  30

<210> SEQ ID NO 46
<211> LENGTH: 30
<212> TYPE: PRT
<213> ORGANISM: Homo sapiens

<400> SEQUENCE: 46

Ser Val Ser Glu Ile Gln Leu Met His Asn Arg Gly Lys His Leu Asn
1               5                   10                  15

Ser Met Glu Arg Val Glu Trp Leu Arg Lys Lys Leu Gln Asp
            20                  25                  30

<210> SEQ ID NO 47
<211> LENGTH: 30
<212> TYPE: PRT
<213> ORGANISM: Homo sapiens

<400> SEQUENCE: 47

Ser Val Ser Glu Ile Gln Leu Met His Asn Lys Gly Lys His Leu Asn
1               5                   10                  15

Ser Met Glu Arg Val Glu Trp Leu Arg Lys Lys Leu Gln Asp
            20                  25                  30

<210> SEQ ID NO 48
<211> LENGTH: 30
<212> TYPE: PRT
<213> ORGANISM: Homo sapiens

<400> SEQUENCE: 48

Ser Val Ser Glu Ile Gln Leu Met His Asn Leu Gly Lys His Leu Asn
1               5                   10                  15

Ser Met Arg Arg Val Glu Trp Leu Arg Lys Lys Leu Gln Asp
            20                  25                  30

<210> SEQ ID NO 49
<211> LENGTH: 30
<212> TYPE: PRT
<213> ORGANISM: Homo sapiens

<400> SEQUENCE: 49

Tyr Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp
            20                  25                  30

<210> SEQ ID NO 50
<211> LENGTH: 30
<212> TYPE: PRT
<213> ORGANISM: Homo sapiens

<400> SEQUENCE: 50

Ser Val Ser Glu Ile Gln Leu Leu His Asn Leu Gly Lys His Leu Asn
1               5                   10                  15

Ser Leu Glu Arg Val Glu Trp Leu Arg Lys Lys Leu Gln Asp
            20                  25                  30

<210> SEQ ID NO 51
<211> LENGTH: 30
<212> TYPE: PRT
<213> ORGANISM: Bos taurus

<400> SEQUENCE: 51

Ala Val Ser Glu Ile Gln Phe Met His Asn Leu Gly Lys His Leu Ser
1               5                   10                  15

Ser Met Glu Arg Val Glu Trp Leu Arg Lys Lys Leu Gln Asp
            20                  25                  30

<210> SEQ ID NO 52
<211> LENGTH: 30
<212> TYPE: PRT
<213> ORGANISM: Bos taurus

<400> SEQUENCE: 52

Ala Val Ser Glu Ile Gln Phe Leu His Asn Leu Gly Lys His Leu Ser
1               5                   10                  15

Ser Leu Glu Arg Val Glu Trp Leu Arg Lys Lys Leu Gln Asp
            20                  25                  30

<210> SEQ ID NO 53
<211> LENGTH: 30
<212> TYPE: PRT
<213> ORGANISM: Sus scrofa

<400> SEQUENCE: 53

Ser Val Ser Glu Ile Gln Leu Met His Asn Leu Gly Lys His Leu Ser
1               5                   10                  15

Ser Leu Glu Arg Val Glu Trp Leu Arg Lys Lys Leu Gln Asp
            20                  25                  30

<210> SEQ ID NO 54
<211> LENGTH: 30
<212> TYPE: PRT
<213> ORGANISM: Rattus sp.

<400> SEQUENCE: 54

Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp
            20                  25                  30

<210> SEQ ID NO 55
<211> LENGTH: 30
<212> TYPE: PRT
<213> ORGANISM: Rattus sp.

<400> SEQUENCE: 55

Ala Val Ser Glu Ile Gln Leu Leu His Asn Leu Gly Lys His Leu Ala
1               5                   10                  15

Ser Val Glu Arg Leu Gln Trp Leu Arg Lys Lys Leu Gln Asp
            20                  25                  30

<210> SEQ ID NO 56
<211> LENGTH: 30
<212> TYPE: PRT
<213> ORGANISM: Homo sapiens

<400> SEQUENCE: 56

Ser Val Ser Glu Ile Gln Leu Met His Asn Leu Gly Lys His Leu Asn
1               5                   10                  15

Ser Met Glu Arg Val Glu Trp Leu Arg Lys Leu Leu Gln Asp
            20                  25                  30

<210> SEQ ID NO 57
<211> LENGTH: 29
<212> TYPE: PRT
<213> ORGANISM: Homo sapiens

<400> SEQUENCE: 57

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln
            20                  25

<210> SEQ ID NO 58
<211> LENGTH: 28
<212> TYPE: PRT
<213> ORGANISM: Homo sapiens

<400> SEQUENCE: 58

Ser Val Ser Glu Ile Gln Leu Met His Asn Leu Gly Lys His Leu Asn
1               5                   10                  15

Ser Met Glu Arg Val Glu Trp Leu Arg Lys Lys Leu
            20                  25

-continued

<210> SEQ ID NO 59
<211> LENGTH: 28
<212> TYPE: PRT
<213> ORGANISM: Homo sapiens

<400> SEQUENCE: 59

Ser Glu Ile Gln Leu Leu His Asn Leu Gly Lys His Leu Asn Ser Leu
1               5                   10                  15

Glu Arg Val Glu Trp Leu Arg Lys Lys Leu Gln Asp
            20                  25

<210> SEQ ID NO 60
<211> LENGTH: 28
<212> TYPE: PRT
<213> ORGANISM: Bos taurus

<400> SEQUENCE: 60

Ser Glu Ile Gln Phe Met His Asn Leu Gly Lys His Leu Ser Ser Met
1               5                   10                  15

Glu Arg Val Glu Trp Leu Arg Lys Lys Leu Gln Asp
            20                  25

<210> SEQ ID NO 61
<211> LENGTH: 28
<212> TYPE: PRT
<213> ORGANISM: Bos taurus

<400> SEQUENCE: 61

Ser Glu Ile Gln Phe Leu His Asn Leu Gly Lys His Leu Ser Ser Leu
1               5                   10                  15

Glu Arg Val Glu Trp Leu Arg Lys Lys Leu Gln Asp
            20                  25

<210> SEQ ID NO 62
<211> LENGTH: 24
<212> TYPE: PRT
<213> ORGANISM: Homo sapiens

<400> SEQUENCE: 62

Leu Met His Asn Leu Gly Lys His Leu Asn Ser Met Glu Arg Val Glu
1               5                   10                  15

Trp Leu Arg Lys Lys Leu Gln Asp
            20

<210> SEQ ID NO 63
<211> LENGTH: 24
<212> TYPE: PRT
<213> ORGANISM: Homo sapiens

<400> SEQUENCE: 63

Leu Leu His Asn Leu Gly Lys His Leu Asn Ser Leu Glu Arg Val Glu
1               5                   10                  15

Trp Leu Arg Lys Lys Leu Gln Asp
            20

<210> SEQ ID NO 64
<211> LENGTH: 24
<212> TYPE: PRT
<213> ORGANISM: Bos taurus

<400> SEQUENCE: 64

Phe Met His Asn Leu Gly Lys His Leu Ser Ser Met Glu Arg Val Glu

```
1               5                   10                  15
Trp Leu Arg Lys Lys Leu Gln Asp
            20

<210> SEQ ID NO 65
<211> LENGTH: 24
<212> TYPE: PRT
<213> ORGANISM: Bos taurus

<400> SEQUENCE: 65

Phe Leu His Asn Leu Gly Lys His Leu Ser Ser Leu Glu Arg Val Glu
1               5                   10                  15

Trp Leu Arg Lys Lys Leu Gln Asp
            20

<210> SEQ ID NO 66
<211> LENGTH: 24
<212> TYPE: PRT
<213> ORGANISM: Bos taurus

<400> SEQUENCE: 66

Phe Leu His Asn Leu Trp Lys His Leu Ser Ser Leu Glu Arg Val Glu
1               5                   10                  15

Trp Leu Arg Lys Lys Leu Gln Asp
            20

<210> SEQ ID NO 67
<211> LENGTH: 24
<212> TYPE: PRT
<213> ORGANISM: Bos taurus
<220> FEATURE:
<221> NAME/KEY: MOD_RES
<222> LOCATION: (6)
<223> OTHER INFORMATION: D-Trp

<400> SEQUENCE: 67

Phe Met His Asn Leu Trp Lys His Leu Ser Ser Met Glu Arg Val Glu
1               5                   10                  15

Trp Leu Arg Lys Lys Leu Gln Asp
            20

<210> SEQ ID NO 68
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Cys Asn Phe
        35

<210> SEQ ID NO 69
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 69

Ser Val Ser Glu Ile Gln Leu Met His Asn Leu Gly Lys His Leu Asn
1               5                   10                  15

Ser Met Glu Arg Val Glu Trp Leu Arg Lys Cys Leu Gln Asp Val His
            20                  25                  30

Cys Asn Phe
        35

<210> SEQ ID NO 70
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Cys Phe

<210> SEQ ID NO 71
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Cys

<210> SEQ ID NO 72
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Val Ser Glu Ile Gln Leu Met His Asn Leu Gly Lys Cys Leu Asn
1               5                   10                  15

Ser Met Glu Arg Val Glu Trp Leu Arg Lys Lys Leu Gln Asp Val His
            20                  25                  30

Asn Phe

<210> SEQ ID NO 73
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73
```

-continued

Ser Val Ser Glu Ile Gln Leu Met His Asn Leu Gly Lys His Cys Asn
1               5                   10                  15

Ser Met Glu Arg Val Glu Trp Leu Arg Lys Lys Leu Gln Asp Val His
            20                  25                  30

Asn Phe

<210> SEQ ID NO 74
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Val Ser Glu Ile Gln Leu Met His Asn Leu Gly Lys His Leu Cys
1               5                   10                  15

Ser Met Glu Arg Val Glu Trp Leu Arg Lys Lys Leu Gln Asp Val His
            20                  25                  30

Asn Phe

<210> SEQ ID NO 75
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Val Ser Glu Ile Gln Leu Met His Asn Leu Gly Lys His Leu Asn
1               5                   10                  15

Cys Met Glu Arg Val Glu Trp Leu Arg Lys Lys Leu Gln Asp Val His
            20                  25                  30

Asn Phe

<210> SEQ ID NO 76
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Val Ser Glu Ile Gln Leu Met His Asn Leu Gly Lys His Leu Asn
1               5                   10                  15

Ser Cys Glu Arg Val Glu Trp Leu Arg Lys Lys Leu Gln Asp Val His
            20                  25                  30

Asn Phe

<210> SEQ ID NO 77
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Val Ser Glu Ile Gln Leu Met His Asn Leu Gly Lys His Leu Asn
1               5                   10                  15

Ser Met Cys Arg Val Glu Trp Leu Arg Lys Lys Leu Gln Asp Val His
            20                  25                  30

Asn Phe

<210> SEQ ID NO 78
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ser Val Ser Glu Ile Gln Leu Met His Asn Leu Gly Lys His Leu Asn
1               5                   10                  15

Ser Met Glu Cys Val Glu Trp Leu Arg Lys Lys Leu Gln Asp Val His
            20                  25                  30

Asn Phe

<210> SEQ ID NO 79
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Val Ser Glu Ile Gln Leu Met His Asn Leu Gly Lys His Leu Asn
1               5                   10                  15

Ser Met Glu Arg Cys Glu Trp Leu Arg Lys Lys Leu Gln Asp Val His
            20                  25                  30

Asn Phe

<210> SEQ ID NO 80
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Val Ser Glu Ile Gln Leu Met His Asn Leu Gly Lys His Leu Asn
1               5                   10                  15

Ser Met Glu Arg Val Cys Trp Leu Arg Lys Lys Leu Gln Asp Val His
            20                  25                  30

Asn Phe

<210> SEQ ID NO 81
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Val Ser Glu Ile Gln Leu Met His Asn Leu Gly Lys His Leu Asn
1               5                   10                  15

Ser Met Glu Arg Val Glu Trp Cys Arg Lys Lys Leu Gln Asp Val His
            20                  25                  30

Asn Phe

<210> SEQ ID NO 82
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Val Ser Glu Ile Gln Leu Met His Asn Leu Gly Lys His Leu Asn
1               5                   10                  15

Ser Met Glu Arg Val Glu Trp Leu Cys Lys Lys Leu Gln Asp Val His
            20                  25                  30

Asn Phe

<210> SEQ ID NO 83
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ser Val Ser Glu Ile Gln Leu Met His Asn Leu Gly Lys His Leu Asn
1               5                   10                  15

Ser Met Glu Arg Val Glu Trp Leu Arg Cys Lys Leu Gln Asp Val His
            20                  25                  30

Asn Phe

<210> SEQ ID NO 84
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Val Ser Glu Ile Gln Leu Met His Asn Leu Gly Lys His Leu Asn
1               5                   10                  15

Ser Met Glu Arg Val Glu Trp Leu Arg Lys Cys Leu Gln Asp Val His
            20                  25                  30

Asn Phe

<210> SEQ ID NO 85
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Val Ser Glu Ile Gln Leu Met His Asn Leu Gly Lys His Leu Asn
1               5                   10                  15

Ser Met Glu Arg Val Glu Trp Leu Arg Lys Lys Cys Gln Asp Val His
            20                  25                  30

Asn Phe

-continued

<210> SEQ ID NO 86
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Val Ser Glu Ile Gln Leu Met His Asn Leu Gly Lys His Leu Asn
1               5                   10                  15

Ser Met Glu Arg Val Glu Trp Leu Arg Lys Lys Leu Cys Asp Val His
            20                  25                  30

Asn Phe

<210> SEQ ID NO 87
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Cys Val His
            20                  25                  30

Asn Phe

<210> SEQ ID NO 88
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Cys His
            20                  25                  30

Asn Phe

<210> SEQ ID NO 89
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val Cys
            20                  25                  30

Asn Phe

<210> SEQ ID NO 90
<211> LENGTH: 86

<212> TYPE: PRT
<213> ORGANISM: Homo sapiens

<400> SEQUENCE: 90

```
Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile Arg Ala Thr Ser Glu Val Ser Pro Asn Ser Lys Pro
        35                  40                  45

Ser Pro Asn Thr Lys Asn His Pro Val Arg Phe Gly Ser Asp Asp Glu
    50                  55                  60

Gly Arg Tyr Leu Thr Gln Glu Thr Asn Lys Val Glu Thr Tyr Lys Glu
65                  70                  75                  80

Gln Pro Leu Lys Thr Pro
                85
```

<210> SEQ ID NO 91
<211> LENGTH: 34
<212> TYPE: PRT
<213> ORGANISM: Homo sapiens

<400> SEQUENCE: 91

```
Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala
```

<210> SEQ ID NO 92
<211> LENGTH: 36
<212> TYPE: PRT
<213> ORGANISM: Homo sapiens

<400> SEQUENCE: 92

```
Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Tyr
        35
```

<210> SEQ ID NO 93
<211> LENGTH: 36
<212> TYPE: PRT
<213> ORGANISM: Homo sapiens

<400> SEQUENCE: 93

```
Ala Val Ser Glu Ile Gln Leu Leu His Asp Lys Gly Lys Ser Ile Gln
1               5                   10                  15

Asp Leu Arg Arg Arg Phe Trp Leu His His Leu Ile Ala Glu Ile His
            20                  25                  30

Thr Ala Glu Tyr
        35
```

<210> SEQ ID NO 94
<211> LENGTH: 35
<212> TYPE: PRT
<213> ORGANISM: Homo sapiens

```
<400> SEQUENCE: 94

Tyr Ala Val Ser Glu His Gln Leu Leu His Asp Lys Gly Lys Ser Ile
1               5                   10                  15

Gln Asp Leu Arg Arg Arg Phe Phe Leu His His Leu Ile Ala Glu Ile
                20                  25                  30

His Thr Ala
        35

<210> SEQ ID NO 95
<211> LENGTH: 34
<212> TYPE: PRT
<213> ORGANISM: Homo sapiens
<220> FEATURE:
<221> NAME/KEY: MOD_RES
<222> LOCATION: (12)
<223> OTHER INFORMATION: D-Phe

<400> SEQUENCE: 95

Ala Val Ser Glu His Gln Leu Leu His Asn Leu Phe Lys Ser Ile Gln
1               5                   10                  15

Asp Leu Arg Arg Arg Phe Phe Leu His His Leu Ile Ala Glu Ile His
                20                  25                  30

Thr Ala

<210> SEQ ID NO 96
<211> LENGTH: 28
<212> TYPE: PRT
<213> ORGANISM: Homo sapiens

<400> SEQUENCE: 96

Leu Leu His Asp Lys Gly Lys Ser Ile Gln Asp Leu Arg Arg Arg Phe
1               5                   10                  15

Phe Leu His His Leu Ile Ala Glu Ile His Thr Ala
                20                  25

<210> SEQ ID NO 97
<211> LENGTH: 28
<212> TYPE: PRT
<213> ORGANISM: Homo sapiens

<400> SEQUENCE: 97

Leu Leu His Asn Leu Gly Lys Ser Ile Gln Asp Leu Arg Arg Arg Phe
1               5                   10                  15

Phe Leu His His Leu Ile Ala Glu Ile His Thr Ala
                20                  25

<210> SEQ ID NO 98
<211> LENGTH: 28
<212> TYPE: PRT
<213> ORGANISM: Homo sapiens

<400> SEQUENCE: 98

Leu Leu His Asp Lys Gly Lys Ser Ile Asn Leu Leu Arg Arg Arg Phe
1               5                   10                  15

Phe Leu His His Leu Ile Ala Glu Ile His Thr Ala
                20                  25

<210> SEQ ID NO 99
<211> LENGTH: 28
<212> TYPE: PRT
<213> ORGANISM: Homo sapiens
<220> FEATURE:
```

US 8,992,925 B2

157                                                                    158

-continued

<221> NAME/KEY: MOD_RES
<222> LOCATION: (6)
<223> OTHER INFORMATION: D-Trp

<400> SEQUENCE: 99

Leu Leu His Asp Leu Trp Lys Ser Ile Gln Asp Leu Arg Arg Arg Phe
1               5                   10                  15

Phe Leu His His Leu Ile Ala Glu Ile His Thr Ala
            20                  25

<210> SEQ ID NO 100
<211> LENGTH: 28
<212> TYPE: PRT
<213> ORGANISM: Homo sapiens
<220> FEATURE:
<221> NAME/KEY: MOD_RES
<222> LOCATION: (6)
<223> OTHER INFORMATION: D-Trp

<400> SEQUENCE: 100

Leu Leu His Asn Leu Trp Lys Ser Ile Gln Asp Leu Arg Arg Arg Phe
1               5                   10                  15

Phe Leu His His Leu Ile Ala Glu Ile His Thr Ala
            20                  25

<210> SEQ ID NO 101
<211> LENGTH: 27
<212> TYPE: PRT
<213> ORGANISM: Homo sapiens
<220> FEATURE:
<221> NAME/KEY: MOD_RES
<222> LOCATION: (5)
<223> OTHER INFORMATION: D-Trp

<400> SEQUENCE: 101

Leu His Asn Leu Trp Lys Ser Ile Gln Asp Leu Arg Arg Arg Phe Phe
1               5                   10                  15

Leu His His Leu Ile Ala Glu Ile His Thr Ala
            20                  25

<210> SEQ ID NO 102
<211> LENGTH: 27
<212> TYPE: PRT
<213> ORGANISM: Homo sapiens
<220> FEATURE:
<221> NAME/KEY: MOD_RES
<222> LOCATION: (5)
<223> OTHER INFORMATION: D-Phe

<400> SEQUENCE: 102

Leu His Asn Leu Phe Lys Ser Ile Gln Asp Leu Arg Arg Arg Phe Phe
1               5                   10                  15

Leu His His Leu Ile Ala Glu Ile His Thr Ala
            20                  25

<210> SEQ ID NO 103
<211> LENGTH: 28
<212> TYPE: PRT
<213> ORGANISM: Homo sapiens
<220> FEATURE:
<221> NAME/KEY: MOD_RES
<222> LOCATION: (6)
<223> OTHER INFORMATION: D-Trp

<400> SEQUENCE: 103

Leu Leu His Asn Leu Trp Lys Ser Ile Gln Asp Leu Arg Arg Arg Phe

```
                1               5                   10                  15
Phe Leu His His Leu Ile Ala Glu Ile His Thr Ala
                20                  25
```

<210> SEQ ID NO 104
<211> LENGTH: 30
<212> TYPE: PRT
<213> ORGANISM: Homo sapiens

<400> SEQUENCE: 104

```
Ala Val Ser Glu His Gln Leu Leu His Asp Lys Gly Lys Ser Ile Gln
1               5                   10                  15
Asp Leu Arg Arg Arg Phe Phe Leu His His Leu Ile Ala Glu
                20                  25                  30
```

<210> SEQ ID NO 105
<211> LENGTH: 30
<212> TYPE: PRT
<213> ORGANISM: Homo sapiens

<400> SEQUENCE: 105

```
Ala Val Ser Glu Ile Gln Leu Leu His Asp Lys Gly Lys Ser Ile Gln
1               5                   10                  15
Asp Leu Arg Arg Arg Phe Trp Leu His His Leu Ile Ala Glu
                20                  25                  30
```

<210> SEQ ID NO 106
<211> LENGTH: 31
<212> TYPE: PRT
<213> ORGANISM: Homo sapiens

<400> SEQUENCE: 106

```
Tyr Ala Val Ser Glu His Gln Leu Leu His Asp Lys Gly Lys Ser Ile
1               5                   10                  15
Gln Asp Leu Arg Arg Arg Phe Phe Leu His His Leu Ile Ala Glu
                20                  25                  30
```

<210> SEQ ID NO 107
<211> LENGTH: 30
<212> TYPE: PRT
<213> ORGANISM: Homo sapiens
<220> FEATURE:
<221> NAME/KEY: MOD_RES
<222> LOCATION: (12)
<223> OTHER INFORMATION: D-Phe

<400> SEQUENCE: 107

```
Ala Val Ser Glu His Gln Leu Leu His Asn Leu Phe Lys Ser Ile Gln
1               5                   10                  15
Asp Leu Arg Arg Arg Phe Phe Leu His His Leu Ile Ala Glu
                20                  25                  30
```

<210> SEQ ID NO 108
<211> LENGTH: 24
<212> TYPE: PRT
<213> ORGANISM: Homo sapiens

<400> SEQUENCE: 108

```
Leu Leu His Asp Lys Gly Lys Ser Ile Gln Asp Leu Arg Arg Arg Phe
1               5                   10                  15
Phe Leu His His Leu Ile Ala Glu
                20
```

<210> SEQ ID NO 109
<211> LENGTH: 24
<212> TYPE: PRT
<213> ORGANISM: Homo sapiens

<400> SEQUENCE: 109

Leu Leu His Asn Leu Gly Lys Ser Ile Gln Asp Leu Arg Arg Arg Phe
1               5                   10                  15

Phe Leu His His Leu Ile Ala Glu
            20

<210> SEQ ID NO 110
<211> LENGTH: 24
<212> TYPE: PRT
<213> ORGANISM: Homo sapiens

<400> SEQUENCE: 110

Leu Leu His Asp Lys Gly Lys Ser Ile Asn Leu Leu Arg Arg Arg Phe
1               5                   10                  15

Phe Leu His His Leu Ile Ala Glu
            20

<210> SEQ ID NO 111
<211> LENGTH: 24
<212> TYPE: PRT
<213> ORGANISM: Homo sapiens
<220> FEATURE:
<221> NAME/KEY: MOD_RES
<222> LOCATION: (6)
<223> OTHER INFORMATION: D-Trp

<400> SEQUENCE: 111

Leu Leu His Asp Leu Trp Lys Ser Ile Gln Asp Leu Arg Arg Arg Phe
1               5                   10                  15

Phe Leu His His Leu Ile Ala Glu
            20

<210> SEQ ID NO 112
<211> LENGTH: 24
<212> TYPE: PRT
<213> ORGANISM: Homo sapiens
<220> FEATURE:
<221> NAME/KEY: MOD_RES
<222> LOCATION: (6)
<223> OTHER INFORMATION: D-Trp

<400> SEQUENCE: 112

Leu Leu His Asn Leu Trp Lys Ser Ile Gln Asp Leu Arg Arg Arg Phe
1               5                   10                  15

Phe Leu His His Leu Ile Ala Glu
            20

<210> SEQ ID NO 113
<211> LENGTH: 23
<212> TYPE: PRT
<213> ORGANISM: Homo sapiens
<220> FEATURE:
<221> NAME/KEY: MOD_RES
<222> LOCATION: (5)
<223> OTHER INFORMATION: D-Trp

<400> SEQUENCE: 113

Leu His Asn Leu Trp Lys Ser Ile Gln Asp Leu Arg Arg Arg Phe Phe
1               5                   10                  15

Leu His His Leu Ile Ala Glu
            20

<210> SEQ ID NO 114
<211> LENGTH: 23
<212> TYPE: PRT
<213> ORGANISM: Homo sapiens
<220> FEATURE:
<221> NAME/KEY: MOD_RES
<222> LOCATION: (5)
<223> OTHER INFORMATION: D-Phe

<400> SEQUENCE: 114

Leu His Asn Leu Phe Lys Ser Ile Gln Asp Leu Arg Arg Arg Phe Phe
1               5                   10                  15

Leu His His Leu Ile Ala Glu
            20

<210> SEQ ID NO 115
<211> LENGTH: 24
<212> TYPE: PRT
<213> ORGANISM: Homo sapiens
<220> FEATURE:
<221> NAME/KEY: MOD_RES
<222> LOCATION: (6)
<223> OTHER INFORMATION: D-Trp

<400> SEQUENCE: 115

Leu Leu His Asn Leu Trp Lys Ser Ile Gln Asp Leu Arg Arg Arg Phe
1               5                   10                  15

Phe Leu His His Leu Ile Ala Glu
            20

<210> SEQ ID NO 116
<211> LENGTH: 34
<212> TYPE: PRT
<213> ORGANISM: Homo sapiens

<400> SEQUENCE: 116

Ser Val Ser Glu Ile Gln Leu Met His Asn Leu Gly Lys His Leu Asn
1               5                   10                  15

Ser Met Glu Arg Val Glu Leu Leu Glu Lys Leu Leu Glu Lys Leu His
            20                  25                  30

Asn Phe

<210> SEQ ID NO 117
<211> LENGTH: 34
<212> TYPE: PRT
<213> ORGANISM: Homo sapiens

<400> SEQUENCE: 117

Ser Val Ser Glu Ile Gln Leu Met His Asn Leu Gly Lys His Leu Asn
1               5                   10                  15

Ser Met Glu Arg Val Glu Leu Leu Glu Lys Leu Leu Lys Lys Leu His
            20                  25                  30

Asn Phe

<210> SEQ ID NO 118
<211> LENGTH: 34
<212> TYPE: PRT
<213> ORGANISM: Homo sapiens

<400> SEQUENCE: 118

-continued

Ser Val Ser Glu Ile Gln Leu Met His Asn Leu Gly Lys His Leu Asn
1               5                   10                  15

Ser Met Glu Arg Val Ala Leu Ala Glu Ala Leu Ala Glu Ala Leu His
            20                  25                  30

Asn Phe

<210> SEQ ID NO 119
<211> LENGTH: 34
<212> TYPE: PRT
<213> ORGANISM: Homo sapiens

<400> SEQUENCE: 119

Ser Val Ser Glu Ile Gln Leu Met His Asn Leu Gly Lys His Leu Asn
1               5                   10                  15

Ser Met Glu Arg Val Ser Leu Leu Ser Ser Leu Leu Ser Ser Leu His
            20                  25                  30

Asn Phe

<210> SEQ ID NO 120
<211> LENGTH: 34
<212> TYPE: PRT
<213> ORGANISM: Homo sapiens

<400> SEQUENCE: 120

Ser Val Ser Glu Ile Gln Leu Met His Asn Leu Gly Lys His Leu Asn
1               5                   10                  15

Ser Met Glu Arg Val Ala Phe Tyr Asp Lys Val Ala Glu Lys Leu His
            20                  25                  30

Asn Phe

<210> SEQ ID NO 121
<211> LENGTH: 28
<212> TYPE: PRT
<213> ORGANISM: Homo sapiens

<400> SEQUENCE: 121

Leu Met His Asn Leu Gly Lys His Leu Asn Ser Met Glu Arg Val Glu
1               5                   10                  15

Leu Leu Glu Lys Leu Leu Glu Lys Leu His Asn Phe
            20                  25

<210> SEQ ID NO 122
<211> LENGTH: 28
<212> TYPE: PRT
<213> ORGANISM: Homo sapiens

<400> SEQUENCE: 122

Leu Met His Asn Leu Gly Lys His Leu Asn Ser Met Glu Arg Val Glu
1               5                   10                  15

Leu Leu Glu Lys Leu Leu Lys Lys Leu His Asn Phe
            20                  25

<210> SEQ ID NO 123
<211> LENGTH: 28
<212> TYPE: PRT
<213> ORGANISM: Homo sapiens

<400> SEQUENCE: 123

Leu Met His Asn Leu Gly Lys His Leu Asn Ser Met Glu Arg Val Ala
1               5                   10                  15

Leu Ala Glu Ala Leu Ala Glu Ala Leu His Asn Phe
            20                  25

<210> SEQ ID NO 124
<211> LENGTH: 28
<212> TYPE: PRT
<213> ORGANISM: Homo sapiens

<400> SEQUENCE: 124

Leu Met His Asn Leu Gly Lys His Leu Asn Ser Met Glu Arg Val Ser
1               5                   10                  15

Leu Leu Ser Ser Leu Leu Ser Ser Leu His Asn Phe
            20                  25

<210> SEQ ID NO 125
<211> LENGTH: 28
<212> TYPE: PRT
<213> ORGANISM: Homo sapiens

<400> SEQUENCE: 125

Leu Met His Asn Leu Gly Lys His Leu Asn Ser Met Glu Arg Val Ala
1               5                   10                  15

Phe Tyr Asp Lys Val Ala Glu Lys Leu His Asn Phe
            20                  25

<210> SEQ ID NO 126
<211> LENGTH: 34
<212> TYPE: PRT
<213> ORGANISM: Homo sapiens

<400> SEQUENCE: 126

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys Leu His
            20                  25                      30

Thr Ala

<210> SEQ ID NO 127
<211> LENGTH: 34
<212> TYPE: PRT
<213> ORGANISM: Homo sapiens

<400> SEQUENCE: 127

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Lys Lys Leu His
            20                  25                      30

Thr Ala

<210> SEQ ID NO 128
<211> LENGTH: 34
<212> TYPE: PRT
<213> ORGANISM: Homo sapiens

<400> SEQUENCE: 128

Ala Val Ser Glu His Gln Leu Leu His Asp Lys Gly Lys Ser Ile Gln
1               5                   10                  15

Asp Leu Arg Arg Arg Ala Leu Ala Glu Ala Leu Ala Glu Ala Leu His
            20                  25                      30

Thr Ala

<210> SEQ ID NO 129
<211> LENGTH: 34
<212> TYPE: PRT
<213> ORGANISM: Homo sapiens

<400> SEQUENCE: 129

Ala Val Ser Glu His Gln Leu Leu His Asp Lys Gly Lys Ser Ile Gln
1               5                   10                  15

Asp Leu Arg Arg Arg Ser Leu Leu Ser Ser Leu Leu Ser Ser Leu His
            20                  25                  30

Thr Ala

<210> SEQ ID NO 130
<211> LENGTH: 34
<212> TYPE: PRT
<213> ORGANISM: Homo sapiens

<400> SEQUENCE: 130

Ala Val Ser Glu His Gln Leu Leu His Asp Lys Gly Lys Ser Ile Gln
1               5                   10                  15

Asp Leu Arg Arg Arg Ala Phe Tyr Asp Lys Val Ala Glu Lys Leu His
            20                  25                  30

Thr Ala

<210> SEQ ID NO 131
<211> LENGTH: 28
<212> TYPE: PRT
<213> ORGANISM: Homo sapiens

<400> SEQUENCE: 131

Leu Leu His Asp Lys Gly Lys Ser Ile Gln Asp Leu Arg Arg Arg Glu
1               5                   10                  15

Leu Leu Glu Lys Leu Leu Glu Lys Leu His Thr Ala
            20                  25

<210> SEQ ID NO 132
<211> LENGTH: 28
<212> TYPE: PRT
<213> ORGANISM: Homo sapiens

<400> SEQUENCE: 132

Leu Leu His Asp Lys Gly Lys Ser Ile Gln Asp Leu Arg Arg Arg Glu
1               5                   10                  15

Leu Leu Glu Lys Leu Leu Lys Lys Leu His Thr Ala
            20                  25

<210> SEQ ID NO 133
<211> LENGTH: 28
<212> TYPE: PRT
<213> ORGANISM: Homo sapiens

<400> SEQUENCE: 133

Leu Leu His Asp Lys Gly Lys Ser Ile Gln Asp Leu Arg Arg Arg Ala
1               5                   10                  15

Leu Ala Glu Ala Leu Ala Glu Ala Leu His Thr Ala
            20                  25

<210> SEQ ID NO 134
<211> LENGTH: 28
<212> TYPE: PRT
<213> ORGANISM: Homo sapiens

<400> SEQUENCE: 134

Leu Leu His Asp Lys Gly Lys Ser Ile Gln Asp Leu Arg Arg Ser
1               5                   10                  15

Leu Leu Ser Ser Leu Leu Ser Ser Leu His Thr Ala
            20                  25

<210> SEQ ID NO 135
<211> LENGTH: 28
<212> TYPE: PRT
<213> ORGANISM: Homo sapiens

<400> SEQUENCE: 135

Leu Leu His Asp Lys Gly Lys Ser Ile Gln Asp Leu Arg Arg Ala
1               5                   10                  15

Phe Tyr Asp Lys Val Ala Glu Lys Leu His Thr Ala
            20                  25

<210> SEQ ID NO 136
<211> LENGTH: 34
<212> TYPE: PRT
<213> ORGANISM: Homo sapiens

<400> SEQUENCE: 136

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Arg Lys Leu His
            20                  25                  30

Thr Ala

<210> SEQ ID NO 137
<211> LENGTH: 34
<212> TYPE: PRT
<213> ORGANISM: Homo sapiens

<400> SEQUENCE: 137

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys Leu His
            20                  25                  30

Thr Ser

<210> SEQ ID NO 138
<211> LENGTH: 37
<212> TYPE: PRT
<213> ORGANISM: Homo sapiens

<400> SEQUENCE: 138

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys Leu His
            20                  25                  30

Thr Ala Gly Arg Arg
        35

<210> SEQ ID NO 139
<211> LENGTH: 34
<212> TYPE: PRT
<213> ORGANISM: Homo sapiens

<400> SEQUENCE: 139

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys Leu Lys
            20                  25                  30

Glu Leu

<210> SEQ ID NO 140
<211> LENGTH: 34
<212> TYPE: PRT
<213> ORGANISM: Homo sapiens

<400> SEQUENCE: 140

Ala Val Ser Glu His Gln Leu Leu His Asp Lys Gly Lys Ser Ile Gln
1               5                   10                  15

Asp Leu Ala Arg Arg Glu Leu Leu Glu Lys Leu Leu Glu Lys Leu His
            20                  25                  30

Thr Ala

<210> SEQ ID NO 141
<211> LENGTH: 34
<212> TYPE: PRT
<213> ORGANISM: Homo sapiens

<400> SEQUENCE: 141

Ala Val Ser Glu His Gln Leu Leu His Asp Lys Gly Lys Ser Ile Gln
1               5                   10                  15

Asp Leu Arg Arg Ala Glu Leu Leu Glu Lys Leu Leu Glu Lys Leu His
            20                  25                  30

Thr Ala

<210> SEQ ID NO 142
<211> LENGTH: 34
<212> TYPE: PRT
<213> ORGANISM: Homo sapiens

<400> SEQUENCE: 142

Ala Val Ser Glu Ala Gln Leu Leu His Asp Leu Gly Lys Ser Ile Gln
1               5                   10                  15

Asp Leu Arg Arg Arg Glu Leu Leu Glu Lys Leu Leu Glu Lys Leu His
            20                  25                  30

Ala Leu

<210> SEQ ID NO 143
<211> LENGTH: 34
<212> TYPE: PRT
<213> ORGANISM: Homo sapiens

<400> SEQUENCE: 143

Ala Val Ser Glu His Gln Leu Leu His Asp Lys Gly Lys Ser Ile Gln
1               5                   10                  15

Asp Leu Arg Arg Arg Glu Leu Leu Glu Arg Leu Leu Glu Arg Leu His
            20                  25                  30

Thr Ala

<210> SEQ ID NO 144
<211> LENGTH: 33
<212> TYPE: PRT
<213> ORGANISM: Homo sapiens

```
<400> SEQUENCE: 144

Ala Val Ser Glu His Gln Leu Leu His Asp Arg Gly Arg Ser Ile Gln
1               5                   10                  15

Asp Arg Arg Arg Glu Leu Leu Glu Arg Leu Leu Glu Arg Leu His Thr
                20                  25                  30

Ala

<210> SEQ ID NO 145
<211> LENGTH: 34
<212> TYPE: PRT
<213> ORGANISM: Homo sapiens

<400> SEQUENCE: 145

Ala Val Ser Glu His Gln Leu Leu His Asp Arg Gly Lys Ser Ile Gln
1               5                   10                  15

Asp Leu Arg Arg Arg Glu Leu Leu Glu Arg Leu Leu Lys Arg Leu His
                20                  25                  30

Thr Ala

<210> SEQ ID NO 146
<211> LENGTH: 34
<212> TYPE: PRT
<213> ORGANISM: Homo sapiens

<400> SEQUENCE: 146

Ala Val Ser Glu His Gln Leu Leu His Asp Arg Gly Arg Ser Ile Gln
1               5                   10                  15

Asp Leu Arg Arg Arg Glu Leu Leu Glu Arg Leu Leu Lys Arg Leu His
                20                  25                  30

Thr Ala

<210> SEQ ID NO 147
<211> LENGTH: 34
<212> TYPE: PRT
<213> ORGANISM: Homo sapiens

<400> SEQUENCE: 147

Ala Val Ser Glu His Gln Leu Leu His Asp Lys Gly Lys Ser Ile Gln
1               5                   10                  15

Asp Leu Arg Arg Arg Ala Leu Ala Glu Ala Leu Ala Glu Ala Leu His
                20                  25                  30

Thr Ala

<210> SEQ ID NO 148
<211> LENGTH: 34
<212> TYPE: PRT
<213> ORGANISM: Homo sapiens

<400> SEQUENCE: 148

Ala Val Ser Glu His Gln Leu Leu His Asp Lys Gly Lys Ser Ile Gln
1               5                   10                  15

Asp Leu Arg Arg Arg Ser Leu Leu Ser Ser Leu Leu Ser Ser Leu His
                20                  25                  30

Thr Ala

<210> SEQ ID NO 149
<211> LENGTH: 34
<212> TYPE: PRT
<213> ORGANISM: Homo sapiens
```

```
<400> SEQUENCE: 149

Ala Val Ser Glu His Gln Leu Leu His Asp Lys Gly Lys Ser Ile Gln
1               5                   10                  15

Asp Leu Arg Arg Arg Ala Phe Tyr Asp Lys Val Ala Glu Lys Leu His
            20                  25                  30

Thr Ala

<210> SEQ ID NO 150
<211> LENGTH: 34
<212> TYPE: PRT
<213> ORGANISM: Homo sapiens

<400> SEQUENCE: 150

Ala Val Ser Glu Ile Gln Phe Met His Asn Leu Gly Lys His Leu Ser
1               5                   10                  15

Ser Met Glu Arg Val Glu Leu Leu Glu Lys Leu Leu Glu Lys Leu His
            20                  25                  30

Asn Tyr

<210> SEQ ID NO 151
<211> LENGTH: 34
<212> TYPE: PRT
<213> ORGANISM: Homo sapiens

<400> SEQUENCE: 151

Ala Val Ser Glu Ile Gln Phe Met His Asn Leu Gly Lys His Leu Ser
1               5                   10                  15

Ser Met Arg Arg Arg Glu Leu Leu Glu Lys Leu Leu Glu Lys Leu His
            20                  25                  30

Asn Tyr

<210> SEQ ID NO 152
<211> LENGTH: 30
<212> TYPE: PRT
<213> ORGANISM: Homo sapiens

<400> SEQUENCE: 152

Ser Val Ser Glu Ile Gln Leu Met His Asn Leu Gly Lys His Leu Asn
1               5                   10                  15

Ser Met Glu Arg Val Glu Leu Leu Glu Lys Leu Leu Glu Lys
            20                  25                  30

<210> SEQ ID NO 153
<211> LENGTH: 30
<212> TYPE: PRT
<213> ORGANISM: Homo sapiens

<400> SEQUENCE: 153

Ser Val Ser Glu Ile Gln Leu Met His Asn Leu Gly Lys His Leu Asn
1               5                   10                  15

Ser Met Glu Arg Val Glu Leu Leu Glu Lys Leu Leu Lys Lys
            20                  25                  30

<210> SEQ ID NO 154
<211> LENGTH: 30
<212> TYPE: PRT
<213> ORGANISM: Homo sapiens

<400> SEQUENCE: 154
```

-continued

Ser Val Ser Glu Ile Gln Leu Met His Asn Leu Gly Lys His Leu Asn
1               5                   10                  15

Ser Met Glu Arg Val Ala Leu Ala Glu Ala Leu Ala Glu Ala
            20                  25                  30

<210> SEQ ID NO 155
<211> LENGTH: 30
<212> TYPE: PRT
<213> ORGANISM: Homo sapiens

<400> SEQUENCE: 155

Ser Val Ser Glu Ile Gln Leu Met His Asn Leu Gly Lys His Leu Asn
1               5                   10                  15

Ser Met Glu Arg Val Ser Leu Leu Ser Ser Leu Leu Ser Ser
            20                  25                  30

<210> SEQ ID NO 156
<211> LENGTH: 34
<212> TYPE: PRT
<213> ORGANISM: Homo sapiens

<400> SEQUENCE: 156

Ser Val Ser Glu Ile Gln Leu Met His Asn Leu Gly Lys His Leu Asn
1               5                   10                  15

Ser Met Glu Arg Val Ala Phe Tyr Asp Lys Val Ala Glu Lys Leu His
            20                  25                  30

Asn Phe

<210> SEQ ID NO 157
<211> LENGTH: 24
<212> TYPE: PRT
<213> ORGANISM: Homo sapiens

<400> SEQUENCE: 157

Leu Met His Asn Leu Gly Lys His Leu Asn Ser Met Glu Arg Val Glu
1               5                   10                  15

Leu Leu Glu Lys Leu Leu Glu Lys
            20

<210> SEQ ID NO 158
<211> LENGTH: 24
<212> TYPE: PRT
<213> ORGANISM: Homo sapiens

<400> SEQUENCE: 158

Leu Met His Asn Leu Gly Lys His Leu Asn Ser Met Glu Arg Val Glu
1               5                   10                  15

Leu Leu Glu Lys Leu Leu Lys Lys
            20

<210> SEQ ID NO 159
<211> LENGTH: 24
<212> TYPE: PRT
<213> ORGANISM: Homo sapiens

<400> SEQUENCE: 159

Leu Met His Asn Leu Gly Lys His Leu Asn Ser Met Glu Arg Val Ala
1               5                   10                  15

Leu Ala Glu Ala Leu Ala Glu Ala
            20

```
<210> SEQ ID NO 160
<211> LENGTH: 24
<212> TYPE: PRT
<213> ORGANISM: Homo sapiens

<400> SEQUENCE: 160

Leu Met His Asn Leu Gly Lys His Leu Asn Ser Met Glu Arg Val Ser
1               5                   10                  15

Leu Leu Ser Ser Leu Leu Ser Ser
            20

<210> SEQ ID NO 161
<211> LENGTH: 24
<212> TYPE: PRT
<213> ORGANISM: Homo sapiens

<400> SEQUENCE: 161

Leu Met His Asn Leu Gly Lys His Leu Asn Ser Met Glu Arg Val Ala
1               5                   10                  15

Phe Tyr Asp Lys Val Ala Glu Lys
            20

<210> SEQ ID NO 162
<211> LENGTH: 30
<212> TYPE: PRT
<213> ORGANISM: Homo sapiens

<400> SEQUENCE: 162

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys
            20                  25                  30

<210> SEQ ID NO 163
<211> LENGTH: 30
<212> TYPE: PRT
<213> ORGANISM: Homo sapiens

<400> SEQUENCE: 163

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Lys Lys
            20                  25                  30

<210> SEQ ID NO 164
<211> LENGTH: 30
<212> TYPE: PRT
<213> ORGANISM: Homo sapiens

<400> SEQUENCE: 164

Ala Val Ser Glu His Gln Leu Leu His Asp Lys Gly Lys Ser Ile Gln
1               5                   10                  15

Asp Leu Arg Arg Arg Ala Leu Ala Glu Ala Leu Ala Glu Ala
            20                  25                  30

<210> SEQ ID NO 165
<211> LENGTH: 30
<212> TYPE: PRT
<213> ORGANISM: Homo sapiens

<400> SEQUENCE: 165

Ala Val Ser Glu His Gln Leu Leu His Asp Lys Gly Lys Ser Ile Gln
1               5                   10                  15
```

```
Asp Leu Arg Arg Arg Ser Leu Leu Ser Ser Leu Leu Ser Ser
        20                  25                  30

<210> SEQ ID NO 166
<211> LENGTH: 30
<212> TYPE: PRT
<213> ORGANISM: Homo sapiens

<400> SEQUENCE: 166

Ala Val Ser Glu His Gln Leu Leu His Asp Lys Gly Lys Ser Ile Gln
1               5                   10                  15

Asp Leu Arg Arg Arg Ala Phe Tyr Asp Lys Val Ala Glu Lys
        20                  25                  30

<210> SEQ ID NO 167
<211> LENGTH: 24
<212> TYPE: PRT
<213> ORGANISM: Homo sapiens

<400> SEQUENCE: 167

Leu Leu His Asp Lys Gly Lys Ser Ile Gln Asp Leu Arg Arg Arg Glu
1               5                   10                  15

Leu Leu Glu Lys Leu Leu Glu Lys
        20

<210> SEQ ID NO 168
<211> LENGTH: 24
<212> TYPE: PRT
<213> ORGANISM: Homo sapiens

<400> SEQUENCE: 168

Leu Leu His Asp Lys Gly Lys Ser Ile Gln Asp Leu Arg Arg Arg Glu
1               5                   10                  15

Leu Leu Glu Lys Leu Leu Lys Lys
        20

<210> SEQ ID NO 169
<211> LENGTH: 24
<212> TYPE: PRT
<213> ORGANISM: Homo sapiens

<400> SEQUENCE: 169

Leu Leu His Asp Lys Gly Lys Ser Ile Gln Asp Leu Arg Arg Arg Ala
1               5                   10                  15

Leu Ala Glu Ala Leu Ala Glu Ala
        20

<210> SEQ ID NO 170
<211> LENGTH: 24
<212> TYPE: PRT
<213> ORGANISM: Homo sapiens

<400> SEQUENCE: 170

Leu Leu His Asp Lys Gly Lys Ser Ile Gln Asp Leu Arg Arg Arg Ser
1               5                   10                  15

Leu Leu Ser Ser Leu Leu Ser Ser
        20

<210> SEQ ID NO 171
<211> LENGTH: 24
<212> TYPE: PRT
<213> ORGANISM: Homo sapiens
```

<400> SEQUENCE: 171

Leu Leu His Asp Lys Gly Lys Ser Ile Gln Asp Leu Arg Arg Ala
1               5                   10                  15

Phe Tyr Asp Lys Val Ala Glu Lys
            20

<210> SEQ ID NO 172
<211> LENGTH: 30
<212> TYPE: PRT
<213> ORGANISM: Homo sapiens

<400> SEQUENCE: 172

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Arg Lys
            20                  25                  30

<210> SEQ ID NO 173
<211> LENGTH: 30
<212> TYPE: PRT
<213> ORGANISM: Homo sapiens

<400> SEQUENCE: 173

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys
            20                  25                  30

<210> SEQ ID NO 174
<211> LENGTH: 33
<212> TYPE: PRT
<213> ORGANISM: Homo sapiens

<400> SEQUENCE: 174

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys Leu His
            20                  25                  30

Thr

<210> SEQ ID NO 175
<211> LENGTH: 30
<212> TYPE: PRT
<213> ORGANISM: Homo sapiens

<400> SEQUENCE: 175

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys
            20                  25                  30

<210> SEQ ID NO 176
<211> LENGTH: 30
<212> TYPE: PRT
<213> ORGANISM: Homo sapiens

<400> SEQUENCE: 176

Ala Val Ser Glu His Gln Leu Leu His Asp Lys Gly Lys Ser Ile Gln
1               5                   10                  15

Asp Leu Ala Arg Arg Glu Leu Leu Glu Lys Leu Leu Glu Lys 20                  25                  30

<210> SEQ ID NO 177
<211> LENGTH: 30
<212> TYPE: PRT
<213> ORGANISM: Homo sapiens

<400> SEQUENCE: 177

Ala Val Ser Glu His Gln Leu Leu His Asp Lys Gly Lys Ser Ile Gln
1               5                   10                  15

Asp Leu Arg Arg Ala Glu Leu Leu Glu Lys Leu Leu Glu Lys
                20                  25                  30

<210> SEQ ID NO 178
<211> LENGTH: 30
<212> TYPE: PRT
<213> ORGANISM: Homo sapiens

<400> SEQUENCE: 178

Ala Val Ser Glu Ala Gln Leu Leu His Asp Leu Gly Lys Ser Ile Gln
1               5                   10                  15

Asp Leu Arg Arg Arg Glu Leu Leu Glu Lys Leu Leu Glu Lys
                20                  25                  30

<210> SEQ ID NO 179
<211> LENGTH: 30
<212> TYPE: PRT
<213> ORGANISM: Homo sapiens

<400> SEQUENCE: 179

Ala Val Ser Glu His Gln Leu Leu His Asp Lys Gly Lys Ser Ile Gln
1               5                   10                  15

Asp Leu Arg Arg Arg Glu Leu Leu Glu Arg Leu Leu Glu Arg
                20                  25                  30

<210> SEQ ID NO 180
<211> LENGTH: 29
<212> TYPE: PRT
<213> ORGANISM: Homo sapiens

<400> SEQUENCE: 180

Ala Val Ser Glu His Gln Leu Leu His Asp Arg Gly Arg Ser Ile Gln
1               5                   10                  15

Asp Arg Arg Arg Glu Leu Leu Glu Arg Leu Leu Glu Arg
                20                  25

<210> SEQ ID NO 181
<211> LENGTH: 30
<212> TYPE: PRT
<213> ORGANISM: Homo sapiens

<400> SEQUENCE: 181

Ala Val Ser Glu His Gln Leu Leu His Asp Arg Gly Lys Ser Ile Gln
1               5                   10                  15

Asp Leu Arg Arg Arg Glu Leu Leu Glu Arg Leu Leu Lys Arg
                20                  25                  30

<210> SEQ ID NO 182
<211> LENGTH: 30
<212> TYPE: PRT
<213> ORGANISM: Homo sapiens

<400> SEQUENCE: 182

```
Ala Val Ser Glu His Gln Leu Leu His Asp Arg Gly Arg Ser Ile Gln
1               5                   10                  15

Asp Leu Arg Arg Arg Glu Leu Leu Glu Arg Leu Leu Lys Arg
            20                  25                  30
```

<210> SEQ ID NO 183
<211> LENGTH: 30
<212> TYPE: PRT
<213> ORGANISM: Homo sapiens

<400> SEQUENCE: 183

```
Ala Val Ser Glu His Gln Leu Leu His Asp Lys Gly Lys Ser Ile Gln
1               5                   10                  15

Asp Leu Arg Arg Arg Ala Leu Ala Glu Ala Leu Ala Glu Ala
            20                  25                  30
```

<210> SEQ ID NO 184
<211> LENGTH: 30
<212> TYPE: PRT
<213> ORGANISM: Homo sapiens

<400> SEQUENCE: 184

```
Ala Val Ser Glu His Gln Leu Leu His Asp Lys Gly Lys Ser Ile Gln
1               5                   10                  15

Asp Leu Arg Arg Arg Ser Leu Leu Ser Ser Leu Leu Ser Ser
            20                  25                  30
```

<210> SEQ ID NO 185
<211> LENGTH: 30
<212> TYPE: PRT
<213> ORGANISM: Homo sapiens

<400> SEQUENCE: 185

```
Ala Val Ser Glu His Gln Leu Leu His Asp Lys Gly Lys Ser Ile Gln
1               5                   10                  15

Asp Leu Arg Arg Arg Ala Phe Tyr Asp Lys Val Ala Glu Lys
            20                  25                  30
```

<210> SEQ ID NO 186
<211> LENGTH: 30
<212> TYPE: PRT
<213> ORGANISM: Homo sapiens

<400> SEQUENCE: 186

```
Ala Val Ser Glu Ile Gln Phe Met His Asn Leu Gly Lys His Leu Ser
1               5                   10                  15

Ser Met Glu Arg Val Glu Leu Leu Glu Lys Leu Leu Glu Lys
            20                  25                  30
```

<210> SEQ ID NO 187
<211> LENGTH: 30
<212> TYPE: PRT
<213> ORGANISM: Homo sapiens

<400> SEQUENCE: 187

```
Ala Val Ser Glu Ile Gln Phe Met His Asn Leu Gly Lys His Leu Ser
1               5                   10                  15

Ser Met Arg Arg Arg Glu Leu Leu Glu Lys Leu Leu Glu Lys
            20                  25                  30
```

<210> SEQ ID NO 188

```
<211> LENGTH: 31
<212> TYPE: PRT
<213> ORGANISM: Homo sapiens

<400> SEQUENCE: 188

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg
            20                  25                  30

<210> SEQ ID NO 189
<211> LENGTH: 31
<212> TYPE: PRT
<213> ORGANISM: Rattus norvegicus

<400> SEQUENCE: 189

Met Met Ser Ala Ser Thr Met Ala Lys Val Met Ile Leu Met Leu Ala
1               5                   10                  15

Val Cys Leu Leu Thr Gln Ala Asp Gly Lys Pro Val Lys Lys Arg
            20                  25                  30

<210> SEQ ID NO 190
<211> LENGTH: 31
<212> TYPE: PRT
<213> ORGANISM: Sus scrofa

<400> SEQUENCE: 190

Met Met Ser Ala Lys Asp Thr Val Lys Val Met Val Val Met Leu Ala
1               5                   10                  15

Ile Cys Phe Leu Ala Arg Ser Asp Gly Lys Pro Ile Lys Lys Arg
            20                  25                  30

<210> SEQ ID NO 191
<211> LENGTH: 31
<212> TYPE: PRT
<213> ORGANISM: Gallus gallus

<400> SEQUENCE: 191

Met Thr Ser Thr Lys Asn Leu Ala Lys Ala Ile Val Ile Leu Tyr Ala
1               5                   10                  15

Ile Cys Phe Phe Thr Asn Ser Asp Gly Arg Pro Met Met Lys Arg
            20                  25                  30

<210> SEQ ID NO 192
<211> LENGTH: 31
<212> TYPE: PRT
<213> ORGANISM: Bos taurus

<400> SEQUENCE: 192

Met Met Ser Ala Lys Asp Met Val Lys Val Met Ile Val Met Leu Ala
1               5                   10                  15

Ile Cys Phe Leu Ala Arg Ser Asp Gly Lys Ser Val Lys Lys Arg
            20                  25                  30

<210> SEQ ID NO 193
<211> LENGTH: 31
<212> TYPE: PRT
<213> ORGANISM: Felis cattus

<400> SEQUENCE: 193

Met Met Ser Ala Lys Asp Met Val Lys Val Met Val Val Met Phe Ala
1               5                   10                  15
```

```
Ile Cys Phe Leu Ala Lys Ser Asp Gly Lys Pro Val Lys Lys Arg
            20                  25                  30
```

<210> SEQ ID NO 194
<211> LENGTH: 31
<212> TYPE: PRT
<213> ORGANISM: Canis familiaris

<400> SEQUENCE: 194

```
Met Met Ser Ala Lys Asp Met Val Lys Val Met Ile Val Met Phe Ala
1               5                   10                  15

Ile Cys Phe Leu Ala Lys Ser Asp Gly Lys Pro Val Lys Lys Arg
            20                  25                  30
```

<210> SEQ ID NO 195
<211> LENGTH: 31
<212> TYPE: PRT
<213> ORGANISM: Mus musculus

<400> SEQUENCE: 195

```
Met Met Ser Ala Asn Thr Val Ala Lys Val Met Ile Ile Met Leu Ala
1               5                   10                  15

Val Cys Leu Leu Thr Gln Thr Asp Gly Lys Pro Val Arg Lys Arg
            20                  25                  30
```

<210> SEQ ID NO 196
<211> LENGTH: 36
<212> TYPE: PRT
<213> ORGANISM: Homo sapiens

<400> SEQUENCE: 196

```
Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Lys Arg
        35
```

<210> SEQ ID NO 197
<211> LENGTH: 36
<212> TYPE: PRT
<213> ORGANISM: Rattus norvegicus

<400> SEQUENCE: 197

```
Met Leu Arg Arg Leu Val Gln Gln Trp Ser Val Leu Val Phe Leu Leu
1               5                   10                  15

Ser Tyr Ser Val Pro Ser Arg Gly Arg Ser Val Glu Gly Leu Gly Arg
            20                  25                  30

Arg Leu Lys Arg
        35
```

<210> SEQ ID NO 198
<211> LENGTH: 36
<212> TYPE: PRT
<213> ORGANISM: Sus scrofa

<400> SEQUENCE: 198

```
Met Leu Trp Arg Leu Val Gln Gln Trp Ser Val Ala Val Phe Leu Leu
1               5                   10                  15

Ser Tyr Ser Val Pro Ser Cys Gly Arg Ser Val Glu Glu Leu Gly Arg
            20                  25                  30
```

Arg Leu Lys Arg
        35

<210> SEQ ID NO 199
<211> LENGTH: 37
<212> TYPE: PRT
<213> ORGANISM: Gallus gallus

<400> SEQUENCE: 199

Met Met Phe Thr Lys Leu Phe Gln Gln Trp Ser Phe Ala Val Phe Leu
1               5                   10                  15

Leu Ser Tyr Ser Val Pro Ser Tyr Gly Arg Ser Val Glu Gly Ile Ser
                20                  25                  30

Arg Arg Leu Lys Arg
        35

<210> SEQ ID NO 200
<211> LENGTH: 36
<212> TYPE: PRT
<213> ORGANISM: Bos taurus

<400> SEQUENCE: 200

Met Leu Trp Arg Leu Val Gln Gln Trp Ser Val Ala Val Phe Leu Leu
1               5                   10                  15

Ser Tyr Ser Val Pro Ser Cys Gly Arg Ser Val Glu Glu Leu Gly Arg
                20                  25                  30

Arg Leu Lys Arg
        35

<210> SEQ ID NO 201
<211> LENGTH: 22
<212> TYPE: PRT
<213> ORGANISM: Felis cattus

<400> SEQUENCE: 201

Leu Leu Ser Tyr Ser Val Pro Ser Cys Gly Arg Ser Val Glu Glu Leu
1               5                   10                  15

Gly Arg Arg Leu Lys Arg
                20

<210> SEQ ID NO 202
<211> LENGTH: 36
<212> TYPE: PRT
<213> ORGANISM: Canis familiaris

<400> SEQUENCE: 202

Met Leu Arg Arg Leu Val Gln Gln Trp Gly Val Ala Val Phe Leu Leu
1               5                   10                  15

Ser Tyr Ser Val Pro Ser Cys Gly Arg Ser Val Glu Glu Leu Gly Arg
                20                  25                  30

Arg Leu Lys Arg
        35

<210> SEQ ID NO 203
<211> LENGTH: 36
<212> TYPE: PRT
<213> ORGANISM: Mus musculus

<400> SEQUENCE: 203

Met Leu Arg Arg Leu Val Gln Gln Trp Ser Val Leu Val Phe Leu Leu
1               5                   10                  15

-continued

```
Ser Tyr Ser Val Pro Ser Arg Gly Arg Ser Val Glu Gly Leu Gly Arg
            20                  25                  30

Arg Leu Lys Arg
        35

<210> SEQ ID NO 204
<211> LENGTH: 36
<212> TYPE: PRT
<213> ORGANISM: Oryctolagus cuniculus

<400> SEQUENCE: 204

Met Leu Arg Arg Leu Val Gln Gln Trp Ser Val Ala Val Phe Leu Leu
1               5                   10                  15

Ser Tyr Ser Val Pro Ser Cys Gly Arg Ser Val Glu Gly Pro Gly Arg
            20                  25                  30

Arg Leu Lys Arg
        35

<210> SEQ ID NO 205
<211> LENGTH: 36
<212> TYPE: PRT
<213> ORGANISM: Phoca vitulina

<400> SEQUENCE: 205

Met Leu Arg Arg Leu Val Gln Gln Trp Ser Val Ala Val Phe Leu Leu
1               5                   10                  15

Ser Tyr Ser Val Pro Ser Cys Gly Arg Ser Val Glu Glu Leu Gly Arg
            20                  25                  30

Arg Leu Lys Arg
        35

<210> SEQ ID NO 206
<211> LENGTH: 29
<212> TYPE: PRT
<213> ORGANISM: Cervus elaphus
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (9)
<223> OTHER INFORMATION: Variable amino acid

<400> SEQUENCE: 206

Gln Trp Ser Val Xaa Val Phe Leu Xaa Ser Tyr Ser Val Pro Ser Cys
1               5                   10                  15

Gly Arg Ser Val Glu Glu Leu Gly Arg Arg Leu Lys Arg
            20                  25

<210> SEQ ID NO 207
<211> LENGTH: 26
<212> TYPE: PRT
<213> ORGANISM: Ovis aries

<400> SEQUENCE: 207

Val Gly Val Phe Leu Leu Ser Tyr Ser Val Pro Ser Cys Gly Arg Ser
1               5                   10                  15

Val Glu Glu Leu Gly Arg Arg Leu Lys Arg
            20                  25

<210> SEQ ID NO 208
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Gly Gly Lys Gly Gly Gly Gly
1               5

<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Gly Gly Asn Gly Ser Gly Gly
1               5

<210> SEQ ID NO 210
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Gly Gly Cys Gly Gly Gly Gly
1               5

<210> SEQ ID NO 211
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gly Pro Asn Gly Gly
1               5

<210> SEQ ID NO 212
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gly Gly Gly Ala Pro
1               5

<210> SEQ ID NO 213
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
acccgctcga ggatactagt gatggagcaa catg                                  34
```

<210> SEQ ID NO 214
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (6)..(32)

<400> SEQUENCE: 214 aactt ggc gcg ccc gaa att gtg ttg acg cag                        32
      Gly Ala Pro Glu Ile Val Leu Thr Gln
      1               5

<210> SEQ ID NO 215
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
cttgtcgact caacactctc ccctgttgaa gctc                            34

<210> SEQ ID NO 216
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (6)..(32)

<400> SEQUENCE: 216 aactt ggc gcg ccc gag gtg cag ctg ttg gag                        32
      Gly Ala Pro Glu Val Gln Leu Leu Glu
      1               5

<210> SEQ ID NO 217
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
gcatgtcgac tcatttaccc ggagacaggg agag                            34

<210> SEQ ID NO 218
<211> LENGTH: 22
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 218
gcatcatgaa acatcgggaa gc                                         22

<210> SEQ ID NO 219

<211> LENGTH: 22
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 219
cccaaagtac gtcgcatctt ga                                              22

<210> SEQ ID NO 220
<211> LENGTH: 22
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 220
gttaagcaac ggaaaactaa gg                                              22

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 221
caaagtacgt cgcatcttga t                                               21

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 222
gcaaggtagg gttcaactga                                                 20

<210> SEQ ID NO 223
<211> LENGTH: 22
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 223
gtcctgtatg ggtggtagtc tt                                              22

<210> SEQ ID NO 224
<211> LENGTH: 34
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 224
attgcgatcg cgttactggg agaagtgcag attt                                 34

<210> SEQ ID NO 225
<211> LENGTH: 34

```
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 225
aatggcgcgc ccatagcgta gcgttcatta tcct                                    34

<210> SEQ ID NO 226
<211> LENGTH: 22
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 226
tgcaatctgc gcctcagtct tc                                                 22

<210> SEQ ID NO 227
<211> LENGTH: 22
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 227
atttctcacc gtcggcatct cc                                                 22

<210> SEQ ID NO 228
<211> LENGTH: 38
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 228
attctcgagg tatacctata gcttaagggc aggataga                                38

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 229
ctttatggga acctagagag aaac                                               24

<210> SEQ ID NO 230
<211> LENGTH: 26
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 230
tctaggttcc cataaagtga gtctgt                                             26

<210> SEQ ID NO 231
<211> LENGTH: 41
<212> TYPE: DNA
```

<213> ORGANISM: Artificial Sequence
<220> FEATURE:
<223> OTHER INFORMATION: Description of Artificial Sequence: Synthetic
      peptide

<400> SEQUENCE: 231
ttccacgaaa tgagtctcaa tctatatctc gaactttaaa a                    41

<210> SEQ ID NO 232
<211> LENGTH: 39
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 232
gttcgagata tagattgaga ctcatttcgt ggaacatta                       39

<210> SEQ ID NO 233
<211> LENGTH: 34
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 233
attggccggc cctttggaga aagatagaag ccac                            34

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 234
ccaacatgac ttttagcaat g                                          21

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 235
tcctctccag accgtaactt a                                          21

<210> SEQ ID NO 236
<211> LENGTH: 22
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 236
gatctctcgt gggatcattg tt                                         22

<210> SEQ ID NO 237
<211> LENGTH: 22
<212> TYPE: DNA
<213> ORGANISM: Artificial Sequence

```
<220> FEATURE:
<223> OTHER INFORMATION: Description of Artificial Sequence: Synthetic
      peptide

<400> SEQUENCE: 237
aacccactta gaagatgctg ct                                              22

<210> SEQ ID NO 238
<211> LENGTH: 22
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 238
catggaactt gggagtgact tt                                              22

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 239
tcaaggttct cagtggcaca t                                               21

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Ala Pro Glu Ile Val Leu Thr Gln
1               5

<210> SEQ ID NO 241
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ser Phe Asn Arg Gly Glu Cys
1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Ala Pro Glu Val Gln Leu Leu Glu
1               5

<210> SEQ ID NO 243
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Leu Ser Leu Ser Pro Gly Lys
1               5

<210> SEQ ID NO 244
<211> LENGTH: 33
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 244
attgcggccg cagtggactt actcaaacct tct                                  33

<210> SEQ ID NO 245
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser Tyr Met His Lys
            20                  25                  30

Leu Leu Val Leu Asp Ala Pro
        35

<210> SEQ ID NO 246
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Gly Gly Gly
1

<210> SEQ ID NO 247
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gly Gly Gly Gly Gly
1               5
```